US012084662B2

(12) United States Patent
Saxena et al.

(10) Patent No.: US 12,084,662 B2
(45) Date of Patent: Sep. 10, 2024

(54) COMPOSITIONS AND METHODS FOR MODULATING PNPLA3 EXPRESSION

(71) Applicant: Dicerna Pharmaceuticals, Inc., Lexington, MA (US)

(72) Inventors: Utsav Saxena, Watertown, MA (US); Henryk T. Dudek, Belmont, MA (US); Marc Abrams, Natick, MA (US); Anton Turanov, Revere, MA (US); Bob Dale Brown, Littleton, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 17/719,821

(22) Filed: Apr. 13, 2022

(65) Prior Publication Data

US 2022/0364098 A1 Nov. 17, 2022

Related U.S. Application Data

(60) Provisional application No. 63/174,932, filed on Apr. 14, 2021.

(51) Int. Cl.
*C12N 15/113* (2010.01)
*A61K 31/7125* (2006.01)
(Continued)

(52) U.S. Cl.
CPC ...... *C12N 15/1137* (2013.01); *A61K 31/7125* (2013.01); *C07H 21/02* (2013.01); *C12N 2310/315* (2013.01); *C12N 2310/32* (2013.01); *C12N 2310/321* (2013.01); *C12N 2310/3515* (2013.01); *C12P 19/34* (2013.01)

(58) Field of Classification Search
CPC .......... C12N 15/1137; C12N 2310/315; C12N 2310/32; C12N 2310/321; A61K 31/7125; C07H 21/02
See application file for complete search history.

(56) References Cited

U.S. PATENT DOCUMENTS 10,231,988 B2 * 3/2019 Fitzgerald .......... C12N 15/1137
10,675,295 B2 * 6/2020 Abrams ............. A61K 31/7125

FOREIGN PATENT DOCUMENTS

WO 2005000201 A2 1/2005
WO 2014179625 A1 11/2014
(Continued)

OTHER PUBLICATIONS

Song and Rossi, The effect of Dicer knockout on RNA interference using various Dicer substrate interfering RNA structures, 2020, bioRxiv preprint doi: https://doi.org/10.1101/2020.04.19.049817, p. 1-30 (Year: 2020).*
(Continued)

*Primary Examiner* — J. E. Angell
*Assistant Examiner* — Keyur A Vyas
(74) *Attorney, Agent, or Firm* — Dechert LLP; Andrea L.C. Reid; Gang Wang

(57) ABSTRACT

Oligonucleotides and compositions including the same are disclosed for inhibiting or reducing patatin-like phospholipase domain-containing protein 3 (PNPLA3) gene expression. Methods of making and using the oligonucleotides also are disclosed, particularly uses relating to treating diseases, disorders and/or conditions associated with PNPLA3 expression.

3 Claims, 2 Drawing Sheets

Specification includes a Sequence Listing.

M1405-M2028

The arrow indicates the nick between the sense strand and the antisense strand.

Sense Mod (5'→3')

M1405

Antisense Mod (3'→5')

M2028

G G N N N N N N N N N N N N N N N N N N N U

(51) Int. Cl.
*C07H 21/02* (2006.01)
*C12P 19/34* (2006.01)

(56) References Cited

FOREIGN PATENT DOCUMENTS

| | | | |
|---|---|---|---|
| WO | 2015085158 | A1 | 6/2015 |
| WO | WO-2016130806 | A2 | 8/2016 |
| WO | 2018223081 | A1 | 12/2018 |
| WO | WO-2019118638 | A2 | 6/2019 |
| WO | WO-2020061200 | A1 | 3/2020 |
| WO | 2020123508 | A2 | 6/2020 |
| WO | 2021067744 | A1 | 4/2021 |
| WO | 2022221430 | A1 | 10/2022 |

OTHER PUBLICATIONS

Carlsson et al., "Review article: the emerging role of genetics in precision medicine for patients with non-alcoholic steatohepatitis," Aliment Pharmacol Ther. 2020;51(12):1305-1320.
PCT International Search Report and Written Opinion from PCT/US2022/024657 dated Jul. 18, 2022.
Kumari et al., "Adiponutrin functions as a nutritionally regulated lysophosphatidic acid acyltransferase," Cell Metab. 2012; 15(5):691-702.
Pingitore and Romeo, "The role of PNPLA3 in health and disease," Biochim Biophys Acta Mol Cell Biol Lipids. 2019;1864(6):900-906.

* cited by examiner

COMPOSITIONS AND METHODS FOR MODULATING PNPLA3 EXPRESSION

CROSS-REFERENCE TO RELATED APPLICATIONS

The present application claims priority under 35 U.S.C. § 119(e) from U.S. Provisional Application No. 63/174,932, filed Apr. 14, 2021, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 12, 2022, is named 400930-028US_190155_SL.txt and is 344,678 bytes in size.

TECHNICAL FIELD

The disclosure relates generally to biology and medicine, and more particularly it relates to the use of oligonucleotide compositions for inhibiting or reducing patatin-like phospholipase domain-containing protein 3 (PNPLA3) gene expression, as well as to uses thereof, particularly uses relating to treating diseases, disorders and/or conditions associated with PNPLA3.

BACKGROUND

PNPLA3 is a protein encoded by PNPLA3 and is a protein having triacylglycerol lipase and acylglycerol transacylase activities. Human PNPLA3 is expressed highly in the liver and moderately in the adipose tissue, brain, kidney, and skin.

Of particular interest herein is a mutation of an isoleucine (Ile/I) to a methionine (Met/M) at position 148 in human PNPLA3 (1148M or PNPLA3 148M; i.e., PNPLA3 rs738409). See, Pingitore & Romeo (2019) Biochim. Biophys. Acta Mol. Cell Biol. Lipids 1864:900-906. Compared to wild-type PNPLA3, PNPLA3 148M lacks lipase activity but appears to have increased transacylase activity. See, Kumari et al. (2012) Cell Metab. 15:691-702.

PNPLA3 148M is strongly associated with a wide spectrum of liver diseases resulting from triglyceride (TG) accumulation, liver injury and fibrosis, including alcoholic hepatitis (AH), alcoholic liver disease (ALD), cirrhosis, hepatocellular carcinoma (HCC), non-alcoholic fatty liver disease (NAFLD), and non-alcoholic steatohepatitis (NASH). It appears that PNPLA3 148M degradation by proteasomes is delayed, which results in an accumulation of the protein on the surface of lipid droplets and which does not allow other proteins to metabolize TGs in hepatocytes. As such, reducing PNPLA3 148M expression may allow other lipases to function normally and reverse the adverse effects of PNPLA3 I148M across a variety of pathologies.

Several RNA-based therapeutics are known for attempting to inhibit or reduce PNPLA3 expression. For example, Intl. Patent Application Publication Nos. WO 2016/130806 and WO 2019/118638 describe double-stranded (ds) RNAi constructs for inhibiting or reducing PNPLA3 expression, as well as methods of using the same for treating or preventing liver diseases such as NAFLD. Also, Intl. Patent Application Publication No. WO 2020/061200 describes antisense oligonucleotides for inhibiting or reducing PNPLA3 expression.

Despite the existence of some therapeutics directed toward PNPLA3, there is a need for additional therapeutics for inhibiting or reducing PNPLA3 expression for treating liver disease.

BRIEF SUMMARY

To address this need, the disclosure describes compositions and methods for treating a disease, disorder, and/or condition related to PNPLA3 expression. The disclosure is based, in part, on discovering and developing ds oligonucleotides (e.g., RNAi oligonucleotides) for selectively inhibiting and/or reducing PNPLA3 expression in, for example, the liver. Accordingly, target sequences within PNPLA3 have been identified, and RNAi oligonucleotides that bind to these target sequences and inhibit PNPLA3 mRNA expression have been generated. As shown herein, the RNAi oligonucleotides inhibit human and cynomolgus monkey PNPLA3 expression in the liver. Without being bound by theory, the RNAi oligonucleotides herein are useful for treating a disease, disorder or condition associated with PNPLA3 expression (e.g., liver disease such as AH, ALD, cirrhosis, HCC, cholangiocarcinoma (CCA), primary sclerosing cholangitis (PSC), NAFLD, and NASH). In general, the RNAi oligonucleotides herein are useful for treating a disease, disorder, or condition associated with aberrant PNPLA3 expression (e.g., mutant PNPLA3 allele expression). In particular, the RNAi oligonucleotides herein are useful for treating a disease, disorder, or condition associated with mutant PNPLA3 expression.

Accordingly, the disclosure describes RNAi oligonucleotides for reducing or inhibiting PNPLA3 expression that includes a sense strand having a sequence as set forth in Table 1 (e.g., SEQ ID NOs: 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, and 775) or Table 3 (e.g., SEQ ID NOs: 777, 779, 781, 783, 785, 787, 789, 791, 793, 795, 797, 799, 801, 803, 805, 807, 809, 811, 813, 815, 817, 819, 821, 823, 825, 827, 829, 831, 833, 835, 837, 839, 841, 843, 845, 847, 849, 851, 853, 855, 857, 859, 861, 863, 865, 867, 869, 871, 873, 875, 877, 879, 881, 883, 885, 887, 889, 891, 893, 895, 897, 899, 901, 903, 905, 907, 909, 911, 913, 915, 917, 919, 921, 923, 925, 927, 929, 931, 933, 935, 937, 939, 941, 943, 945, 947, 949, 951, 953, 955, 957, 959, 961, 963, 965, 967, 969, 971, 973, 975, 977, 979, 981, 983, 985, 987, 989, 991, 993, 995, 997, 999, 1001, 1003, 1005, 1007, 1009, 1011, 1013, 1015, 1017, 1019, 1021, 1023, 1025, 1027, 1029, 1031, 1033, 1035, 1037, 1039, 1041, 1043, 1045, 1047, 1049, 1051, 1053, 1055, 1057, 1059, 1061, 1063, 1065, 1067, 1069, 1071, 1073, 1075, 1077, 1079, 1081, 1083, 1085, 1087, 1089, 1091, 1093, 1095, 1097, 1099, 1101, 1103, 1105, 1107, 1109, 1111, 1113, 1115, 1117, 1119, 1121, 1123, 1125, 1127, 1129, 1131, 1133, 1135, 1137, 1139, 1141, 1143, 1145, 1147, 1149, 1151, 1153, 1155, 1157, 1159, 1161, and 1163), especially any one of SEQ ID NOs: 787, 843, 867, 871, 937, 1003, 1007, 1017, 1161, or 1163.

Alternatively, the disclosure describes RNAi oligonucleotides for reducing or inhibiting PNPLA3 expression that includes an antisense strand having a sequence as set forth in Table 1 (e.g., SEQ ID NOs: 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, and 776) or Table 3 (e.g., SEQ ID NOs: 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, and 1164), especially any one of SEQ ID NOs: 788, 844, 868, 872, 938, 1004, 1008, 1018, 1162, or 1164.

In certain embodiments, the disclosure describes RNAi oligonucleotides for reducing or inhibiting PNPLA3 expression that includes a sense strand having a sequence as set forth in Table A, B, C or D (e.g., SEQ ID NOs: 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, or 1300).

In certain embodiments, the disclosure describes RNAi oligonucleotides for reducing or inhibiting PNPLA3 expression that includes an antisense strand having a sequence as set forth in Table A, B, C or D (e.g., SEQ ID NOs: 1179, 1181, 1183, 1185, 1187, 1189, 1191, 1193, 1195, 1197, 1199, 1201, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, or 1301).

In some embodiments, RNAi oligonucleotides are described for reducing or inhibiting PNPLA3 expression that include an antisense strand and a sense strand, where the antisense strand has a sequence as set forth in Table 1 or Table 3, and where the sense strand has a sequence as set forth in Table 1 or Table 3.

In some embodiments, RNAi oligonucleotides are described for reducing or inhibiting PNPLA3 expression that include an antisense strand and a sense strand, where the antisense strand has a sequence as set forth in Table A, Table B, Table C, or Table D, and where the sense strand has a sequence as set forth in Table A, Table B, Table C, or Table D.

In some embodiments, RNAi oligonucleotides are described for reducing or inhibiting PNPLA3 expression that include an antisense strand and a sense strand, where the antisense and sense strands form a duplex region, and where the antisense strand has a region of complementarity to a PNPLA3 mRNA target sequence of any one of SEQ ID NOS:1167 to 1176.

In any of the embodiments above, the antisense strand is from about 15 nucleotides to about 30 nucleotides in length. In some embodiments, the antisense strand is from about 20 nucleotides to about 25 nucleotides. In some embodiments, the antisense strand is 22 nucleotides in length.

In any of the embodiments above, the sense strand is from about 15 nucleotides to about 50 nucleotides in length. In some instances, the sense strand is from about 20 nucleotides to about 40 nucleotides in length. In some embodiments, the sense strand is 36 nucleotides in length.

In any of the embodiments above, the duplex region is from about 19 nucleotides in length to about 21 nucleotides in length. In certain embodiment, the duplex region is 20 nucleotides in length.

In any of the embodiments above, the region of complementarity is at least 15 contiguous nucleotides in length. In some embodiments, the region of complementarity is from about 19 contiguous nucleotides in length to about 21 contiguous nucleotides in length. In other embodiments, the region of complementarity is 19 contiguous nucleotides in length or 21 contiguous nucleotides in length.

In any of the embodiments above, the RNAi oligonucleotides include on the sense strand a 3' end a stem-loop set forth as: S1-L-S2, where S1 is complementary to S2, and where L forms a loop between S1 and S2 of about 3 to about 5 nucleotides in length.

In any of the embodiments above, the antisense strand, the sense strand, or both have an overhang sequence. In some embodiments, the antisense strand includes a 3'-overhang of 1 or more nucleotides in length. In other embodiments, the 3'-overhang sequence is 2 nucleotides in length such as, for example, GG.

Oligonucleotides also are described that include an antisense strand and a sense strand, where the antisense strand can be from about 21 nucleotides to about 27 nucleotides in length and has a region of complementarity to PNPLA3, wherein the sense strand includes a stem-loop at its 3' end set forth as: S1-L-S2, wherein S1 is complementary to S2, wherein L forms a loop between S1 and S2 from about 3 nucleotides to about 5 nucleotides in length, and wherein the antisense strand and the sense strand form a duplex structure of at least about 19 nucleotides in length but are not covalently linked.

In some embodiments, the loop L is a triloop or a tetraloop. In some instances, L is a tetraloop of 4 nucleotides in length. In other embodiments, L includes a sequence 5'-GAAA-3'.

In some embodiments, S1 and S2 are 1-10 nucleotides in length and have the same length. In other embodiments, S1 and S2 are 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides in length. In other embodiments, S1 and S2 are 6 nucleotides in length. In certain embodiments, the stem-loop comprises the sequence 5'-GCAGCCGAAAGGCUGC-3' (SEQ ID NO:1177).

In some embodiments, the antisense strand is 27 nucleotides in length and the sense strand is 25 nucleotides in length. In other embodiments, the antisense strand is 22 nucleotides in length and the sense strand is 36 nucleotides in length.

In the embodiments above, the duplex region includes a 3'-overhang sequence on the antisense strand. In some embodiments, the 3'-overhang sequence on the antisense strand is 2 nucleotides in length.

In any of the embodiments above, at least one nucleotide in an oligonucleotide is a modified nucleotide. In some instances, the modified nucleotide includes a 2'-modification such as, for example, 2'-aminoethyl, 2'-fluoro, 2'-O-methyl, 2'-O-methoxyethyl and 2'-deoxy-2'-fluoro-β-arabinonucleic acid. In certain instances, all nucleotides in an oligonucleotide include a 2'-modification such as, for example, 2'-fluoro or 2'-O-methyl.

In any of the embodiments above, at least one nucleotide in an oligonucleotide includes a modified internucleotide linkage. In some embodiments, the modified internucleotide linkage is a phosphorothioate linkage.

In any of the embodiments above, a 4'-carbon of a sugar of a 5'-nucleotide of the antisense strand includes a phosphate analog such as, for example, an oxymethylphosphonate, vinylphosphonate or malonylphosphonate. Alternatively, or optionally, the phosphate analog is a 4'-phosphate analog including 5'-methoxyphosphonate-4'-oxy.

In any of the embodiments above, at least one nucleotide of an oligonucleotide can be conjugated to one or more targeting ligands such as, for example, an amino sugar, carbohydrate, cholesterol, lipid, or polypeptide. In some embodiments, the targeting ligand is a N-acetylgalactosamine (GalNAc) moiety. In other embodiments, the GalNAc moiety is a monovalent GalNAc moiety, a bivalent GalNAc moiety, a trivalent GalNAc moiety, or a tetravalent GalNAc moiety.

In some embodiments, the targeting ligands are conjugated to one or more nucleotides of L of the stem loop. In certain instances, up to 4 nucleotides of L of the stem-loop are each conjugated to a monovalent GalNAc moiety.

In any of the embodiments above, the oligonucleotide is an RNAi oligonucleotide. In some instances, the RNAi oligonucleotide includes a sense strand having a nucleotide sequence as set forth in Table 1 or Table 3, especially any one of SEQ ID NOs: 787, 843, 867, 871, 937, 1003, 1007, 1017, 1161, or 1163. In certain embodiments, the RNAi oligonucleotide includes a sense strand having a nucleotide sequence as set forth in Table A, B, C, or D, especially any one of SEQ ID NOs: 1188, 1190, 1220, 1224, 1230, 1232, 1244, 1246, 1250, or 1254. In some instances, the RNAi oligonucleotide includes an antisense strand having a nucleotide sequence as set for the in Table 1 or Table 3, especially any one of SEQ ID NOs: 788, 844, 868, 872, 938, 1004, 1008, 1018, 1162, or 1164. In some embodiments, the RNAi oligonucleotide includes an antisense strand having a nucleotide sequence as set for the in Table A, B, C or D, especially any one of SEQ ID NOs: 1189, 1191, 1221, 1225, 1231, 1233, 1245, 1247, 1251, or 1255. In certain instances, the RNAi oligonucleotide includes a sense strand having a nucleotide sequence of any one of SEQ ID NOs: 787, 843, 867, 871, 937, 1003, 1007, 1017, 1161, or 1163, or any one of SEQ ID NOs: 1188, 1190, 1220, 1224, 1230, 1232, 1244, 1246, 1250, or 1254 and an antisense strand having a nucleotide sequence of any one of SEQ ID NOs: 788, 844, 868, 872, 938, 1004, 1008, 1018, 1162, or 1164, any one of SEQ ID NOs: 1189, 1191, 1221, 1225, 1231, 1233, 1245, 1247, 1251, or 1255. In certain embodiments, the sense strand and the antisense strand of the RNAi oligonucleotide, respectively, are selected from:

(a) SEQ ID NOs: 787 and 788,
(b) SEQ ID NOs: 843 and 844,
(c) SEQ ID NOs: 867 and 868,
(d) SEQ ID NOs: 871 and 872,
(e) SEQ ID NOs: 937 and 938,
(f) SEQ ID NOs: 1003 and 1004,
(g) SEQ ID NOs: 1007 and 1008,
(h) SEQ ID NOs: 1017 and 1018,
(i) SEQ ID NOs: 1161 and 1162, and
(j) SEQ ID NOs: 1163 and 1164.

In some instances, the RNAi oligonucleotide includes a sense strand having a nucleotide sequence as set forth in Table A, Table B, Table C, or Table D, especially any one of SEQ ID NOs: 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, or 1300. In some instances, the RNAi oligonucleotide includes an antisense strand having a nucleotide sequence as set for the in Table A, Table B, Table C, or Table D, especially any one of SEQ ID NOs: 1179, 1181, 1183, 1185, 1187, 1189, 1191, 1193, 1195, 1197, 1199, 1202, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, or 1301. In certain instances, the RNAi oligonucleotide includes a sense strand having a nucleotide sequence of any one of SEQ ID NOs: 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, or 1300, and an antisense strand having a nucleotide sequence of any one of SEQ ID NOs: 1179, 1181, 1183, 1185, 1187, 1189, 1191, 1193, 1195, 1197, 1199, 1201, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, or 1301.

In certain instances, the RNAi oligonucleotide includes a sense strand having a nucleotide sequence of any one of SEQ ID NOs: 1188, 1190, 1200, 1216, 1218, 1220, 1224, 1230, 1232, 1234, 1244, 1246, 1250, 1254, 1262, 1288, 1290, 1292, 1294, 1296, 1298, or 1300, and an antisense strand having a nucleotide sequence of any one of SEQ ID NOs: 1189, 1191, 1201, 1215, 1217, 1219, 1225, 1231, 1233, 1235, 1245, 1247, 1251, 1255, 1263, 1289, 1291, 1295, 1297, 1299, or 1301.

In particular instances, the sense strand and the antisense strand of the RNAi oligonucleotide, respectively, are selected from:

(a) SEQ ID NOs: 1220 and 1221,
(b) SEQ ID NOs: 1224 and 1225,
(c) SEQ ID NOs: 1230 and 1231,
(d) SEQ ID NOs: 1232 and 1233,
(e) SEQ ID NOs: 1188 and 1189,
(f) SEQ ID NOs: 1190 and 1191,
(g) SEQ ID NOs: 1244 and 1245,
(h) SEQ ID NOs: 1250 and 1251-,
(i) SEQ ID NOs: 1254 and 1255, and
(j) SEQ ID NOs: 1246 and 1247.

Oligonucleotides also are described for inhibiting or reducing PNPLA3 expression that include a sense strand and an antisense strand, where the sense strand and the antisense strand form a duplex region, where all nucleotides of the sense strand and the antisense strand include a modification of a base, a sugar and/or an internucleotide linkage, where the antisense strand includes a region of complementarity to a PNPLA3 mRNA target sequence of one of SEQ ID NOs: 1167 to 1176, and where the region of complementarity is at least about 15 contiguous nucleotides in length.

In other aspects, pharmaceutical compositions are described that include at least one oligonucleotide herein and a pharmaceutically acceptable carrier, delivery agent or excipient. In some instances, the pharmaceutical compositions include an additional therapeutic agent such as, for example, an antidiabetic agent or anti-obesity agent.

In other aspects, methods are described for reducing PNPLA3 expression in a cell, a population of cells, a tissue, an organ, or an individual that include at least a step of administering/contacting the cell, the population of cells, the tissue, the organ, or the individual with an oligonucleotide herein or a pharmaceutical composition herein. In some instances, reducing PNPLA3 expression includes reducing an amount or level of PNPLA3 mRNA, an amount or level of PNPLA3 protein, or both in the cell, the population of cells, the tissue, the organ, or the individual. In some instances, the cell, the cell population, the tissue, the organ, or the individual has a disease, disorder, or condition associated with PNPLA3 expression. In certain instances, the disease, disorder, or condition associated with PNPLA3 expression is a cardiometabolic disease, AH, ALD, cirrhosis, HCC, CCA, and other cholangiopathies (such as PSC), NAFLD, and NASH.

In other aspects, methods are described for treating an individual having or suspected of having a disease, disorder or condition associated with PNPLA3 expression. The methods include at least a step of administering to an individual in need thereof an effective amount of an oligonucleotide herein or a pharmaceutical composition herein. In some instances, the disease, disorder, or condition associated with PNPLA3 expression is a cardiometabolic disease, AH, ALD, CCA, cirrhosis, HCC, NAFLD, PSC, and NASH. In some instances, the oligonucleotide or pharmaceutical composition is administered daily, weekly, monthly, quarterly, yearly via SQ administration, especially monthly or quarterly.

In some instances, the individual has cirrhosis, diabetes, hepatic fibrosis, hepatic inflammation, hyperlipidemia, AH, ALD, CCA, cirrhosis, HCC, NAFLD, PSC, NASH, obesity, and/or steatosis.

In any of the embodiments above, the methods comprise additional steps such as measuring or obtaining genotype information, PNPLA3 expression, PNPLA3 protein levels, the individual's weight and/or blood glucose and/or TGs and comparing such obtained values to one or more baseline values or previously obtained values to assess the effectiveness of contacting or administering. In some embodiments, the additional step comprises confirming that the individual has a PNPLA3 I148M variant. In some embodiments, the additional step comprises confirming that the individual does not have a PNPLA3 E434K variant. In some embodiments, the additional step comprises confirming that the individual does not have a protein truncating HSD17B13 variant (rs72613567).

In any of the embodiments above, the methods can include administering the RNAi oligonucleotide or pharmaceutical composition simultaneously, separately, or sequentially with a second composition or a second therapeutic agent. In some embodiments, the second composition or a second therapeutic agent is a PNPLA3 antibody or fragment thereof, an antidiabetic agent or anti-obesity agent. In some embodiments, the second composition or second therapeutic agent is administered with a frequency same as the RNAi oligonucleotide (i.e., every other day, twice a week, or even weekly). In other embodiments, the second composition or second therapeutic agent is administered with a frequency distinct from the RNAi oligonucleotide. Likewise, in other embodiments, the second composition or second therapeutic agent is administered via the same route as the RNAi oligonucleotide (e.g., SQ). In still other embodiments, the second composition or second therapeutic agent is administered via a route that differs from the RNAi oligonucleotide).

In other aspects, uses are described for the RNAi oligonucleotides herein for treating a disease, disorder or condition associated with PNPLA3 expression, which optionally are administered simultaneously, separately, or sequentially (i.e., in combination) with a second composition or second therapeutic agent.

In other aspects, uses are described for the RNAi oligonucleotides herein in manufacturing a medicament for treating a disease, disorder, or condition associated with PNPLA3 expression, where the medicament optionally further includes a second composition or second therapeutic agent.

In other aspects, kits are described that include at least one oligonucleotide herein, an optional pharmaceutically acceptable carrier, and a package insert having instructions for administering the same to an individual having a disease, disorder, or condition associated with PNPLA3 expression.

An advantage of the oligonucleotides and compositions herein is that suppressed PNPLA3 expression, especially PNPLA3 148M, exerts a beneficial effect on the entire spectrum of NAFLD including fibrosis.

BRIEF DESCRIPTION OF THE DRAWINGS

The advantages, effects, features, and objects other than those set forth above will become more readily apparent when consideration is given to the detailed description below. Such detailed description refers to the following drawing(s), where:

FIG. 1 discloses SEQ ID NOS 1302-1303, respectively, in order of appearance. The sense strand has a modification pattern M1405, wherein nucleotides at positions 1, 2, 3, 4, 5, 6, 7, 12, 13, 14, 15, 16, 17, 18, 19, 20, 21, 22, 23, 24, 25, 26, 27, 31, 32, 33, 34, 35, and 36 are modified with 2'-O-methyl; nucleotides at positions 8, 9, 10, and 11 are modified with 2'-fluoro; the internucleotide linkage between nucleotides at positions 1 and 2 is a phosphorothioate linkage; and nucleotides at positions 28, 29, and 30 are modified with adem-GalNAc. The antisense strand has a modification pattern M2028, wherein nucleotides at positions 1. 6, 8, 9, 11, 12, 13, 15, 16, 17, 18, 19, 20, 21, and 22 are modified with 2'-O-methyl; nucleotides at positions 2, 3, 4, 5, 7, 10, and 14 are modified with 2'-fluoro; the internucleotide linkages between nucleotides at positions 1 and 2, positions 2 and 3, positions 3 and 4, positions 20 and 21, and positions 21 and 22 are phosphorothioate linkages; and nucleotide at position 1 is a 4'-phosphate analog comprising 5'-methoxyphosphonate-4'-oxy.

DETAILED DESCRIPTION

Overview

Figure 1:
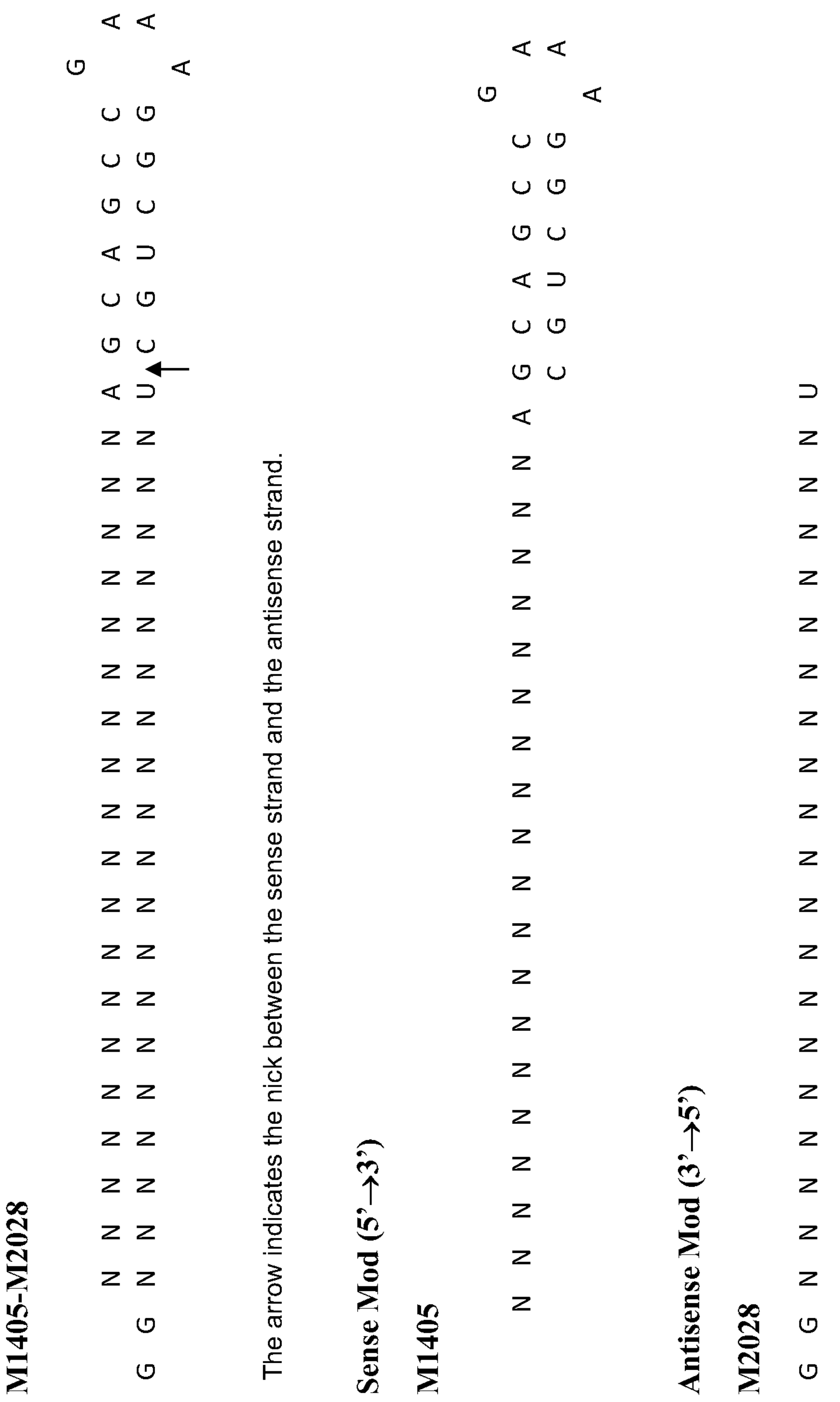
FIG. 1 discloses a schematic depicting the structure and chemical modification pattern of a generic GalNAc-conjugated PNPLA3 oligonucleotide.

ALD and NAFLD are serious public health burdens. ALD and NAFLD are chronic liver disorders that begin with hepatic TG accumulation (steatosis) and progress to hepatic inflammation and fibrosis, cirrhosis, and even liver cancer. PNPLA3 148M is a genetic factor that has been shown to be associated with ALD and NAFLD, as well, as cirrhosis, HCC, and liver-related death.

RNA interference (RNAi) is a process of introducing exogeneous RNA into a cell leading to specific degradation of the mRNA encoding the targeted protein with a resultant decrease in target gene expression.

In humans, PNPLA3 is 481 amino acids in length with a predicted molecular weight of 52.865 kD. Exemplary nucleic acid sequences for PNPLA3 can be found in NCBI Ref. Seq. No. NM_025225 (human), NM_054088 or XM_006520346 (mouse), NM_001282324 (rat), XM_015457081 (primate), XM_005567051 (primate) and XM_001109144 (primate). One of skill in the art, however, understands that additional examples of PNPLA3 mRNA sequences are readily available using publicly available databases such as, for example, GenBank and UniProt.

Definitions

As used herein, “about” means within a statistically meaningful range of a value or values such as, for example, a stated concentration, length, molecular weight, pH, sequence similarity, time frame, temperature, volume, etc. Such a value or range can be within an order of magnitude typically within 20%, more typically within 10%, and even more typically within 5% of a given value or range. The allowable variation encompassed by “about” will depend upon the system under study, and can be readily appreciated by one of skill in the art.

As used herein, “administer,” “administering,” “administration” and the like refers to providing a substance (e.g., an oligonucleotide herein or a composition herein) to an individual in a manner that is pharmacologically useful (e.g., to treat a disease, disorder, or condition in the individual).

As used herein, “antisense strand” means an oligonucleotide herein that is complimentary to a region of a target sequence. Likewise, and as used herein, “sense strand” means an oligonucleotide herein that is complimentary to a region of an antisense strand.

As used herein, “asialoglycoprotein receptor” or “ASGPR” means a bipartite C-type lectin formed by a major 48 kDa subunit (ASGPR-1) and minor 40 kDa subunit (ASGPR-2). ASGPR is primarily expressed on the sinusoidal surface of hepatocyte cells and has a major role in binding, internalizing and subsequent clearing of circulating glycoproteins that contain terminal galactose or GalNAc residues (asialoglycoproteins).

As used herein, “attenuate,” “attenuating,” “attenuation” and the like refers to reducing or effectively halting. As a non-limiting example, one or more of the treatments herein may reduce or effectively halt the onset or progression of AH, ALD, CCA, PSC, cirrhosis, HCC, NAFLD, and NASH, as well as related diseases, disorders, and conditions in an individual. This attenuation may be exemplified by, for example, a decrease in one or more aspects (e.g., symptoms, tissue characteristics, and cellular, inflammatory, or immunological activity, etc.) of AH, ALD, cirrhosis, HCC, CCA, PSC, NAFLD, and NASH, as well as related diseases, disorders and conditions, no detectable progression (worsening) of one or more aspects of AH, ALD, cirrhosis, HCC, CCA, PSC, NAFLD, and NASH, as well as related diseases, disorders and conditions, or no detectable aspects of AH, ALD, cirrhosis, HCC, NAFLD, and NASH, as well as related diseases, disorders and conditions in an individual when they might otherwise be expected.

As used herein, “attenuate,” “attenuating,” “attenuation” and the like means reducing or effectively halting. As a non-limiting example, one or more of the treatments herein may reduce or effectively halt the onset or progression of dyslipidemia/hypertriglyceridemia/hyperlipidemia in a subject. This attenuation may be exemplified by, for example, a decrease in one or more aspects (e.g., symptoms, tissue characteristics, and cellular, inflammatory, or immunological activity, etc.) of AH, ALD, cirrhosis, HCC, CCA, PSC, NAFLD, and NASH, as well as related diseases, disorders, and conditions in an individual when they might otherwise be expected.

As used herein, "complementary" means a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. Complementary nucleotides can base pair in the Watson-Crick manner or in any other manner that allows for the formation of stable duplexes. Likewise, two nucleic acids may have regions of multiple nucleotides that are complementary with each other to form regions of complementarity, as described herein.

As used herein, "contact," "contacting" and the like means directly or indirectly introducing or delivering the RNAi into, for example, a cell by facilitating or effecting uptake or absorption into the cell.

As used herein, "deoxyribonucleotide" means a nucleotide having a hydrogen in place of a hydroxyl at the 2' position of its pentose sugar when compared with a ribonucleotide. A modified deoxyribonucleotide has one or more modifications substitutions of atoms other than at the 2' position, including modifications or substitutions in or of the nucleobase, sugar, or phosphate group.

As used herein, "double-stranded oligonucleotide" or "ds oligonucleotide" means an oligonucleotide that is substantially in a duplex form. The complementary base-pairing of duplex region(s) of a ds oligonucleotide can be formed between antiparallel sequences of nucleotides of covalently separate nucleic acid strands. Likewise, complementary base-pairing of duplex region(s) of a ds oligonucleotide can be formed between antiparallel sequences of nucleotides of nucleic acid strands that are covalently linked. Moreover, complementary base-pairing of duplex region(s) of a ds oligonucleotide can be formed from single nucleic acid strand that is folded (e.g., via a hairpin) to provide complementary antiparallel sequences of nucleotides that base pair together. A ds oligonucleotide can include two covalently separate nucleic acid strands that are fully duplexed with one another. However, a ds oligonucleotide can include two covalently separate nucleic acid strands that are partially duplexed (e.g., having overhangs at one or both ends). A ds oligonucleotide can include an antiparallel sequence of nucleotides that are partially complementary, and thus, may have one or more mismatches, which may include internal mismatches or end mismatches.

As used herein, "duplex," in reference to nucleic acids (e.g., oligonucleotides), means a structure formed through complementary base pairing of two antiparallel sequences of nucleotides.

As used herein, "excipient" means a non-therapeutic agent that may be included in a composition herein, for example, to provide or contribute to a desired consistency or stabilizing effect.

As used herein, "hepatocyte" or "hepatocytes" means cells of the parenchymal tissues of the liver. These cells make up about 70%-85% of the liver's mass and manufacture serum albumin, fibronectin (FBN) and the prothrombin group of clotting factors (except for Factors 3 and 4). Markers for hepatocyte lineage cells include, but are not limited to, transthyretin (Ttr), glutamine synthetase (GluI), hepatocyte nuclear factor 1a (Hnf1a) and hepatocyte nuclear factor 4a (Hnf4a). Markers for mature hepatocytes may include, but are not limited to, cytochrome P450 (Cyp3a11), fumarylacetoacetate hydrolase (Fah), glucose 6-phosphate (G6p), albumin (Alb) and OC2-2F8. See, e.g., Huch et al. (2013) NATURE 494:247-50.

As used herein, a "hepatotoxic agent" means a chemical compound, virus or other substance that is itself toxic to the liver or can be processed to form a metabolite that is toxic to the liver. Hepatotoxic agents may include, but are not limited to, carbon tetrachloride ($CCl_4$), acetaminophen (paracetamol), vinyl chloride, arsenic, chloroform, nonsteroidal anti-inflammatory drugs (such as aspirin and phenylbutazone).

As used herein, "labile linker" means a linker that can be cleaved (e.g., by acidic pH). Likewise, "fairly stable linker" means a linker that cannot be cleaved.

As used herein, "liver inflammation" or "hepatitis" means a physical condition in which the liver becomes swollen, dysfunctional and/or painful, especially as a result of injury or infection, as may be caused by exposure to a hepatotoxic agent. Symptoms may include jaundice, fatigue, weakness, nausea, vomiting, appetite reduction and weight loss. Liver inflammation, if left untreated, may progress to fibrosis, cirrhosis, liver failure or liver cancer.

As used herein, "liver fibrosis," "hepatic fibrosis" or "fibrosis of the liver" refers to an excessive accumulation in the liver of extracellular matrix proteins, which could include collagens (I, III, and IV), FBN, undulin, elastin, laminin, hyaluronan, and proteoglycans resulting from inflammation and liver cell death. Liver fibrosis, if left untreated, may progress to cirrhosis, liver failure or liver cancer.

As used herein, "loop" means an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

As used herein, "modified internucleotide linkage" means an internucleotide linkage having one or more chemical modifications when compared with a reference internucleotide linkage having a phosphodiester bond. A modified nucleotide can be a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

As used herein, "modified nucleotide" refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide, and thymidine deoxyribonucleotide. A modified nucleotide can be a non-naturally occurring nucleotide. A modified nucleotide can have, for example, one or more chemical modification in its sugar, nucleobase, and/or phosphate group. Additionally, or alternatively, a modified nucleotide can have one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc.

As used herein, "nicked tetraloop structure" mean a structure of a RNAi oligonucleotide that is characterized by separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

As used herein, "nucleotide" means an organic molecule having a nucleoside (a nucleobase such as, for example, adenine, cytosine, guanine, thymine, or uracil; and a pentose sugar such as, for example, ribose or 2'-deoxyribose; and a phosphate group, which can serve as a monomeric unit of nucleic acid polymers such as deoxyribonucleic acid (DNA) and ribonucleic acid (RNA).

As used herein, "oligonucleotide" means a short nucleic acid molecule (e.g., less than about 100 nucleotides in length). An oligonucleotide may be single-stranded (ss) or ds. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide (ASO), short siRNA, or ss siRNA. Typically, a ds oligonucleotide is a RNAi oligonucleotide.

As used herein, "overhang" means a terminal non-base pairing nucleotide(s) resulting from one strand or region extending beyond the terminus of a complementary strand with which the one strand or region forms a duplex. An overhang may include one or more unpaired nucleotides extending from a duplex region at the 5' terminus or 3' terminus of a ds oligonucleotide. The overhang can be a 3' or 5' overhang on the antisense strand or sense strand of a ds oligonucleotides.

As used herein, "phosphate analog" means a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. A 5' phosphate analog can include a phosphatase-resistant linkage. Examples of phosphate analogs include, but are not limited to, 5' phosphonates, such as 5' methylene phosphonate (5'-MP) and 5'-(E)-vinylphosphonate (5'-VP). An oligonucleotide can have a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, e.g., Intl. Patent Application Publication No. WO 2018/045317. Other modifications have been developed for the 5' end of oligonucleotides (see, e.g., Intl. Patent Application No. WO 2011/133871; U.S. Pat. No. 8,927,513; and Prakash et al. (2015) NUCLEIC ACIDS RES. 43:2993-3011).

As used herein, "PNPLA3-associated disease," "PNPLA3-associated disorder" or "PNPLA3-associated condition" means conditions where increased PNPLA3 expression and/or the presence of, for example, the PNPLA3 I148M variant. Exemplary PNPLA3-associated conditions, diseases or disorders include, but are not limited to, accumulation of fat in the liver, cirrhosis of the liver, fatty liver (steatosis), hepatocellular necrosis, HCC, liver fibrosis, inflammation of the liver, NASH, NAFLD, or obesity.

As used herein, "reduced expression," and with respect to a gene (e.g., PNPLA3) means a decrease in the amount or level of RNA transcript (e.g., PNPLA3 mRNA) or protein encoded by the gene and/or a decrease in the amount or level of activity of the gene in a cell, a population of cells, a sample, or a subject, when compared to an appropriate reference (e.g., a reference cell, population of cells, sample, or subject). For example, the act of contacting a cell with an oligonucleotide herein (e.g., an oligonucleotide having an antisense strand having a nucleotide sequence that is complementary to a nucleotide sequence including PNPLA3 mRNA) may result in a decrease in the amount or level of mRNA, protein, and/or activity (e.g., via degradation of PNPLA3 mRNA by the RNAi pathway) when compared to a cell that is not treated with the ds oligonucleotide. Similarly, and as used herein, "reducing expression" means an act that results in reduced expression of a gene (e.g., PNPLA3). Specifically, and as used herein, "reduction of PNPLA3 expression" means a decrease in the amount or level of PNPLA3 mRNA, PMPLA3 protein, and/or PNPLA3 activity in a cell, a population of cells, a sample, or a subject when compared to an appropriate reference (e.g., a reference cell, population of cells, tissue, or subject).

As used herein, "region of complementarity" means a sequence of nucleotides of a nucleic acid (e.g., a ds oligonucleotide) that is sufficiently complementary to an antiparallel sequence of nucleotides to permit hybridization between the two sequences of nucleotides under appropriate hybridization conditions (e.g., in a phosphate buffer, in a cell, etc.). An oligonucleotide herein includes a targeting sequence having a region of complementary to a mRNA target sequence.

As used herein, "ribonucleotide" means a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the nucleobase, sugar, or phosphate group.

As used herein, "RNAi oligonucleotide" refers to either (a) a ds oligonucleotide having a sense strand (passenger) and antisense strand (guide), in which the antisense strand or part of the antisense strand is used by the Argonaute 2 (Ago2) endonuclease in the cleavage of a target mRNA or (b) a ss oligonucleotide having a single antisense strand, where that antisense strand (or part of that antisense strand) is used by the Ago2 endonuclease in the cleavage of a target mRNA.

As used herein, "strand" refers to a single, contiguous sequence of nucleotides linked together through internucleotide linkages (e.g., phosphodiester linkages or phosphorothioate linkages). A strand can have two free ends (e.g., a 5' end and a 3' end).

As used herein, "subject" means any mammal, including cats, dogs, mice, rats, and primates, especially humans. Moreover, "individual" or "patient" may be used interchangeably with "subject."

As used herein, "synthetic" refers to a nucleic acid or other molecule that is artificially synthesized (e.g., using a machine such as, for example, a solid-state nucleic acid synthesizer) or that is otherwise not derived from a natural source (e.g., a cell or organism) that normally produces the nucleic acid or other molecule.

As used herein, "targeting ligand" means a molecule (e.g., an amino sugar, carbohydrate, cholesterol, lipid, or polypeptide) that selectively binds to a cognate molecule (e.g., a receptor) of a tissue or cell of interest and that is conjugatable to another substance for targeting another substance to the tissue or cell of interest. For example, a targeting ligand may be conjugated to an oligonucleotide herein for purposes of targeting the oligonucleotide to a specific tissue or cell of interest. A targeting ligand can selectively bind to a cell surface receptor. Accordingly, a targeting ligand, when conjugated to an oligonucleotide, facilitates delivery of the oligonucleotide into a particular cell through selective binding to a receptor expressed on the surface of the cell and endosomal internalization by the cell of the complex comprising the oligonucleotide, targeting ligand, and receptor. Moreover, a targeting ligand can be conjugated to an oligonucleotide via a linker that is cleaved following or during cellular internalization such that the oligonucleotide is released from the targeting ligand in the cell.

As used herein, "tetraloop" means a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a $T_m$ of at least about 50° C., at least about 55° C., at least about 56° C., at least about 58° C., at least about 60° C., at least about 65° C., or at least about 75° C. in 10 mM $NaHPO_4$ to a hairpin comprising a duplex of at least 2 base pairs (bp) in length. A tetraloop also may stabilize a bp in an adjacent stem duplex by stacking interactions. Additionally, interactions among the nucleotides in a tetraloop include, but are not limited to, non-Watson-Crick base pairing, stacking interactions, hydrogen bonding, and contact interactions (Cheong et al. (1990) Nature 346:680-682; Heus & Pardi (1991) Science 253:191-194). Here, a tetraloop can include or can have about 3 to 6 nucleotides, and typically is about 4 to 5 nucleotides. A tetraloop therefore can have 3, 4, 5, or 6 nucleotides, which may or may not be modified (e.g., which may or may not be conjugated to a targeting moiety), especially 4 nucleotides. Any nucleotide may be used in the tetraloop, and standard IUPAC-IUB symbols for such nucleotides may be used as described in Cornish-Bowden (1985) Nucleic Acids Res. 13:3021-30. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA) and the CUUG tetraloop (Woese et al. (1990) Proc. Natl. Acad. Sci. USA 87:8467-71; Antao et al. (1991) Nucleic Acids Res. 19:5901-05). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, e.g., Nakano et al. (2002) Biochem. 41:4281-92; and Shinji et al. (2000) Nippon Kagakkai Koen Yokoshu 78:731. Here, the tetraloop can be within a nicked tetraloop structure.

As used herein, "treat" or "treating" means an act of providing care to an individual in need thereof, for example, by administering a therapeutic agent (e.g., an oligonucleotide herein) to the individual for purposes of improving the health and/or well-being of the individual with respect to an existing condition (e.g., a disease, disorder) or to prevent or decrease the likelihood of the occurrence of a condition. Treating also can involve reducing the frequency or severity of at least one sign, symptom or contributing factor of a condition (e.g., disease, disorder) experienced by the individual.

As used herein, "iRNA," "iRNA agent," "RNAi," "RNAi agent" and "RNA interference agent" means an agent that contains RNA and that mediates the targeted cleavage of an RNA transcript via an RNA-induced silencing complex (RISC) pathway. iRNA directs sequence-specific degradation of mRNA via RNA interference. The iRNA modulates, inhibits, or reduces PNPLA3 expression in a cell.

Compositions

According to some aspects, the disclosure provides oligonucleotides (e.g., double-stranded RNAi oligonucleotides) that reduce, modulate, or inhibit expression of PNPLA3 in the liver. In some embodiments, the oligonucleotides provided herein used to treat of diseases associated with PNPLA3 expression. In some aspects, the disclosure provides methods of treatment a disease associated with PNPLA3 expression by reducing, modulating, or inhibiting PNPLA3 expression in the liver (e.g., in cells comprising the liver).

Oligonucleotide Inhibitors of PNPLA3 Expression

I. PNPLA3 Target Sequences: The oligonucleotides herein (e.g., RNAi oligonucleotides) are targeted to a target sequence comprising PNPLA3 mRNA (i.e., a PNPLA3 target sequence). In some embodiments, the oligonucleotide or a portion, fragment, or strand thereof (e.g., an antisense strand or a guide strand of a ds RNAi oligonucleotide) binds or anneals to a PNPLA3 target sequence, thereby inhibiting PNPLA3 expression. In some embodiments, the oligonucleotide is targeted to a PNPLA3 target sequence for inhibiting PNPLA3 expression in vivo. In some embodiments, the amount or extent of PNPLA3 expression inhibition by an oligonucleotide targeted to a PNPLA3 target sequence correlates with the potency of the oligonucleotide. In some embodiments, the amount or extent of inhibition of PNPLA3 expression by an oligonucleotide targeted to a PNPLA3 target sequence correlates with the amount or extent of therapeutic benefit in an individual having or suspected of having a disease, disorder, or condition associated with PNPLA3 expression treated with the oligonucleotide.

Through examining and analyzing the nucleotide sequence of PNPLA3 mRNAs, including mRNAs of multiple different species (e.g., human, cynomolgus monkey, and rhesus monkey; see, e.g., Example 1) and as a result of in vitro and in vivo testing (see, e.g., Examples 2-3), it is shown herein that certain nucleotide sequences of PNPLA3 mRNA are more amenable than others to oligonucleotide-based inhibition of PNPLA3 expression and are thus useful as target sequences for the oligonucleotides herein. In some embodiments, a sense strand of an oligonucleotide (e.g., a ds RNAi oligonucleotide) described herein (e.g., in Tables 1 or 3, or tables A, B, C or D) comprises a PNPLA3 target sequence. In some embodiments, a portion or region of the sense strand of an oligonucleotide described herein (e.g., in Tables 1 or 3, or tables A, B, C or D) comprises a PNPLA3 target sequence. In some embodiments, the PNPLA3 target sequence comprises, or consists of, a sequence of any one of SEQ ID NOs:1167 to 1176.

II. PNPLA3 mRNA Targeting Sequences: In some embodiments, the oligonucleotides herein have regions of complementarity to PNPLA3 mRNA (e.g., within a target sequence of PNPLA3 mRNA) for targeting PNPLA3 mRNA in cells and inhibiting PNPLA3 expression. In some embodiments, the oligonucleotides herein comprise a PNPLA3 targeting sequence (e.g., an antisense strand or a guide strand of a ds oligonucleotide) having a region of complementarity that binds or anneals to a PNPLA3 mRNA target sequence by complementary (Watson-Crick) base pairing. The targeting sequence or region of complementarity is of a suitable length and base content to enable binding or annealing of the oligonucleotide (or a strand thereof) to PNPLA3 mRNA for inhibiting its expression. In some embodiments, the targeting sequence or region of complementarity is at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, or at least about 30 nucleotides in length. Alternatively, the targeting sequence or region of complementarity is about 12 to about 30 (e.g., 12 to 30, 12 to 22, 15 to 25, 17 to 21, 18 to 27, 19 to 27, or 15 to 30) nucleotides in length. Alternatively, the targeting sequence or region of complementarity is about 12, 13, 14, 15, 16, 17, 18, 19, 20, 21, 22, 23, 24, 25, 26, 27, 28, 29, or 30 nucleotides in length. In certain embodiments, the targeting sequence or region of complementarity is 18 nucleotides in length. In certain embodiments, the targeting sequence or region of complementarity is 19 nucleotides in length. In certain embodiments, the targeting sequence or region of complementarity is 20 nucleotides in length. In certain embodiments, the targeting sequence or region of complementarity is 21 nucleotides in length. In certain embodiments, the targeting sequence or region of complementarity is 22 nucleotides in length. In certain embodiments, the targeting sequence or region of complementarity is 23 nucleotides in length. In certain embodiments, the targeting sequence or region of complementarity is 24 nucleotides in length.

In some embodiments, the oligonucleotides herein comprise a targeting sequence or a region of complementarity (e.g., an antisense strand or a guide strand of a double-stranded oligonucleotide) that is fully complementary to PNPLA3 target sequence. In some embodiments, the targeting sequence or region of complementarity is partially complementary to a PNPLA3 target sequence. In some embodiments, the oligonucleotide comprises a targeting sequence or region of complementarity that is fully complementary to a sequence of any one of SEQ ID NOs: 1167 to 1176. In some embodiments, the oligonucleotide comprises a targeting sequence or region of complementarity that is partially complementary to a sequence of any one of SEQ ID NOs: 1167 to 1176.

Alternatively, in some embodiments, the oligonucleotides herein comprise a targeting sequence or region of complementarity that is complementary to a contiguous sequence of nucleotides comprising a PNPLA3 mRNA, wherein the contiguous sequence of nucleotides is about 12 to about 30 nucleotides in length (e.g., 12 to 30, 12 to 28, 12 to 26, 12 to 24, 12 to 20, 12 to 18, 12 to 16, 14 to 22, 16 to 20, 18 to 20, or 18 to 19 nucleotides in length). In some embodiments, the oligonucleotides comprise a targeting sequence or region of complementarity that is complementary to a contiguous sequence of nucleotides comprising a PNPLA3 mRNA, where the contiguous sequence of nucleotides is 10, 11, 12, 13, 14, 15, 16, 17, 18, 19, or 20 nucleotides in length. In some embodiments, the oligonucleotides comprise a targeting sequence or region of complementarity that is complementary to a contiguous sequence of nucleotides comprising a PNPLA3 mRNA, where the contiguous sequence of nucleotides is 19 nucleotides in length. In some embodiments, the oligonucleotides comprise a targeting sequence or region of complementarity that is complementary to a contiguous sequence of nucleotides comprising a PNPLA3 mRNA, where the contiguous sequence of nucleotides is 20 nucleotides in length. In other embodiments, the oligonucleotides comprise a targeting sequence or a region of complementarity that is complementary to a contiguous sequence of nucleotides of any one of SEQ ID NOs: 1167 to 1176, optionally where the contiguous sequence of nucleotides is 19 nucleotides in length.

With regard to the targeting sequence or region of complementarity of the oligonucleotides herein, it is complementary to contiguous nucleotides of a sequence as set forth in any one of SEQ ID NOs: 1167 to 1176 and spans the entire length of an antisense strand. In some embodiments, the region of complementarity of the oligonucleotides is complementary to contiguous nucleotides of a sequence as set forth in any one of SEQ ID NOs: 1167 to 1176 and spans a portion of the entire length of an antisense strand. In some additional embodiments, the oligonucleotides include a region of complementarity (e.g., on an antisense strand of a ds oligonucleotide) that is at least partially (e.g., fully) complementary to a contiguous stretch of nucleotides spanning nucleotides 1-20 of a sequence as set forth in any one of SEQ ID NOs: 1167 to 1176.

Alternatively, the oligonucleotides herein comprise a targeting sequence or region of complementarity having one or more base pair (bp) mismatches with the corresponding PNPLA3 target sequence. In some embodiments, the targeting sequence or region of complementarity is up to about 1, up to about 2, up to about 3, up to about 4, up to about 5, etc. mismatches with the corresponding PNPLA3 target sequence provided that the ability of the targeting sequence or region of complementarity to bind or anneal to the PNPLA3 mRNA under appropriate hybridization conditions and/or the ability of the oligonucleotide to reduce or inhibit PNPLA3 expression is maintained. Stated differently, the targeting sequence or region of complementarity is no more than 1, no more than 2, no more than 3, no more than 4, or no more than 5 mismatches with the corresponding PNPLA3 target sequence provided that the ability of the targeting sequence or region of complementarity to bind or anneal to the PNPLA3 mRNA under appropriate hybridization conditions and/or the ability of the oligonucleotides to reduce or inhibit PNPLA3 expression is maintained. In some embodiments, the oligonucleotides comprise a targeting sequence or region of complementarity having 1 mismatch with the corresponding target sequence. In some embodiments, the oligonucleotides comprise a targeting sequence or region of complementarity having 2 mismatches with the corresponding target sequence. In some embodiments, the oligonucleotides comprise a targeting sequence or a region of complementarity having 3 mismatches with the corresponding target sequence. In some embodiments, the oligonucleotides comprise a targeting sequence or region of complementarity having 4 mismatches with the corresponding target sequence. In some embodiments, the oligonucleotides comprise a targeting sequence or region of complementarity having 5 mismatches with the corresponding target sequence. In other embodiments, the oligonucleotides comprise a targeting sequence or a region of complementarity more than one mismatch (e.g., 2, 3, 4, 5 or more mismatches) with the corresponding target sequence, where at least 2 (e.g., all) of the mismatches are positioned consecutively (e.g., 2, 3, 4, 5 or more mismatches in a row), or where the mismatches are interspersed in any position throughout the targeting sequence or region of complementarity. In other embodiments, the oligonucleotides comprise a targeting sequence or region of complementarity more than one mismatch (e.g., 2, 3, 4, 5 or more mismatches) with the corresponding target sequence, where at least 2 (e.g., all) of the mismatches are positioned consecutively (e.g., 2, 3, 4, 5 or more mismatches in a row), or where at least one or more non-mismatched base pair is located between the mismatches, or a combination thereof.

III. Types of Oligonucleotides: A variety of oligonucleotide types and/or structures are useful for targeting PNPLA3 mRNA including, but not limited to, RNAi oligonucleotides, antisense oligonucleotides, miRNAs, etc. Any of the oligonucleotide types described herein or elsewhere are contemplated for use as a framework to incorporate a targeting sequence herein for the purposes of inhibiting PNPLA3 expression. In some embodiments, the oligonucleotides herein inhibit PNPLA3 expression by engaging with RNAi pathways upstream or downstream of Dicer involvement. For example, RNAi oligonucleotides have been developed with each strand having sizes of about 19-25 nucleotides with at least one 3' overhang of 1 to 5 nucleotides (see, e.g., U.S. Pat. No. 8,372,968). Longer oligonucleotides also have been developed that are processed by Dicer to generate active RNAi products (see, e.g., U.S. Pat. No. 8,883,996). Further work produced extended ds oligonucleotides where at least one end of at least one strand is extended beyond a duplex targeting region, including structures where one of the strands includes a thermodynamically stabilizing tetraloop structure (see, e.g., U.S. Pat. Nos. 8,513,207 and 8,927,705, as well as Intl. Patent Application Publication No. WO 2010/033225). Such structures include ss extensions (on one or both sides of the molecule) as well as ds extensions.

The oligonucleotides herein engage with the RNAi pathway downstream of the involvement of Dicer (e.g., Dicer cleavage). In some embodiments, the oligonucleotides have an overhang (e.g., of 1, 2, or 3 nucleotides in length) in the 3' end of the sense strand. In some embodiments, the oligonucleotides (e.g., siRNA) include a 21-nucleotide guide strand that is antisense to a target mRNA (e.g., PNPLA3 mRNA) and a complementary passenger strand, in which both strands anneal to form a 19-bp duplex and 2 nucleotide overhangs at either or both 3' ends. Longer oligonucleotide designs also are contemplated, including oligonucleotides having a guide strand of 23 nucleotides and a passenger strand of 21 nucleotides, where there is a blunt end on the right side of the molecule (3' end of passenger strand/5' end of guide strand) and a two nucleotide 3'-guide strand overhang on the left side of the molecule (5' end of the passenger strand/3' end of the guide strand). In such molecules, there is a 21 bp duplex region. See, e.g., U.S. Pat. Nos. 9,012,138; 9,012,621 and 9,193,753.

The oligonucleotides herein comprise sense and antisense strands that are both in the range of about 17 to about 26 (e.g., 17 to 26, 20 to 25, or 21-23) nucleotides in length. In some embodiments, the oligonucleotides comprise a sense and antisense strand that are both in the range of about 19 to about 22 nucleotides in length. In some embodiments, the sense and antisense strands are of equal length. In some embodiments, the oligonucleotides comprise sense and antisense strands, such that there is a 3'-overhang on either the sense strand or the antisense strand, or both the sense and antisense strand. In some instances, for oligonucleotides having sense and antisense strands that are both in the range of about 21 to about 23 nucleotides in length, a 3'-overhang on the sense, antisense or both sense and antisense strands is 1 or 2 nucleotides in length. In some embodiments, the oligonucleotides comprise a guide strand of 22 nucleotides and a passenger strand of 20 nucleotides, where there is a blunt end on the right side of the molecule (3' end of passenger strand/5' end of guide strand) and a 2 nucleotide 3' guide strand overhang on the left side of the molecule (5' end of the passenger strand/3' end of the guide strand). In such molecules, there is a 20-bp duplex region.

Other oligonucleotide designs for use herein include: 16-mer siRNAs (see, e.g., "Nucleic Acids in Chemistry & Biology," Blackburn (ed.), Royal Society of Chemistry, 2006), shRNAs (e.g., having 19 bp or shorter stems; see, e.g., Moore et al. (2010) Methods Mol. Biol. 629:141-58), blunt siRNAs (e.g., of 19 bps in length; see, e.g., Kraynack & Baker (2006) RNA 12:163-76), asymmetrical siRNAs (aiRNA; see, e.g., Sun et al. (2008) Nat. Biotechnol. 26:1379-82), asymmetric shorter-duplex siRNA (see, e.g., Chang et al. (2009) Mol. Ther. 17:725-32), fork siRNAs (see, e.g., Hohjoh (2004) Febs Lett. 557:193-198), ss siRNAs (see, e.g., Elsner (2012) Nat. Biotechnol. 30:1063), dumbbell-shaped circular siRNAs (see, e.g., Abe et al. (2007) J. Am. Chem. Soc. 129:15108-09), and small internally segmented interfering Rna (sisiRNA; see, e.g., Bramsen et al. (2007) Nucleic Acids Res. 35:5886-97). Further non-limiting examples of oligonucleotide structures that may be used herein to reduce or inhibit PNPLA3 expression are miRNA, shRNA, and short siRNA (see, e.g., Hamilton et al. (2002) EMBO J. 21:4671-79; see also, US Patent Application Publication No. 2009/0099115).

Alternatively, the oligonucleotides herein are single-stranded (ss). Such structures include, but are not limited to, ss RNAi molecules. Recent efforts have demonstrated the activity of ss RNAi molecules (see, e.g., Matsui et al. (2016) Mol. Ther. 24:946-55). In some embodiments, the oligonucleotides are ASOs. An ASO is a ss oligonucleotide that has a nucleobase sequence which, when written or depicted in the 5' to 3' direction, includes a reverse complement of a targeted segment of a particular nucleic acid and is suitably modified (e.g., as a gapmer) to induce RNaseH-mediated cleavage of its target RNA in cells or (e.g., as a mixmer) so as to inhibit translation of the target mRNA in cells. ASOs for use herein are modified in any suitable manner known in the art including, for example, as shown in U.S. Pat. No. 9,567,587 (including, for example, length, sugar moieties of the nucleobase (pyrimidine, purine), and alterations of the heterocyclic portion of the nucleobase). Further, ASOs have been used for decades to reduce expression of specific target genes (see, e.g., Bennett et al. (2017) Annu. Rev. Pharmacol. 57:81-105).

IV. Double-Stranded RNAi Oligonucleotides: ds oligonucleotides for targeting PNPLA3 mRNA and inhibiting PNPLA3 expression (e.g., via the RNAi pathway) comprising a sense strand (i.e., a passenger strand) and an antisense strand (i.e., a guide strand). In some embodiments, the sense strand and antisense strand are separate strands and are not covalently linked. In some embodiments, the sense strand and antisense strand are covalently linked.

In some embodiments, the sense strand comprises a first region (R1) and a second region (R2), where R2 comprises a first subregion (S1), a tetraloop (L) or triloop (triL), and a second subregion (S2), where L or triL is located between S1 and S2, and where S1 and S2 form a second duplex (D2). D2 has various lengths. In some embodiments, D2 is about 1 to about 6 bp in length. In some embodiments, D2 is 2-6, 3-6, 4-6, 5-6, 1-5, 2-5, 3-5 or 4-5 bp in length. In other embodiments, D2 is 1, 2, 3, 4, 5 or 6 bp in length. In certain embodiments, D2 is 6 bp in length.

In some embodiments, R1 of the sense strand and the antisense strand forms a first duplex (D1). In some embodiments, D1 is at least about 15 (e.g., at least 15, at least 16, at least 17, at least 18, at least 19, at least 20 or at least 21) nucleotides in length. In some embodiments, D1 is about 12 to about 30 nucleotides in length (e.g., 12 to 30, 12 to 27, 15 to 22, 18 to 22, 18 to 25, 18 to 27, 18 to 30 or 21 to 30 nucleotides in length). In other embodiments, D1 is at least 12 nucleotides in length (e.g., at least 12, at least 15, at least 20, at least 25 or at least 30 nucleotides in length). In other embodiments, D1 is 12, 13, 14, 15, 16, 17, 18, 19, 20, 21, 22, 23, 24, 25, 26, 27, 28, 29 or 30 nucleotides in length. In certain embodiments, D1 is 20 nucleotides in length. In some instances, D1 does not span the entire length of the sense strand and/or antisense strand. In some instances, D1 spans the entire length of either the sense strand or antisense strand or both. In certain instances, D1 spans the entire length of both the sense strand and the antisense strand.

In certain instances, a ds oligonucleotide herein includes a sense strand having a sequence of any one of SEQ ID NOs: 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, and 775, and an antisense strand having a complementary sequence selected from SEQ ID NOs: 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, and 776, as is arranged in Table 1. Alternatively, a ds oligonucleotide herein includes a sense strand having a sequence of any one of SEQ ID NOs: 777, 779, 781, 783, 785, 787, 789, 791, 793, 795, 797, 799, 801, 803, 805, 807, 809, 811, 813, 815, 817, 819, 821, 823, 825, 827, 829, 831, 833, 835, 837, 839, 841, 843, 845, 847, 849, 851, 853, 855, 857, 859, 861, 863, 865, 867, 869, 871, 873, 875, 877, 879, 881, 883, 885, 887, 889, 891, 893, 895, 897, 899, 901, 903, 905, 907, 909, 911, 913, 915, 917, 919, 921, 923, 925, 927, 929, 931, 933, 935, 937, 939, 941, 943, 945, 947, 949, 951, 953, 955, 957, 959, 961, 963, 965, 967, 969, 971, 973, 975, 977, 979, 981, 983, 985, 987, 989, 991, 993, 995, 997, 999, 1001, 1003, 1005, 1007, 1009, 1011, 1013, 1015, 1017, 1019, 1021, 1023, 1025, 1027, 1029, 1031, 1033, 1035, 1037, 1039, 1041, 1043, 1045, 1047, 1049, 1051, 1053, 1055, 1057, 1059, 1061, 1063, 1065, 1067, 1069, 1071, 1073, 1075, 1077, 1079, 1081, 1083, 1085, 1087, 1089, 1091, 1093, 1095, 1097, 1099, 1101, 1103, 1105, 1107, 1109, 1111, 1113, 1115, 1117, 1119, 1121, 1123, 1125, 1127, 1129, 1131, 1133, 1135, 1137, 1139, 1141, 1143, 1145, 1147, 1149, 1151, 1153, 1155, 1157, 1159, 1161, and 1163, and an antisense strand having a complementary sequence selected from SEQ ID NOs: 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, and 1164, as is arranged in Table 3. In certain instances, the sense strand is any one of SEQ ID NOs: 787, 843, 867, 871, 937, 1003, 1007, 1017, 1161, or 1163, and the antisense strand is any one of SEQ ID NOs: 788, 844, 868, 872, 938, 1004, 1008, 1018, 1162, or 1164.

In certain embodiments, the disclosure describes RNAi oligonucleotides for reducing or inhibiting PNPLA3 expression that includes a sense strand having a sequence as set forth in Table A, B, C, or D (e.g., SEQ ID NOs: 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, or 1300).

In certain embodiments, the disclosure describes RNAi oligonucleotides for reducing or inhibiting PNPLA3 expression that includes an antisense strand having a sequence as set forth in Table A, B, C, or D (e.g., SEQ ID NOs: 1179, 1181, 1183, 1185, 1187, 1189, 1191, 1193, 1195, 1197, 1199, 1201, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, or 1301). In certain embodiments, the disclosure describes RNAi oligonucleotides for reducing or inhibiting PNPLA3 expression that includes a sense strand having a sequence as set forth in Table A, B, C, or D (e.g., SEQ ID Nos: 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298 or 1300).

In certain embodiments, the disclosure describes RNAi oligonucleotides for reducing or inhibiting PNPLA3 expression that includes an antisense strand having a sequence as set forth in Table A, B, C, or D (e.g., SEQ ID NOs: 1179, 1181, 1183, 1185, 1187, 1189, 1191, 1193, 1195, 1197, 1199, 1201, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, or 1301).

In some embodiments, RNAi oligonucleotides are described for reducing or inhibiting PNPLA3 expression that include an antisense strand and a sense strand, where the antisense strand has a sequence as set forth in Table A, Table B, Table C, or Table D, and where the sense strand has a sequence as set forth in Table A, Table B, Table C, or Table D.

In some instances, the RNAi oligonucleotide includes a sense strand having a nucleotide sequence as set forth in Table A, Table B, Table C, or Table D, especially any one of SEQ ID NOs: 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, or 1300. In some instances, the RNAi oligonucleotide includes an antisense strand having a nucleotide sequence as set for the in Table A, Table B, Table C, or Table D, especially any one of SEQ ID NOs: 1179, 1181, 1183, 1185, 1187, 1189, 1191, 1193, 1195, 1197, 1199, 1202, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, or 1301. In certain instances, the RNAi oligonucleotide includes a sense strand having a nucleotide sequence of any one of SEQ ID NOs: 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, or 1300, and an antisense strand having a nucleotide sequence of any one of SEQ ID NOs: 1179, 1181, 1183, 1185, 1187, 1189, 1191, 1193, 1195, 1197, 1199, 1201, 1203, 1205, 1207, 1209, 1211, 1213, 1215, 1217, 1219, 1221, 1223, 1225, 1227, 1229, 1231, 1233, 1235, 1237, 1239, 1241, 1243, 1245, 1247, 1249, 1251, 1253, 1255, 1257, 1259, 1261, 1263, 1265, 1267, 1269, 1271, 1273, 1275, 1277, 1279, 1281, 1283, 1285, 1287, 1289, 1291, 1293, 1295, 1297, 1299, or 1301.

In certain instances, the RNAi oligonucleotide includes a sense strand having a nucleotide sequence of any one of SEQ ID NOs: 1188, 1190, 1200, 1216, 1218, 1220, 1224, 1230, 1232, 1234, 1244, 1246, 1250, 1254, 1262, 1288, 1290, 1292, 1294, 1296, 1298, or 1300, and an antisense strand having a nucleotide sequence of any one of SEQ ID NOs: 1189, 1191, 1201, 1215, 1217, 1221, 1225, 1231, 1233, 1235, 1245, 1247, 1251, 1255, 1263, 1289, 1291, 1295, 1297, 1299, or 1301.

In certain instances, the RNAi oligonucleotide includes a sense strand having a nucleotide sequence of any one of SEQ ID NOs: 1188, 1190, 1220, 1224, 1230, 1232, 1244, 1246, 1250, or 1254, and an antisense strand having a nucleotide sequence of any one of SEQ ID NOs: 1189, 1191, 1221, 1225, 1231, 1233, 1245, 1247, 1251, or 1255.

In certain instances, the sense strand and the antisense strand of the RNAi oligonucleotide, respectively, are selected from:

(a) SEQ ID NOs: 1220 and 1221,
(b) SEQ ID NOs: 1224 and 1225,
(c) SEQ ID NOs: 1230 and 1231,
(d) SEQ ID NOs: 1232 and 1233,
(e) SEQ ID NOs: 1188 and 1189,
(f) SEQ ID NOs: 1190 and 1191,
(g) SEQ ID NOs: 1244 and 1245,
(h) SEQ ID NOs: 1250 and 1251-,
(i) SEQ ID NOs: 1254 and 1255, and
(j) SEQ ID NOs: 1246 and 1247.

One of skill in the art appreciates that in some instances, the sequences presented in the Sequence Listing is referred to in describing the structure of an oligonucleotide (e.g., a ds oligonucleotide) or other nucleic acid. In such instances, the actual oligonucleotide or other nucleic acid has one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification when compared with the specified sequence while retaining essentially same or similar complementary properties as the specified sequence.

In some embodiments, a ds oligonucleotide herein includes a 25-nucleotide sense strand and a 27-nucleotide antisense strand that when acted upon by a Dicer enzyme results in an antisense strand that is incorporated into the mature RISC. In certain instances, the sense strand of the ds oligonucleotide is longer than 27 nucleotides (e.g., 28, 29, 30, 31, 32, 33, 34, 35, 36, 37, 38, 39, or 40 nucleotides). In certain instances, the sense strand of the ds oligonucleotide is longer than 25 nucleotides (e.g., 26, 27, 28, 29, or 30 nucleotides).

In some instances, the ds oligonucleotides herein have one 5' end that is thermodynamically less stable when compared to the other 5' end. In some embodiments, the ds oligonucleotide is asymmetric and includes a blunt end at the 3' end of a sense strand and a 3'-overhang at the 3' end of an antisense strand. In some embodiments, the 3'-overhang on the antisense strand is about 1 to about 8 nucleotides in length (e.g., 1, 2, 3, 4, 5, 6, 7 or 8 nucleotides in length). Typically, a ds oligonucleotide for RNAi has a two-nucleotide overhang on the 3' end of the antisense (guide) strand. However, other overhangs are possible. In some embodiments, an overhang is a 3'-overhang having a length of between about 1 to about 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides. However, in other instances, the overhang is a 5'-overhang comprising a length of between about 1 to about 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides.

In some instances, two terminal nucleotides on the 3' end of an antisense strand are modified. In some instances, the two terminal nucleotides on the 3' end of the antisense strand are complementary with the target mRNA (e.g., PNPLA3 mRNA). In other instances, the two terminal nucleotides on the 3' end of the antisense strand are not complementary with the target mRNA. In some instances, two terminal nucleotides on each 3' end of an oligonucleotide in the nicked tetraloop structure are GG. Typically, one or both of the two terminal GG nucleotides on each 3' end of a ds oligonucleotide is not complementary with the target mRNA.

In some instances, there is one or more (e.g., 1, 2, 3, 4, or 5) mismatch(s) between the sense and antisense strand. If there is more than one mismatch between the sense and antisense strand, they may be positioned consecutively (e.g., 2, 3, or more in a row), or interspersed throughout the region of complementarity. In some instances, the 3' end of the sense strand contains one or more mismatches. In certain instances, two mismatches are incorporated at the 3' end of the sense strand. In some instances, base mismatches, or destabilization of segments at the 3' end of the sense strand of the oligonucleotide improves or increases the potency of the ds oligonucleotide.

A. Antisense Strands: The oligonucleotides (e.g., a ds oligonucleotide) herein for targeting PNPLA3 mRNA and inhibiting PNPLA3 expression include an antisense strand including a sequence as set forth in the antisense strands of Table 1 or Table 3, or Table A, B, C or D. In some instances, the oligonucleotides include an antisense strand having at least about 12 (e.g., at least 12, at least 13, at least 14, at least 15, at least 16, at least 17, at least 18, at least 19, at least 20, at least 21, at least 22, or at least 23) contiguous nucleotides of a sequence as set forth in any one of SEQ ID NOs: 788, 844, 868, 872, 938, 1004, 1008, 1018, 1162, or 1164, or an antisense strand having a nucleotide sequence of any one of SEQ ID NOs: 1189, 1191, 1221, 1225, 1231, 1233, 1245, 1247, 1251, or 1255

Further, the oligonucleotides (e.g., a ds oligonucleotide) herein can include an antisense strand of up to about 40 nucleotides in length (e.g., up to 40, up to 35, up to 30, up to 27, up to 25, up to 21, up to 19, up to 17, or up to 12 nucleotides in length). In some instances, the oligonucleotides can have an antisense strand of at least about 12 nucleotides in length (e.g., at least 12, at least 15, at least 19, at least 21, at least 22, at least 25, at least 27, at least 30, at least 35, or at least 38 nucleotides in length). Alternatively, the oligonucleotides can have an antisense strand in a range of about 12 to about 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40, or 32 to 40) nucleotides in length. In certain instances, the oligonucleotide can have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

As noted above, the antisense strand of the oligonucleotides herein may be referred to as the "guide strand." For example, the antisense strand that engages with RISC and that binds to an Argonaute protein such as Ago2, or that engages with or that binds to one or more similar factors, and directs silencing of a target gene, the antisense strand is referred to as a guide strand (or "passenger strand").

B. Sense Strands: The oligonucleotides (e.g., a ds oligonucleotide) herein for targeting PNPLA3 mRNA and inhibiting PNPLA3 expression include a sense strand sequence including a sequence as set forth in the sense strands of Table 1 or Table 3, or Table A, B, C, or D. In some instances, the oligonucleotides include a sense strand that having at least about 12 (e.g., at least 13, at least 14, at least 15, at least 16, at least 17, at least 18, at least 19, at least 20, at least 21, at least 22, or at least 23) contiguous nucleotides of a sequence as set forth in in any one of SEQ ID NOs: 787, 843, 867, 871, 937, 1003, 1007, 1017, 1161, or 1163.

Further, the oligonucleotides (e.g., a ds oligonucleotide) herein include a sense strand (or passenger strand) of up to about 40 nucleotides in length (e.g., up to 40, up to 36, up to 30, up to 27, up to 25, up to 21, up to 19, up to 17, or up to 12 nucleotides in length). In some instances, the oligonucleotides can have a sense strand of at least about 12 nucleotides in length (e.g., at least 12, at least 15, at least 19, at least 21, at least 25, at least 27, at least 30, at least 36, or at least 38 nucleotides in length). Alternatively, the oligonucleotides can have a sense strand in a range of about 12 to about 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In certain instances, the oligonucleotides can have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

Figure 2:
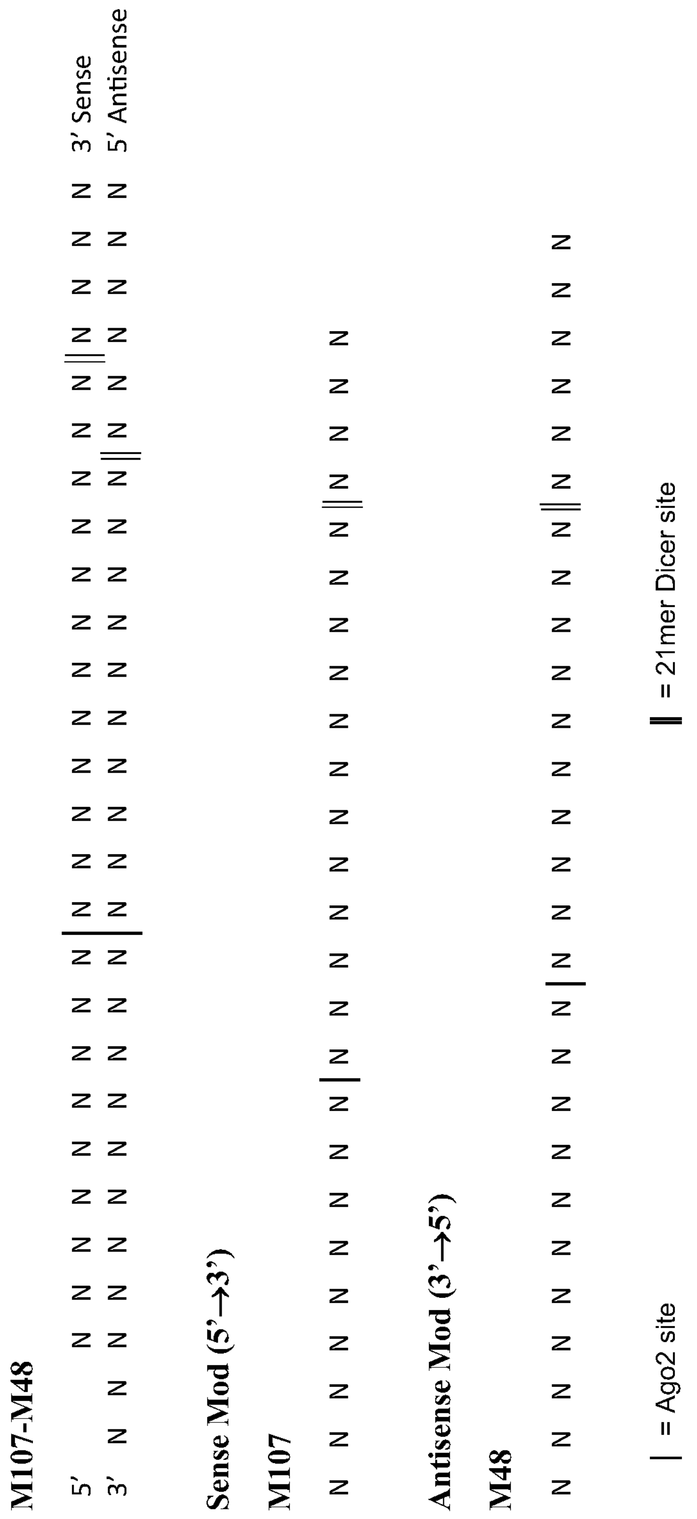
FIG. 2 discloses a schematic depicting the structure and chemical modification pattern of an alternative generic GalNAc-conjugated PNPLA3 oligonucleotide. The sense strand has a modification pattern M107, wherein nucleotides at positions 2, 4, 14 and 16 are modified with 2'-O-methyl; nucleotides at positions 1, 3, 5, 6, 7, 8, 9, 10, 11, 12, 13, 15, 17, 18, 19, 20, 21, 22 and 23 are RNA nucleotides; and nucleotides at positions 24 and 25 are DNA nucleotides. The antisense strand has a modification pattern M48, wherein nucleotides at positions 1, 2, 3, 4, 11, 13, 23, 25, 26 and 27 are modified with 2'-O-methyl; and nucleotides at positions 5, 6, 7, 8, 9, 10, 12, 14, 15, 16, 17, 18 19, 20, 21, 22 and 24 are RNA nucleotides.

In some embodiments, the sense strand comprises a stem-loop structure at its 3' end. In other embodiments, the sense strand comprises a stem-loop structure at its 5' end. In additional embodiments, the stem is a duplex of about 2, 3, 4, 5, 6, 7, 8, 9, 10, 11, 12, 13, or 14 bp in length. In some embodiments, the stem-loop provides the oligonucleotides protection against degradation (e.g., enzymatic degradation) and facilitates or improves targeting and/or delivery to a target cell, tissue, or organ (e.g., the liver), or both. For example, the loop of the stem-loop provides nucleotides having one or more modifications that facilitate, improve, or increase targeting to a target mRNA (e.g., a PNPLA3 mRNA), inhibiting of target gene expression (e.g., PNPLA3 expression), and/or delivering to a target cell, tissue, or organ (e.g., the liver), or both. In some embodiments, the stem-loop itself or modification(s) to the stem-loop do not substantially affect the inherent gene expression inhibition activity of the oligonucleotide, but facilitates, improves, or increases stability (e.g., provides protection against degradation) and/or delivery of the oligonucleotide to a target cell, tissue, or organ (e.g., the liver). In certain embodiments, the oligonucleotides comprise a sense strand including (e.g., at its 3' end) a stem-loop set forth as: S1-L-S2, in which S1 is complementary to S2, and in which L forms a single-stranded loop between S1 and S2 of up to about 10 nucleotides in length (e.g., 3, 4, 5, 6, 7, 8, 9, or 10 nucleotides in length). In certain embodiments, the loop (L) is 4 nucleotides in length. FIGS. 1 and 2 depict non-limiting examples of such an oligonucleotide. In some embodiments the loop (L) of the stem-loop having the structure S1-L-S2 as described above is a tetraloop (e.g., within a nicked tetraloop structure). In some embodiments, the tetraloop comprises ribonucleotides, deoxyribonucleotides, modified nucleotides, delivery ligands and combinations thereof.

V. Oligonucleotide Modifications

A. Sugar Modifications: A modified sugar (also referred to herein as a sugar analog) includes a modified deoxyribose or ribose moiety in which, for example, one or more modifications occur at the 2', 3', 4' and/or 5' carbon position of the sugar. A modified sugar also includes non-natural, alternative, carbon structures such as those present in locked nucleic acids ("LNA"; see, e.g., Koshkin et al. (1998) Tetrahedron 54:3607-3630), unlocked nucleic acids ("UNA"; see, e.g., Snead et al. (2013) Mol. Ther-Nuc. Acids 2:e103) and bridged nucleic acids ("BNA"; see, e.g., Imanishi & Obika (2002) Chem. Commun. 16:1653-1659).

In some embodiments, the nucleotide modification in the sugar is a 2-modification such as, for example, 2'-O-propargyl, 2-O-propylamin, 2'-amino, 2'-ethyl, 2'-fluoro (2'-F), 2'-aminoethyl (EA), 2'-O-methyl (2'-OMe), 2'-O-methoxyethyl (2'-MOE), 2'-O-[2-(methylamino)-2-oxoethyl] (2'-O-NMA), or 2'-deoxy-2'-fluoro-β-d-arabinonucleic acid (2'-FANA). In certain embodiments, the modification is 2'-F, 2'-OMe, or 2'-MOE. In other embodiments, the modification in the sugar is a modification of the sugar ring, which includes modification of one or more carbons of the sugar ring. For example, the modification in the sugar is a 2'-oxygen of the sugar linked to a 1-carbon or 4'-carbon of the sugar, or a 2'-oxygen linked to the 1-carbon or 4'-carbon via an ethylene or methylene bridge. In other embodiments, the modification is an acyclic sugar that lacks a 2'-carbon to 3'-carbon bond. In other embodiments, the modification is a thiol group such as, for example, in the 4' position of the sugar.

The oligonucleotides herein include at least 1 modified nucleotide (e.g., at least 1, at least 5, at least 10, at least 15, at least 20, at least 25, at least 30, at least 35, at least 40, at least 45, at least 50, at least 55, at least 60, or more). In some embodiments, the sense strand comprises at least 1 modified nucleotide (e.g., at least 1, at least 5, at least 10, at least 15, at least 20, at least 25, at least 30, at least 35, or more). In some embodiments, the antisense strand comprises at least 1 modified nucleotide (e.g., at least 1, at least 5, at least 10, at least 15, at least 20, or more).

In certain embodiments, all nucleotides of the sense strand are modified. Likewise, all nucleotides of the antisense strand are modified. In some embodiments, all the nucleotides of the oligonucleotides herein (i.e., both the sense strand and the antisense strand) are modified. As above, and in some embodiments, the modified nucleotide is a 2-modification (e.g., a 2'-F, 2'-OMe, 2'-MOE, and/or 2'-deoxy-2'-fluoro-β-d-arabinonucleic acid). In certain embodiments, the modified nucleotide is a 2'-modification such as, for example, a 2'-F or a 2'-OMe.

Moreover, the oligonucleotides herein have different modification patterns. In some embodiments, the modified oligonucleotides comprise an antisense strand having a modification pattern as set forth in any one of Tables A, B, C or D and comprise a sense strand sequence having a modification pattern as set forth in any one of Tables A, B, C or D (as well as FIG. 1). In some embodiments, one or more of positions 8, 9, 10, or 11 of the sense strand are modified with a 2'-F. In other embodiments, the sugar moiety at each nucleotide at positions 1 to 7 and 12 to 20 in the sense strand is modified with a 2'-OMe.

In some embodiments, the antisense strand includes 3 nucleotides that are modified at the 2'-position of the sugar moiety with a 2'-F. In some embodiments, the sugar moiety at positions 2, 5, and 14 and optionally up to 3 of the nucleotides at positions 1, 3, 7, and 10 of the antisense strand are modified with a 2'-F. In other embodiments, the sugar moiety at positions 2, 5, and 14 of the antisense strand is modified with a 2'-F. In other embodiments, the sugar moiety at positions 1, 2, 5, and 14 of the antisense strand is modified with a 2'-F. In still other instances, the sugar moiety at positions 1, 2, 3, 5, 7, and 14 of the antisense strand is modified with a 2'-F. In yet other embodiments, the sugar moiety at positions 1, 2, 3, 5, 10, and 14 of the antisense strand is modified with a 2'-F. In yet other embodiments, the sugar moiety at positions 2, 3, 5, 7, 10, and 14 of the antisense strand is modified with a 2'-F.

B. 5'-Terminal Phosphates: 5'-terminal phosphate groups can be used to enhance the interaction of the oligonucleotides herein with Ago2. However, oligonucleotides having a 5'-phosphate group may be susceptible to degradation via phosphatases or other enzymes, which can limit their bioavailability in vivo. In some embodiments, the oligonucleotides (e.g., a ds oligonucleotide) comprise analogs of 5' phosphates that are resistant to such degradation. Examples of such phosphate analogs include, but are not limited to, oxymethylphosphonate, vinylphosphonate, malonyl phosphonate, or a combination thereof. In certain embodiments the 3' end of a strand of the oligonucleotides is attached to a chemical moiety that mimics the electrostatic and steric properties of a natural 5-phosphate group ("phosphate mimic").

Alternatively, or additionally, the oligonucleotides herein have a phosphate analog at a 4'-carbon position of the sugar (referred to as a "4'-phosphate analog"). See, e.g., Intl. Patent Application Publication No. WO 2018/045317. In some embodiments, the oligonucleotides herein include a 4'-phosphate analog at a 5'-terminal nucleotide. In some embodiments, the phosphate analog is an oxymethylphosphonate, in which the oxygen atom of the oxymethyl group is bound to the sugar moiety (e.g., at its 4'-carbon) or analog thereof. In other embodiments, the 4'-phosphate analog is a thiomethylphosphonate or an aminomethylphosphonate, in which the sulfur atom of the thiomethyl group or the nitrogen atom of the amino methyl group is bound to the 4'-carbon of the sugar moiety or analog thereof. In certain embodiments, the 4'-phosphate analog is an oxymethylphosphonate, which is represented by the formula $—O—CH_2—PO(OH)_2$ or $—O—CH_2—PO(OR)_2$, in which R is independently selected from H, $CH_3$, an alkyl group, $CH_2CH_2CN$, $CH_2OCOC(CH_3)_3$, $CH_2OCH_2CH_2Si(CH_3)_3$, or a protecting group. In certain embodiments, the alkyl group is $CH_2CH_3$. In certain other embodiments, R is independently selected from H, $CH_3$, or $CH_2CH_3$.

C. Modified Internucleoside Linkages: In addition to the above modifications, the oligonucleotides herein comprise a modified internucleoside linkage. In some instances, phosphate modifications or substitutions result in oligonucleotides that comprise at least about 1 (e.g., at least 1, at least 2, at least 3, or at least 5) modified internucleotide linkages. In some embodiments, the oligonucleotides comprise about 1 to about 10 (e.g., 1 to 10, 2 to 8, 4 to 6, 3 to 10, 5 to 10, 1 to 5, 1 to 3, or 1 to 2) modified internucleotide linkages. In certain additional embodiments, the oligonucleotides comprise 1, 2, 3, 4, 5, 6, 7, 8, 9, or 10 modified internucleotide linkages.

Examples of modified internucleotide linkages include, but are not limited, to, a phosphorodithioate linkage, a phosphorothioate linkage, a phosphotriester linkage, a thionoalkylphosphonate linkage, a thionalkylphosphotriester linkage, a phosphoramidite linkage, a phosphonate linkage, or a boranophosphate linkage. In some embodiments, at least one modified internucleotide linkage of any one of the oligonucleotides as disclosed herein is a phosphorothioate linkage.

In some embodiments, the oligonucleotides herein comprise a phosphorothioate linkage between one or more of positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In other embodiments, the oligonucleotides comprise a phosphorothioate linkage between each of positions 1 and 2 of the sense strand, positions 1 and 2 of the antisense strand, positions 2 and 3 of the antisense strand, positions 20 and 21 of the antisense strand, and positions 21 and 22 of the antisense strand.

D. Base Modifications: In addition to the above modifications, the oligonucleotides herein also comprise one or more modified nucleobases. In some embodiments, modified nucleobases (also referred to herein as base analogs) are linked at the 1' position of a nucleotide sugar moiety. In certain embodiments, the modified nucleobase is a nitrogenous base. In certain other embodiments, the modified nucleobase does not contain nitrogen atom. See, e.g., US Patent Application Publication No. 2008/0274462. In some embodiments, the modified nucleotide is a universal base. However, in certain embodiments, the modified nucleotide does not contain a nucleobase (abasic).

With regard to universal bases, they comprise a heterocyclic moiety located at the 1' position of a nucleotide sugar moiety in a modified nucleotide, or the equivalent position in a nucleotide sugar moiety substitution, that, when present in a duplex, is positioned opposite more than one type of base without substantially altering structure of the duplex. Moreover, and compared to a reference ss nucleic acid (e.g., oligonucleotide) that is fully complementary to a target nucleic acid, a ss nucleic acid having a universal base forms a duplex with the target nucleic acid that has a lower $T_m$ than a duplex formed with the complementary nucleic acid. However, when compared to a reference ss nucleic acid in which the universal base has been replaced with a base to generate a single mismatch, the ss nucleic acid having the universal base forms a duplex with the target nucleic acid that has a higher $T_m$ than a duplex formed with the nucleic acid having the mismatched base.

Exemplary universal-binding nucleotides include, but are not limited to, inosine, 1-(3-D-ribofuranosyl-5-nitroindole and/or 1-β-D-ribofuranosyl-3-nitropyrrole (see, e.g., US Patent Application Publication No. 2007/0254362; Van Aerschot et al. (1995) Nucleic Acids Res. 23:4363-70; Loakes et al. (1995) Nucleic Acids Res. 23:2361-66; and Loakes & Brown (1994) Nucleic Acids Res. 22:4039-43).

E. Reversible Modifications: While certain modifications to protect the oligonucleotides herein from the in vivo environment before reaching target cells can be made, they also can reduce the potency or activity of the oligonucleotides once they reach the cytosol of the target cell. Reversible modifications therefore can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules are chemically modified with cyclic disulfide moieties to mask the negative charge created by the internucleotide diphosphate linkages and to improve cellular uptake and nuclease resistance. See, US Patent Application Publication No. 2011/0294869, Intl. Patent Application Publication Nos. WO 2014/088920 and WO 2015/188197, and Meade et al. (2014) Nat. Biotechnol. 32:1256-63. This reversible modification of the internucleotide diphosphate linkages is designed to be cleaved intracellularly by the reducing environment of the cytosol (e.g., glutathione). Earlier examples include neutralizing phosphotriester modifications that are reported to be cleavable inside cells (see, e.g., Dellinger et al. (2003) J. Am. Chem. Soc. 125:940-50).

Some reversible modifications protect the oligonucleotides during in vivo administration (e.g., transit through the blood and/or lysosomal/endosomal compartments of a cell) where the oligonucleotides will be exposed to nucleases and other harsh environmental conditions (e.g., pH). When released into the cytosol of a cell where the levels of glutathione are higher compared to extracellular space, the modification is reversed, and the result is cleaved oligonucleotides. Using reversible, glutathione-sensitive moieties, it is possible to introduce sterically larger chemical groups into the oligonucleotides when compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the oligonucleotides, such as nuclease resistance, lipophilicity, charge, thermal stability, specificity, and reduced immunogenicity. In some instances, the structure of the glutathione-sensitive moiety can be engineered to modify the kinetics of its release.

In some embodiments, the glutathione-sensitive moiety is attached to the sugar of the nucleotide. In certain embodiments, the glutathione-sensitive moiety is attached to the 2'-carbon of the sugar of a modified nucleotide. Additionally, or alternatively, the glutathione-sensitive moiety is attached to the 5'-carbon of a sugar, particularly when the modified nucleotide is the 5'-terminal nucleotide of the oligonucleotides. Additionally, or alternatively, the glutathione-sensitive moiety is attached to the 3'-carbon of sugar, particularly when the modified nucleotide is the 3'-terminal nucleotide of the oligonucleotides. In some embodiments, the glutathione-sensitive moiety includes a sulfonyl group (see, e.g., Intl. Patent Application Publication No. WO 2018/039364).

VI. Targeting Ligands

It is desirable to target the oligonucleotides herein to one or more cells or one or more organs. Such a strategy can help to avoid undesirable effects in other organs or to avoid undue loss of the oligonucleotides to cells, tissue or organs that would not benefit therefrom. Accordingly, the oligonucleotides can be modified to facilitate targeting and/or delivering to a tissue, cell, or organ (e.g., to facilitate delivering the oligonucleotides to the liver). In some embodiments, the oligonucleotides are modified to facilitate delivery of the oligonucleotide to the hepatocytes of the liver. In certain embodiments, the oligonucleotides comprise at least one nucleotide (e.g., 1, 2, 3, 4, 5, 6, or more nucleotides) conjugated to one or more targeting ligand(s).

Exemplary targeting ligands include, but are not limited to, a carbohydrate, amino sugar, cholesterol, peptide, polypeptide, protein, or part of a protein (e.g., an antibody or antibody fragment), or lipid. In some embodiments, the targeting ligand is an aptamer. For example, the targeting ligand is an RGD peptide for targeting tumor vasculature or glioma cells, CREKA peptide for targeting tumor vasculature or stoma, transferrin, lactoferrin or an aptamer for targeting transferrin receptors expressed on CNS vasculature, or an anti-EGFR antibody for targeting EGFR on glioma cells. In certain embodiments, the targeting ligand is one or more GalNAc moieties.

In some embodiments, 1 or more (e.g., 1, 2, 3, 4, 5, or 6) nucleotides of the oligonucleotides each can be conjugated to a separate targeting ligand. In some embodiments, 2 to 4 nucleotides of the oligonucleotides each are conjugated to a separate targeting ligand. In some embodiments, targeting ligands can be conjugated to 2 to 4 nucleotides at either ends of the sense strand or antisense strand (e.g., targeting ligands are conjugated to a 2 to 4 nucleotide overhang or extension on the 5' or 3' end of the sense strand or antisense strand) such that the targeting ligands resemble bristles of a toothbrush and the oligonucleotides resemble a toothbrush. For example, the oligonucleotides comprise a stem-loop at either the 5' or 3' end of the sense strand and 1, 2, 3, or 4 nucleotides of the loop of the stem may be individually conjugated to a targeting ligand. In some embodiments, the oligonucleotides (e.g., a ds oligonucleotide) comprise a stem-loop at the 3' end of the sense strand, where the loop of the stem-loop includes a triloop or a tetraloop, and where the 3 or 4 nucleotides of the triloop or tetraloop, respectfully, are individually conjugated to a targeting ligand.

GalNAc is a high affinity ligand for the ASGPR, which is primarily expressed on the sinusoidal surface of hepatocyte cells and has a major role in binding, internalizing and subsequent clearing circulating glycoproteins that contain terminal galactose or GalNAc residues (asialoglycoproteins). Conjugation (either indirect or direct) of GalNAc moieties to the oligonucleotides herein are used to target them to the ASGPR expressed on cells. In some embodiments, the oligonucleotides are conjugated to at least one or more GalNAc moieties, where the GalNAc moieties target the oligonucleotides to an ASGPR expressed on human liver cells (e.g., human hepatocytes).

The oligonucleotides herein are conjugated directly or indirectly to a monovalent GalNAc. In some embodiments, the oligonucleotides are conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, the oligonucleotides are conjugated to one or more bivalent GalNAc, trivalent GalNAc or tetravalent GalNAc moieties.

In some embodiments, 1 or more (e.g., 1, 2, 3, 4, 5, or 6) nucleotides of the oligonucleotides herein each can be conjugated to a GalNAc moiety. In some embodiments, 2 to 4 nucleotides of a tetraloop each are conjugated to a separate GalNAc. In other embodiments, 1 to 3 nucleotides of a triloop each are conjugated to a separate GalNAc. In some embodiments, the targeting ligands are conjugated to 2 to 4 nucleotides at either end of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotides resemble a toothbrush. In some embodiments, the GalNAc moieties are conjugated to a nucleotide of the sense strand. For example, 4 GalNAc moieties are conjugated to nucleotides in the tetraloop of the sense strand, where each GalNAc moiety is conjugated to 1 nucleotide. In certain embodiments, 3 GalNAc moieties are conjugated to nucleotides in the tetraloop of the sense strand, where each GalNAc moiety is conjugated to 1 nucleotide.

In certain embodiments, the oligonucleotides comprise a monovalent GalNAc attached to a guanine nucleotide referred to as [ademG-GalNAc] or 2'-aminodiethoxymethanol-Guanine-GalNAc, as depicted below:

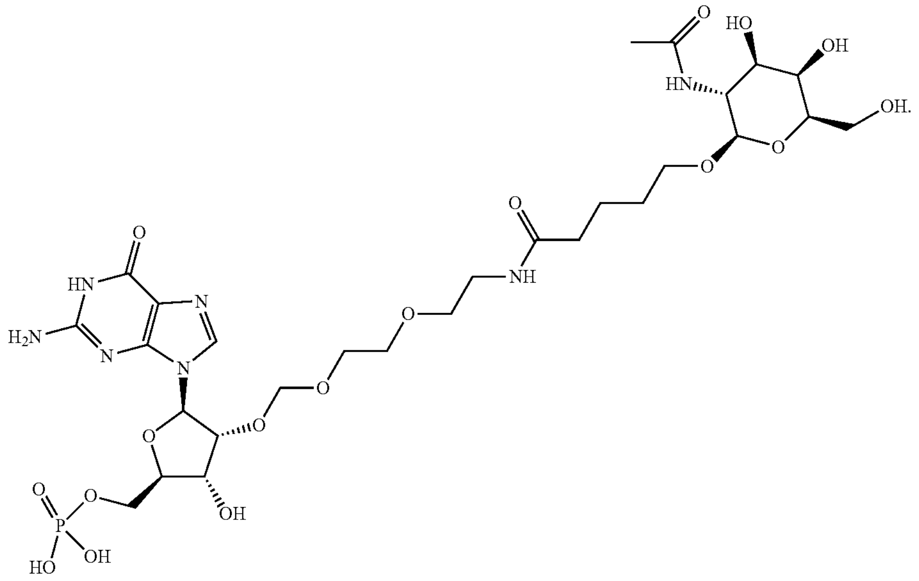 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(=O)[nH]c(N)nc32)O[C@H](CO)[C@H](O)[C@@H]1O]

In certain embodiments, the oligonucleotides herein comprise a monovalent GalNAc attached to an adenine nucleotide, referred to as [ademA-GalNAc] or 2'-aminodiethoxymethanol-Adenine-GalNAc, as depicted below:

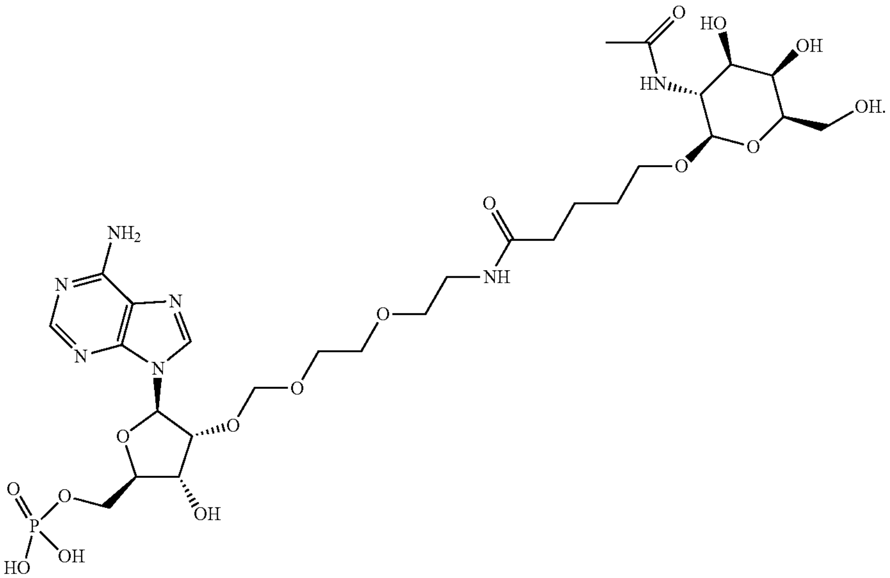

An example of such conjugation is shown below for a loop having from 5' to 3', the nucleotide sequence GAAA (L=linker, X=heteroatom), where stem attachment points are shown. Such a loop is present, for example, at positions 27-30 of the sense strand listed in Table 3, A, B, C or D and as shown in FIG. 1. In the chemical formula,

is used to describe an attachment point to the oligonucleotide strand:

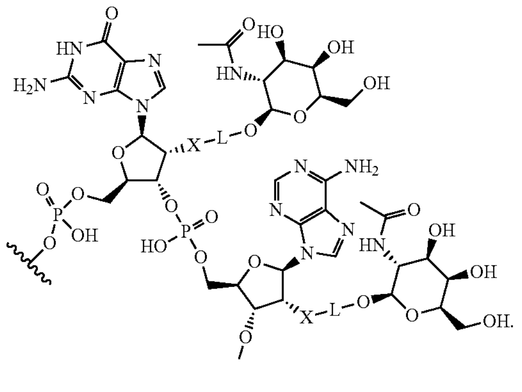

-continued

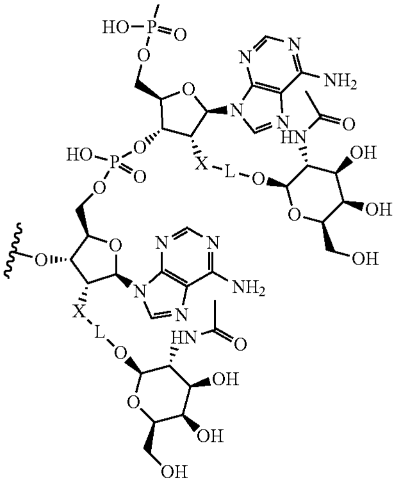

Appropriate methods or chemistry (e.g., click chemistry) are used to link a targeting ligand to a nucleotide. One way of conjugating the targeting ligand to a nucleotide is by using a click linker. In some embodiments, an acetal-based linker is used to conjugate the targeting ligand to a nucleotide of any one of the oligonucleotides herein. Acetal-based linkers are disclosed, for example, in Intl. Patent Application Publication No. WO 2016/100401. In some instances, the linker is a labile linker. However, in other instances, the linker is stable. An example is shown below for a loop having from 5' to 3', the nucleotides GAAA, in which GalNAc moieties are attached to nucleotides of the loop using an acetal linker. Such a loop is present, for example, at positions 27-30 of the any one of the sense strands listed in Table 3, A, B, C or D. In the chemical formula,

is an attachment point to the oligonucleotide strand:

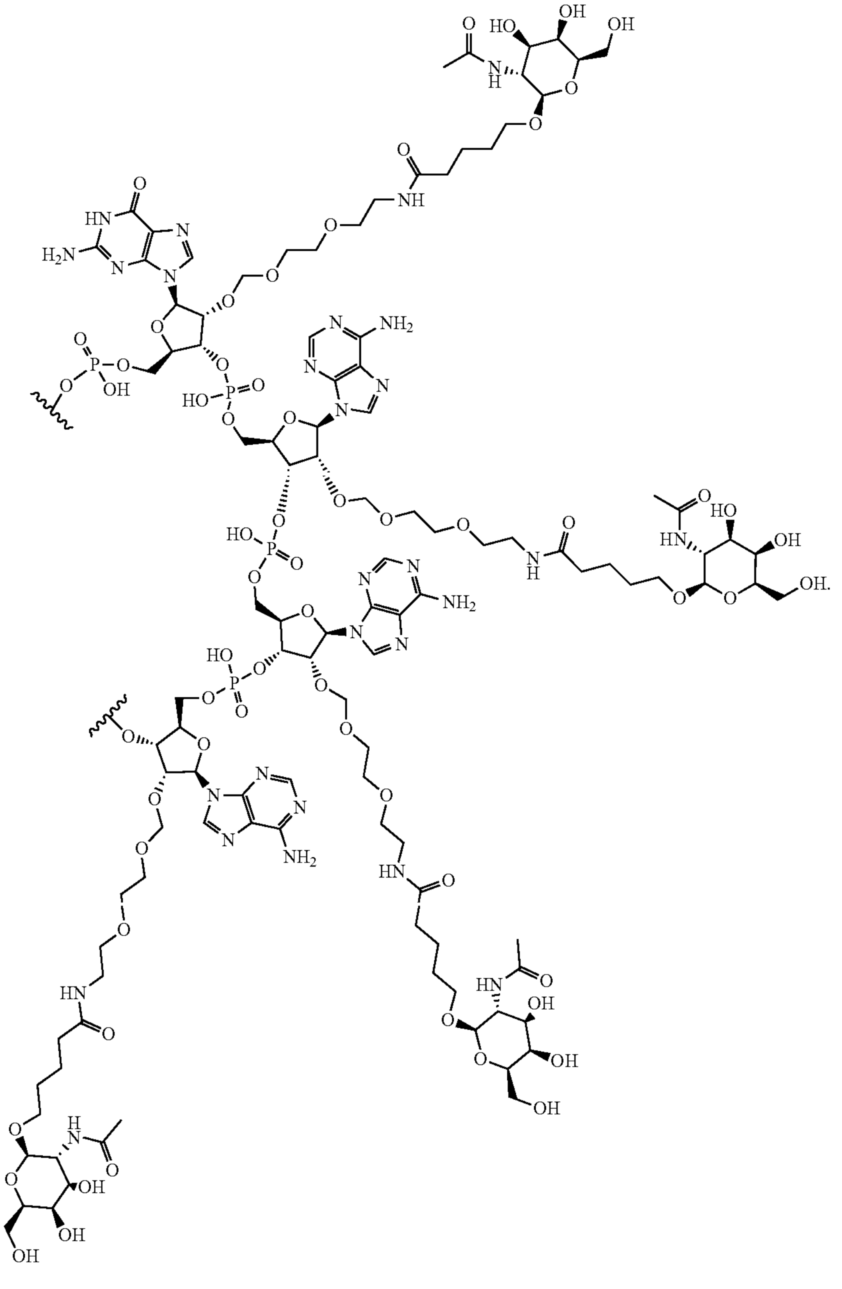

In some embodiments, a duplex extension (e.g., of up to 3, 4, 5, or 6 bp in length) is provided between the targeting ligand (e.g., a GalNAc moiety) and the oligonucleotides herein (e.g., a ds oligonucleotide). In other embodiments, the oligonucleotides do not have a GalNAc conjugated thereto.

Formulations and Pharmaceutical Compositions

The oligonucleotides herein are incorporated into a formulation or pharmaceutical composition. Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, the oligonucleotides herein are formulated in buffer solutions such as phosphate buffered saline solutions, liposomes, micellar structures, and capsids.

Formulations of oligonucleotides with cationic lipids are used to facilitate transfection of the oligonucleotides into cells. For example, cationic lipids, such as lipofectin, cationic glycerol derivatives, and polycationic molecules (e.g., polylysine) can be used. Suitable lipids include Oligofectamine, Lipofectamine (Life Technologies), NC388 (Ribozyme Pharmaceuticals, Inc.), or FuGene 6 (Roche), all of which are used according to the manufacturer's instructions.

Accordingly, in some embodiments, the formulations herein comprise a liposome, a lipid, a lipid complex, a microsphere, a microparticle, a nanosphere, or a nanoparticle (such as a lipid nanoparticle) or may be otherwise formulated for administration to the cells, tissues, organs, or body of an individual in need thereof (see, e.g., Remington, "The Science and Practice of Pharmacy" (L. V. Allen Jr., ed., $22^{nd}$ Edition, Pharmaceutical Press, 2013).

In some embodiments, the formulations herein further comprise an excipient, which can confer to a composition improved stability, improved absorption, improved solubility and/or therapeutic enhancement of the active ingredient. In some embodiments, the excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, the oligonucleotides herein are lyophilized for extending shelf-life and then made into a solution before use (e.g., administration to an individual). Accordingly, the excipient in a pharmaceutical composition including one or more of the oligonucleotides is a lyoprotectant (e.g., mannitol, lactose, polyethylene glycol, or polyvinylpyrrolidone) or a collapse temperature modifier (e.g., dextran, Ficoll™, or gelatin).

Pharmaceutical compositions are formulated to be compatible with its intended route of administration. Routes of administration include, but are not limited to, parenteral (e.g., intravenous, intramuscular, intraperitoneal, intradermal, and subcutaneous), oral (e.g., inhalation), transdermal (e.g., topical), transmucosal, and rectal administration.

Pharmaceutical compositions suitable for injectable use comprise sterile aqueous solutions (where water soluble) or dispersions and sterile powders for the extemporaneous preparation of sterile injectable solutions or dispersion. For intravenous administration, suitable carriers include, but are not limited to, physiological saline, bacteriostatic water, Cremophor EL™ (BASF) or phosphate buffered saline (PBS). The carrier is a solvent or dispersion medium containing, for example, water, ethanol, polyol (e.g., glycerol, propylene glycol, liquid polyethylene glycol, and the like), as well as suitable mixtures thereof. In many embodiments, it will be preferable to comprise in the compositions with isotonic agents such as, for example, sugars, polyalcohols such as mannitol, sorbitol and/or sodium chloride. Sterile injectable solutions are prepared by incorporating the oligonucleotides herein in a required amount in a selected solvent with one or a combination of ingredients enumerated above, as required, followed by filtered sterilization.

Moreover, the pharmaceutical compositions comprise at least about 0.1% of a therapeutic agent (e.g., one or more of the oligonucleotides herein) or more, although the percentage of the therapeutic agent may be between about 1% to about 80% or more of the weight or volume of the total composition. Factors such as solubility, bioavailability, biological half-life, route of administration, product shelf life, as well as other pharmacological considerations will be contemplated by one of skill in the art of preparing such pharmaceutical formulations, and as such, a variety of dosages and treatment regimens may be desirable.

Even though several examples are directed toward liver-targeted delivery of at least one of the oligonucleotides herein, targeting of other tissues also is contemplated.

Kits

The oligonucleotides herein can be incorporated into a kit comprising one or more of the oligonucleotides herein, and instructions for use. In some embodiments, the kit comprises one or more of the oligonucleotides, and a package insert containing instructions for use of the kit and/or any component thereof. In other embodiments, the kit comprises a suitable container, one or more of the oligonucleotides, one or more controls, and various buffers, reagents, enzymes, and other standard ingredients as are known in the art.

In some embodiments, the container can be at least one vial, well, test tube, flask, bottle, syringe, or other container means, into which the one or more oligonucleotides are placed, and in some instances, suitably aliquoted. In other embodiments, where an additional component is provided, the kit contains additional containers into which this component is placed. The kits also comprise a means for containing the one or more oligonucleotides and any other reagent in close confinement for commercial sale. Such containers include injection or blow-molded plastic containers into which the desired vials are retained. Containers and/or kits comprise labeling with instructions for use and/or warnings.

In some embodiments, the kit comprises one or more oligonucleotides herein, and a pharmaceutically acceptable carrier, or a pharmaceutical composition comprising one or more of the oligonucleotides and instructions for treating or delaying progression of a disease, disorder, or condition associated with PNPLA3 expression in an individual in need thereof.

Methods

Methods of Making

The oligonucleotides herein are made using methods and/or techniques known to one of skill in the art such as, for example, by using conventional nucleic acid solid phase synthesis. The polynucleotides of the oligonucleotides are assembled on a suitable nucleic acid synthesizer utilizing standard nucleotide or nucleoside precursors (e.g., phosphoramidites). Automated nucleic acid synthesizers, including DNA/RNA synthesizers, are commercially available from, for example, Applied Biosystems (Foster City, CA), BioAutomation (Irving, TX), and GE Healthcare Life Sciences (Pittsburgh, PA).

As one of skill in the art understands, other methods and/or techniques of synthesizing the oligonucleotides herein are used. Additionally, the various synthetic steps are performed in an alternate sequence or order to give the desired compounds. Other synthetic chemistry transformations, protecting groups (e.g., for hydroxyl, amino, etc. present on the bases), and protecting group methodologies (protection and deprotection) useful in synthesizing the oligonucleotides are known in the art and are described in, for example, Larock, "Comprehensive Organic Transformations," VCH Publishers (1989); Greene & Wuts, Protective Groups in Organic Synthesis, $2^{nd}$ Ed., John Wiley & Sons (1991); Fieser & Fieser, *Fieser and Fieser's Reagents for Organic Synthesis*, John Wiley & Sons (1994); and Paquette, ed., Encyclopedia of Reagents for Organic Synthesis, John Wiley & Sons (1995).

Methods of Using

I. Methods of Reducing PNPLA3 Expression in Cells, Tissue, Organs, and Organisms The oligonucleotides herein are used to reduce PNPLA3 mRNA in cells, tissues, organs, or individuals. The methods comprise the steps described herein, and these may be, but not necessarily, carried out in the sequence as described. Other sequences, however, also are conceivable. Moreover, individual, or multiple steps are carried out either in parallel and/or overlapping in time and/or individually or in multiply repeated steps. Furthermore, the methods comprise additional, unspecified steps.

The methods comprise contacting or delivering to a cell, population of cells, tissues, organs, or individuals an effective amount any of the oligonucleotides herein (e.g., a ds oligonucleotide) for reducing PNPLA3 expression. In some embodiments, reduced PNPLA3 expression is determined by measuring a reduction in the amount or level of PNPLA3 mRNA, PNPLA3 protein, or PNPLA3 activity in a cell.

With regard to an appropriate cell type, the cell type is any cell that expresses mRNA (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose and soft tissue, and skin). In some embodiments, the cell is a primary cell obtained from an individual. In some embodiments, the primary cell has undergone a limited number of passages such that the cell substantially maintains is natural phenotypic properties. In some embodiments, the cell is an ex vivo, in vivo, or in vitro cell (i.e., such that one or more of the oligonucleotides herein can be delivered to the cell in culture or to an organism in which the cell resides).

In some embodiments, the oligonucleotides herein are delivered to a cell or population of cells using a nucleic acid delivery method known in the art including, but not limited to, injecting a solution containing the oligonucleotides, bombarding by particles covered by the oligonucleotides, exposing the cell or population of cells to a solution containing the oligonucleotides, or electroporating cell membranes in the presence of the oligonucleotides. Other methods known in the art for delivering oligonucleotides to cells are used such as, for example, lipid-mediated carrier transport, chemical-mediated transport, and cationic liposome transfection such as calcium phosphate, and others.

Reduced PNPLA3 expression is determined by an assay or technique that evaluates one or more molecules, properties or characteristics of a cell or population of cells associated with PNPLA3 expression (e.g., using a PNPLA3 expression biomarker) or by an assay or technique that evaluates molecules that are directly indicative of PNPLA3 expression in a cell or population of cells (e.g., PNPLA3 mRNA or PNPLA3 protein). In some embodiments, the extent to which the oligonucleotides reduce PNPLA3 expression are evaluated by comparing PNPLA3 expression in a cell or population of cells contacted with the oligonucleotides to a control cell or population of cells (e.g., a cell or population of cells not contacted with the oligonucleotides or contacted with a control oligonucleotide). In some embodiments, a control amount or level of PNPLA3 expression in a control cell or population of cells is predetermined, such that the control amount or level need not be measured in every instance the assay or technique is performed. The predetermined level or value takes a variety of forms including, but not limited to, a single cut-off value, such as a median or mean.

Contacting or delivering the oligonucleotides herein (e.g., a ds oligonucleotide) to a cell or a population of cells result in reduced PNPLA3 expression. In some embodiments, reduced PNPLA3 expression is relative to a control amount or level of PNPLA3 expression in the cell or the population of cells not contacted with the oligonucleotides or contacted with a control oligonucleotide. In some embodiments, reduced PNPLA3 expression is about 1% or lower, about 5% or lower, about 10% or lower, about 15% or lower, about 20% or lower, about 25% or lower, about 30% or lower, about 35% or lower, about 40% or lower, about 45% or lower, about 50% or lower, about 55% or lower, about 60% or lower, about 70% or lower, about 80% or lower, or about 90% or lower relative to a control amount or level of PNPLA3 expression. In some embodiments, the control amount or level of PNPLA3 expression is an amount or level of PNPLA3 mRNA and/or PNPLA3 protein in the cell or the population of cells that has not been contacted with oligonucleotides herein. In some embodiments, the effect of delivery of the oligonucleotides to the cell or the population of cells according to a method herein is assessed after any finite period or amount of time (e.g., minutes, hours, days, weeks, and/or months). For example, PNPLA3 expression is determined in the cell or the population of cells at least about 4 hours, about 8 hours, about 12 hours, about 18 hours, or about 24 hours. Alternatively, PNPLA3 expression is determined in the cell or the population of cells at least about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, about 42 days, about 49 days, about 56 days, about 63 days, about 70 days, about 77 days, or about 84 days or more after contacting or delivering the oligonucleotides to the cell or population of cells. In other embodiments, PNPLA3 expression is determined in the cell or the population of cells at least about 1 month, about 2 months, about 3 months, about 4 months, about 5 months, or about 6 months or more after contacting or delivering the oligonucleotides to the cell or the population of cells.

In some embodiments, the oligonucleotides herein are delivered in the form of a transgene that is engineered to express in a cell one or more of the oligonucleotides or strands (e.g., sense and antisense strands). For example, the oligonucleotides are delivered using a transgene engineered to express any oligonucleotide herein. Transgenes may be delivered using viral vectors (e.g., adenovirus, retrovirus, vaccinia virus, poxvirus, adeno-associated virus, or herpes simplex virus) or non-viral vectors (e.g., plasmids or synthetic mRNAs). In some embodiments, the transgenes are injected directly to an individual.

II. Methods of Treatment:

Methods for treating an individual having, suspected of having or at risk of developing, a disease, disorder, or condition associated with PNPLA3 expression comprise administering at least one or more of the oligonucleotides herein. Additionally, methods for treating or attenuating in an individual, an onset or progression of a disease, disorder, or condition associated with PNPLA3 expression comprise using one or more of the oligonucleotides herein. Furthermore, methods for achieving one or more therapeutic benefits in an individual having a disease, disorder, or condition associated with PNPLA3 expression comprise providing one or more of the oligonucleotides herein. In some embodiments, the individual can be treated by administering a therapeutically effective amount of any one or more of the oligonucleotides of any of the above disclosed embodiments. In some embodiments, the treatment comprises reducing PNPLA3 expression. In some embodiments, the individual is treated therapeutically. In some embodiments, the individual is treated prophylactically. In all of these embodiments, the oligonucleotide is selected from Table A, B, C or D.

In some embodiments, the one or more oligonucleotides, or a pharmaceutical composition including the same, is administered to the individual having a disease, disorder, or condition associated with PNPLA3 expression such that PNPLA3 expression is reduced in the individual, thereby treating the individual. In some embodiments, an amount or level of PNPLA3 mRNA is reduced in the individual. In other embodiments, an amount or level of PNPLA3 protein is reduced in the individual. In still other embodiments, an amount or level of PNPLA3 activity is reduced in the individual. In yet other embodiments, an amount or level of liver TG (e.g., one or more TG(s) or total TGs in liver) is reduced in the individual, especially in the liver. In still other instances, an amount or level of liver inflammation can be reduced. In still other instances, an amount of level of liver fibrosis is reduced. In still other embodiments, an amount or level of plasma AST, plasma ALT, or even Pro-C3 is reduced. In any of the above disclosed embodiments, the oligonucleotides comprise a sense strand having a nucleotide sequence of any one of SEQ ID NOs: 1188, 1190, 1220, 1224, 1230, 1232, 1244, 1246, 1250 or 1254, and an antisense strand having a nucleotide sequence of any one of SEQ ID NOs: 1189, 1191, 1221, 1225, 1231, 1233, 1245, 1247, 1251 or 1255.

In some embodiments, PNPLA3 expression is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to PNPLA3 expression prior to administering the one or more oligonucleotides or pharmaceutical composition thereof. In other embodiments, PNPLA3 expression is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to PNPLA3 expression in an individual (e.g., a reference or control subject) not receiving the one or more oligonucleotides or pharmaceutical composition or receiving a control oligonucleotide, pharmaceutical composition or treatment.

In certain embodiments, an amount or level of PNPLA3 mRNA is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of PNPLA3 mRNA prior to administering the one or more oligonucleotides or pharmaceutical composition thereof. In some embodiments, the amount or level of PNPLA3 mRNA is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of PNPLA3 mRNA in an individual (e.g., a reference or control subject) not administered the one or more oligonucleotides or pharmaceutical composition or administered a control oligonucleotide, pharmaceutical composition, or treatment.

In certain embodiments, an amount or level of PNPLA3 protein is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of PNPLA3 protein prior to administering the one or more oligonucleotides or pharmaceutical composition thereof. In other embodiments, an amount or level of PNPLA3 protein is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of PNPLA3 protein in an individual (e.g., a reference or control subject) not administered the one or more oligonucleotides or pharmaceutical composition or administered a control oligonucleotide, pharmaceutical composition or treatment.

In certain embodiments, an amount or level of PNPLA3 activity is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of PNPLA3 activity prior to administering the one or more oligonucleotides or pharmaceutical composition thereof. In some embodiments, the amount or level of PNPLA3 activity is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of PNPLA3 activity in an individual (e.g., a reference or control subject) not administered the one or more oligonucleotides or pharmaceutical composition or administered a control oligonucleotide, pharmaceutical composition or treatment.

In certain embodiments, an amount or level of TG, especially liver TG, can be reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of TG prior to administering the one or more oligonucleotides or pharmaceutical composition thereof. In some embodiments, the amount or level of TG is reduced in the individual by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of TG in an individual (e.g., a reference or control subject) not administered the one or more oligonucleotides or pharmaceutical composition or administered a control oligonucleotide, pharmaceutical composition or treatment.

Here, PNPLA3 expression, the amount or level of PNPLA3 mRNA, PNPLA3 protein, PNPLA3 activity, liver TG, or any combination thereof, is reduced in a cell (e.g., a hepatocyte), a population or a group of cells (e.g., an organoid), a tissue (e.g., liver tissue), a sample (e.g., a liver biopsy sample), an organ (e.g., liver), blood or a fraction thereof (e.g., plasma), or any other biological material obtained or isolated from the individual. In some embodiments, PNPLA3 expression, the amount or level of PNPLA3 mRNA, PNPLA3 protein, PNPLA3 activity, TG, or any combination thereof, is reduced in more than one type of cell (e.g., a hepatocyte and one or more other type(s) of cell), more than one groups of cells, more than one type of tissue (e.g., liver tissue and one or more other type(s) of tissue), more than one type of sample (e.g., a liver biopsy sample and one or more other type(s) of biopsy sample), more than one organ (e.g., liver and one or more other organ(s)), more than one fraction of blood (e.g., plasma and one or more other blood fraction(s)) obtained or isolated from the subject.

Examples of a disease, disorder, or condition associated with PNPLA3 expression include, but are not limited to, AH, ALD, HCC, CCA, PSC, NAFLD, NASH, fatty liver (steatosis), inflammation of the liver, liver fibrosis, cirrhosis of the liver, or a combination thereof.

Because of their high specificity, the oligonucleotides herein specifically target mRNAs of target genes of cells, tissues, or organs (e.g., liver). In preventing disease, the target gene is the one that is required for initiation or maintenance of the disease or that has been identified as being associated with a higher risk of contracting the disease. In treating disease, one or more of the oligonucleotides are brought into contact with the cells, tissue or organ exhibiting or responsible for mediating the disease. For example, an oligonucleotide substantially identical to all or part of a wild-type (i.e., native) or mutated gene associated with a disorder or condition associated with PNPLA3 expression is brought into contact with or introduced into a cell or tissue type of interest such as a hepatocyte or other liver cell.

In some embodiments, the target gene is from any mammal, such as a human. Any gene may be silenced according to the methods herein. Moreover, the methods herein typically involve administering to an individual a therapeutically effective amount of one or more oligonucleotides herein, that is, an amount capable of producing a desirable therapeutic result. The therapeutically acceptable amount is an amount that therapeutically treats a disease or disorder or condition. The appropriate dosage for any one individual will depend on certain factors, including the individual's size, body surface area, age, the composition to be administered, the active ingredient(s) in the composition, time and route of administration, general health, and other therapeutic agents being administered concurrently.

In the methods, the individual is administered any one of the oligonucleotides or compositions herein either enterally (e.g., orally, by gastric feeding tube, by duodenal feeding tube, via gastrostomy, or rectally), parenterally (e.g., subcutaneous injection, intravenous injection or infusion, intra-arterial injection or infusion, intraosseous infusion, intramuscular injection, intracerebral injection, intracerebroventricular injection, or intrathecal), topically (e.g., epicutaneous, inhalational, via eye drops, or through a mucous membrane), or by direct injection into a target organ (e.g., the liver of a subject). Typically, the oligonucleotides or compositions are administered intravenously or subcutaneously.

As a non-limiting set of examples, the oligonucleotides or compositions herein typically are administered quarterly (once every three months), bi-monthly (once every two months), monthly or weekly. For example, the oligonucleotides or compositions are administered every week or at intervals of two, or three weeks. In certain embodiments, the oligonucleotides, or compositions are administered daily. In some embodiments, an individual is administered one or more loading doses of the oligonucleotides or compositions followed by one or more maintenance doses of the oligonucleotides or compositions.

In some embodiments, the individual is a human, a non-human primate, or other mammalian subject. In other embodiments, the individual is a domesticated animal such as a dog or a cats; livestock such as a horse, cattle, pig, sheep, goat, or chicken; and animals such as a mouse, rat, guinea pig or hamster.

III. Medical Uses

The oligonucleotides herein can be used, or adapted for use, to treat an individual (e.g., a human having a disease, disorder, or condition associated with PNPLA3 expression) that would benefit from reducing PNPLA3 expression. In some embodiments, the oligonucleotides are provided for use, or adapted for use, to treat an individual having a disease, disorder, or condition associated with PNPLA3 expression. Also, the oligonucleotides are provided for use, or adaptable for use, in the manufacture of a medicament or pharmaceutical composition for treating a disease, disorder, or condition associated with PNPLA3 expression. In other embodiments, the oligonucleotides are provided for use, or adaptable for use, in targeting PNPLA3 mRNA and reducing PNPLA3 expression (e.g., via the RNAi pathway). In other embodiments, the oligonucleotides are provided for use, or adaptable for use, in targeting PNPLA3 mRNA and reducing an amount or level of PNPLA3 mRNA, PNPLA3 protein, and/or PNPLA3 activity.

In some embodiments, the methods comprise selecting an individual for treatment based upon the individual having a marker (e.g., a biomarker) for a disease, disorder, or condition associated with PNPLA3 expression, or someone predisposed to the same, such as, but not limited to, PNPLA3 mRNA, PNPLA3 protein or a combination thereof. Likewise, and as detailed below, the methods also comprise additional steps such as, for example, measuring or obtaining a baseline value for a marker of PNPLA3 expression (e.g., PNPLA3 protein) and then comparing such obtained value to one or more other baseline values or values obtained after the individual is administered one or more of the oligonucleotides to assess the effectiveness of treatment.

EXAMPLES

The following non-limiting examples are offered for purposes of illustration, not limitation.

Synthesis of Oligonucleotides

Example 1: Preparing ds RNAi Oligonucleotides

Oligonucleotide synthesizing and purifying: The ds RNAi oligonucleotides in the Examples are chemically synthesized using methods described herein. Generally, ds RNAi oligonucleotides are synthesized using solid phase oligonucleotide synthesis methods as described for 19-23mer siRNAs (see, e.g., Scaringe et al. (1990) Nucleic Acids Res. 18:5433-41 and Usman et al. (1987) J. Am. Chem. Soc. 109:7845-45; see also, U.S. Pat. Nos. 5,804,683; 5,831,071; 5,998,203; 6,008,400; 6,111,086; 6,117,657; 6,353,098; 6,362,323; 6,437,117 and 6,469,158).

Individual RNA strands are synthesized and HPLC purified according to standard methods (Integrated DNA Technologies). For example, RNA oligonucleotides are synthesized using solid phase phosphoramidite chemistry, deprotected, and desalted on NAP-5 columns (Amersham Pharmacia Biotech; Piscataway, NJ) using standard techniques (Damha & Olgivie (1993) Methods Mol. Biol. 20:81-114; Wincott et al. (1995) Nucleic Acids Res. 23:2677-84). The oligomers are purified using ion-exchange high performance liquid chromatography (IE-HPLC) on an Amersham Source 15Q column (1.0 cm×25 cm; Amersham Pharmacia Biotech) using a 15 min step-linear gradient. The gradient varies from 90:10 Buffers A:B to 52:48 Buffers A:B, where Buffer A is 100 mM Tris pH 8.5 and Buffer B is 100 mM Tris pH 8.5, 1 M NaCl. Samples are monitored at 260 nm and peaks corresponding to the full-length oligonucleotide species are collected, pooled, desalted on NAP-5 columns, and lyophilized.

The purity of each oligomer is determined by capillary electrophoresis (CE) on a Beckman PACE 5000 (Beckman Coulter, Inc.). The CE capillaries have a 100 μm inner diameter and contain ssDNA 100R Gel (Beckman-Coulter). Typically, about 0.6 nmole of oligonucleotide is injected into a capillary, is run in an electric field of 444 V/cm and is detected by UV absorbance at 260 nm. Denaturing Tris-Borate-7 M-urea running buffer is purchased from Beckman-Coulter. Oligoribonucleotides are obtained that are at least 90% pure as assessed by CE for use in experiments described below. Compound identity is verified by matrix-assisted laser desorption ionization time-of-flight (MALDI-TOF) mass spectroscopy on a Voyager DE™ Biospectometry Work Station (Applied Biosystems) following the manufacturer's recommended protocol. Relative molecular masses of all oligomers are obtained, often within 0.2% of expected molecular mass.

Preparing duplexes: ss RNA oligomers are resuspended (e.g., at 100 μM concentration) in duplex buffer having 100 mM potassium acetate, 30 mM HEPES, pH 7.5. Complementary sense and antisense strands are mixed in equal molar amounts to yield a final solution of, for example, 50 μM duplex. Samples are heated to 100° C. for 5 min in RNA buffer (IDT) and are allowed to cool to room temperature before use. The ds RNA oligonucleotides are stored at −20° C. ss RNA oligomers are stored lyophilized or in nuclease-free water at −80° C.

In Vitro Function

Example 2: RNAi Oligonucleotide Inhibition of PNPLA3 Expression In Vitro

PNPLA3 target sequence identifying: To identify RNAi oligonucleotide inhibitors of PNPLA3 expression, a computer-based algorithm is used to computationally generate PNPLA3 target sequences suitable for assaying PNPLA3 expression inhibition by the RNAi pathway. The algorithm provides RNAi oligonucleotide guide (antisense) strand sequences that are complementary to suitable PNPLA3 target sequences of human PNPLA3 mRNA (e.g., SEQ ID NO:1). Some of the guide strand sequences identified by the algorithm also are complementary to the corresponding PNPLA3 target sequence of monkey PNPLA mRNA. Some of the antisense (guide) strand sequences identified by the algorithm also are complementary to the corresponding PNPLA3 target sequence of monkey PNPLA3 mRNA (e.g., SEQ ID NO:5). From this, 384 ds RNAi oligonucleotides (formatted as DsiRNA oligonucleotides) are generated, each with a unique antisense strand having a region of complementarity to a PNPLA3 target sequence identified by the algorithm.

TABLE 1

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 1 | UCUGCAGGUCCUCUCAGAUCUUGUG | 9 | CACAAGAUCUGAGAGGACCUGCAGAGU | 10 |
| 2 | AGGUCCUCUCAGAUCUUGUGCGGAA | 11 | UUCCGCACAAGAUCUGAGAGGACCUGC | 12 |
| 3 | AUUGGCAUCUUCCAUCCAUCCUUCA | 13 | UGAAGGAUGGAUGGAAGAUGCCAAUGU | 14 |
| 4 | AUCUUCCAUCCAUCCUUCAACUUAA | 15 | UUAAGUUGAAGGAUGGAUGGAAGAUGC | 16 |
| 5 | UCUUCCAUCCAUCCUUCAACUUAAG | 17 | CUUAAGUUGAAGGAUGGAUGGAAGAUG | 18 |
| 6 | CCAGAGUGUCUGAUGGGGAAAACGU | 19 | ACGUUUUCCCCAUCAGACACUCUGGUA | 20 |
| 7 | GAGUGUCUGAUGGGGAAAACGUUCU | 21 | AGAACGUUUUCCCCAUCAGACACUCUG | 22 |
| 8 | AUGGGGAAAACGUUCUGGUGUCUGA | 23 | UCAGACACCAGAACGUUUUCCCCAUCA | 24 |
| 9 | GGGGAAAACGUUCUGGUGUCUGACU | 25 | AGUCAGACACCAGAACGUUUUCCCCAU | 26 |
| 10 | GGGAAAACGUUCUGGUGUCUGACUU | 27 | AAGUCAGACACCAGAACGUUUUCCCCA | 28 |
| 11 | GGAAAACGUUCUGGUGUCUGACUUU | 29 | AAAGUCAGACACCAGAACGUUUUCCCC | 30 |
| 12 | GAAAACGUUCUGGUGUCUGACUUUC | 31 | GAAAGUCAGACACCAGAACGUUUUCCC | 32 |
| 13 | AAAACGUUCUGGUGUCUGACUUUCG | 33 | CGAAAGUCAGACACCAGAACGUUUUCC | 34 |
| 14 | AAACGUUCUGGUGUCUGACUUUCGG | 35 | CCGAAAGUCAGACACCAGAACGUUUUC | 36 |
| 15 | AACGUUCUGGUGUCUGACUUUCGGU | 37 | ACCGAAAGUCAGACACCAGAACGUUUU | 38 |
| 16 | ACGUUCUGGUGUCUGACUUUCGGUC | 39 | GACCGAAAGUCAGACACCAGAACGUUU | 40 |
| 17 | GUUCUGGUGUCUGACUUUCGGUCCA | 41 | UGGACCGAAAGUCAGACACCAGAACGU | 42 |
| 18 | GACGAAGUCGUGGAUGCCUUGGUAU | 43 | AUACCAAGGCAUCCACGACUUCGUCUU | 44 |
| 19 | ACGAAGUCGUGGAUGCCUUGGUAUG | 45 | CAUACCAAGGCAUCCACGACUUCGUCU | 46 |
| 20 | CGAAGUCGUGGAUGCCUUGGUAUGU | 47 | ACAUACCAAGGCAUCCACGACUUCGUC | 48 |
| 21 | CAGAGGCGUGCGAUAUGUGGAUGGA | 49 | UCCAUCCACAUAUCGCACGCCUCUGAA | 50 |
| 22 | GCGAUAUGUGGAUGGAGGAGUGAGU | 51 | ACUCACUCCUCCAUCCACAUAUCGCAC | 52 |
| 23 | GAUGGAGGAGUGAGUGACAACGUAC | 53 | GUACGUUGUCACUCACUCCUCCAUCCA | 54 |
| 24 | GAGGAGUGAGUGACAACGUACCCUU | 55 | AAGGGUACGUUGUCACUCACUCCUCCA | 56 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 25 | GAGUGAGUGACAACGUACCCUUCAU | 57 | AUGAAGGGUACGUUGUCACUCACUCCU | 58 |
| 26 | AGUGAGUGACAACGUACCCUUCAUU | 59 | AAUGAAGGGUACGUUGUCACUCACUCC | 60 |
| 27 | GUGAGUGACAACGUACCCUUCAUUG | 61 | CAAUGAAGGGUACGUUGUCACUCACUC | 62 |
| 28 | UGAGUGACAACGUACCCUUCAUUGA | 63 | UCAAUGAAGGGUACGUUGUCACUCACU | 64 |
| 29 | GAGUGACAACGUACCCUUCAUUGAU | 65 | AUCAAUGAAGGGUACGUUGUCACUCAC | 66 |
| 30 | AGUGACAACGUACCCUUCAUUGAUG | 67 | CAUCAAUGAAGGGUACGUUGUCACUCA | 68 |
| 31 | GUGACAACGUACCCUUCAUUGAUGC | 69 | GCAUCAAUGAAGGGUACGUUGUCACUC | 70 |
| 32 | UGACAACGUACCCUUCAUUGAUGCC | 71 | GGCAUCAAUGAAGGGUACGUUGUCACU | 72 |
| 33 | GACAACGUACCCUUCAUUGAUGCCA | 73 | UGGCAUCAAUGAAGGGUACGUUGUCAC | 74 |
| 34 | CAACGUACCCUUCAUUGAUGCCAAA | 75 | UUUGGCAUCAAUGAAGGGUACGUUGUC | 76 |
| 35 | AACGUACCCUUCAUUGAUGCCAAAA | 77 | UUUUGGCAUCAAUGAAGGGUACGUUGU | 78 |
| 36 | ACGUACCCUUCAUUGAUGCCAAAAC | 79 | GUUUUGGCAUCAAUGAAGGGUACGUUG | 80 |
| 37 | CGUACCCUUCAUUGAUGCCAAAACA | 81 | UGUUUUGGCAUCAAUGAAGGGUACGUU | 82 |
| 38 | UACCCUUCAUUGAUGCCAAAACAAC | 83 | GUUGUUUUGGCAUCAAUGAAGGGUACG | 84 |
| 39 | UUGAUGCCAAAACAACCAUCACCGU | 85 | ACGGUGAUGGUUGUUUUGGCAUCAAUG | 86 |
| 40 | GAUGCCAAAACAACCAUCACCGUGU | 87 | ACACGGUGAUGGUUGUUUUGGCAUCAA | 88 |
| 41 | AUGGGGAGUACGACAUCUGCCCUAA | 89 | UUAGGGCAGAUGUCGUACUCCCCAUAG | 90 |
| 42 | GUACGACAUCUGCCCUAAAGUCAAG | 91 | CUUGACUUUAGGGCAGAUGUCGUACUC | 92 |
| 43 | GACAUCUGCCCUAAAGUCAAGUCCA | 93 | UGGACUUGACUUUAGGGCAGAUGUCGU | 94 |
| 44 | ACAUCUGCCCUAAAGUCAAGUCCAC | 95 | GUGGACUUGACUUUAGGGCAGAUGUCG | 96 |
| 45 | GUCAAGUCCACGAACUUUCUUCAUG | 97 | CAUGAAGAAAGUUCGUGGACUUGACUU | 98 |
| 46 | UCAAGUCCACGAACUUUCUUCAUGU | 99 | ACAUGAAGAAAGUUCGUGGACUUGACU | 100 |
| 47 | CAAGUCCACGAACUUUCUUCAUGUG | 101 | CACAUGAAGAAAGUUCGUGGACUUGAC | 102 |
| 48 | GUCCACGAACUUUCUUCAUGUGGAC | 103 | GUCCACAUGAAGAAAGUUCGUGGACUU | 104 |
| 49 | CCACGAACUUUCUUCAUGUGGACAU | 105 | AUGUCCACAUGAAGAAAGUUCGUGGAC | 106 |
| 50 | CACGAACUUUCUUCAUGUGGACAUC | 107 | GAUGUCCACAUGAAGAAAGUUCGUGGA | 108 |
| 51 | ACGAACUUUCUUCAUGUGGACAUCA | 109 | UGAUGUCCACAUGAAGAAAGUUCGUGG | 110 |
| 52 | CGAACUUUCUUCAUGUGGACAUCAC | 111 | GUGAUGUCCACAUGAAGAAAGUUCGUG | 112 |
| 53 | GAACUUUCUUCAUGUGGACAUCACC | 113 | GGUGAUGUCCACAUGAAGAAAGUUCGU | 114 |
| 54 | AACUUUCUUCAUGUGGACAUCACCA | 115 | UGGUGAUGUCCACAUGAAGAAAGUUCG | 116 |
| 55 | ACUUUCUUCAUGUGGACAUCACCAA | 117 | UUGGUGAUGUCCACAUGAAGAAAGUUC | 118 |
| 56 | CUUUCUUCAUGUGGACAUCACCAAG | 119 | CUUGGUGAUGUCCACAUGAAGAAAGUU | 120 |
| 57 | UUUCUUCAUGUGGACAUCACCAAGC | 121 | GCUUGGUGAUGUCCACAUGAAGAAAGU | 122 |
| 58 | UUCUUCAUGUGGACAUCACCAAGCU | 123 | AGCUUGGUGAUGUCCACAUGAAGAAAG | 124 |
| 59 | CUUCAUGUGGACAUCACCAAGCUCA | 125 | UGAGCUUGGUGAUGUCCACAUGAAGAA | 126 |
| 60 | UUCAUGUGGACAUCACCAAGCUCAG | 127 | CUGAGCUUGGUGAUGUCCACAUGAAGA | 128 |
| 61 | UCAUGUGGACAUCACCAAGCUCAGU | 129 | ACUGAGCUUGGUGAUGUCCACAUGAAG | 130 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 62 | CAUGUGGACAUCACCAAGCUCAGUC | 131 | GACUGAGCUUGGUGAUGUCCACAUGAA | 132 |
| 63 | AUGUGGACAUCACCAAGCUCAGUCU | 133 | AGACUGAGCUUGGUGAUGUCCACAUGA | 134 |
| 64 | UGUGGACAUCACCAAGCUCAGUCUA | 135 | UAGACUGAGCUUGGUGAUGUCCACAUG | 136 |
| 65 | GUGGACAUCACCAAGCUCAGUCUAC | 137 | GUAGACUGAGCUUGGUGAUGUCCACAU | 138 |
| 66 | UGGACAUCACCAAGCUCAGUCUACG | 139 | CGUAGACUGAGCUUGGUGAUGUCCACA | 140 |
| 67 | AGCUUUUGUCCCCCCGGAUCUCAAG | 141 | CUUGAGAUCCGGGGGGACAAAAGCUCU | 142 |
| 68 | AAGGUGCUGGGAGAGAUAUGCCUUC | 143 | GAAGGCAUAUCUCUCCCAGCACCUUGA | 144 |
| 69 | GGGAGAGAUAUGCCUUCGAGGAUAU | 145 | AUAUCCUCGAAGGCAUAUCUCUCCCAG | 146 |
| 70 | GGAGAGAUAUGCCUUCGAGGAUAUU | 147 | AAUAUCCUCGAAGGCAUAUCUCUCCCA | 148 |
| 71 | AGAGAUAUGCCUUCGAGGAUAUUUG | 149 | CAAAUAUCCUCGAAGGCAUAUCUCUCC | 150 |
| 72 | GAGAUAUGCCUUCGAGGAUAUUUGG | 151 | CCAAAUAUCCUCGAAGGCAUAUCUCUC | 152 |
| 73 | AGAUAUGCCUUCGAGGAUAUUUGGA | 153 | UCCAAAUAUCCUCGAAGGCAUAUCUCU | 154 |
| 74 | GAUAUGCCUUCGAGGAUAUUUGGAU | 155 | AUCCAAAUAUCCUCGAAGGCAUAUCUC | 156 |
| 72 | AUAUGCCUUCGAGGAUAUUUGGAUG | 157 | CAUCCAAAUAUCCUCGAAGGCAUAUCU | 158 |
| 76 | AUGCCUUCGAGGAUAUUUGGAUGCA | 159 | UGCAUCCAAAUAUCCUCGAAGGCAUAU | 160 |
| 77 | UGCCUUCGAGGAUAUUUGGAUGCAU | 161 | AUGCAUCCAAAUAUCCUCGAAGGCAUA | 162 |
| 78 | GCCUUCGAGGAUAUUUGGAUGCAUU | 163 | AAUGCAUCCAAAUAUCCUCGAAGGCAU | 164 |
| 79 | UCAGGUUCUUGGAAGAGAAGGGCAU | 165 | AUGCCCUUCUCUUCCAAGAACCUGAAU | 166 |
| 80 | CAGGUUCUUGGAAGAGAAGGGCAUC | 167 | GAUGCCCUUCUCUUCCAAGAACCUGAA | 168 |
| 81 | AGGUUCUUGGAAGAGAAGGGCAUCU | 169 | AGAUGCCCUUCUCUUCCAAGAACCUGA | 170 |
| 82 | GGUUCUUGGAAGAGAAGGGCAUCUG | 171 | CAGAUGCCCUUCUCUUCCAAGAACCUG | 172 |
| 83 | UGGAAGAGAAGGGCAUCUGCAACAG | 173 | CUGUUGCAGAUGCCCUUCUCUUCCAAG | 174 |
| 84 | UGAAGUCAUCCUCAGAAGGGAUGGA | 175 | UCCAUCCCUUCUGAGGAUGACUUCAGG | 176 |
| 85 | GAAGUCAUCCUCAGAAGGGAUGGAU | 177 | AUCCAUCCCUUCUGAGGAUGACUUCAG | 178 |
| 86 | AAGUCAUCCUCAGAAGGGAUGGAUC | 179 | GAUCCAUCCCUUCUGAGGAUGACUUCA | 180 |
| 87 | GUCAUCCUCAGAAGGGAUGGAUCCU | 181 | AGGAUCCAUCCCUUCUGAGGAUGACUU | 182 |
| 88 | CAUCCUCAGAAGGGAUGGAUCCUGA | 183 | UCAGGAUCCAUCCCUUCUGAGGAUGAC | 184 |
| 89 | AUCCUCAGAAGGGAUGGAUCCUGAG | 185 | CUCAGGAUCCAUCCCUUCUGAGGAUGA | 186 |
| 90 | CUAGACCACCUGCGUCUCAGCAUCC | 187 | GGAUGCUGAGACGCAGGUGGUCUAGCA | 188 |
| 91 | AGUGAAGAAAUGAAAGACAAAGGUG | 189 | CACCUUUGUCUUUCAUUUCUUCACUCA | 190 |
| 92 | GUGAAGAAAUGAAAGACAAAGGUGG | 191 | CCACCUUUGUCUUUCAUUUCUUCACUC | 192 |
| 93 | UGAAGAAAUGAAAGACAAAGGUGGA | 193 | UCCACCUUUGUCUUUCAUUUCUUCACU | 194 |
| 94 | GAAGAAAUGAAAGACAAAGGUGGAU | 195 | AUCCACCUUUGUCUUUCAUUUCUUCAC | 196 |
| 95 | AAGAAAUGAAAGACAAAGGUGGAUA | 197 | UAUCCACCUUUGUCUUUCAUUUCUUCA | 198 |
| 96 | AGAAAUGAAAGACAAAGGUGGAUAC | 199 | GUAUCCACCUUUGUCUUUCAUUUCUUC | 200 |
| 97 | GAAAUGAAAGACAAAGGUGGAUACA | 201 | UGUAUCCACCUUUGUCUUUCAUUUCUU | 202 |
| 98 | AAAUGAAAGACAAAGGUGGAUACAU | 203 | AUGUAUCCACCUUUGUCUUUCAUUUCU | 204 |
| 99 | AAUGAAAGACAAAGGUGGAUACAUG | 205 | CAUGUAUCCACCUUUGUCUUUCAUUUC | 206 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 100 | AUGAAAGACAAAGGUGGAUACAUGA | 207 | UCAUGUAUCCACCUUUGUCUUUCAUUU | 208 |
| 101 | UGAAAGACAAAGGUGGAUACAUGAG | 209 | CUCAUGUAUCCACCUUUGUCUUUCAUU | 210 |
| 102 | GAAAGACAAAGGUGGAUACAUGAGC | 211 | GCUCAUGUAUCCACCUUUGUCUUUCAU | 212 |
| 103 | AAGACAAAGGUGGAUACAUGAGCAA | 213 | UUGCUCAUGUAUCCACCUUUGUCUUUC | 214 |
| 104 | AGACAAAGGUGGAUACAUGAGCAAG | 215 | CUUGCUCAUGUAUCCACCUUUGUCUUU | 216 |
| 105 | GACAAAGGUGGAUACAUGAGCAAGA | 217 | UCUUGCUCAUGUAUCCACCUUUGUCUU | 218 |
| 106 | ACAAAGGUGGAUACAUGAGCAAGAU | 219 | AUCUUGCUCAUGUAUCCACCUUUGUCU | 220 |
| 107 | AAGGUGGAUACAUGAGCAAGAUUUG | 221 | CAAAUCUUGCUCAUGUAUCCACCUUUG | 222 |
| 108 | AGGUGGAUACAUGAGCAAGAUUUGC | 223 | GCAAAUCUUGCUCAUGUAUCCACCUUU | 224 |
| 109 | UGGAUACAUGAGCAAGAUUUGCAAC | 225 | GUUGCAAAUCUUGCUCAUGUAUCCACC | 226 |
| 110 | GGAUACAUGAGCAAGAUUUGCAACU | 227 | AGUUGCAAAUCUUGCUCAUGUAUCCAC | 228 |
| 111 | GAUACAUGAGCAAGAUUUGCAACUU | 229 | AAGUUGCAAAUCUUGCUCAUGUAUCCA | 230 |
| 112 | AUACAUGAGCAAGAUUUGCAACUUG | 231 | CAAGUUGCAAAUCUUGCUCAUGUAUCC | 232 |
| 113 | UACAUGAGCAAGAUUUGCAACUUGC | 233 | GCAAGUUGCAAAUCUUGCUCAUGUAUC | 234 |
| 114 | ACAUGAGCAAGAUUUGCAACUUGCU | 235 | AGCAAGUUGCAAAUCUUGCUCAUGUAU | 236 |
| 115 | CAUGAGCAAGAUUUGCAACUUGCUA | 237 | UAGCAAGUUGCAAAUCUUGCUCAUGUA | 238 |
| 116 | AUGAGCAAGAUUUGCAACUUGCUAC | 239 | GUAGCAAGUUGCAAAUCUUGCUCAUGU | 240 |
| 117 | UGAGCAAGAUUUGCAACUUGCUACC | 241 | GGUAGCAAGUUGCAAAUCUUGCUCAUG | 242 |
| 118 | GAGCAAGAUUUGCAACUUGCUACCC | 243 | GGGUAGCAAGUUGCAAAUCUUGCUCAU | 244 |
| 119 | AGCAAGAUUUGCAACUUGCUACCCA | 245 | UGGGUAGCAAGUUGCAAAUCUUGCUCA | 246 |
| 120 | GCAAGAUUUGCAACUUGCUACCCAU | 247 | AUGGGUAGCAAGUUGCAAAUCUUGCUC | 248 |
| 121 | CAAGAUUUGCAACUUGCUACCCAUU | 249 | AAUGGGUAGCAAGUUGCAAAUCUUGCU | 250 |
| 122 | AAGAUUUGCAACUUGCUACCCAUUA | 251 | UAAUGGGUAGCAAGUUGCAAAUCUUGC | 252 |
| 123 | AGAUUUGCAACUUGCUACCCAUUAG | 253 | CUAAUGGGUAGCAAGUUGCAAAUCUUG | 254 |
| 124 | GAUUUGCAACUUGCUACCCAUUAGG | 255 | CCUAAUGGGUAGCAAGUUGCAAAUCUU | 256 |
| 125 | AUUUGCAACUUGCUACCCAUUAGGA | 257 | UCCUAAUGGGUAGCAAGUUGCAAAUCU | 258 |
| 126 | UUUGCAACUUGCUACCCAUUAGGAU | 259 | AUCCUAAUGGGUAGCAAGUUGCAAAUC | 260 |
| 127 | UUGCAACUUGCUACCCAUUAGGAUA | 261 | UAUCCUAAUGGGUAGCAAGUUGCAAAU | 262 |
| 128 | UGCAACUUGCUACCCAUUAGGAUAA | 263 | UUAUCCUAAUGGGUAGCAAGUUGCAAA | 264 |
| 129 | GCAACUUGCUACCCAUUAGGAUAAU | 265 | AUUAUCCUAAUGGGUAGCAAGUUGCAA | 266 |
| 130 | CAACUUGCUACCCAUUAGGAUAAUG | 267 | CAUUAUCCUAAUGGGUAGCAAGUUGCA | 268 |
| 131 | CUUGCUACCCAUUAGGAUAAUGUCU | 269 | AGACAUUAUCCUAAUGGGUAGCAAGUU | 270 |
| 132 | UUGCUACCCAUUAGGAUAAUGUCUU | 271 | AAGACAUUAUCCUAAUGGGUAGCAAGU | 272 |
| 133 | UGCUACCCAUUAGGAUAAUGUCUUA | 273 | UAAGACAUUAUCCUAAUGGGUAGCAAG | 274 |
| 134 | AUUAGGAUAAUGUCUUAUGUAAUGC | 275 | GCAUUACAUAAGACAUUAUCCUAAUGG | 276 |
| 135 | UUAGGAUAAUGUCUUAUGUAAUGCU | 277 | AGCAUUACAUAAGACAUUAUCCUAAUG | 278 |
| 136 | CUGUGGAAUCUGCCAUUGCGAUUGU | 279 | ACAAUCGCAAUGGCAGAUUCCACAGGC | 280 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 137 | GGAAUCUGCCAUUGCGAUUGUCCAG | 281 | CUGGACAAUCGCAAUGGCAGAUUCCAC | 282 |
| 138 | GAAUCUGCCAUUGCGAUUGUCCAGA | 283 | UCUGGACAAUCGCAAUGGCAGAUUCCA | 284 |
| 139 | AAUCUGCCAUUGCGAUUGUCCAGAG | 285 | CUCUGGACAAUCGCAAUGGCAGAUUCC | 286 |
| 140 | AUCUGCCAUUGCGAUUGUCCAGAGA | 287 | UCUCUGGACAAUCGCAAUGGCAGAUUC | 288 |
| 141 | CCAUUGCGAUUGUCCAGAGACUGGU | 289 | ACCAGUCUCUGGACAAUCGCAAUGGCA | 290 |
| 142 | CAUUGCGAUUGUCCAGAGACUGGUG | 291 | CACCAGUCUCUGGACAAUCGCAAUGGC | 292 |
| 143 | AUUGCGAUUGUCCAGAGACUGGUGA | 293 | UCACCAGUCUCUGGACAAUCGCAAUGG | 294 |
| 144 | UUGCGAUUGUCCAGAGACUGGUGAC | 295 | GUCACCAGUCUCUGGACAAUCGCAAUG | 296 |
| 145 | UGCGAUUGUCCAGAGACUGGUGACA | 297 | UGUCACCAGUCUCUGGACAAUCGCAAU | 298 |
| 146 | GCGAUUGUCCAGAGACUGGUGACAU | 299 | AUGUCACCAGUCUCUGGACAAUCGCAA | 300 |
| 147 | CGAUUGUCCAGAGACUGGUGACAUG | 301 | CAUGUCACCAGUCUCUGGACAAUCGCA | 302 |
| 148 | AUUGUCCAGAGACUGGUGACAUGGC | 303 | GCCAUGUCACCAGUCUCUGGACAAUCG | 304 |
| 149 | GUCCAGAGACUGGUGACAUGGCUUC | 305 | GAAGCCAUGUCACCAGUCUCUGGACAA | 306 |
| 150 | CCAGAGACUGGUGACAUGGCUUCCA | 307 | UGGAAGCCAUGUCACCAGUCUCUGGAC | 308 |
| 151 | CAGAGACUGGUGACAUGGCUUCCAG | 309 | CUGGAAGCCAUGUCACCAGUCUCUGGA | 310 |
| 152 | AGAGACUGGUGACAUGGCUUCCAGA | 311 | UCUGGAAGCCAUGUCACCAGUCUCUGG | 312 |
| 153 | GAGACUGGUGACAUGGCUUCCAGAU | 313 | AUCUGGAAGCCAUGUCACCAGUCUCUG | 314 |
| 154 | AGACUGGUGACAUGGCUUCCAGAUA | 315 | UAUCUGGAAGCCAUGUCACCAGUCUCU | 316 |
| 155 | GACUGGUGACAUGGCUUCCAGAUAU | 317 | AUAUCUGGAAGCCAUGUCACCAGUCUC | 318 |
| 156 | ACUGGUGACAUGGCUUCCAGAUAUG | 319 | CAUAUCUGGAAGCCAUGUCACCAGUCU | 320 |
| 157 | CUGGUGACAUGGCUUCCAGAUAUGC | 321 | GCAUAUCUGGAAGCCAUGUCACCAGUC | 322 |
| 158 | GACAUGGCUUCCAGAUAUGCCCGAC | 323 | GUCGGGCAUAUCUGGAAGCCAUGUCAC | 324 |
| 159 | CAUGGCUUCCAGAUAUGCCCGACGA | 325 | UCGUCGGGCAUAUCUGGAAGCCAUGUC | 326 |
| 160 | CAGAUAUGCCCGACGAUGUCCUGUG | 327 | CACAGGACAUCGUCGGGCAUAUCUGGA | 328 |
| 161 | CUCACAGGUGUUCACUCGAGUGCUG | 329 | CAGCACUCGAGUGAACACCUGUGAGGU | 330 |
| 162 | CACUCGAGUGCUGAUGUGUCUGCUC | 331 | GAGCAGACACAUCAGCACUCGAGUGAA | 332 |
| 163 | CUCGAGUGCUGAUGUGUCUGCUCCC | 333 | GGGAGCAGACACAUCAGCACUCGAGUG | 334 |
| 164 | CCCAAAUGCCAGUGAGCAGCCAACA | 335 | UGUUGGCUGCUCACUGGCAUUUGGGAC | 336 |
| 165 | UCAGGUCCAGCCUGAACUUCUUCUU | 337 | AAGAAGAAGUUCAGGCUGGACCUGAGG | 338 |
| 166 | CAGGUCCAGCCUGAACUUCUUCUUG | 339 | CAAGAAGAAGUUCAGGCUGGACCUGAG | 340 |
| 167 | AGGUCCAGCCUGAACUUCUUCUUGG | 341 | CCAAGAAGAAGUUCAGGCUGGACCUGA | 342 |
| 168 | CAAUAAAGUACCUGCUGGUGCUGAG | 343 | CUCAGCACCAGCAGGUACUUUAUUGCC | 344 |
| 169 | AAUAAAGUACCUGCUGGUGCUGAGG | 345 | CCUCAGCACCAGCAGGUACUUUAUUGC | 346 |
| 170 | AUAAAGUACCUGCUGGUGCUGAGGG | 347 | CCCUCAGCACCAGCAGGUACUUUAUUG | 348 |
| 171 | CUCUCCACCUUUCCCAGUUUUUCAC | 349 | GUGAAAAACUGGGAAAGGUGGAGAGCC | 350 |
| 172 | CUCCACCUUUCCCAGUUUUUCACUA | 351 | UAGUGAAAAACUGGGAAAGGUGGAGAG | 352 |
| 173 | UCCACCUUUCCCAGUUUUUCACUAG | 353 | CUAGUGAAAAACUGGGAAAGGUGGAGA | 354 |
| 174 | CCACCUUUCCCAGUUUUUCACUAGA | 355 | UCUAGUGAAAAACUGGGAAAGGUGGAG | 356 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 175 | CACCUUUCCCAGUUUUUCACUAGAG | 357 | CUCUAGUGAAAAACUGGGAAAGGUGGA | 358 |
| 176 | ACCUUUCCCAGUUUUUCACUAGAGA | 359 | UCUCUAGUGAAAAACUGGGAAAGGUGG | 360 |
| 177 | CCUUUCCCAGUUUUUCACUAGAGAA | 361 | UUCUCUAGUGAAAAACUGGGAAAGGUG | 362 |
| 178 | AGUUUUUCACUAGAGAAGAGUCUGU | 363 | ACAGACUCUUCUCUAGUGAAAAACUGG | 364 |
| 179 | UCUAGCAGAUUCUUUCAGAGGUGCU | 365 | AGCACCUCUGAAAGAAUCUGCUAGACU | 366 |
| 180 | AGCAGAUUCUUUCAGAGGUGCUAAA | 367 | UUUAGCACCUCUGAAAGAAUCUGCUAG | 368 |
| 181 | GCAGAUUCUUUCAGAGGUGCUAAAG | 369 | CUUUAGCACCUCUGAAAGAAUCUGCUA | 370 |
| 182 | CAGAUUCUUUCAGAGGUGCUAAAGU | 371 | ACUUUAGCACCUCUGAAAGAAUCUGCU | 372 |
| 183 | AGAUUCUUUCAGAGGUGCUAAAGUU | 373 | AACUUUAGCACCUCUGAAAGAAUCUGC | 374 |
| 184 | GAUUCUUUCAGAGGUGCUAAAGUUU | 375 | AAACUUUAGCACCUCUGAAAGAAUCUG | 376 |
| 185 | AUUCUUUCAGAGGUGCUAAAGUUUC | 377 | GAAACUUUAGCACCUCUGAAAGAAUCU | 378 |
| 186 | AGGUGCUAAAGUUUCCCAUCUUUGU | 379 | ACAAAGAUGGGAAACUUUAGCACCUCU | 380 |
| 187 | GGUGCUAAAGUUUCCCAUCUUUGUG | 381 | CACAAAGAUGGGAAACUUUAGCACCUC | 382 |
| 188 | GUGCUAAAGUUUCCCAUCUUUGUGC | 383 | GCACAAAGAUGGGAAACUUUAGCACCU | 384 |
| 189 | GCUAAAGUUUCCCAUCUUUGUGCAG | 385 | CUGCACAAAGAUGGGAAACUUUAGCAC | 386 |
| 190 | CUAAAGUUUCCCAUCUUUGUGCAGC | 387 | GCUGCACAAAGAUGGGAAACUUUAGCA | 388 |
| 191 | UAAAGUUUCCCAUCUUUGUGCAGCU | 389 | AGCUGCACAAAGAUGGGAAACUUUAGC | 390 |
| 192 | AAAGUUUCCCAUCUUUGUGCAGCUA | 391 | UAGCUGCACAAAGAUGGGAAACUUUAG | 392 |
| 193 | AAGUUUCCCAUCUUUGUGCAGCUAC | 393 | GUAGCUGCACAAAGAUGGGAAACUUUA | 394 |
| 194 | AGUUUCCCAUCUUUGUGCAGCUACC | 395 | GGUAGCUGCACAAAGAUGGGAAACUUU | 396 |
| 195 | GUUUCCCAUCUUUGUGCAGCUACCU | 397 | AGGUAGCUGCACAAAGAUGGGAAACUU | 398 |
| 196 | AUCUUUGUGCAGCUACCUCCGCAUU | 399 | AAUGCGGAGGUAGCUGCACAAAGAUGG | 400 |
| 197 | GUGCAGCUACCUCCGCAUUGCUGUG | 401 | CACAGCAAUGCGGAGGUAGCUGCACAA | 402 |
| 198 | CCAGCCUCUGAGCUGAGUUGGUUUU | 403 | AAAACCAACUCAGCUCAGAGGCUGGGA | 404 |
| 199 | CAGCCUCUGAGCUGAGUUGGUUUUA | 405 | UAAAACCAACUCAGCUCAGAGGCUGGG | 406 |
| 200 | AGCCUCUGAGCUGAGUUGGUUUUAU | 407 | AUAAAACCAACUCAGCUCAGAGGCUGG | 408 |
| 201 | GCCUCUGAGCUGAGUUGGUUUUAUG | 409 | CAUAAAACCAACUCAGCUCAGAGGCUG | 410 |
| 202 | CCUCUGAGCUGAGUUGGUUUUAUGA | 411 | UCAUAAAACCAACUCAGCUCAGAGGCU | 412 |
| 203 | CUCUGAGCUGAGUUGGUUUUAUGAA | 413 | UUCAUAAAACCAACUCAGCUCAGAGGC | 414 |
| 204 | UCUGAGCUGAGUUGGUUUUAUGAAA | 415 | UUUCAUAAAACCAACUCAGCUCAGAGG | 416 |
| 205 | UGAGCUGAGUUGGUUUUAUGAAAAG | 417 | CUUUUCAUAAAACCAACUCAGCUCAGA | 418 |
| 206 | UGAGUUGGUUUUAUGAAAAGCUAGG | 419 | CCUAGCUUUUCAUAAAACCAACUCAGC | 420 |
| 207 | GAGUUGGUUUUAUGAAAAGCUAGGA | 421 | UCCUAGCUUUUCAUAAAACCAACUCAG | 422 |
| 208 | UUGGUUUUAUGAAAAGCUAGGAAGC | 423 | GCUUCCUAGCUUUUCAUAAAACCAACU | 424 |
| 209 | UGGUUUUAUGAAAAGCUAGGAAGCA | 425 | UGCUUCCUAGCUUUUCAUAAAACCAAC | 426 |
| 210 | GGUUUUAUGAAAAGCUAGGAAGCAA | 427 | UUGCUUCCUAGCUUUUCAUAAAACCAA | 428 |
| 211 | UUUUAUGAAAAGCUAGGAAGCAACC | 429 | GGUUGCUUCCUAGCUUUUCAUAAAACC | 430 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 212 | UUAUGAAAAGCUAGGAAGCAACCUU | 431 | AAGGUUGCUUCCUAGCUUUUCAUAAAA | 432 |
| 213 | UAUGAAAAGCUAGGAAGCAACCUUU | 433 | AAAGGUUGCUUCCUAGCUUUUCAUAAA | 434 |
| 214 | AUGAAAAGCUAGGAAGCAACCUUUC | 435 | GAAAGGUUGCUUCCUAGCUUUUCAUAA | 436 |
| 215 | CCAGCACUUAACUCUAAUACAUCAG | 437 | CUGAUGUAUUAGAGUUAAGUGCUGGAC | 438 |
| 216 | CAGCACUUAACUCUAAUACAUCAGC | 439 | GCUGAUGUAUUAGAGUUAAGUGCUGGA | 440 |
| 217 | UAAUACAUCAGCAUGCGUUAAUUCA | 441 | UGAAUUAACGCAUGCUGAUGUAUUAGA | 442 |
| 218 | AAUACAUCAGCAUGCGUUAAUUCAG | 443 | CUGAAUUAACGCAUGCUGAUGUAUUAG | 444 |
| 219 | AGCAUGCGUUAAUUCAGCUGGUUGG | 445 | CCAACCAGCUGAAUUAACGCAUGCUGA | 446 |
| 220 | GCAUGCGUUAAUUCAGCUGGUUGGG | 447 | CCCAACCAGCUGAAUUAACGCAUGCUG | 448 |
| 221 | UGCGUUAAUUCAGCUGGUUGGGAAA | 449 | UUUCCCAACCAGCUGAAUUAACGCAUG | 450 |
| 222 | GCGUUAAUUCAGCUGGUUGGGAAAU | 451 | AUUUCCCAACCAGCUGAAUUAACGCAU | 452 |
| 223 | CGUUAAUUCAGCUGGUUGGGAAAUG | 453 | CAUUUCCCAACCAGCUGAAUUAACGCA | 454 |
| 224 | GUUAAUUCAGCUGGUUGGGAAAUGA | 455 | UCAUUUCCCAACCAGCUGAAUUAACGC | 456 |
| 225 | UUAAUUCAGCUGGUUGGGAAAUGAC | 457 | GUCAUUUCCCAACCAGCUGAAUUAACG | 458 |
| 226 | UAAUUCAGCUGGUUGGGAAAUGACA | 459 | UGUCAUUUCCCAACCAGCUGAAUUAAC | 460 |
| 227 | AUUCAGCUGGUUGGGAAAUGACACC | 461 | GGUGUCAUUUCCCAACCAGCUGAAUUA | 462 |
| 228 | UUCAGCUGGUUGGGAAAUGACACCA | 463 | UGGUGUCAUUUCCCAACCAGCUGAAUU | 464 |
| 229 | UCAGCUGGUUGGGAAAUGACACCAG | 465 | CUGGUGUCAUUUCCCAACCAGCUGAAU | 466 |
| 230 | CAGCUGGUUGGGAAAUGACACCAGG | 467 | CCUGGUGUCAUUUCCCAACCAGCUGAA | 468 |
| 231 | AGCUGGUUGGGAAAUGACACCAGGA | 469 | UCCUGGUGUCAUUUCCCAACCAGCUGA | 470 |
| 232 | GCUGGUUGGGAAAUGACACCAGGAA | 471 | UUCCUGGUGUCAUUUCCCAACCAGCUG | 472 |
| 233 | GCAGAGGGUCCCUUACUGACUGUUU | 473 | AAACAGUCAGUAAGGGACCCUCUGCAC | 474 |
| 234 | CAGAGGGUCCCUUACUGACUGUUUC | 475 | GAAACAGUCAGUAAGGGACCCUCUGCA | 476 |
| 235 | AGAGGGUCCCUUACUGACUGUUUCG | 477 | CGAAACAGUCAGUAAGGGACCCUCUGC | 478 |
| 236 | CCUAUUAAUGGUCAGACUGUUCCAG | 479 | CUGGAACAGUCUGACCAUUAAUAGGGC | 480 |
| 237 | CUAUUAAUGGUCAGACUGUUCCAGC | 481 | GCUGGAACAGUCUGACCAUUAAUAGGG | 482 |
| 238 | UAUUAAUGGUCAGACUGUUCCAGCA | 483 | UGCUGGAACAGUCUGACCAUUAAUAGG | 484 |
| 239 | AUUAAUGGUCAGACUGUUCCAGCAU | 485 | AUGCUGGAACAGUCUGACCAUUAAUAG | 486 |
| 240 | UUAAUGGUCAGACUGUUCCAGCAUG | 487 | CAUGCUGGAACAGUCUGACCAUUAAUA | 488 |
| 241 | UAAUGGUCAGACUGUUCCAGCAUGA | 489 | UCAUGCUGGAACAGUCUGACCAUUAAU | 490 |
| 242 | AAUGGUCAGACUGUUCCAGCAUGAG | 491 | CUCAUGCUGGAACAGUCUGACCAUUAA | 492 |
| 243 | AGAACGACACUGCCUGUCAGGUGGU | 493 | ACCACCUGACAGGCAGUGUCGUUCUUG | 494 |
| 244 | CGACACUGCCUGUCAGGUGGUCUGC | 495 | GCAGACCACCUGACAGGCAGUGUCGUU | 496 |
| 245 | AACCUUGACUACUAAAAACGUCUCC | 497 | GGAGACGUUUUUAGUAGUCAAGGUUAU | 498 |
| 246 | UUUAGAACACCUUUUUCACCUAACU | 499 | AGUUAGGUGAAAAAGGUGUUCUAAAAU | 500 |
| 247 | UUAGAACACCUUUUUCACCUAACUA | 501 | UAGUUAGGUGAAAAAGGUGUUCUAAAA | 502 |
| 248 | UAGAACACCUUUUUCACCUAACUAA | 503 | UUAGUUAGGUGAAAAAGGUGUUCUAAA | 504 |
| 249 | AGAACACCUUUUUCACCUAACUAAA | 505 | UUUAGUUAGGUGAAAAAGGUGUUCUAA | 506 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 250 | GAACACCUUUUUCACCUAACUAAAA | 507 | UUUUAGUUAGGUGAAAAAGGUGUUCUA | 508 |
| 251 | AACACCUUUUUCACCUAACUAAAAU | 509 | AUUUUAGUUAGGUGAAAAAGGUGUUCU | 510 |
| 252 | ACACCUUUUUCACCUAACUAAAAUA | 511 | UAUUUUAGUUAGGUGAAAAAGGUGUUC | 512 |
| 253 | CACCUUUUUCACCUAACUAAAAUAA | 513 | UUAUUUUAGUUAGGUGAAAAAGGUGUU | 514 |
| 254 | ACCUUUUUCACCUAACUAAAAUAAU | 515 | AUUAUUUUAGUUAGGUGAAAAAGGUGU | 516 |
| 255 | CUUUUUCACCUAACUAAAAUAAUGU | 517 | ACAUUAUUUUAGUUAGGUGAAAAAGGU | 518 |
| 256 | UUUUCACCUAACUAAAAUAAUGUUU | 519 | AAACAUUAUUUUAGUUAGGUGAAAAAG | 520 |
| 257 | UUCACCUAACUAAAAUAAUGUUUAA | 521 | UUAAACAUUAUUUUAGUUAGGUGAAAA | 522 |
| 258 | UCACCUAACUAAAAUAAUGUUUAAA | 523 | UUUAAACAUUAUUUUAGUUAGGUGAAA | 524 |
| 259 | CACCUAACUAAAAUAAUGUUUAAAG | 525 | CUUUAAACAUUAUUUUAGUUAGGUGAA | 526 |
| 260 | ACCUAACUAAAAUAAUGUUUAAAGA | 527 | UCUUUAAACAUUAUUUUAGUUAGGUGA | 528 |
| 261 | CCUAACUAAAAUAAUGUUUAAAGAG | 529 | CUCUUUAAACAUUAUUUUAGUUAGGUG | 530 |
| 262 | CUAACUAAAAUAAUGUUUAAAGAGU | 531 | ACUCUUUAAACAUUAUUUUAGUUAGGU | 532 |
| 263 | UAACUAAAAUAAUGUUUAAAGAGUU | 533 | AACUCUUUAAACAUUAUUUUAGUUAGG | 534 |
| 264 | AACUAAAAUAAUGUUUAAAGAGUUU | 535 | AAACUCUUUAAACAUUAUUUUAGUUAG | 536 |
| 265 | ACUAAAAUAAUGUUUAAAGAGUUUU | 537 | AAAACUCUUUAAACAUUAUUUUAGUUA | 538 |
| 266 | CUAAAAUAAUGUUUAAAGAGUUUUG | 539 | CAAAACUCUUUAAACAUUAUUUUAGUU | 540 |
| 267 | UAAAAUAAUGUUUAAAGAGUUUUGU | 541 | ACAAAACUCUUUAAACAUUAUUUUAGU | 542 |
| 268 | AAGAGUUUUGUAUAAAAAUGUAAGG | 543 | CCUUACAUUUUUAUACAAAACUCUUUA | 544 |
| 269 | GUUUUGUAUAAAAAUGUAAGGAAGC | 545 | GCUUCCUUACAUUUUUAUACAAAACUC | 546 |
| 270 | UUUUGUAUAAAAAUGUAAGGAAGCG | 547 | CGCUUCCUUACAUUUUUAUACAAAACU | 548 |
| 271 | UUUGUAUAAAAAUGUAAGGAAGCGU | 549 | ACGCUUCCUUACAUUUUUAUACAAAAC | 550 |
| 272 | UUGUAUAAAAAUGUAAGGAAGCGUU | 551 | AACGCUUCCUUACAUUUUUAUACAAAA | 552 |
| 273 | UGUAUAAAAAUGUAAGGAAGCGUUG | 553 | CAACGCUUCCUUACAUUUUUAUACAAA | 554 |
| 274 | GUAUAAAAAUGUAAGGAAGCGUUGU | 555 | ACAACGCUUCCUUACAUUUUUAUACAA | 556 |
| 275 | AUGUAAGGAAGCGUUGUUACCUGUU | 557 | AACAGGUAACAACGCUUCCUUACAUUU | 558 |
| 276 | UUUUGUAUUAUGUGAAUCAGUGAGA | 559 | UCUCACUGAUUCACAUAAUACAAAAUU | 560 |
| 277 | UUUGUAUUAUGUGAAUCAGUGAGAU | 561 | AUCUCACUGAUUCACAUAAUACAAAAU | 562 |
| 278 | UUGUAUUAUGUGAAUCAGUGAGAUG | 563 | CAUCUCACUGAUUCACAUAAUACAAAA | 564 |
| 279 | UGUAUUAUGUGAAUCAGUGAGAUGU | 565 | ACAUCUCACUGAUUCACAUAAUACAAA | 566 |
| 280 | GUAUUAUGUGAAUCAGUGAGAUGUU | 567 | AACAUCUCACUGAUUCACAUAAUACAA | 568 |
| 281 | UAUUAUGUGAAUCAGUGAGAUGUUA | 569 | UAACAUCUCACUGAUUCACAUAAUACA | 570 |
| 282 | AUUAUGUGAAUCAGUGAGAUGUUAG | 571 | CUAACAUCUCACUGAUUCACAUAAUAC | 572 |
| 283 | UUAUGUGAAUCAGUGAGAUGUUAGU | 573 | ACUAACAUCUCACUGAUUCACAUAAUA | 574 |
| 284 | UAUGUGAAUCAGUGAGAUGUUAGUA | 575 | UACUAACAUCUCACUGAUUCACAUAAU | 576 |
| 285 | AUGUGAAUCAGUGAGAUGUUAGUAG | 577 | CUACUAACAUCUCACUGAUUCACAUAA | 578 |
| 286 | UGUGAAUCAGUGAGAUGUUAGUAGA | 579 | UCUACUAACAUCUCACUGAUUCACAUA | 580 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 287 | GUGAAUCAGUGAGAUGUUAGUAGAA | 581 | UUCUACUAACAUCUCACUGAUUCACAU | 582 |
| 288 | GUGAGAUGUUAGUAGAAUAAGCCUU | 583 | AAGGCUUAUUCUACUAACAUCUCACUG | 584 |
| 289 | UUUUCUAUUUAUGCAUUUGAGUACA | 585 | UGUACUCAAAUGCAUAAAUAGAAAAAA | 586 |
| 290 | UUUCUAUUUAUGCAUUUGAGUACAG | 587 | CUGUACUCAAAUGCAUAAAUAGAAAAA | 588 |
| 291 | UUCUAUUUAUGCAUUUGAGUACAGT | 589 | ACUGUACUCAAAUGCAUAAAUAGAAAA | 590 |
| 292 | CUAUUUAUGCAUUUGAGUACAGUAC | 591 | GUACUGUACUCAAAUGCAUAAAUAGAA | 592 |
| 293 | UGCUCAAACUGUUAAAUGUUGGAAA | 593 | UUUCCAACAUUUAACAGUUUGAGCACA | 594 |
| 294 | GCUCAAACUGUUAAAUGUUGGAAAA | 595 | UUUUCCAACAUUUAACAGUUUGAGCAC | 596 |
| 295 | CUCAAACUGUUAAAUGUUGGAAAAG | 597 | CUUUUCCAACAUUUAACAGUUUGAGCA | 598 |
| 296 | UCAAACUGUUAAAUGUUGGAAAAGA | 599 | UCUUUUCCAACAUUUAACAGUUUGAGC | 600 |
| 297 | CAAACUGUUAAAUGUUGGAAAAGAA | 601 | UUCUUUUCCAACAUUUAACAGUUUGAG | 602 |
| 298 | AAACUGUUAAAUGUUGGAAAAGAAA | 603 | UUUCUUUUCCAACAUUUAACAGUUUGA | 604 |
| 299 | AACUGUUAAAUGUUGGAAAAGAAAG | 605 | CUUUCUUUUCCAACAUUUAACAGUUUG | 606 |
| 300 | ACUGUUAAAUGUUGGAAAAGAAAGA | 607 | UCUUUCUUUUCCAACAUUUAACAGUUU | 608 |
| 301 | CUGUUAAAUGUUGGAAAAGAAAGAT | 609 | AUCUUUCUUUUCCAACAUUUAACAGUU | 610 |
| 302 | UGUUAAAUGUUGGAAAAGAAAGATA | 611 | UAUCUUUCUUUUCCAACAUUUAACAGU | 612 |
| 303 | GUUAAAUGUUGGAAAAGAAAGAUAC | 613 | GUAUCUUUCUUUUCCAACAUUUAACAG | 614 |
| 304 | UUAAAUGUUGGAAAAGAAAGAUACA | 615 | UGUAUCUUUCUUUUCCAACAUUUAACA | 616 |
| 305 | UAAAUGUUGGAAAAGAAAGAUACAA | 617 | UUGUAUCUUUCUUUUCCAACAUUUAAC | 618 |
| 306 | GCACUUGACUGAGAAGACAGACCCT | 619 | AGGGUCUGUCUUCUCAGUCAAGUGCUU | 620 |
| 307 | GAGAAAAGAGGCUACUUGUGAAAAT | 621 | AUUUUCACAAGUAGCCUCUUUUCUCAA | 622 |
| 308 | AGAAAAGAGGCUACUUGUGAAAATA | 623 | UAUUUUCACAAGUAGCCUCUUUUCUCA | 624 |
| 309 | GAAAAGAGGCUACUUGUGAAAAUAA | 625 | UUAUUUUCACAAGUAGCCUCUUUUCUC | 626 |
| 310 | AAAAGAGGCUACUUGUGAAAAUAAT | 627 | AUUAUUUUCACAAGUAGCCUCUUUUCU | 628 |
| 311 | AAAGAGGCUACUUGUGAAAAUAATG | 629 | CAUUAUUUUCACAAGUAGCCUCUUUUC | 630 |
| 312 | AAGAGGCUACUUGUGAAAAUAAUGA | 631 | UCAUUAUUUUCACAAGUAGCCUCUUUU | 632 |
| 313 | AGAGGCUACUUGUGAAAAUAAUGAG | 633 | CUCAUUAUUUUCACAAGUAGCCUCUUU | 634 |
| 314 | GAGGCUACUUGUGAAAAUAAUGAGC | 635 | GCUCAUUAUUUUCACAAGUAGCCUCUU | 636 |
| 315 | GGCUACUUGUGAAAAUAAUGAGCCC | 637 | GGGCUCAUUAUUUUCACAAGUAGCCUC | 638 |
| 316 | CUACUUGUGAAAAUAAUGAGCCCCC | 639 | GGGGGCUCAUUAUUUUCACAAGUAGCC | 640 |
| 317 | UGAACCUGCCUUCUUACAUCUUGAG | 641 | CUCAAGAUGUAAGAAGGCAGGUUCAAA | 642 |
| 318 | AAAGUUACAAGUUUCUUUUCCCAAG | 643 | CUUGGGAAAAGAAACUUGUAACUUUCC | 644 |
| 319 | AAGUUACAAGUUUCUUUUCCCAAGT | 645 | ACUUGGGAAAAGAAACUUGUAACUUUC | 646 |
| 320 | AGUUACAAGUUUCUUUUCCCAAGTT | 647 | AACUUGGGAAAAGAAACUUGUAACUUU | 648 |
| 321 | AGUUUCUUUUCCCAAGUUUCCCAGT | 649 | ACUGGGAAACUUGGGAAAAGAAACUUG | 650 |
| 322 | CAACAGUAUUUUCUAAUAACCAGTA | 651 | UACUGGUUAUUAGAAAAUACUGUUGGC | 652 |
| 323 | AACAGUAUUUUCUAAUAACCAGUAT | 653 | AUACUGGUUAUUAGAAAAUACUGUUGG | 654 |
| 324 | ACAGUAUUUUCUAAUAACCAGUATA | 655 | UAUACUGGUUAUUAGAAAAUACUGUUG | 656 |

TABLE 1-continued

DsiRNAs (unmodified) Targeting Human PNPLA3 mRNA and Controls Evaluated in Cells.

| DsiRNA | Passenger (sense) | SEQ ID NO: | Guide (antisense) | SEQ ID NO: |
|---|---|---|---|---|
| 325 | CAGUAUUUUCUAAUAACCAGUAUAT | 657 | AUAUACUGGUUAUUAGAAAAUACUGUU | 658 |
| 326 | UUGUGAUUGUUAUCAGGAAAAAAATA | 659 | UAUUUUUUCCUGAUAACAAUCACAAUA | 660 |
| 327 | UGUGAUUGUUAUCAGGAAAAAAUAT | 661 | AUAUUUUUUCCUGAUAACAAUCACAAU | 662 |
| 328 | GUGAUUGUUAUCAGGAAAAAAUATA | 663 | UAUAUUUUUUCCUGAUAACAAUCACAA | 664 |
| 329 | UGAUUGUUAUCAGGAAAAAAUAUAT | 665 | AUAUAUUUUUUCCUGAUAACAAUCACA | 666 |
| 330 | GAUUGUUAUCAGGAAAAAAUAUATT | 667 | AAUAUAUUUUUUCCUGAUAACAAUCAC | 668 |
| 331 | AUUGUUAUCAGGAAAAAAUAUAUTA | 669 | UAAUAUAUUUUUUCCUGAUAACAAUCA | 670 |
| 332 | UUGUUAUCAGGAAAAAAUAUAUUAA | 671 | UUAAUAUAUUUUUUCCUGAUAACAAUC | 672 |
| 333 | UGUUAUCAGGAAAAAAUAUAUUAAA | 673 | UUUAAUAUAUUUUUUCCUGAUAACAAU | 674 |
| 334 | GUUAUCAGGAAAAAAUAUAUUAAAT | 675 | AUUUAAUAUAUUUUUUCCUGAUAACAA | 676 |
| 335 | UUAUCAGGAAAAAAUAUAUUAAATG | 677 | CAUUUAAUAUAUUUUUUCCUGAUAACA | 678 |
| 336 | UAUCAGGAAAAAAUAUAUUAAAUGG | 679 | CCAUUUAAUAUAUUUUUUCCUGAUAAC | 680 |
| 337 | AUCAGGAAAAAAUAUAUUAAAUGGC | 681 | GCCAUUUAAUAUAUUUUUUCCUGAUAA | 682 |
| 338 | AGGAAAAAAUAUAUUAAAUGGCUGA | 683 | UCAGCCAUUUAAUAUAUUUUUUCCUGA | 684 |
| 339 | GGAAAAAAUAUAUUAAAUGGCUGAT | 685 | AUCAGCCAUUUAAUAUAUUUUUUCCUG | 686 |
| 340 | GAAAAAAUAUAUUAAAUGGCUGATA | 687 | UAUCAGCCAUUUAAUAUAUUUUUUCCU | 688 |
| 341 | AAAAAAUAUAUUAAAUGGCUGAUAG | 689 | CUAUCAGCCAUUUAAUAUAUUUUUUCC | 690 |
| 342 | UAUUUUCUUUCUGCUUUUAAAAATT | 691 | AAUUUUUAAAAGCAGAAAGAAAAUACG | 692 |
| 343 | AUUUUCUUUCUGCUUUUAAAAAUTA | 693 | UAAUUUUUAAAAGCAGAAAGAAAAUAC | 694 |
| 344 | UCUUUCUGCUUUUAAAAAUUAUUCA | 695 | UGAAUAAUUUUUAAAAGCAGAAAGAAA | 696 |
| 345 | CUUUCUGCUUUUAAAAAUUAUUCAG | 697 | CUGAAUAAUUUUUAAAAGCAGAAAGAA | 698 |
| 346 | UUUCUGCUUUUAAAAAUUAUUCAGG | 699 | CCUGAAUAAUUUUUAAAAGCAGAAAGA | 700 |
| 347 | CUACUAAAAACACAAAAAUUAGCCA | 701 | UGGCUAAUUUUUGUGUUUUUAGUAGAG | 702 |
| 348 | CAAGAUAAGGAAAUCAGGAAGUGTA | 703 | UACACUUCCUGAUUUCCUUAUCUUGAU | 704 |
| 349 | AAGAUAAGGAAAUCAGGAAGUGUAA | 705 | UUACACUUCCUGAUUUCCUUAUCUUGA | 706 |
| 350 | AGAUAAGGAAAUCAGGAAGUGUAAT | 707 | AUUACACUUCCUGAUUUCCUUAUCUUG | 708 |
| 351 | GAUAAGGAAAUCAGGAAGUGUAATA | 709 | UAUUACACUUCCUGAUUUCCUUAUCUU | 710 |
| 352 | AUAAGGAAAUCAGGAAGUGUAAUAT | 711 | AUAUUACACUUCCUGAUUUCCUUAUCU | 712 |
| 353 | UAAGGAAAUCAGGAAGUGUAAUATT | 713 | AAUAUUACACUUCCUGAUUUCCUUAUC | 714 |
| 354 | AAGGAAAUCAGGAAGUGUAAUAUTC | 715 | GAAUAUUACACUUCCUGAUUUCCUUAU | 716 |
| 355 | AGGAAAUCAGGAAGUGUAAUAUUCT | 717 | AGAAUAUUACACUUCCUGAUUUCCUUA | 718 |
| 356 | GGAAAUCAGGAAGUGUAAUAUUCTT | 719 | AAGAAUAUUACACUUCCUGAUUUCCUU | 720 |
| 357 | GAAAUCAGGAAGUGUAAUAUUCUTA | 721 | UAAGAAUAUUACACUUCCUGAUUUCCU | 722 |
| 358 | CUAUGAAUGCAUUCUUAUUUCUUCT | 723 | AGAAGAAAUAAGAAUGCAUUCAUAGGC | 724 |
| 359 | UAUGAAUGCAUUCUUAUUUCUUCTT | 725 | AAGAAGAAAUAAGAAUGCAUUCAUAGG | 726 |
| 360 | CUACCACACCCAGCUAGUUUUUUTT | 727 | AAAAAAAACUAGCUGGGUGUGGUAGUG | 728 |
| 361 | CCACACCCAGCUAGUUUUUUUUUGT | 729 | ACAAAAAAAAACUAGCUGGGUGUGGUA | 730 |

TABLE 1-continued

| DsiRNAs (unmodified) Targeting Human PNPLA3 mRNA and Controls Evaluated in Cells. | | | | |
|---|---|---|---|---|
| DsiRNA | Passenger (sense) | SEQ ID NO: | Guide (antisense) | SEQ ID NO: |
| 362 | CACACCCAGCUAGUUUUUUUUUGTA | 731 | UACAAAAAAAAACUAGCUGGGUGUGGU | 732 |
| 363 | GCUAGGAUUACAGGUGUGAGCUACC | 733 | GGUAGCUCACACCUGUAAUCCUAGCAC | 734 |
| 364 | CUAGGAUUACAGGUGUGAGCUACCA | 735 | UGGUAGCUCACACCUGUAAUCCUAGCA | 736 |
| 365 | CCAUGCCUGGUCCAACAUUCUUCAT | 737 | AUGAAGAAUGUUGGACCAGGCAUGGUA | 738 |
| 366 | UGCAGAGUAUGAGCCUGAUUUUGTT | 739 | AACAAAAUCAGGCUCAUACUCUGCACU | 740 |
| 367 | GCAGAGUAUGAGCCUGAUUUUGUTT | 741 | AAACAAAAUCAGGCUCAUACUCUGCAC | 742 |
| 368 | CAGAGUAUGAGCCUGAUUUUGUUTA | 743 | UAAACAAAAUCAGGCUCAUACUCUGCA | 744 |
| 369 | AGAGUAUGAGCCUGAUUUUGUUUAA | 745 | UUAAACAAAAUCAGGCUCAUACUCUGC | 746 |
| 370 | GAGUAUGAGCCUGAUUUUGUUUAAA | 747 | UUUAAACAAAAUCAGGCUCAUACUCUG | 748 |
| 371 | GGGUGAAACCCCAUCUCUACUAAAA | 749 | UUUUAGUAGAGAUGGGGUUUCACCCAG | 750 |
| 372 | GUGAAACCCCAUCUCUACUAAAAAA | 751 | UUUUUUAGUAGAGAUGGGGUUUCACCC | 752 |
| 373 | UGAAACCCCAUCUCUACUAAAAAAT | 753 | AUUUUUUAGUAGAGAUGGGGUUUCACC | 754 |
| 374 | GAAACCCCAUCUCUACUAAAAAATG | 755 | CAUUUUUUAGUAGAGAUGGGGUUUCAC | 756 |
| 375 | AAACCCCAUCUCUACUAAAAAAUGC | 757 | GCAUUUUUUAGUAGAGAUGGGGUUUCA | 758 |
| 376 | AACCCCAUCUCUACUAAAAAAUGCA | 759 | UGCAUUUUUUAGUAGAGAUGGGGUUUC | 760 |
| 377 | CCCAUCUCUACUAAAAAAUGCAAAA | 761 | UUUUGCAUUUUUUAGUAGAGAUGGGGU | 762 |
| 378 | AUCAAAACCCUUAUGGCAGACUGTT | 763 | AACAGUCUGCCAUAAGGGUUUUGAUAU | 764 |
| 379 | UAUUUUAUUUGUCGUGCUUAUAUGT | 765 | ACAUAUAAGCACGACAAAUAAAAUACA | 766 |
| 380 | GUGUUGCCCAAGUUUCUAUGGUGAA | 767 | UUCACCAUAGAAACUUGGGCAACACAU | 768 |
| 381 | GCCCAAGUUUCUAUGGUGAACGGTA | 769 | UACCGUUCACCAUAGAAACUUGGGCAA | 770 |
| 382 | CCCAAGUUUCUAUGGUGAACGGUAT | 771 | AUACCGUUCACCAUAGAAACUUGGGCA | 772 |
| 383 | ACUUUCAGCAUGAGAAAAUAACUCC | 773 | GGAGUUAUUUUCUCAUGCUGAAAGUGA | 774 |
| 384 | CUUUCAGCAUGAGAAAAUAACUCCT | 775 | AGGAGUUAUUUUCUCAUGCUGAAAGUG | 776 |

In vitro cell-based assays: The ability of each of the 384 DsiRNAs listed in Table 1 to inhibit PNPLA3 expression is determined using in vitro cell-based assays. Further, the nucleotide sequences for the passenger strand and guide strand of the DsiRNAs have a distinct pattern of modified nucleotides and phosphorothioate linkages (see, e.g., FIG. 2). Briefly, HuH-7 human liver cells stably expressing PNPLA3 are transfected with each of the DsiRNAs (0.5 nM) in separate wells of a multi-well cell culture plate. Cells are maintained for 24 hr. following transfection, and then levels of remaining PNPLA3 mRNA from the transfected cells are determined using TAQMAN®-based qPCR assays. Two qPCR assays, a 3' assay and a 5' assay, are used to determine mRNA levels as measured by HEX and FAM probes, respectively.

The results of the HuH-7 cell-based assay with the DsiRNAs are shown in Table 2. Table 2 shows the results of the HuH-7 cell-based assay with 384 DsiRNAs that have guide strands that are complementary to human and monkey PNPLA3 mRNA ("double-common"). Transfection of a double-common DsiRNA that results in less than or equal to 30% PNPLA3 mRNA remaining in the cells when compared to negative controls is considered a candidate PNPLA3 expression inhibitor (referred to herein as a "hit").

TABLE 2

Double-Common DsiRNA PNPLA3 Knockdown in HuH-7 Cells, 0.5 nM 24 hr-5' and -3' Assays % mRNA Remaining (normalized to HPRT1 and SFRS9 vs Mock Control).

| | PNPLA3-F495 | | PNPLA3-F595 | | Averages | |
|---|---|---|---|---|---|---|
| DsiRNA | % Remaining | % SEM | % Remaining | % SEM | Average % Remaining | Average % SEM |
| 1 | — | — | 41.276 | 5.253 | 41.2760 | 5.2530 |
| 2 | 24.048 | 5.091 | 33.293 | 8.521 | 28.6705 | 6.8060 |

TABLE 2-continued

Double-Common DsiRNA PNPLA3 Knockdown in HuH-7 Cells, 0.5 nM 24 hr-5' and -3' Assays % mRNA Remaining (normalized to HPRT1 and SFRS9 vs Mock Control).

| | PNPLA3-F495 | | PNPLA3-F595 | | Averages | |
|---|---|---|---|---|---|---|
| DsiRNA | % Remaining | % SEM | % Remaining | % SEM | Average % Remaining | Average % SEM |
| 3 | 23.686 | 3.496 | 36.027 | 2.441 | 29.8565 | 2.9685 |
| 4 | 20.851 | 2.728 | 31.34 | 4.013 | 26.0955 | 3.3705 |
| 5 | 19.609 | 4.442 | 30.014 | 4.678 | 24.8115 | 4.5600 |
| 6 | 17.737 | 2.25 | 38.518 | 5.495 | 28.1275 | 3.8725 |
| 7 | 42.296 | 6.654 | — | — | 42.2960 | 6.6540 |
| 8 | 30.019 | 2.843 | 35.275 | 5.401 | 32.6470 | 4.1220 |
| 9 | 107.259 | 15.824 | 77.986 | 22.381 | 92.6225 | 19.1025 |
| 10 | 69.476 | 36.895 | 83.554 | 28.116 | 76.5150 | 32.5055 |
| 11 | 39.447 | 10.162 | 31.949 | 3.604 | 35.6980 | 6.8830 |
| 12 | — | — | 31.418 | 19.31 | 31.4180 | 19.3100 |
| 13 | 82.71 | 31.376 | 81.104 | 20.936 | 81.9070 | 26.1560 |
| 14 | 35.657 | 4.964 | 54.326 | 6.388 | 44.9915 | 5.6760 |
| 15 | 32.849 | 4.61 | 28.693 | 2.08 | 30.7710 | 3.3450 |
| 16 | — | — | — | — | — | — |
| 17 | — | — | 38.503 | 11.845 | 38.5030 | 11.8450 |
| 18 | 35.771 | 6.677 | 53.554 | 4.637 | 44.6625 | 5.6570 |
| 19 | 13.754 | 5.708 | 23.172 | 6.037 | 18.4630 | 5.8725 |
| 20 | 30.11 | 15.649 | 40.907 | 11.249 | 35.5085 | 13.4490 |
| 21 | 29.368 | 4.354 | 51.409 | 11.578 | 40.3885 | 7.9660 |
| 22 | 55.824 | 19.324 | 56.734 | 15.375 | 56.2790 | 17.3495 |
| 23 | 27.853 | 4.585 | 30.09 | 5.153 | 28.9715 | 4.8690 |
| 24 | 38.262 | 20.656 | 42.106 | 12.679 | 40.1840 | 16.6675 |
| 25 | 27.359 | 2.988 | 33.97 | 4.654 | 30.6645 | 3.8210 |
| 26 | 34.444 | 22.868 | 75.891 | 39.63 | 55.1675 | 31.2490 |
| 27 | 52.207 | 13.773 | 37.602 | 4.715 | 44.9045 | 9.2440 |
| 28 | 27.654 | 4.589 | 26.822 | 3.115 | 27.2380 | 3.8520 |
| 29 | 40.199 | 5.272 | 35.055 | 4.257 | 37.6270 | 4.7645 |
| 30 | 27.071 | 6.617 | 27.672 | 4.172 | 27.3715 | 5.3945 |
| 31 | 26.453 | 4.251 | 31.149 | 2.751 | 28.8010 | 3.5010 |
| 32 | 44.932 | 8.656 | 32.93 | 3.5 | 38.9310 | 6.0780 |
| 33 | 97.873 | 67.085 | 132.571 | 104.973 | 115.2220 | 86.0290 |
| 34 | 27.054 | 5.653 | 44.814 | 11.339 | 35.9340 | 8.4960 |
| 35 | 178.389 | 145.305 | 220.361 | 218.004 | 199.3750 | 181.6545 |
| 36 | 22.973 | 7.112 | 39.55 | 6.188 | 31.2615 | 6.6500 |
| 37 | 32.844 | 4.1 | 40.917 | 5.782 | 36.8805 | 4.9410 |
| 38 | 36.642 | 13.921 | 34.387 | 13.321 | 35.5145 | 13.6210 |
| 39 | 43.801 | 18.504 | 54.98 | 32.264 | 49.3905 | 25.3840 |
| 40 | 38.178 | 18.519 | 103.356 | 40.968 | 70.7670 | 29.7435 |
| 41 | 33.309 | 13.99 | 36.814 | 10.58 | 35.0615 | 12.2850 |
| 42 | 25.27 | 4.156 | 26.624 | 4.591 | 25.9470 | 4.3735 |
| 43 | 22.02 | 2.478 | 39.928 | 6.08 | 30.9740 | 4.2790 |
| 44 | 19.086 | 1.83 | 28.238 | 2.134 | 23.6620 | 1.9820 |
| 45 | 60.907 | 30.543 | 77.064 | 28.815 | 68.9855 | 29.6790 |
| 46 | 32.715 | 4.298 | 45.502 | 4.177 | 39.1085 | 4.2375 |
| 47 | 32.36 | 7.13 | 50.54 | 6.722 | 41.4500 | 6.9260 |
| 48 | 28.239 | 8.334 | 52.43 | 10.568 | 40.3345 | 9.4510 |
| 49 | 49.22 | 7.374 | 44.676 | 7.588 | 46.9480 | 7.4810 |
| 50 | 64.843 | 20.454 | 53.307 | 13.88 | 59.0750 | 17.1670 |
| 51 | 31.516 | 10.842 | 28.143 | 3.648 | 29.8295 | 7.2450 |
| 52 | 38.404 | 7.542 | 29.373 | 4.595 | 33.8885 | 6.0685 |
| 53 | 55.094 | 5.175 | 65.67 | 8.678 | 60.3820 | 6.9265 |
| 54 | 56.104 | 4.672 | 48.547 | 3.664 | 52.3255 | 4.1680 |
| 55 | 78.803 | 6.549 | 50.57 | 4.167 | 64.6865 | 5.3580 |
| 56 | 56.816 | 6.257 | 42.303 | 4.046 | 49.5595 | 5.1515 |
| 57 | 22.321 | 1.477 | 24.024 | 1.797 | 23.1725 | 1.6370 |
| 58 | 42.104 | 8.901 | 86.02 | 10.205 | 64.0620 | 9.5530 |
| 59 | 37.617 | 4.933 | 41.69 | 3.548 | 39.6535 | 4.2405 |
| 60 | 49.219 | 7.084 | 45.388 | 4.609 | 47.3035 | 5.8465 |
| 61 | 28.515 | 4.427 | 34.695 | 4.696 | 31.6050 | 4.5615 |
| 62 | 24.048 | 2.942 | 27.275 | 2.209 | 25.6615 | 2.5755 |
| 63 | 33.399 | 2.377 | 34.226 | 3.995 | 33.8125 | 3.1860 |
| 64 | 17.981 | 2.846 | 34.171 | 6.769 | 26.0760 | 4.8075 |
| 65 | 27.426 | 1.916 | 31.928 | 4.955 | 29.6770 | 3.4355 |
| 66 | 26.094 | 3.248 | 23.97 | 3.488 | 25.0320 | 3.3680 |
| 67 | 21.158 | 2.466 | 24.938 | 2.599 | 23.0480 | 2.5325 |
| 68 | 35.62 | 4.572 | 34.261 | 2.97 | 34.9405 | 3.7710 |
| 69 | 21.882 | 3.332 | 33.373 | 3.622 | 27.6275 | 3.4770 |
| 70 | 40.405 | 4.812 | 42.552 | 4.601 | 41.4785 | 4.7065 |
| 71 | 22.1 | 2.422 | 34.351 | 2.553 | 28.2255 | 2.4875 |
| 72 | 33.555 | 4.796 | 36.455 | 3.012 | 35.0050 | 3.9040 |
| 73 | 25.822 | 3.189 | 34.328 | 2.337 | 30.0750 | 2.7630 |
| 74 | 35.156 | 8.593 | 42.12 | 6.588 | 38.6380 | 7.5905 |

TABLE 2-continued

Double-Common DsiRNA PNPLA3 Knockdown in HuH-7 Cells, 0.5 nM 24 hr-5' and -3' Assays % mRNA Remaining (normalized to HPRT1 and SFRS9 vs Mock Control).

| | PNPLA3-F495 | | PNPLA3-F595 | | Averages | |
|---|---|---|---|---|---|---|
| DsiRNA | % Remaining | % SEM | % Remaining | % SEM | Average % Remaining | Average % SEM |
| 75 | 30.278 | 2.948 | 39.251 | 2.5 | 34.7645 | 2.7240 |
| 76 | 54.252 | 11.633 | 55.948 | 7.739 | 55.1000 | 9.6860 |
| 77 | 32.7 | 2.948 | 32.575 | 2.223 | 32.6375 | 2.5855 |
| 78 | 47.513 | 9.443 | 41.285 | 5.205 | 44.3990 | 7.3240 |
| 79 | 27.208 | 6.712 | 30.186 | 2.302 | 28.6970 | 4.5070 |
| 80 | 41.53 | 8.596 | 40.294 | 7.195 | 40.9120 | 7.8955 |
| 81 | 24.351 | 5.957 | 30.338 | 1.908 | 27.3445 | 3.9325 |
| 82 | 32.801 | 2.291 | 36.67 | 2.213 | 34.7355 | 2.2520 |
| 83 | 24.892 | 2.701 | 31.062 | 3.006 | 27.9770 | 2.8535 |
| 84 | 37.631 | 5.376 | 33.714 | 3.496 | 35.6725 | 4.4360 |
| 85 | 36.987 | 1.676 | 39.783 | 1.568 | 38.3850 | 1.6220 |
| 86 | 54.723 | 3.207 | 55.297 | 3.214 | 55.0100 | 3.2105 |
| 87 | 77.564 | 4.28 | 69.537 | 3.448 | 73.5505 | 3.8640 |
| 88 | 52.849 | 5.817 | 56.297 | 6.566 | 54.5730 | 6.1915 |
| 89 | 26.699 | 2.653 | 41.509 | 3.837 | 34.1040 | 3.2450 |
| 90 | 30.182 | 4.019 | 42.498 | 2.662 | 36.3400 | 3.3405 |
| 91 | 25.266 | 4.57 | 27.045 | 2.857 | 26.1555 | 3.7135 |
| 92 | 26.577 | 3.612 | 30.034 | 2.501 | 28.3055 | 3.0565 |
| 93 | 26.538 | 2.286 | 34 | 2.564 | 30.2690 | 2.4250 |
| 94 | 48.767 | 5.695 | 30.921 | 2.911 | 39.8440 | 4.3030 |
| 95 | 30.369 | 4.104 | 32.567 | 4.019 | 31.4680 | 4.0615 |
| 96 | 33.205 | 8.907 | 38.475 | 5.665 | 35.8400 | 7.2860 |
| 97 | 14.726 | 1.561 | 11.303 | 0.555 | 13.0145 | 1.0580 |
| 98 | 22.478 | 4.813 | 16.728 | 2.957 | 19.6030 | 3.8850 |
| 99 | 18.627 | 2.295 | 16.015 | 1.822 | 17.3210 | 2.0585 |
| 100 | 13.055 | 2.262 | 11.896 | 1.013 | 12.4755 | 1.6375 |
| 101 | 15.753 | 2.573 | 11.243 | 0.971 | 13.4980 | 1.7720 |
| 102 | 24.287 | 1.728 | 15.82 | 0.749 | 20.0535 | 1.2385 |
| 103 | 17.645 | 3.371 | 10.338 | 1.306 | 13.9915 | 2.3385 |
| 104 | 22.114 | 6.098 | 12.625 | 2.184 | 17.3695 | 4.1410 |
| 105 | 33.791 | 5.469 | 18.178 | 2.526 | 25.9845 | 3.9975 |
| 106 | 34.826 | 4.934 | 16.945 | 1.304 | 25.8855 | 3.1190 |
| 107 | 25.682 | 1.01 | 13.707 | 0.505 | 19.6945 | 0.7575 |
| 108 | 23.086 | 1.758 | 12.884 | 1.012 | 17.9850 | 1.3850 |
| 109 | 20.041 | 3.132 | 10.126 | 1.13 | 15.0835 | 2.1310 |
| 110 | 28.606 | 2.003 | 13.448 | 0.804 | 21.0270 | 1.4035 |
| 111 | 43.662 | 4.981 | 20.448 | 1.281 | 32.0550 | 3.1310 |
| 112 | 20.181 | 1.863 | 12.302 | 1.629 | 16.2415 | 1.7460 |
| 113 | 20.934 | 6.186 | 15.977 | 2.091 | 18.4555 | 4.1385 |
| 114 | 38.491 | 7.949 | 23.525 | 4.479 | 31.0080 | 6.2140 |
| 115 | 21.566 | 1.511 | 14.963 | 0.928 | 18.2645 | 1.2195 |
| 116 | 18.051 | 1.808 | 11.863 | 1.114 | 14.9570 | 1.4610 |
| 117 | 15.962 | 2.707 | 11.739 | 0.976 | 13.8505 | 1.8415 |
| 118 | 37.771 | 4.761 | 25.737 | 2.365 | 31.7540 | 3.5630 |
| 119 | 47.032 | 11.179 | 22.511 | 4.506 | 34.7715 | 7.8425 |
| 120 | 66.607 | 3.571 | 32.035 | 2.004 | 49.3210 | 2.7875 |
| 121 | 35.025 | 9.645 | 15.594 | 4.295 | 25.3095 | 6.9700 |
| 122 | 33.49 | 9.414 | 14.094 | 2.996 | 23.7920 | 6.2050 |
| 123 | 27.725 | 6.288 | 15.172 | 2.581 | 21.4485 | 4.4345 |
| 124 | 29.415 | 3.434 | 10.892 | 1.452 | 20.1535 | 2.4430 |
| 125 | 21.307 | 2.786 | 12.129 | 1.254 | 16.7180 | 2.0200 |
| 126 | 26.243 | 4.681 | 8.668 | 1.375 | 17.4555 | 3.0280 |
| 127 | 27.085 | 4.693 | 10.576 | 1.527 | 18.8305 | 3.1100 |
| 128 | 20.768 | 4.12 | 12.92 | 2.463 | 16.8440 | 3.2915 |
| 129 | 18.319 | 1.349 | 13.094 | 1.028 | 15.7065 | 1.1885 |
| 130 | 28.795 | 2.276 | 15.029 | 1.164 | 21.9120 | 1.7200 |
| 131 | 17.799 | 2.265 | 12.145 | 0.808 | 14.9720 | 1.5365 |
| 132 | 27.693 | 7.219 | 12.343 | 1.574 | 20.0180 | 4.3965 |
| 133 | 24.005 | 2.76 | 13.061 | 0.765 | 18.5330 | 1.7625 |
| 134 | 21.903 | 3.009 | 11.031 | 1.763 | 16.4670 | 2.3860 |
| 135 | 14.058 | 1.645 | 10.457 | 1.234 | 12.2575 | 1.4395 |
| 136 | 15.21 | 4.068 | 12.22 | 0.846 | 13.7150 | 2.4570 |
| 137 | 21.482 | 3.191 | 15.113 | 1.482 | 18.2975 | 2.3365 |
| 138 | 24.386 | 4.677 | 13.694 | 1.354 | 19.0400 | 3.0155 |
| 139 | 26.608 | 4.511 | 17.112 | 1.574 | 21.8600 | 3.0425 |
| 140 | 32.503 | 3.692 | 20.895 | 3.738 | 26.6990 | 3.7150 |
| 141 | 23.794 | 1.508 | 16.334 | 1.555 | 20.0640 | 1.5315 |
| 142 | 31.213 | 7.279 | 15.566 | 3.053 | 23.3895 | 5.1660 |
| 143 | 27.265 | 4.596 | 18.117 | 2.525 | 22.6910 | 3.5605 |
| 144 | 36.408 | 5.816 | 22.612 | 3.627 | 29.5100 | 4.7215 |
| 145 | 57.79 | 8.838 | 24.119 | 3.876 | 40.9545 | 6.3570 |
| 146 | 49.794 | 6.232 | 59.38 | 7.58 | 54.5870 | 6.9060 |

TABLE 2-continued

Double-Common DsiRNA PNPLA3 Knockdown in HuH-7 Cells, 0.5 nM 24 hr-5' and -3' Assays % mRNA Remaining (normalized to HPRT1 and SFRS9 vs Mock Control).

| | PNPLA3-F495 | | PNPLA3-F595 | | Averages | |
|---|---|---|---|---|---|---|
| DsiRNA | % Remaining | % SEM | % Remaining | % SEM | Average % Remaining | Average % SEM |
| 147 | 47.063 | 10.454 | 33.805 | 4.167 | 40.4340 | 7.3105 |
| 148 | 37.932 | 3.753 | 30.31 | 3.198 | 34.1210 | 3.4755 |
| 149 | 61.573 | 12.448 | 30.541 | 3.873 | 46.0570 | 8.1605 |
| 150 | 58.524 | 6.231 | 39.629 | 3.33 | 49.0765 | 4.7805 |
| 151 | 43.03 | 4.916 | 21.046 | 2.885 | 32.0380 | 3.9005 |
| 152 | 44.872 | 8.77 | 21.007 | 2.636 | 32.9395 | 5.7030 |
| 153 | 40.396 | 5.688 | 22.825 | 2.132 | 31.6105 | 3.9100 |
| 154 | 65.539 | 13.255 | 45.417 | 6.461 | 55.4780 | 9.8580 |
| 155 | 48.703 | 9.937 | 31.374 | 2.867 | 40.0385 | 6.4020 |
| 156 | 37.181 | 4.937 | 29.617 | 2.937 | 33.3990 | 3.9370 |
| 157 | 35.186 | 4.535 | 17.878 | 1.581 | 26.5320 | 3.0580 |
| 158 | 51.661 | 2.695 | 33.002 | 1.991 | 42.3315 | 2.3430 |
| 159 | 30.77 | 4.109 | 19.233 | 1.542 | 25.0015 | 2.8255 |
| 160 | 36.094 | 3.542 | 17.974 | 1.657 | 27.0340 | 2.5995 |
| 161 | 35.409 | 2.366 | 33.483 | 2.737 | 34.4460 | 2.5515 |
| 162 | 33.433 | 2.074 | 26.398 | 3.543 | 29.9155 | 2.8085 |
| 163 | 42.491 | 4.39 | 22.276 | 1.604 | 32.3835 | 2.9970 |
| 164 | 33.078 | 3.228 | 32.84 | 3.386 | 32.9590 | 3.3070 |
| 165 | 45.275 | 3.204 | 39.092 | 3.755 | 42.1835 | 3.4795 |
| 166 | 29.602 | 1.738 | 24.219 | 1.898 | 26.9105 | 1.8180 |
| 167 | 27.784 | 3.443 | 22.843 | 1.792 | 25.3135 | 2.6175 |
| 168 | 74.683 | 10.617 | 49.732 | 3.286 | 62.2075 | 6.9515 |
| 169 | 48.336 | 4.662 | 44.463 | 3.058 | 46.3995 | 3.8600 |
| 170 | 50.128 | 9.574 | 41.486 | 4.115 | 45.8070 | 6.8445 |
| 171 | 47.25 | 9.041 | 37.456 | 4.455 | 42.3530 | 6.7480 |
| 172 | 53.153 | 7.175 | 30.582 | 6.503 | 41.8675 | 6.8390 |
| 173 | 39.084 | 6.244 | 25.727 | 2.191 | 32.4055 | 4.2175 |
| 174 | 45.005 | 1.875 | 33.581 | 2.379 | 39.2930 | 2.1270 |
| 175 | 47.646 | 6.625 | 26.629 | 4.836 | 37.1375 | 5.7305 |
| 176 | 55.395 | 7.326 | 34.511 | 6.658 | 44.9530 | 6.9920 |
| 177 | 33.771 | 3.981 | 34.434 | 3.484 | 34.1025 | 3.7325 |
| 178 | 67.077 | 10.657 | 56.357 | 7.847 | 61.7170 | 9.2520 |
| 179 | 35.008 | 4.54 | 28.283 | 2.932 | 31.6455 | 3.7360 |
| 180 | 42.068 | 3.42 | 28.527 | 1.676 | 35.2975 | 2.5480 |
| 181 | 40.143 | 2.884 | 23.643 | 3.134 | 31.8930 | 3.0090 |
| 182 | 55.98 | 12.403 | 27.675 | 2.591 | 41.8275 | 7.4970 |
| 183 | 45.856 | 4.074 | 26.554 | 3.411 | 36.2050 | 3.7425 |
| 184 | 47.638 | 13.905 | 23.569 | 4.462 | 35.6035 | 9.1835 |
| 185 | 29.627 | 2.072 | 28.727 | 2.788 | 29.1770 | 2.4300 |
| 186 | 25.87 | 1.617 | 24.308 | 1.641 | 25.0890 | 1.6290 |
| 187 | 28.469 | 3.789 | 28.409 | 2.228 | 28.4390 | 3.0085 |
| 188 | 43.256 | 3.532 | 29.637 | 1.678 | 36.4465 | 2.6050 |
| 189 | 35.294 | 2.99 | 26.036 | 1.809 | 30.6650 | 2.3995 |
| 190 | 41.63 | 3.818 | 31.807 | 1.941 | 36.7185 | 2.8795 |
| 191 | 33.432 | 2.727 | 26.418 | 1.23 | 29.9250 | 1.9785 |
| 192 | 38.533 | 3.055 | 26.167 | 2.676 | 32.3500 | 2.8655 |
| 193 | 52.145 | 7.633 | 66.647 | 7.649 | 59.3960 | 7.6410 |
| 194 | 78.674 | 19.973 | 77.211 | 18.407 | 77.9425 | 19.1900 |
| 195 | 61.3 | 14.568 | 47.323 | 8.818 | 54.3115 | 11.6930 |
| 196 | 82.319 | 28.729 | 49.804 | 10.153 | 66.0615 | 19.4410 |
| 197 | 47.078 | 7.783 | 46.383 | 6.365 | 46.7305 | 7.0740 |
| 198 | 43.554 | 13.721 | 39.919 | 8.064 | 41.7365 | 10.8925 |
| 199 | 40.89 | 12.488 | 44.564 | 5.499 | 42.7270 | 8.9935 |
| 200 | 46.423 | 6.179 | 34.111 | 2.888 | 40.2670 | 4.5335 |
| 201 | 44.093 | 8.793 | 52.982 | 7.827 | 48.5375 | 8.3100 |
| 202 | 51.569 | 12.11 | 47.774 | 10.111 | 49.6715 | 11.1105 |
| 203 | 39.021 | 4.874 | 51.153 | 5.821 | 45.0870 | 5.3475 |
| 204 | 52.055 | 9.223 | 31.552 | 3.951 | 41.8035 | 6.5870 |
| 205 | 41.044 | 5.775 | 34.923 | 3.705 | 37.9835 | 4.7400 |
| 206 | 31.351 | 3.687 | 32.129 | 2.472 | 31.7400 | 3.0795 |
| 207 | 43.82 | 4.633 | 28.098 | 1.853 | 35.9590 | 3.2430 |
| 208 | 36.337 | 6.743 | 29.077 | 3.006 | 32.7070 | 4.8745 |
| 209 | 36.945 | 7.059 | 29.934 | 3.642 | 33.4395 | 5.3505 |
| 210 | 37.592 | 3.376 | 37.793 | 2.909 | 37.6925 | 3.1425 |
| 211 | 36.686 | 3.72 | 35.615 | 3.93 | 36.1505 | 3.8250 |
| 212 | 36.654 | 4.758 | 32.036 | 2.656 | 34.3450 | 3.7070 |
| 213 | 42.177 | 6.122 | 31.067 | 4.128 | 36.6220 | 5.1250 |
| 214 | 37.527 | 8.471 | 32.699 | 4.645 | 35.1130 | 6.5580 |
| 215 | 37.302 | 6.865 | 29.908 | 3.386 | 33.6050 | 5.1255 |
| 216 | 39.019 | 8.467 | 28.36 | 2.817 | 33.6895 | 5.6420 |
| 217 | 53.521 | 13.053 | 25.512 | 3.686 | 39.5165 | 8.3695 |
| 218 | 41.043 | 11.011 | 27.355 | 5.791 | 34.1990 | 8.4010 |

TABLE 2-continued

Double-Common DsiRNA PNPLA3 Knockdown in HuH-7 Cells, 0.5 nM 24 hr-5' and -3' Assays % mRNA Remaining (normalized to HPRT1 and SFRS9 vs Mock Control).

| | PNPLA3-F495 | | PNPLA3-F595 | | Averages | |
|---|---|---|---|---|---|---|
| DsiRNA | % Remaining | % SEM | % Remaining | % SEM | Average % Remaining | Average % SEM |
| 219 | 51.988 | 10.693 | 31.329 | 3.319 | 41.6585 | 7.0060 |
| 220 | 54.023 | 6.301 | 41.112 | 4.76 | 47.5675 | 5.5305 |
| 221 | 58.76 | 6.462 | 39.758 | 2.97 | 49.2590 | 4.7160 |
| 222 | 236.787 | 43.566 | 243.617 | 53.774 | 240.2020 | 48.6700 |
| 223 | 61.825 | 6.104 | 39.095 | 4.733 | 50.4600 | 5.4185 |
| 224 | 60.335 | 8.345 | 42.762 | 5.15 | 51.5485 | 6.7475 |
| 225 | 42.422 | 4.628 | 33.442 | 3.115 | 37.9320 | 3.8715 |
| 226 | 48.764 | 5.455 | 26.922 | 2.335 | 37.8430 | 3.8950 |
| 227 | 57.581 | 7.579 | 42.222 | 4.06 | 49.9015 | 5.8195 |
| 228 | 46.242 | 5.713 | 32.37 | 2.362 | 39.3060 | 4.0375 |
| 229 | 59.85 | 6.227 | 37.452 | 3.019 | 48.6510 | 4.6230 |
| 230 | 42.275 | 3.602 | 32.725 | 2.969 | 37.5000 | 3.2855 |
| 231 | 54.799 | 3.621 | 33.443 | 2.238 | 44.1210 | 2.9295 |
| 232 | 52.778 | 5.345 | 35.823 | 3.952 | 44.3005 | 4.6485 |
| 233 | 54.107 | 6.101 | 33.629 | 3.781 | 43.8680 | 4.9410 |
| 234 | 57.658 | 5.363 | 42.349 | 3.414 | 50.0035 | 4.3885 |
| 235 | 39.81 | 6.669 | 29.299 | 2.818 | 34.5545 | 4.7435 |
| 236 | 49.078 | 4.885 | 31.99 | 2.007 | 40.5340 | 3.4460 |
| 237 | 57.23 | 6.733 | 36.45 | 3.148 | 46.8400 | 4.9405 |
| 238 | 51.689 | 4.587 | 33.588 | 2.816 | 42.6385 | 3.7015 |
| 239 | 44.895 | 5.883 | 33.621 | 3.034 | 39.2580 | 4.4585 |
| 240 | 59.327 | 4.174 | 43.637 | 4.972 | 51.4820 | 4.5730 |
| 241 | 63.766 | 13.264 | 50.677 | 5.209 | 57.2215 | 9.2365 |
| 242 | 66.835 | 12.5 | 52.004 | 7.592 | 59.4195 | 10.0460 |
| 243 | 54.29 | 6.239 | 38.992 | 4.219 | 46.6410 | 5.2290 |
| 244 | 72.508 | 13.528 | 36.851 | 5.599 | 54.6795 | 9.5635 |
| 245 | 65.646 | 9.098 | 55.163 | 6.389 | 60.4045 | 7.7435 |
| 246 | 51.051 | 6.557 | 46.828 | 6.46 | 48.9395 | 6.5085 |
| 247 | 60.801 | 6.585 | 41.571 | 5.728 | 51.1860 | 6.1565 |
| 248 | 50.195 | 6.174 | 39.365 | 4.661 | 44.7800 | 5.4175 |
| 249 | 37.378 | 5.543 | 42.906 | 6.632 | 40.1420 | 6.0875 |
| 250 | 43.321 | 5.067 | 30.966 | 3.133 | 37.1435 | 4.1000 |
| 251 | 45.472 | 4.875 | 32.346 | 3.885 | 38.9090 | 4.3800 |
| 252 | 43.062 | 3.621 | 28.848 | 2.106 | 35.9550 | 2.8635 |
| 253 | 37.701 | 3.518 | 25.509 | 2.268 | 31.6050 | 2.8930 |
| 254 | 58.2 | 18.808 | 36.005 | 9.635 | 47.1025 | 14.2215 |
| 255 | 31.77 | 3.926 | 27.901 | 4.411 | 29.8355 | 4.1685 |
| 256 | 38.708 | 3.847 | 36.377 | 3.262 | 37.5425 | 3.5545 |
| 257 | 30.508 | 3.645 | 31.26 | 2.622 | 30.8840 | 3.1335 |
| 258 | 44.359 | 5 | 34.497 | 2.636 | 39.4280 | 3.8180 |
| 259 | 67.139 | 7.485 | 40.465 | 2.943 | 53.8020 | 5.2140 |
| 260 | 66.589 | 6.837 | 39.106 | 3.29 | 52.8475 | 5.0635 |
| 261 | 48.322 | 10.679 | 26.008 | 2.39 | 37.1650 | 6.5345 |
| 262 | 50.546 | 4.737 | 32.219 | 2.427 | 41.3825 | 3.5820 |
| 263 | 59.307 | 7.82 | 29.231 | 2.967 | 44.2690 | 5.3935 |
| 264 | 97.302 | 11.857 | 53.08 | 6.094 | 75.1910 | 8.9755 |
| 265 | 76.539 | 14.949 | 85.905 | 13.021 | 81.2220 | 13.9850 |
| 266 | 57.905 | 6.615 | 64.596 | 7.651 | 61.2505 | 7.1330 |
| 267 | 69.77 | 6.607 | 53.074 | 4.276 | 61.4220 | 5.4415 |
| 268 | 48.668 | 10.684 | 40.916 | 5.466 | 44.7920 | 8.0750 |
| 269 | 47.46 | 7.531 | 42.844 | 4.1 | 45.1520 | 5.8155 |
| 270 | 70.579 | 11.73 | 61.976 | 6.502 | 66.2775 | 9.1160 |
| 271 | 115.007 | 12.121 | 67.306 | 4.174 | 91.1565 | 8.1475 |
| 272 | 82.348 | 12.571 | 104.237 | 16.188 | 93.2925 | 14.3795 |
| 273 | 72.215 | 14.678 | 53.943 | 7.425 | 63.0790 | 11.0515 |
| 274 | 49.167 | 8.023 | 49.69 | 6.118 | 49.4285 | 7.0705 |
| 275 | 41.439 | 3.584 | 29.44 | 2.996 | 35.4395 | 3.2900 |
| 276 | 53.402 | 8.54 | 50.701 | 3.872 | 52.0515 | 6.2060 |
| 277 | 56.148 | 3.835 | 32.342 | 3.153 | 44.2450 | 3.4940 |
| 278 | 67.762 | 15.057 | 45.771 | 7.974 | 56.7665 | 11.5155 |
| 279 | 53.393 | 3.781 | 31.896 | 2.753 | 42.6445 | 3.2670 |
| 280 | 62.738 | 14.71 | 39.414 | 4.46 | 51.0760 | 9.5850 |
| 281 | 40.384 | 8.034 | 38.263 | 3.196 | 39.3235 | 5.6150 |
| 282 | 40.763 | 5.446 | 40.712 | 4.898 | 40.7375 | 5.1720 |
| 283 | 46.465 | 10.212 | 46.647 | 6.183 | 46.5560 | 8.1975 |
| 284 | 38.536 | 4.547 | 41.452 | 2.836 | 39.9940 | 3.6915 |
| 285 | 42.301 | 4.416 | 43.768 | 4.259 | 43.0345 | 4.3375 |
| 286 | 46.313 | 8.357 | 38.798 | 5.187 | 42.5555 | 6.7720 |
| 287 | 50.769 | 6.505 | 43.597 | 4.509 | 47.1830 | 5.5070 |
| 288 | 38.562 | 8.297 | 37.896 | 4.33 | 38.2290 | 6.3135 |
| 289 | 97.407 | 9.944 | 84.032 | 7.979 | 90.7195 | 8.9615 |
| 290 | 96.276 | 16.596 | 80.344 | 14.757 | 88.3100 | 15.6765 |

TABLE 2-continued

Double-Common DsiRNA PNPLA3 Knockdown in HuH-7 Cells, 0.5 nM 24 hr-5' and -3' Assays % mRNA Remaining (normalized to HPRT1 and SFRS9 vs Mock Control).

| | PNPLA3-F495 | | PNPLA3-F595 | | Averages | |
|---|---|---|---|---|---|---|
| DsiRNA | % Remaining | % SEM | % Remaining | % SEM | Average % Remaining | Average % SEM |
| 291 | 97.306 | 19.495 | 65.589 | 6.382 | 81.4475 | 12.9385 |
| 292 | 55.475 | 9.264 | 45.599 | 8.096 | 50.5370 | 8.6800 |
| 293 | 62.494 | 8.981 | 44.842 | 6.356 | 53.6680 | 7.6685 |
| 294 | 64.097 | 10.104 | 45.876 | 4.721 | 54.9865 | 7.4125 |
| 295 | 54.142 | 14.352 | 44.557 | 6.065 | 49.3495 | 10.2085 |
| 296 | 45.915 | 5.238 | 42.595 | 4.868 | 44.2550 | 5.0530 |
| 297 | 52.489 | 10.839 | 40.88 | 3.707 | 46.6845 | 7.2730 |
| 298 | 63.515 | 15.058 | 48.368 | 7.137 | 55.9415 | 11.0975 |
| 299 | 68.855 | 5.952 | 39.142 | 4.218 | 53.9985 | 5.0850 |
| 300 | 41.279 | 2.923 | 42.539 | 2.744 | 41.9090 | 2.8335 |
| 301 | 61.222 | 5.21 | 35.294 | 2.489 | 48.2580 | 3.8495 |
| 302 | 61.31 | 7.946 | 54.541 | 6.669 | 57.9255 | 7.3075 |
| 303 | 72.478 | 6.439 | 34.292 | 3.108 | 53.3850 | 4.7735 |
| 304 | 67.572 | 16.336 | 42.125 | 6.87 | 54.8485 | 11.6030 |
| 305 | 50.921 | 8.983 | 33.358 | 4.008 | 42.1395 | 6.4955 |
| 306 | 57.53 | 5.6 | 69.86 | 6.547 | 63.6950 | 6.0735 |
| 307 | 64.026 | 11.056 | 39.867 | 4.008 | 51.9465 | 7.5320 |
| 308 | 49.409 | 3.059 | 42.979 | 2.509 | 46.1940 | 2.7840 |
| 309 | 54.897 | 4.814 | 31.307 | 1.962 | 43.1020 | 3.3880 |
| 310 | 41.554 | 2.628 | 37.128 | 1.841 | 39.3410 | 2.2345 |
| 311 | 51.666 | 8.47 | 40.257 | 4.367 | 45.9615 | 6.4185 |
| 312 | 49.509 | 6.575 | 28.02 | 4.538 | 38.7645 | 5.5565 |
| 313 | — | — | 194.826 | 68.134 | 194.8260 | 68.1340 |
| 314 | 121.989 | 16.822 | 138.651 | 21 | 130.3200 | 18.9110 |
| 315 | 80.309 | 31.932 | 61.6 | 21.185 | 70.9545 | 26.5585 |
| 316 | 92.927 | 25.688 | 67.475 | 19.158 | 80.2010 | 22.4230 |
| 317 | 90.794 | 26.314 | 68.783 | 17.49 | 79.7885 | 21.9020 |
| 318 | 78.946 | 5.722 | 89.051 | 5.366 | 83.9985 | 5.5440 |
| 319 | 78.528 | 22.516 | 68.248 | 14.662 | 73.3880 | 18.5890 |
| 320 | 88.504 | 27.66 | 74.364 | 17.313 | 81.4340 | 22.4865 |
| 321 | 80.819 | 11.586 | 72.082 | 9.362 | 76.4505 | 10.4740 |
| 322 | 66.905 | 11.106 | 59.407 | 7.519 | 63.1560 | 9.3125 |
| 323 | 56.665 | 7.201 | 65.996 | 7.423 | 61.3305 | 7.3120 |
| 324 | 58.472 | 14.789 | 52.989 | 6.283 | 55.7305 | 10.5360 |
| 325 | 73.835 | 10.27 | 45.629 | 3.865 | 59.7320 | 7.0675 |
| 326 | 83.653 | 12.949 | 55.705 | 5.376 | 69.6790 | 9.1625 |
| 327 | 48.135 | 5.765 | 47.686 | 2.973 | 47.9105 | 4.3690 |
| 328 | 58.846 | 13.768 | 64.173 | 8.7 | 61.5095 | 11.2340 |
| 329 | 46.418 | 3.234 | 43.86 | 4.767 | 45.1390 | 4.0005 |
| 330 | 48.925 | 5.8 | 47.32 | 5.483 | 48.1225 | 5.6415 |
| 331 | 60.81 | 13.53 | 36.129 | 3.04 | 48.4695 | 8.2850 |
| 332 | 56.142 | 10.276 | 41.861 | 5.196 | 49.0015 | 7.7360 |
| 333 | 57.072 | 5.485 | 46.44 | 1.828 | 51.7560 | 3.6565 |
| 334 | 57.031 | 14.153 | 47.644 | 5.986 | 52.3375 | 10.0695 |
| 335 | 63.616 | 8.355 | 62.766 | 7.336 | 63.1910 | 7.8455 |
| 336 | 61.994 | 10.795 | 49.157 | 4.36 | 55.5755 | 7.5775 |
| 337 | 109.966 | 11.513 | 73.307 | 11.438 | 91.6365 | 11.4755 |
| 338 | 110.715 | 15.908 | 92.237 | 13.006 | 101.4760 | 14.4570 |
| 339 | 75.364 | 14.03 | 67.654 | 10.63 | 71.5090 | 12.3300 |
| 340 | 109.658 | 7.631 | 67.114 | 6.374 | 88.3860 | 7.0025 |
| 341 | 81.366 | 8.105 | 61.479 | 4 | 71.4225 | 6.0525 |
| 342 | 64.415 | 15.53 | 79.511 | 24.66 | 71.9630 | 20.0950 |
| 343 | 74.24 | 10.057 | 46.431 | 5.731 | 60.3355 | 7.8940 |
| 344 | 86.963 | 13.807 | 54.298 | 8.525 | 70.6305 | 11.1660 |
| 345 | 71.074 | 6.207 | 57.396 | 6.551 | 64.2350 | 6.3790 |
| 346 | 91.626 | 10.114 | 74.902 | 8.206 | 83.2640 | 9.1600 |
| 347 | 77.149 | 8.202 | 53.758 | 5.371 | 65.4535 | 6.7865 |
| 348 | 80.631 | 9.944 | 56.546 | 8.401 | 68.5885 | 9.1725 |
| 349 | 60.505 | 5.38 | 37.207 | 4.379 | 48.8560 | 4.8795 |
| 350 | 64.783 | 11.132 | 46.827 | 8.602 | 55.8050 | 9.8670 |
| 351 | 70.732 | 7.768 | 42.967 | 3.442 | 56.8495 | 5.6050 |
| 352 | 85.716 | 13.405 | 56.756 | 5.896 | 71.2360 | 9.6505 |
| 353 | 49.942 | 6.657 | 49.317 | 3.253 | 49.6295 | 4.9550 |
| 354 | 38.757 | 3.56 | 37.798 | 2.633 | 38.2775 | 3.0965 |
| 355 | 45.029 | 2.934 | 38.812 | 2.665 | 41.9205 | 2.7995 |
| 356 | 38.688 | 3.896 | 34.3 | 2.617 | 36.4940 | 3.2565 |
| 357 | 52.918 | 9.736 | 35.223 | 3.54 | 44.0705 | 6.6380 |
| 358 | 52.294 | 3.336 | 44.793 | 5.552 | 48.5435 | 4.4440 |
| 359 | 53.158 | 3.096 | 41.327 | 3.233 | 47.2425 | 3.1645 |
| 360 | 103.51 | 27.753 | 62.923 | 11.824 | 83.2165 | 19.7885 |
| 361 | 122.759 | 25.999 | 106.083 | 13.134 | 114.4210 | 19.5665 |
| 362 | 106.559 | 19.744 | 101.161 | 14.303 | 103.8600 | 17.0235 |

TABLE 2-continued

Double-Common DsiRNA PNPLA3 Knockdown in HuH-7 Cells, 0.5 nM 24 hr-5' and -3' Assays % mRNA Remaining (normalized to HPRT1 and SFRS9 vs Mock Control).

| | PNPLA3-F495 | | PNPLA3-F595 | | Averages | |
|---|---|---|---|---|---|---|
| DsiRNA | % Remaining | % SEM | % Remaining | % SEM | Average % Remaining | Average % SEM |
| 363 | 109.834 | 19.943 | 79.727 | 14.271 | 94.7805 | 17.1070 |
| 364 | 102.297 | 10.688 | 78.932 | 9.566 | 90.6145 | 10.1270 |
| 365 | 82.014 | 8.363 | 73.591 | 5.609 | 77.8025 | 6.9860 |
| 366 | 67.391 | 23.514 | 69.264 | 11.51 | 68.3275 | 17.5120 |
| 367 | 95.165 | 15.862 | 42.233 | 5.102 | 68.6990 | 10.4820 |
| 368 | 95.977 | 20.567 | 51.602 | 9.654 | 73.7895 | 15.1105 |
| 369 | 65.153 | 14.652 | 46.363 | 7.328 | 55.7580 | 10.9900 |
| 370 | 58.571 | 7.578 | 50.496 | 6.145 | 54.5335 | 6.8615 |
| 371 | 84.037 | 13.739 | 52.431 | 5.879 | 68.2340 | 9.8090 |
| 372 | 67.564 | 8.585 | 48.839 | 4.307 | 58.2015 | 6.4460 |
| 373 | 57.82 | 10.735 | 38.625 | 4.956 | 48.2225 | 7.8455 |
| 374 | 84.402 | 27.865 | 37.659 | 6.895 | 61.0305 | 17.3800 |
| 375 | 72.533 | 12.7 | 45.661 | 5.549 | 59.0970 | 9.1245 |
| 376 | 68.34 | 7.43 | 44.068 | 4.428 | 56.2040 | 5.9290 |
| 377 | 70.417 | 6.309 | 53.79 | 6.279 | 62.1035 | 6.2940 |
| 378 | 61.427 | 3.64 | 47.649 | 2.676 | 54.5380 | 3.1580 |
| 379 | 95.519 | 18.074 | 57.492 | 7.143 | 76.5055 | 12.6085 |
| 380 | 65.481 | 5.625 | 42.825 | 2.2 | 54.1530 | 3.9125 |
| 381 | 59.761 | 9.824 | 33.808 | 2.686 | 46.7845 | 6.2550 |
| 382 | 58.179 | 4.499 | 36.306 | 3.105 | 47.2425 | 3.8020 |
| 383 | 73.232 | 3.793 | 41.961 | 2.581 | 57.5965 | 3.1870 |
| 384 | 69.482 | 14.129 | 34.575 | 5.662 | 52.0285 | 9.8955 |

These results show that DsiRNAs designed to target human PNPLA3 mRNA inhibit PNPLA3 expression in cells (as determined by a reduced amount of PNPLA3 mRNA in DsiRNA-transfected cells) and that the nucleotide sequences including the DsiRNA hits are useful for generating RNAi oligonucleotides to inhibit PNPLA3 expression. Further, these results demonstrate that multiple PNPLA3 target sequences are suitable for the RNAi-mediated inhibition of PNPLA3 expression.

In Vivo Function

Example 3: RNAi Oligonucleotide Inhibition of PNPLA3 Expression In Vivo

Of the 384 DsiRNAs screened in the HuH-7 cell-based assays described in Example 2, the nucleotide sequences of 192 DsiRNAs hits (Table 3) are selected for further evaluation in vivo. Briefly, the nucleotide sequences the selected DsiRNAs are used to generate 194 corresponding ds RNAi oligonucleotides including a nicked tetraloop GalNAc-conjugated structure (referred to herein as "GalNAc-conjugated PNPLA3 oligonucleotides") having a 36-mer sense (passenger) strand and a 22-mer antisense (guide) strand. Further, the nucleotide sequences for the passenger strand and guide strand of the GalNAc-conjugated PNPLA3 oligonucleotides have a distinct pattern of modified nucleotides and phosphorothioate linkages (see, e.g., FIG. 1 for a schematic of the generic structure and chemical modification pattern of the GalNAc-conjugated PNPLA3 oligonucleotides). The three adenosine nucleotides of the tetraloop each are conjugated to a GalNAc moiety (CAS #: 14131-60-3).

TABLE 3

GalXC-PNPLA3: 192 GalXC Compound In Vitro Screen.

| PNPLA3 | Passenger | Guide | PNPLA3-F495 | | PNPLA3-F595 | |
|---|---|---|---|---|---|---|
| Oligo-nucleotide | (sense) (SEQ ID NO:) | (antisense) (SEQ ID NO:) | % Remaining | % SEM | % Remaining | % SEM |
| 1 | 777 | 778 | 47.485 | 10.196 | 42.315 | 9.325 |
| 2 | 779 | 780 | 88.393 | 13.374 | 74.853 | 8.613 |
| 3 | 781 | 782 | 71.522 | 13.389 | 62.163 | 8.489 |
| 4 | 783 | 784 | 48.2 | 12.808 | 59.051 | 15.527 |
| 5 | 785 | 786 | 87.111 | 20.654 | 74.136 | 14.422 |
| 6 | 787 | 788 | 52.772 | 4.946 | 32.37 | 3.842 |
| 7 | 789 | 790 | 60 | 4.856 | 56.847 | 3.105 |
| 8 | 791 | 792 | 89.452 | 17.034 | 90.454 | 16.078 |
| 9 | 793 | 794 | 76.773 | 16.13 | 58.479 | 11.665 |
| 10 | 795 | 796 | 85.463 | 9.685 | 66.419 | 7.575 |
| 11 | 797 | 798 | 108.216 | 4.243 | 70.258 | 3.457 |
| 12 | 799 | 800 | 57.964 | 8.916 | 47.12 | 9.746 |
| 13 | 801 | 802 | 91.802 | 15.466 | 80.834 | 14.834 |
| 14 | 803 | 804 | 108.246 | 8.747 | 102.424 | 9.238 |
| 15 | 805 | 806 | 102.556 | 8.612 | 91.909 | 8.507 |
| 16 | 807 | 808 | 123.63 | 8.863 | 110.429 | 6.112 |
| 17 | 809 | 810 | 70.82 | 7.935 | 48.198 | 3.957 |

TABLE 3-continued

GalXC-PNPLA3: 192 GalXC Compound In Vitro Screen.

| PNPLA3 Oligo-nucleotide | Passenger (sense) (SEQ ID NO:) | Guide (antisense) (SEQ ID NO:) | PNPLA3-F495 % Remaining | PNPLA3-F495 % SEM | PNPLA3-F595 % Remaining | PNPLA3-F595 % SEM |
|---|---|---|---|---|---|---|
| 18 | 811 | 812 | 105.252 | 5.434 | 76.73 | 5.427 |
| 19 | 813 | 814 | 73.737 | 7.411 | 63.414 | 3.163 |
| 20 | 815 | 816 | 53.275 | 5.084 | 40.621 | 3.768 |
| 21 | 817 | 818 | 73.13 | 8.636 | 54.227 | 4.991 |
| 22 | 819 | 820 | 69.662 | 5.077 | 65.603 | 4.833 |
| 23 | 821 | 822 | 115.648 | 7.396 | 93.812 | 6.834 |
| 24 | 823 | 824 | 113.539 | 8.877 | 95.22 | 8.13 |
| 25 | 825 | 826 | 72.315 | 22.04 | 65.007 | 19.295 |
| 26 | 827 | 828 | 52.756 | 8.42 | 52.681 | 4.521 |
| 27 | 829 | 830 | 50.002 | 5.36 | 45.103 | 6.461 |
| 28 | 831 | 832 | 65.906 | 5.919 | 61.42 | 3.683 |
| 29 | 833 | 834 | 85.13 | 15.786 | 81.4 | 13.245 |
| 30 | 835 | 836 | 94.2 | 7.683 | 92.984 | 6.53 |
| 31 | 837 | 838 | 79.41 | 9.652 | 78.856 | 9.311 |
| 32 | 839 | 840 | 110.611 | 10.798 | 121.904 | 11.977 |
| 33 | 841 | 842 | 61.132 | 15.106 | 54.942 | 10.832 |
| 34 | 843 | 844 | 22.997 | 2.613 | 26.894 | 3.012 |
| 35 | 845 | 846 | 69.893 | 7.912 | 71.053 | 6.942 |
| 36 | 847 | 848 | 42.209 | 6.514 | 37.063 | 6.765 |
| 37 | 849 | 850 | 32.369 | 6.443 | 30.326 | 5.18 |
| 38 | 851 | 852 | 98.013 | 5.195 | 99.493 | 5.551 |
| 39 | 853 | 854 | 108.745 | 12.02 | 109.98 | 14.348 |
| 40 | 855 | 856 | 108.242 | 5.703 | 106.183 | 7.088 |
| 41 | 857 | 858 | 62.227 | 18.716 | 47.683 | 7.008 |
| 42 | 859 | 860 | 77.369 | 5.452 | 72.082 | 4.805 |
| 43 | 861 | 862 | 97.72 | 6.492 | 104.918 | 2.468 |
| 44 | 863 | 864 | 95.316 | 16.953 | 81.092 | 8.169 |
| 45 | 865 | 866 | 65.563 | 3.105 | 63.593 | 5.933 |
| 46 | 867 | 868 | 45.891 | 2.704 | 41.178 | 2.034 |
| 47 | 869 | 870 | 70.44 | 8.4 | 69.907 | 11.675 |
| 48 | 871 | 872 | 42.793 | 4.981 | 41.802 | 4.578 |
| 49 | 873 | 874 | 69.377 | 12.858 | 75.563 | 14.64 |
| 50 | 875 | 876 | 94.54 | 12.65 | 113.746 | 13.701 |
| 51 | 877 | 878 | 96.644 | 9.928 | 88.742 | 7.236 |
| 52 | 879 | 880 | 57.675 | 7.9 | 54.023 | 9.11 |
| 53 | 881 | 882 | 45.257 | 4.671 | 41.066 | 8.781 |
| 54 | 883 | 884 | 64.216 | 13.821 | 57.326 | 9.308 |
| 55 | 885 | 886 | 80.64 | 10.056 | 83.19 | 12.71 |
| 56 | 887 | 888 | 53.489 | 6.288 | 60.359 | 10.933 |
| 57 | 889 | 890 | 43.058 | 8.468 | 67.338 | 7.905 |
| 58 | 891 | 892 | 92.209 | 4.675 | 88.981 | 4.725 |
| 59 | 893 | 894 | 125.612 | 12.186 | 131.574 | 15.729 |
| 60 | 895 | 896 | 56.646 | 7.227 | 58.75 | 7.18 |
| 61 | 897 | 898 | 63.963 | 4.129 | 64.01 | 3.511 |
| 62 | 899 | 900 | 35.42 | 4.93 | 43.575 | 3.839 |
| 63 | 901 | 902 | 80.942 | 5.673 | 99.785 | 7.605 |
| 64 | 903 | 904 | 28.438 | 9.671 | 41.409 | 10.949 |
| 65 | 905 | 906 | 78.01 | 12.28 | 70.329 | 13.215 |
| 66 | 907 | 908 | 63.519 | 7.735 | 56.465 | 6.226 |
| 67 | 909 | 910 | 102.482 | 9.653 | 86.816 | 7.212 |
| 68 | 911 | 912 | 73.153 | 6.21 | 76.354 | 7.251 |
| 69 | 913 | 914 | 115.319 | 14.233 | 109.375 | 11.395 |
| 70 | 915 | 916 | 50.507 | 16.055 | 61.744 | 17.75 |
| 71 | 917 | 918 | 64.122 | 18.86 | 67.106 | 19.792 |
| 72 | 919 | 920 | 45.025 | 11.057 | 36.962 | 8.699 |
| 73 | 921 | 922 | 64.691 | 7.735 | 70.342 | 7.008 |
| 74 | 923 | 924 | 91.612 | 17.728 | 73.763 | 9.075 |
| 75 | 925 | 926 | 30.626 | 5.128 | 34.089 | 2.646 |
| 76 | 927 | 928 | 85.724 | 5.965 | 98.425 | 5.178 |
| 77 | 929 | 930 | 77.837 | 24.988 | 65.493 | 20.924 |
| 78 | 931 | 932 | 66.549 | 13.96 | 70.219 | 13.374 |
| 79 | 933 | 934 | 88.812 | 9.773 | 93.579 | 14.174 |
| 80 | 935 | 936 | 126.281 | 13.138 | 125.405 | 9.847 |
| 81 | 937 | 938 | 33.474 | 12.471 | 36.472 | 7.102 |
| 82 | 939 | 940 | 36.521 | 6.105 | 36.344 | 12.791 |
| 83 | 941 | 942 | 79.756 | 28.563 | 79.725 | 24.95 |
| 84 | 943 | 944 | 91.352 | 9.565 | 103.633 | 12.963 |
| 85 | 945 | 946 | 79.374 | 11.693 | 88.146 | 11.711 |
| 86 | 947 | 948 | 104.203 | 12.127 | 111.907 | 13.828 |
| 87 | 949 | 950 | 78.157 | 5.154 | 100.371 | 7.36 |
| 88 | 951 | 952 | 117.96 | 7.199 | 130.066 | 9.106 |
| 89 | 953 | 954 | 84.233 | 7.043 | 78.918 | 4.772 |
| 90 | 955 | 956 | 70.825 | 5.146 | 76.977 | 8.968 |

TABLE 3-continued

GalXC-PNPLA3: 192 GalXC Compound In Vitro Screen.

| PNPLA3 Oligo-nucleotide | Passenger (sense) (SEQ ID NO:) | Guide (antisense) (SEQ ID NO:) | PNPLA3-F495 % Remaining | PNPLA3-F495 % SEM | PNPLA3-F595 % Remaining | PNPLA3-F595 % SEM |
|---|---|---|---|---|---|---|
| 91 | 957 | 958 | 59.621 | 7.853 | 65.538 | 7.22 |
| 92 | 959 | 960 | 91.443 | 6.954 | 99.109 | 6.096 |
| 93 | 961 | 962 | 46.844 | 11.633 | 51.957 | 9.244 |
| 94 | 963 | 964 | 81.508 | 6.389 | 87.195 | 8.633 |
| 95 | 965 | 966 | 91.805 | 8.83 | 108.782 | 9.098 |
| 96 | 967 | 968 | 96.733 | 4.922 | 125.597 | 5.479 |
| 97 | 969 | 970 | 92.658 | 10.451 | 110.074 | 12.159 |
| 98 | 971 | 972 | 100.916 | 7.648 | 107.715 | 9.441 |
| 99 | 973 | 974 | 108.731 | 9.204 | 130.037 | 11.933 |
| 100 | 975 | 976 | 80.886 | 6.51 | 82.486 | 5.492 |
| 101 | 977 | 978 | 114.601 | 6.354 | 125.063 | 7.668 |
| 102 | 979 | 980 | 64.486 | 7.636 | 81.933 | 8.887 |
| 103 | 981 | 982 | 48.127 | 7.673 | 70.594 | 9.464 |
| 104 | 983 | 984 | 98.266 | 10.023 | 125.396 | 13.292 |
| 105 | 985 | 986 | 78.835 | 8.422 | 85.896 | 6.258 |
| 106 | 987 | 988 | 65.38 | 6.01 | 75.699 | 5.561 |
| 107 | 989 | 990 | 82.332 | 16.715 | 110.985 | 21.204 |
| 108 | 991 | 992 | 50.805 | 3.714 | 49.059 | 3.238 |
| 109 | 993 | 994 | 82.297 | 10.387 | 74.612 | 6.957 |
| 110 | 995 | 996 | 56.254 | 4.26 | 51.783 | 3.569 |
| 111 | 997 | 998 | 37.191 | 3.673 | 43.781 | 4.781 |
| 112 | 999 | 1000 | 54.832 | 3.334 | 45.421 | 4.277 |
| 113 | 1001 | 1002 | 24.729 | 2.434 | 22.466 | 2.637 |
| 114 | 1003 | 1004 | 34.923 | 6.177 | 40.356 | 5.286 |
| 115 | 1005 | 1006 | 42.682 | 3.081 | 57.453 | 2.391 |
| 116 | 1007 | 1008 | 30.325 | 3.011 | 34.404 | 1.82 |
| 117 | 1009 | 1010 | 70.118 | 7.78 | 89.223 | 8.905 |
| 118 | 1011 | 1012 | 43.339 | 6.479 | 44.854 | 6.904 |
| 119 | 1013 | 1014 | 104.192 | 5.672 | 110.895 | 6.371 |
| 120 | 1015 | 1016 | 95.131 | 8.872 | 108.847 | 8.363 |
| 121 | 1017 | 1018 | 22.097 | 2.259 | 25.862 | 3.07 |
| 122 | 1019 | 1020 | 50.635 | 11.129 | 59.072 | 10.096 |
| 123 | 1021 | 1022 | 68.368 | 9.482 | 90.191 | 15.479 |
| 124 | 1023 | 1024 | 50.658 | 2.598 | 62.686 | 2.149 |
| 125 | 1025 | 1026 | 67.692 | 4.608 | 104.474 | 6.486 |
| 126 | 1027 | 1028 | 60.169 | 6.81 | 103.156 | 11.309 |
| 127 | 1029 | 1030 | 37.137 | 3.679 | 49.778 | 7.312 |
| 128 | 1031 | 1032 | 87.29 | 4.881 | 127.439 | 10.802 |
| 129 | 1033 | 1034 | 41.409 | 6.549 | 47.012 | 11.236 |
| 130 | 1035 | 1036 | 32.213 | 7.175 | 43.875 | 10.706 |
| 131 | 1037 | 1038 | 77.807 | 7.013 | 109.299 | 9.799 |
| 132 | 1039 | 1040 | 37.026 | 6.758 | 49.133 | 8.307 |
| 133 | 1041 | 1042 | 57.723 | 5.921 | 70.531 | 6.977 |
| 134 | 1043 | 1044 | 94.403 | 10.058 | 130.999 | 12.973 |
| 135 | 1045 | 1046 | 42.258 | 3.137 | 56.368 | 4.699 |
| 136 | 1047 | 1048 | 77.667 | 6.622 | 106.147 | 4.946 |
| 137 | 1049 | 1050 | 51.002 | 3.36 | 62.009 | 6.073 |
| 138 | 1051 | 1052 | 38.522 | 4.21 | 43.297 | 7.219 |
| 139 | 1053 | 1054 | 75.103 | 5.866 | 115.191 | 7.77 |
| 140 | 1055 | 1056 | 46.405 | 3.737 | 57.89 | 3.035 |
| 141 | 1057 | 1058 | 34.308 | 4.135 | 44.278 | 3.532 |
| 142 | 1059 | 1060 | 36.66 | 3.327 | 48.931 | 4.389 |
| 143 | 1061 | 1062 | 36.323 | 6.447 | 50.414 | 7.284 |
| 144 | 1063 | 1064 | 48.346 | 4.964 | 69.682 | 5.951 |
| 145 | 1065 | 1066 | 71.349 | 8.498 | 63.576 | 12.402 |
| 146 | 1067 | 1068 | 66.855 | 7.354 | 54.028 | 10.308 |
| 147 | 1069 | 1070 | 58.02 | 6.725 | 81.61 | 6.225 |
| 148 | 1071 | 1072 | 46.107 | 4.599 | 47.578 | 5.721 |
| 149 | 1073 | 1074 | 79.89 | 11.647 | 94.885 | 12.091 |
| 150 | 1075 | 1076 | 51.93 | 6.887 | 60.564 | 5.631 |
| 151 | 1077 | 1078 | 67.023 | 11.379 | 78.549 | 9.92 |
| 152 | 1079 | 1080 | 69.029 | 12.304 | 64.36 | 9.232 |
| 153 | 1081 | 1082 | 56.372 | 11.395 | 50.897 | 6.456 |
| 154 | 1083 | 1084 | 54.923 | 8.02 | 56.301 | 7.96 |
| 155 | 1085 | 1086 | 47.848 | 4.993 | 52.756 | 4.92 |
| 156 | 1087 | 1088 | 72.997 | 5.423 | 89.098 | 8.279 |
| 157 | 1089 | 1090 | 49.577 | 9.222 | 61.752 | 9.967 |
| 158 | 1091 | 1092 | 57.345 | 5.967 | 55.082 | 5.124 |
| 159 | 1093 | 1094 | 49.719 | 8.465 | 50.474 | 6.318 |
| 160 | 1095 | 1096 | 66.221 | 8.527 | 60.526 | 6.042 |
| 161 | 1097 | 1098 | 59.431 | 5.38 | 51.367 | 4.575 |
| 162 | 1099 | 1100 | 44.241 | 2.416 | 42.17 | 2.266 |
| 163 | 1101 | 1102 | 67.893 | 7.786 | 85.144 | 7.578 |

TABLE 3-continued

| GalXC-PNPLA3: 192 GalXC Compound In Vitro Screen. | | | | | | |
|---|---|---|---|---|---|---|
| PNPLA3 | Passenger | Guide | PNPLA3-F495 | | PNPLA3-F595 | |
| Oligo-nucleotide | (sense) (SEQ ID NO:) | (antisense) (SEQ ID NO:) | % Remaining | % SEM | % Remaining | % SEM |
| 164 | 1103 | 1104 | 54.101 | 3.156 | 64.663 | 5.874 |
| 165 | 1105 | 1106 | 74.353 | 11.203 | 73.215 | 11.059 |
| 166 | 1107 | 1108 | 91.603 | 5.407 | 78.535 | 4.566 |
| 167 | 1109 | 1110 | 86.259 | 4.861 | 84.54 | 5.247 |
| 168 | 1111 | 1112 | 100.862 | 9.39 | 83.472 | 3.848 |
| 169 | 1113 | 1114 | 64.233 | 6.416 | 55.446 | 5.259 |
| 170 | 1115 | 1116 | 82.913 | 8.265 | 67.499 | 6.098 |
| 171 | 1117 | 1118 | 63.834 | 4.157 | 66.965 | 7.54 |
| 172 | 1119 | 1120 | 87.059 | 6.502 | 80.608 | 3.299 |
| 173 | 1121 | 1122 | 52.896 | 8.619 | 50.91 | 8.301 |
| 174 | 1123 | 1124 | 89.834 | 8.687 | 60.792 | 7.648 |
| 175 | 1125 | 1126 | 56.928 | 16.722 | 55.37 | 13.438 |
| 176 | 1127 | 1128 | 91.989 | 35.495 | 98.901 | 26.361 |
| 177 | 1129 | 1130 | 78.111 | 6.12 | 85.965 | 5.555 |
| 178 | 1131 | 1132 | 81.351 | 5.528 | 68.852 | 4.702 |
| 179 | 1133 | 1134 | 82.851 | 10.171 | 87.313 | 8.301 |
| 180 | 1135 | 1136 | 94.367 | 3.317 | 87.13 | 5.434 |
| 181 | 1137 | 1138 | 108.095 | 11.973 | 99.858 | 9.769 |
| 182 | 1139 | 1140 | 95.753 | 5.346 | 87.366 | 6.613 |
| 183 | 1141 | 1142 | 88.199 | 15.408 | 67.131 | 13.665 |
| 184 | 1143 | 1144 | 102.928 | 9.669 | 84.541 | 9.709 |
| 185 | 1145 | 1146 | 48.692 | 11.647 | 48.288 | 10.808 |
| 186 | 1147 | 1148 | 84.114 | 6.361 | 82.348 | 3.469 |
| 187 | 1149 | 1150 | 89.182 | 14.563 | 92.44 | 12.983 |
| 188 | 1151 | 1152 | 85.958 | 10.066 | 85.508 | 8.055 |
| 189 | 1153 | 1154 | 56.68 | 12.506 | 63.775 | 15.034 |
| 190 | 1155 | 1156 | 77.223 | 11.068 | 75.609 | 8.161 |
| 191 | 1157 | 1158 | 85.696 | 6.162 | 92.128 | 6.673 |
| 192 | 1159 | 1160 | 50.761 | 3.422 | 51.217 | 2.474 |

Mouse studies: Various GalNAc-conjugated PNPLA3 oligonucleotides, some of which are listed in Table 3, are evaluated in hydrodynamic injection (HDI) mouse model. Additional HDI studies are listed in tables 4, 5 and 6. For these HDI studies, the mice are engineered to transiently express human PNPLA3 mRNA in hepatocytes. A GalNAc-conjugated PNPLA3 oligonucleotide control (SEQ ID NOs: 1165 & 1166) is used as a benchmark control. Briefly, 6-8-week-old female CD-1 mice are treated SQ with a GalNAc-conjugated PNPLA3 oligonucleotide at a dose level of 1 mg/kg. Three days later (72 hr.), the mice are hydrodynamically injected with a DNA plasmid encoding the full human PNPLA3 gene under control of a ubiquitous cytomegalovirus (CMV) promoter sequence. One day after introduction of the plasmid, liver samples are collected. Total RNA derived from these mice are subjected to qRT-PCR analysis for PNPLA3 mRNA, relative to mice treated only with an identical volume of PBS. The values are normalized for transfection efficiency using the NeoR gene included on the plasmid.

As shown in Tables 4, 5 and 6 a number of the GalNAc-conjugated PNPLA3 oligonucleotides tested inhibited PNPLA3 expression, as determined by a reduced amount of PNPLA3 mRNA in liver samples from oligonucleotide-treated mice relative to mice treated with PBS. The mean % of remaining PNPLA3 mRNA in liver samples of mice treated with the benchmark GalNAc-conjugated PNPLA3 oligonucleotide control relative to mice treated with PBS. Table 4 shows that 18 of the 21 GalNAc-conjugated PNPLA3 oligonucleotides inhibit PNPLA3 expression to a greater extent than the reference GalNAc-conjugated PNPLA3 oligonucleotide used as control. Sequences of these oligonucleotides along with the modification patterns and SEQ ID NOs. is disclosed in Table A

TABLE 4

| discloses single 0.5 mg/kg GalXC-PNPLA3 S.c. Dose, Day 3 HDI, Day 4 Takedown, Liver qPCR | | | | | | | | | | | | |
|---|---|---|---|---|---|---|---|---|---|---|---|---|
| | Group | | | | | | | | | | | |
| Animal | PBS | −1170 (Ref.) | −643 | −1110 | −1162 | −1170 | −1699 | −1703 | −1708 | −2104 | −2143 | −2155 |
| 1 | 105.7 | 96.7 | 78.2 | | 69.2 | 76.5 | 65.0 | 41.6 | 68.1 | 56.7 | 82.5 | 60.7 |
| 2 | 104.5 | 66.6 | 101.7 | 88.0 | 72.0 | 89.3 | 82.9 | 81.8 | 98.1 | 69.3 | 61.6 | 81.5 |
| 3 | 89.9 | 115.5 | 96.8 | 99.7 | 54.2 | 23.3 | 53.0 | 46.5 | 85.6 | 41.6 | 77.7 | 70.0 |
| 4 | 99.9 | 57.1 | 64.1 | 92.2 | 84.4 | 26.7 | 69.6 | 48.6 | 61.8 | 29.3 | 92.5 | 81.0 |
| 5 | | 107.2 | 64.2 | 70.4 | 118.2 | 75.0 | 39.4 | 63.4 | 39.7 | 35.5 | 89.1 | 61.2 |
| Average: | 100.0 | 88.6 | 81.0 | 87.6 | 79.6 | 58.1 | 62.0 | 56.4 | 70.6 | 46.5 | 80.7 | 70.9 |
| SEM: | 3.6 | 11.4 | 7.9 | 6.2 | 10.8 | 13.8 | 7.4 | 7.3 | 10.0 | 7.3 | 5.4 | 4.5 |

TABLE 4-continued discloses single 0.5 mg/kg GalXC-PNPLA3 S.c. Dose, Day 3 HDI, Day 4 Takedown, Liver qPCR

| | Group | | | | | | | | | |
|---|---|---|---|---|---|---|---|---|---|---|
| Animal | −2156 | −2157 | −2163 | −2165 | −2170 | −2195 | −2200 | −2204 | −2205 | −2210 |
| 1 | 63.1 | 104.4 | 41.1 | 93.9 | 66.8 | 91.3 | 144.7 | 76.6 | 57.0 | 64.5 |
| 2 | 76.4 | 81.6 | 31.0 | 50.7 | 48.1 | 57.0 | 109.8 | 77.0 | 33.9 | |
| 3 | 80.5 | 123.1 | 30.8 | 36.6 | 47.8 | 28.7 | 87.5 | 104.5 | 26.8 | 58.7 |
| 4 | 83.0 | 107.6 | 36.3 | 52.3 | 46.8 | 56.0 | 102.6 | 64.1 | 41.6 | 60.3 |
| 5 | 42.4 | 153.9 | 50.1 | 23.5 | 89.2 | 48.6 | 84.1 | 173.5 | 36.6 | 83.0 |
| Average: | 69.1 | 114.1 | 37.9 | 51.4 | 59.7 | 56.3 | 105.7 | 99.1 | 39.2 | 66.6 |
| SEM: | 7.5 | 11.9 | 3.6 | 11.8 | 8.3 | 10.1 | 10.8 | 19.7 | 5.1 | 5.6 |

Table 5 and 6 show 2 additional sets of HDI Studies with 18 GalNAc-conjugated PNPLA3 oligonucleotides in each set using the same reference oligonucleotide. Sequences of these oligonucleotides along with the modification patterns and SEQ ID NOs. are disclosed in Table B and Table C respectively.

Based on these results, 10 GalNAc-conjugated PNPLA3 oligonucleotides are selected for evaluation of their ability to inhibit PNPLA3 expression in non-human primates (NHPs). The GalNAc-conjugated PNPLA3 oligonucleotides have chemically modified nucleotides of the pattern as shown in FIG. 1.

TABLE 5 discloses a Single 1 mg/kg s.c. dose, HDI 3 days post-dose, harvest 4 days post-dose

| | Group | | | | | | | | | | | | | | | | | | |
|---|---|---|---|---|---|---|---|---|---|---|---|---|---|---|---|---|---|---|---|
| Animal | PBS | −644 | −745 | −1126 | −1129 | −1130 | −1143 | −1147 | −1152 | −1229 | −1698 | −2137 | −2138 | −2140 | −2142 | −2144 | −2146 | −2149 | −2205 (ref) |
| 1 | | 57.2 | 116.3 | 35.0 | 66.3 | 108.6 | 41.3 | 60.4 | | 111.7 | 60.0 | 80.2 | 101.1 | 39.0 | 96.0 | 48.4 | 53.5 | | 18.1 |
| 2 | 120.1 | 55.2 | 121.8 | 41.0 | 82.9 | 68.5 | | 59.3 | 55.1 | 80.1 | 112.9 | 68.0 | 69.9 | 24.1 | 47.9 | | 78.1 | | 38.9 |
| 3 | 129.1 | 143.6 | 82.2 | 94.9 | 53.4 | 91.1 | 30.0 | | | 86.2 | 71.9 | 120.8 | 45.0 | 41.4 | 78.2 | 34.9 | | 23.5 | 65.7 |
| 4 | 50.8 | | 102.2 | 57.9 | 77.6 | 145.3 | 34.4 | 43.4 | 39.8 | 101.5 | 88.7 | | 47.0 | 41.0 | 95.5 | 37.6 | 47.1 | 26.2 | 36.7 |
| 5 | | 27.0 | 114.3 | 42.3 | 117.2 | 125.9 | 13.9 | 41.8 | 64.5 | 89.1 | 116.6 | 44.5 | 29.1 | 47.1 | 54.0 | 25.5 | | 16.5 | 38.2 |
| Average: | 100.0 | 70.7 | 107.4 | 54.2 | 79.5 | 107.9 | 29.9 | 51.3 | 53.1 | 93.7 | 90.0 | 78.4 | 58.4 | 38.5 | 74.3 | 36.6 | 59.6 | 22.1 | 39.5 |
| SEM: | 24.8 | 25.2 | 7.1 | 10.9 | 10.7 | 13.3 | 5.8 | 5.0 | 7.2 | 5.7 | 11.1 | 16.0 | 12.5 | 3.9 | 10.1 | 4.7 | 9.5 | 2.9 | 7.6 |

TABLE 6 discloses a Single 1 mg/kg s.c. dose, HDI 3 days post-dose, harvest 4 days post-dose

| | Group | | | | | | | | | | | | | | | | | | |
|---|---|---|---|---|---|---|---|---|---|---|---|---|---|---|---|---|---|---|---|
| Animal | PBS | −637 | −641 | −923 | −1116 | −1125 | −1136 | −1151 | −1157 | −1158 | −1173 | −1541 | −1163 | −1614 | −1697 | −2136 | −2176 | −2222 | −2205 (ref) |
| 1 | | 80.3 | 114.9 | 88.9 | 48.9 | 203.5 | 156.1 | 49.0 | 113.6 | 113.6 | 42.2 | 91.1 | 62.5 | 56.4 | 24.4 | 145.3 | 64.1 | 97.3 | 26.9 |
| 2 | 76.6 | 140.7 | 116.7 | 122.7 | 78.6 | 115.6 | | 101.3 | 72.8 | 95.2 | 99.6 | 50.1 | | 79.5 | 57.3 | 85.7 | 28.2 | 137.8 | 58.6 |
| 3 | 78.7 | 115.4 | 57.8 | 142.4 | 122.0 | 119.8 | 130.1 | 91.9 | 186.4 | 134.1 | 20.5 | 135.3 | 110.5 | 60.2 | 104.6 | 65.7 | 71.4 | 107.5 | 34.6 |
| 4 | 133.6 | 90.3 | 84.3 | 85.6 | 150.0 | 80.0 | | | 98.2 | 113.6 | 25.0 | | 203.1 | 44.8 | | 132.5 | 44.8 | 50.1 | 52.7 |
| 5 | 111.1 | 119.9 | 198.0 | 75.0 | 41.6 | 166.4 | 84.6 | 121.0 | 114.0 | | 44.2 | 45.9 | 96.0 | 44.9 | 52.0 | 179.6 | 35.4 | 90.3 | 55.6 |
| Average: | 100.0 | 109.4 | 114.3 | 102.9 | 88.2 | 137.1 | 123.6 | 90.8 | 117.0 | 114.1 | 46.3 | 80.6 | 118.0 | 57.2 | 59.6 | 121.8 | 48.8 | 96.6 | 45.7 |
| SEM: | 13.7 | 10.8 | 23.6 | 12.7 | 20.9 | 21.6 | 20.9 | 15.2 | 18.9 | 7.9 | 14.1 | 20.9 | 30.1 | 6.4 | 16.7 | 20.6 | 8.3 | 14.2 | 6.3 |

Table 7 discloses an additional HDI Study using the best GalNAc-conjugated PNPLA3 oligonucleotides (hits) based on the results obtained from the previous studies and previous 3 HDI screens, as disclosed in tables 4, 5 and 6. Sequences of the oligonucleotides along with the modification patterns and SEQ ID NOs. used in this HDI screen are disclosed in Table D.

TABLE 7 comparison of hits from earlier studies and 3 HDI screens with Single 1 mg/kg s.c. dose, HDI 3 days post-dose, harvest 4 days post-dose.

| Animal | Group PBS | −639 | −644 | −729 | −735 | −743 | −744 | −838 | −1126 | −1143 | −1147 | −1152 | −1173 |
|---|---|---|---|---|---|---|---|---|---|---|---|---|---|
| 1 | 98.7 | 58.8 | 22.9 | 114.6 | 119.1 | 106.5 | 94.7 | 45.3 | 64.6 | 24.8 | 70.5 | 55.2 | 26.0 |
| 2 | 99.9 | 62.3 | 30.7 | 108.6 | 85.0 | 105.4 | 55.4 | 48.1 | 30.4 | 16.8 | 24.7 | 71.6 | 10.7 |
| 3 | 143.0 | 87.9 | 10.1 | 106.3 | 97.4 | 76.2 | 61.1 | 91.8 | 39.1 | 18.4 | 33.4 | 50.5 | 18.2 |
| 4 | 115.1 | 89.6 | 19.2 | 99.5 | 84.0 | 99.8 | 56.5 | 68.5 | 61.2 | 26.7 | 59.3 | 58.2 | 10.8 |
| 5 | 89.2 | 91.4 | 41.1 | 94.5 | 105.8 | 115.0 | 113.8 | 48.6 | 54.6 | 30.3 | 47.2 | 59.8 | 35.5 |
| Average: | 109.2 | 78.0 | 24.8 | 104.7 | 98.3 | 100.6 | 76.3 | 60.5 | 50.0 | 23.4 | 47.0 | 59.1 | 20.2 |
| SEM: | 9.4 | 7.2 | 5.3 | 3.5 | 6.6 | 6.6 | 11.9 | 8.9 | 6.6 | 2.5 | 8.3 | 3.5 | 4.7 |

| Animal | Group −1697 | −1699 | −1703 | −2140 | −2144 | −2149 | −2156 | −2195 | −2205 | PBS |
|---|---|---|---|---|---|---|---|---|---|---|
| 1 | 88.2 | 18.7 | 44.9 | 29.4 | 13.4 | 32.7 | 76.2 | 62.3 | 36.2 | 85.1 |
| 2 | 53.5 | 27.3 | 34.6 | 22.1 | 20.4 | 20.1 | 56.4 | 48.8 | 29.2 | 127.9 |
| 3 | 72.2 | 43.1 | 34.3 | 51.1 | 31.8 | 21.1 | 55.1 | 31.2 | 40.9 | 97.7 |
| 4 | 27.8 | 33.0 | 22.2 | 34.2 | 73.1 | 17.1 | 40.8 | 43.5 | 30.7 | 74.6 |
| 5 | 25.0 | 26.1 | 23.9 | 19.1 | 59.8 | 16.7 | 62.5 | 88.6 | 30.5 | 68.9 |
| Average: | 53.3 | 29.6 | 32.0 | 31.2 | 39.7 | 21.5 | 58.2 | 54.9 | 33.5 | 90.8 |
| SEM: | 12.3 | 4.1 | 4.1 | 5.6 | 11.5 | 2.9 | 5.7 | 9.8 | 2.2 | 10.5 |

NHP studies: 10 GalNAc-conjugated PNPLA3 oligonucleotides selected from table 7 are evaluated in cynomolgus monkeys (*Macaca fascicularis*). Here, the NHPs are grouped so that their mean body weights (about 5.4 kg) are comparable between the control and experimental groups. Each cohort contains two male and three female subjects. The GalNAc-conjugated PNPLA3 oligonucleotides are administered SQ on Study Day 0. Blood samples are collected on Study Days −8, −5 and 0, and weekly after dosing. Ultrasound-guided core needle liver biopsies are collected on Study Days −7, 28 and 56. At each time point, total RNA derived from the liver biopsy samples is subjected to qRT-PCR analysis to measure PNPLA3 mRNA in oligonucleotide-treated monkeys relative to monkeys treated with a comparable volume of PBS. To normalize the data, the measurements are made relative to the geometric mean of two reference genes, PPIB and 18S rRNA. As shown in Table 8 (Day −7), Table 9 (Day 28), and Table 10 (Day 56), treating NHPs with the GalNAc-conjugated PNPLA3 oligonucleotides inhibits PNPLA3 expression in the liver, as determined by a reduced amount of PNPLA3 mRNA in liver samples from oligonucleotide-treated NHPs relative to NHPs treated with PBS. For all time points evaluated, PNPLA3 oligonucleotides 34, 81 and 121 inhibit PNPLA3 expression to a greater extent than the benchmark PBS and time-matched controls. From the same NHP study, inhibition of PNPLA3 expression is also determined by measuring PNPLA3 protein in serum prepared from the pre-dose and weekly blood samples by ELISA. Taken together, these results demonstrate that treating NHPs with GalNAc-conjugated PNPLA3 oligonucleotides reduces the amount of PNPLA3 mRNA in the liver and concomitantly reduces the amount of PNPLA3 protein in the serum.

TABLE 8

PNPLA3 mRNA Knockdown of Select GalNAc-Conjugated PNPLA3 Oligonucleotides in NHP at Day −7.

| Sequence | Passenger (sense) (SEQ ID NO:) | Guide (antisense) (SEQ ID NO:) | Mean % KD, Rel To Time-Matched PBS |
|---|---|---|---|
| PBS | — | — | 0 |
| 644 | 1220 | 1221 | 29 |
| 1126 | 1224 | 1225 | −4.9 |
| 1143 | 1230 | 1231 | 43 |
| 1147 | 1232 | 1233 | −2.5 |
| 1699 | 1188 | 1189 | 44 |
| 1703 | 1190 | 1191 | 28 |
| 2140 | 1244 | 1245 | 27 |
| 2149 | 1250 | 1251 | 20 |
| 1697 | 1254 | 1255 | 5.9 |
| 2144 | 1246 | 1247 | −15 |

TABLE 9

PNPLA3 mRNA Knockdown of Select GalNAc-Conjugated PNPLA3 Oligonucleotides in NHP at Day 28.

| Sequence | Passenger (sense) (SEQ ID NO:) | Guide (antisense) (SEQ ID NO:) | Mean % KD, Rel To Time-Matched PBS | Mean % KD, Rel to mean of pre-dose | Mean % KD, Rel To Individual Animal Predose |
|---|---|---|---|---|---|
| PBS | — | — | 0 | −9.8 | −30 |
| 644 | 1220 | 1221 | 34 | −3 | −17 |
| 1126 | 1224 | 1225 | 50 | 48 | 36 |
| 1143 | 1230 | 1231 | 54 | 11 | −0.1 |
| 1147 | 1232 | 1233 | −2.4 | −9.8 | 11 |
| 1699 | 1188 | 1189 | 65 | 32 | 30 |
| 1703 | 1190 | 1191 | 60 | 39 | 19 |
| 2140 | 1244 | 1245 | 65 | 47 | 40 |
| 2149 | 1250 | 1251 | 64 | 51 | 48 |
| 1697 | 1254 | 1255 | 49 | 40 | 42 |
| 2144 | 1246 | 1247 | 50 | 53 | 51 |

TABLE 10

| PNPLA3 mRNA Knockdown of Select GalNAc-Conjugated PNPLA3 Oligonucleotides in NHP at Day 56. | | | | | |
|---|---|---|---|---|---|
| Sequence | Passenger (sense) (SEQ ID NO:) | Guide (antisense) (SEQ ID NO:) | Mean % KD, Rel to Time-Matched PBS | Mean % KD, Rel to Mean of Pre-Dose | Mean % KD, Rel to Individual Animal Predose |
| PBS | — | — | 0 | 5 | −12 |
| 644 | 1220 | 1221 | 46 | 28 | 28 |
| 1126 | 1224 | 1225 | 39 | 45 | 27 |
| 1143 | 1230 | 1231 | 35 | −9.2 | −32 |
| 1147 | 1232 | 1233 | 28 | 34 | 29 |
| 1699 | 1188 | 1189 | 51 | 18 | 14 |
| 1703 | 1190 | 1191 | 5.5 | −24 | −45 |
| 2140 | 1244 | 1245 | −34 | −73 | −100 |
| 2149 | 1250 | 1251 | 48 | 39 | 36 |
| 1697 | 1254 | 1255 | 32 | 31 | 31 |
| 2144 | 1246 | 1247 | −9.8 | 9.7 | 4.4 |

Taken together, these results show that GalNAc-conjugated PNPLA3 oligonucleotides designed to target human PNPLA3 mRNA inhibit PNPLA3 expression in vivo (as determined by the reduction of the amount of PNPLA3 mRNA and PNPLA3 protein in treated animals).

SEQUENCES

The following nucleic acid sequences and/or amino acid sequences are referred to in the disclosure and are provided below for reference.

```
SEQ ID NO: 1 - wild-type human PNPLA3 (2753 bp; NCBI Ref. Seq. No. NM_025225.3)
agagagcgcttgcgggcgccgggcggagctgctgcggatcaggacccgagccgattcccgatcccgacccagatcctaacccgc

gcccccgccccgccgccgccgccatgtacgacgcagagcgcggctggagcttgtccttcgcgggctgcggcttcctgggcttctac

cacgtcggggcgacccgctgcctgagcgagcacgccccgcacctcctccgcgacgcgcgcatgttgttcggcgcttcggccgggg

cgttgcactgcgtcggcgtcctctccggtatcccgctggagcagactctgcaggtcctctcagatcttgtgcggaaggccaggagtcg

gaacattggcatcttccatccatccttcaacttaagcaagttcctccgacagggtctctgcaaatgcctcccggccaatgtccaccagctc

atctccggcaaaataggcatctctcttaccagagtgtctgatggggaaaacgttctggtgtctgactttcggtccaaagacgaagtcgtg

gatgccttggtatgttcctgcttcatccccttctacagtggccttatccctccttccttcagaggcgtgcgatatgtggatggaggagtgag

tgacaacgtacccttcattgatgccaaaacaaccatcaccgtgtccccttctatggggagtacgacatctgccctaaagtcaagtccac

gaactttcttcatgtggacatcaccaagctcagtctacgcctctgcacagggaacctctaccttctctcgagagcttttgtcccccggat

ctcaaggtgctgggagagatatgccttcgaggatatttggatgcattcaggttcttggaagagaagggcatctgcaacaggccccagc

caggcctgaagtcatcctcagaagggatggatcctgaggtcgccatgcccagctgggcaaacatgagtctggattcttccccggagtc

ggctgccttggctgtgaggctggagggagatgagctgctagaccacctgcgtctcagcatcctgccctgggatgagagcatcctgga

caccctctcgcccaggctcgctacagcactgagtgaagaaatgaaagacaaaggtggatacatgagcaagatttgcaacttgctaccc

attaggataatgtcttatgtaatgctgccctgtaccctgcctgtggaatctgccattgcgattgtccagagactggtgacatggcttccaga

tatgcccgacgatgtcctgtggttgcagtgggtgacctcacaggtgttcactcgagtgctgatgtgtctgctccccgcctccaggtccca

aatgccagtgagcagccaacaggcctccccatgcacacctgagcaggactggccctgctggactccctgctcccccaagggctgtc

cagcagagaccaaagcagaggccaccccgcggtccatcctcaggtccagcctgaacttcttcttgggcaataaagtacctgctggtg

ctgaggggctctccacctttcccagtttttcactagagaagagtctgtgagtcacttgaggaggcgagtctagcagattctttcagaggtg

ctaaagtttcccatctttgtgcagctacctccgcattgctgtgtagtgacccctgcctgtgacgtggaggatcccagcctctgagctgagt

tggttttatgaaaagctaggaagcaacctttcgcctgtgcagcggtccagcacttaactctaatacatcagcatgcgttaattcagctggtt

gggaaatgacaccaggaagcccagtgcagagggtcccttactgactgtttcgtggccctattaatggtcagactgttccagcatgaggt

tcttagaatgacaggtgtttggatgggtgggggccttgtgatgggggtaggctggcccatgtgtgatcttgtggggtggagggaaga

gaatagcatgatcccacttccccatgctgtgggaaggggtgcagttcgtccccaagaacgacactgcctgtcaggtggtctgcaaaga

tgataaccttgactactaaaaacgtctccatggcgggggtaacaagatgataatctacttaattttagaacacctttttcacctaactaaaat

aatgtttaaagagttttgtataaaaatgtaaggaagcgttgttacctgttgaattttgtattatgtgaatcagtgagatgttagtagaataagcc
```

-continued ttaaaaaaaaaaaaatcggttgggtgcagtggcacacggctgtaatcccagcactttgggaggccaaggttggcagatcacctgaggt caggagttcaagaccagtctggccaacatagcaaaaccctgtctctactaaaaatacaaaaattatctgggcatggtggtgcatgcctgt aatcccagctattcggaaggctgaggcaggagaatcacttgaacccaggaggcggaggttgcggtgagctgagattgcaccatttca ttccagcctgggcaacatgagtgaaagtctgactcaaaaaaaaaaaatttaaaaaacaaaataatctagtgtgcagggcattcacctca gccccccaggcaggagccaagcacagcaggagcttccgcctcctctccactggagcacacaacttgaacctggcttattttctgcagg gaccagccccacatggtcagtgagtttctccccatgtgtggcgatgagagagtgtagaaataaagacacaagacaaagaga SEQ ID NO: 2 - wild-type human PNPLA3 (481 aa; NCBI Ref. Seq. No. NP_079501.2)
MYDAERGWSLSFAGCGFLGFYHVGATRCLSEHAPHLLRDARMLFGASAGALHCVG

VLSGIPLEQTLQVLSDLVRKARSRNIGIFHPSFNLSKFLRQGLCKCLPANVHQLISGKI

GISLTRVSDGENVLVSDFRSKDEVVDALVCSCFIPFYSGLIPPSFRGVRYVDGGVSDN

VPFIDAKTTITVSPFYGEYDICPKVKSTNFLHVDITKLSLRLCTGNLYLLSRAFVPPDL

KVLGEICLRGYLDAFRFLEEKGICNRPQPGLKSSSEGMDPEVAMPSWANMSLDSSPE

SAALAVRLEGDELLDHLRLSILPWDESILDTLSPRLATALSEEMKDKGGYMSKICNLL

PIRIMSYVMLPCTLPVESAIAIVQRLVTWLPDMPDDVLWLQWVTSQVFTRVLMCLLP

ASRSQMPVSSQQASPCTPEQDWPCWTPCSPKGCPAETKAEATPRSILRSSLNFFLGNK

VPAGAEGLSTFPSFSLEKSL

SEQ ID NO: 3 - human PNPLA3 I148M (variant) mRNA
agagagcgcttgcgggcgccgggcggagctgctgcggatcaggacccgagccgattcccgatcccgacccagatcctaacccgc gcccccgccccgccgccgccgccatgtacgacgcagagcgcggctggagcttgtccttcgcgggctgcggcttcctgggcttctac cacgtcggggcgacccgctgcctgagcgagcacgccccgcacctcctccgcgacgcgcgcatgttgttcggcgcttcggccgggg cgttgcactgcgtcggcgtcctctccggtatcccgctggagcagactctgcaggtcctctcagatcttgtgcggaaggccaggagtcg gaacattggcatcttccatccatccttcaacttaagcaagttcctccgacagggtctctgcaaatgcctcccggccaatgtccaccagctc atctccggcaaaataggcatctctcttaccagagtgtctgatggggaaaacgttctggtgtctgactttcggtccaaagacgaagtcgtg gatgccttggtatgttcctgcttcatgcccttctacagtggccttatccctccttccttcagaggcgtgcgatatgtggatggaggagtgag tgacaacgtacccttcattgatgccaaaacaaccatcaccgtgtccccttctatggggagtacgacatctgccctaaagtcaagtccac gaactttcttcatgtggacatcaccaagctcagtctacgcctctgcacagggaacctctaccttctctcgagagcttttgtcccccggat ctcaaggtgctgggagagatatgccttcgaggatatttggatgcattcaggttcttggaagagaagggcatctgcaacaggccccagc caggcctgaagtcatcctcagaagggatggatcctgaggtcgccatgcccagctgggcaaacatgagtctggattcttccccggagtc ggctgccttggctgtgaggctggagggagatgagctgctagaccacctgcgtctcagcatcctgccctgggatgagagcatcctgga cacccctctcgcccaggctcgctacagcactgagtgaagaaatgaaagacaaaggtggatacatgagcaagatttgcaacttgctaccc attaggataatgtcttatgtaatgctgccctgtaccctgcctgtggaatctgccattgcgattgtccagagactggtgacatggcttccaga tatgcccgacgatgtcctgtggttgcagtgggtgacctcacaggtgttcactcgagtgctgatgtgtctgctccccgcctccaggtccca aatgccagtgagcagccaacaggcctccccatgcacacctgagcaggactggccctgctggactccctgctcccccaagggctgtc cagcagagaccaaagcagaggccaccccgcggtccatcctcaggtccagcctgaacttcttcttgggcaataaagtacctgctggtg ctgaggggctctccacctttcccagtttttcactagagaagagtctgtgagtcacttgaggaggcgagtctagcagattctttcagaggtg ctaaagtttcccatctttgtgcagctacctccgcattgctgtgtagtgacccctgcctgtgacgtggaggatcccagcctctgagctgagt tggttttatgaaaagctaggaagcaacctttcgcctgtgcagcggtccagcacttaactctaatacatcagcatgcgttaattcagctggtt gggaaatgacaccaggaagcccagtgcagagggtcccttactgactgtttcgtggccctattaatggtcagactgttccagcatgaggt tcttagaatgacaggtgtttggatgggtgggggccttgtgatggggggtaggctggcccatgtgtgatcttgtggggtggagggaaga gaatagcatgatcccacttccccatgctgtgggaaggggtgcagttcgtccccaagaacgacactgcctgtcaggtggtctgcaaaga tgataaccttgactactaaaaacgtctccatggcgggggtaacaagatgataatctacttaattttagaacaccttttttcacctaactaaaat aatgtttaaagagttttgtataaaaatgtaaggaagcgttgttacctgttgaattttgtattatgtgaatcagtgagatgttagtagaataagcc -continued ttaaaaaaaaaaaaaatcggttgggtgcagtggcacacggctgtaatcccagcactttgggaggccaaggttggcagatcacctgaggt caggagttcaagaccagtctggccaacatagcaaaaccctgtctctactaaaaatacaaaaattatctgggcatggtggtgcatgcctgt aatcccagctattcggaaggctgaggcaggagaatcacttgaacccaggaggcggaggttgcggtgagctgagattgcaccatttca ttccagcctgggcaacatgagtgaaagtctgactcaaaaaaaaaaaaatttaaaaaacaaaataatctagtgtgcagggcattcacctca gccccccaggcaggagccaagcacagcaggagcttccgcctcctctccactggagcacacaacttgaacctggcttattttctgcagg gaccagccccacatggtcagtgagtttctccccatgtgtggcgatgagagagtgtagaaataaagacacaagacaaagaga SEQ ID NO: 4 - human PNPLA3 I148M (variant)
MYDAERGWSLSFAGCGFLGFYHVGATRCLSEHAPHLLRDARMLFGASAGALHCVG

VLSGIPLEQTLQVLSDLVRKARSRNIGIFHPSFNLSKFLRQGLCKCLPANVHQLISGKI

GISLTRVSDGENVLVSDFRSKDEVVDALVCSCFMPFYSGLIPPSFRGVRYVDGGVSD

NVPFIDAKTTITVSPFYGEYDICPKVKSTNFLHVDITKLSLRLCTGNLYLLSRAFVPPD

LKVLGEICLRGYLDAFRFLEEKGICNRPQPGLKSSSEGMDPEVAMPSWANMSLDSSP

ESAALAVRLEGDELLDHLRLSILPWDESILDTLSPRLATALSEEMKDKGGYMSKICNL

LPIRIMSYVMLPCTLPVESAIAIVQRLVTWLPDMPDDVLWLQWVTSQVFTRVLMCLL

PASRSQMPVSSQQASPCTPEQDWPCWTPCSPKGCPAETKAEATPRSILRSSLNFFLGN

KVPAGAEGLSTFPSFSLEKSL

SEQ ID NO: 5 - primate PNPLA3 (2291 bp; NCBI Ref. Seq. No. XM_015457081.1)
cgagggaggcggggcggacgtcgcgcgtggaaagcccgggcggagacgcggcggctgggtcacgagcgcttgcgggcgccc ggcggagctgctgcggatcaggacccgagccgatccccgatcccgactccgatccggatccgcgcccccgcccccgccccgccat gtacgacgccgagcgcggctggagcttgtccttcgcgggctgcggcttcctgggcttctaccacgtcggggcgacccggtgcctga gcgagcacgccccgcacctcctccgcgacgcgcgcatgttgttcggcgcctcggccggggcgttgcactgcgtcggcgtcctctcc gggatcccgctggagcagactctgcaggtcctctcagatcttgtccggaaggccaggagtcggaacattggtatcttccatccatcctt caacataggcaagttcctccgacaggatctctacaaatacctcccggccaatgtccaccagctcatctctggcaaaatatgcgtctcact caccagagtgtctgatggggaaaacgttctggtgtctgactttcagtccaaagacgaagtcgtggatgccttgatttgttcctgcttcatcc ctttctacagtggccttatccctccttccttcagaggcgtgcgatatgtggatggaggagcgagtgacaacgtacccttcattgatgccaa gacaaccatcaccgtgtcgcccttctatggggagtacgacatctgccctaaagtcaagtccaccaactttcttcatgtggacatcaccaa gctcagcctacgcctctgcacagggaacctctaccttctctcaagagcgtttgtcccccccggatctcaaggtgctgggagagatatgcc ttcgaggatatttggacgcgttcaggttcttggaagagaagggcatctgcaacaagccccagcggggtctgaagtcatcctcagaagg gatggattctgaggtcactgcgcccggctgggaaaacacaagtctggattcttccccggagccggctgccttggctatgaggctggat ggagatgagctgctagaccacctgcgtctcagcatcctgccctgggatgagagcatcctggacaccctgtcgcccgagctcgctaca gtgagtgaagcaatgaaagacaaaggtggatacatgagcaagatttgcaacttgctacccattaggataatatcttatgtgatgctgccc tgtaccctgcctgtggagtctgccattgcgattgtccagagactggtgacatggcttccagatatgcccgacgatgtgcagtggctgca gtgggtgacctcacaggtcttcactcgagcgctgatgtgtctgcttcccgcctccaggtcccaaatgccagtgagcagcgaacaggcc tccccatgcaaaccggagcaggactggcactgctggactccctgctcccccgaggactgtcctgcagaggccaaagcagaggctac cccacggtccatcctcaggtccagcctgaacttcttctggggcaataaagtacctgctggtgctgaggggctctccacctttcccagtttt tcactggagaagaatttgtgagtcatttgaggaggcgagtctaggagattctttcagaggtgctaaagcttcccatctttgtgcagctacct ccgcattgccgtgtagtgacccctgcctgtgacgtggaggatcccagcctctgagctgagttggttttatgaaaagctaggaagcaatg tttggtctgtgcagcagtccagcacttaagtctaatacgtcagcatgcgttagttcagctggttgggaaatgacaccgggaagcctagcg cagagggtcccttactgactatttcatggtcctattaatggtcagactgttccagtgtgaggttcttagaatgactagtgtttggatgggtgg gggccttgtggtggggggtgggctggcctatgtgtgatcttgtggggtggaaggaagagagtagcacaatcccacctccccatgccg tgggaaggggtgcacttggttcccaagaaggacactgcctgtcaggtggcctgcaaatataataaccttgacaactaaaaacctctcca -continued tgggggtgggaggtaccaagataataaccgatttacattttagagcacctttttcacctaactaaaataatgtttaaagagttttatataaaa atgtaaggaagagttgttatctgttgaattttgtattatatgaatcagtgagatgttaatagaataagcctt SEQ ID NO: 6 - primate PNPLA3 (480 aa; NCBI Ref. Seq. No. XP_015312567.1)
MYDAERGWSLSFAGCGFLGFYHVGATRCLSEHAPHLLRDARMLFGASAGALHCVG

VLSGIPLEQTLQVLSDLVRKARSRNIGIFHPSFNIGKFLRQDLYKYLPANVHQLISGKI

CVSLTRVSDGENVLVSDFQSKDEVVDALICSCFIPFYSGLIPPSFRGVRYVDGGASDN

VPFIDAKTTITVSPFYGEYDICPKVKSTNFLHVDITKLSLRLCTGNLYLLSRAFVPPDL

KVLGEICLRGYLDAFRFLEEKGICNKPQRGLKSSSEGMDSEVTAPGWENTSLDSSPEP

AALAMRLDGDELLDHLRLSILPWDESILDTLSPELATVSEAMKDKGGYMSKICNLLPI

RIISYVMLPCTLPVESAIAIVQRLVTWLPDMPDDVQWLQWVTSQVFTRALMCLLPAS

RSQMPVSSEQASPCKPEQDWHCWTPCSPEDCPAEAKAEATPRSILRSSLNFFWGNKV

PAGAEGLSTFPSFSLEKNL

SEQ ID NO: 7 - mouse PNPLA3 (4675 bp; NCBI Ref. Seq. No. XM_006520346.5)
caccccgaagacagcttaggcggctgcggctctttaagctcagagcagcaacaccgggagcagagctgaactgcagcgccgcccgg agcttcaagcaccatgtatgacccagagcgccgctggagcctgtcgtttgcaggctgcggcttcctgggcttctaccacgtcggggct acgctatgtctgagcgagcgcgccccgcacctcctccgcgatgcgcgcactttctttggctgctcggccggtgcactgcacgcggtca ccttcgtgtgcagtctccctctcggtgcgtccacggccactacccaggccccgcgtgcggggaggggttgctacacctggggaatcg gtaacactttccggggtgcccgaagaaacctgtccggagagctctcatccttcccggtgccgttgagcactcagctggagaccctggg cctgtcacctggcgtgggatttcccggggccggctggagcagacgcgctccgagcatcttcttcctgacccgctctggcgccctggtc ctgtcagctgggtcatccctgagcagcagggaacgacgcaggtttgccgggtcctctggtccctgagccgcagaaggccgtataatg gagatcctcatggacctcgtgcggaaagccaggagccgcaacatcggcaccctccacccgttcttcaacattaacaagtgcatcaga gacgggctccaggagagcctcccagacaatgtccaccaggtcatttctggcaaggttcacatctcactcaccagggtgtcggatggg gagaacgtgctggtgtctgagttccattccaaagacgaagtcgtggatgccctggtgtgttcctgcttcattcccctcttctctggcctaat ccctccttccttccgaggcgagcggtacgtggacggaggagtgagcgacaacgtccctgtgctggatgccaaaaccaccatcacggt gtcacctttctacggtgagcatgacatctgccccaaagtcaagtccaccaacttcttccacgtgaatatcaccaacctcagcctccgcct ctgcactgggaacctccaacttctgaccagagcgctcttcccgtctgatgtgaaggtgatgggagagctgtgctatcaagggtacctgg acgccttccggttcctggaggagaatggcatctgtaacgggccacagcgcagcctgagtctgtccttggtggcgccagaagcctgctt ggaaaatggcaaacttgtgggagacaaggtgccagtcagcctatgctttacagatgagaacatctgggagacactgtcccccgagct cagcacagctctgagtgaagcgattaaggacagggagggctacctgagcaaagtctgcaacctcctgcccgtcaggatcctgtccta catcatgctgccctgcagtctgcccgtggagtcggctatcgctgcagtccacaggctggtgacatggctccctgatatccaggatgata tccagtggctacaatgggcgacatcccaggtttgtgcccgaatgacgatgtgcctgctcccctctaccagcatgagattcctgggacaa tcccaattccttggcctccattgtatcaaagggctgaaaaccaaagggaaggcacagctgtctcttcagcatgcctcttctgccagaacc actgcaaggtttggtgctcaggctgtgcaaacattctagcaatgtttgactcagtgtcaagcaggtgacaaggaacatggtgctgtgtgg ggggaacccatggcccaggtgagggcttattggtgggtgaagctgtgggtgttcaggtggtggagaaggccttaagggatgggact gacacctcagcactgaaggcaggaggaagctgtggctctgggttgcacccctgcctggctccaccctctctggcatctgtagaagtta cagctggttcttcctctcagccccatgctcccagaaataagactcagacccaaattatagttacaaataccttggccatatagctaggctc ttctcagactagctcataacttaactcattaattttaacctccatcctgccacatggctggtggcctgtgctcaggtaccatgagtccagctc ttcacatctttccggatgaatcttccataattctttctgcctcctggatgttccaccttctattccaccttttcctataggccatggttttgtttttgt tttttttttccaaatttaatttaattaattaatttatttatttttggtttttcgagacagggtttctctgtatcgccctggctgtcctggaactcactatg taagccaggctggcctcaaactcagaaatccgcctgcctctgcctcctgagtgctgggattaaaggcgtgcgcaaccatgcccggtgt ggtttttttttttttttaattgacaggtggatgcatctatataatccataacatattctctctacaggtatctattaggttttgggtgaggtgtggag ttctagggaactctgagagaaattcctggggagtaagtggtttatcaagttgattggaggagtttttaatgctatggacagacagacagaa -continued ggacaacagcatagtcggggctaccagggagttcaggccccggcatcggagatagaagcaggatggggtctttgaagagattctga gcccacacagcagaggagggactctctctttagagcttttgaggatgagggaggttgactgcaagagcctacagccaggctcgaggc aggcagggggtggggagcaggatgtaaacccccttcgatgctgacagactcacttctggggtaaaatattatgagatgcctgtcagtgt ctgtgaagagacctgagcagagtctggattctgacatcaatcatgttcttacaatactgaagacctgagagcctgcaatcttggtttgtaa attgctggtctccgtgcttccagtgaacttggacattcttctcatggttggtccaggagaggccaaagctgagggcaccctgccttccac ccccagtccagcttgaccttttatctggagcaacagtgtctagatgatgggtgggtgaggggtgctatactgtctgtccctctgggaagg gttctgttacttttggaggcagctaggaagtttctctgtgcagctgccccctggtgctgtgtggtgacctcattgcctgtgaccccaggatc acaggatctgggctaaagtggtagtccatagaaaccaaagacaatgatttggtgtttagaaagctactcttggtctgggtgaagtctggt gcttaagggctatcacaaagagcgtgtcaaaccatctctcagcctgtgagtcagtggggagcccaagggcatcagtgtttggaaactg gaatccaaaccgggcaatctcggaaggaaactgtttaggaattgtgatgggacgggccgtggctgtctctgaaaagggcctgccaga taacttattacttttaaggacacctttggctcttactaatttataaagcattttatataaacacaccagggagtgcatggtgaactacacgtat gatcagttaagtggggctagaattaggtagggagagcatcggacctctgcctcctcaacctcaacttgcttgctttctccactggctcca aatctttgtatagtcatcagccatgaccacctctctccctccccatctactaccagcagcgttaatgggaataagtacccacttctctcagg tgtactatacagctgtgggtgtggtgtgtgtttcctgtaattcacactttagaaaggaaacaagcaaacaaaagaaaccaggtgctgccc atactcctaagtgtagacagtgaaggtgtgtgtctcccatgcctgagtctcctggaggcctagtgagctccaggttcatgcaagcacatc aggaggaatcatataatctcagcacggttgatccagatgggataagaaaggactctgggagagagaatgtggttctagagacaaagt gtctaggctacacagaagataagactgtcccaaggaaagaaaagaaaccaggaactagggtgcagctcagttgtcagaggacttctc taggcttgaagcccagagtccaatctcagcaccttataaactgtggagtgacaggcagtgacatcggcctgtaatcccaacactcaag cagtagaggcaagaggatcataagttcaaggtcttccttggctatttagggagttggaggttagctctggctacatgagaccctgtctca aaaaaaaaaaaaaaaaaaagtagaaacttctgccttgctttgagctgcccctttctggacgtttctcatcagtagagaatattcctgccac cctatcagacaaaactcccactggtttggagtctctccattctcaggaacacctcaggagtcagacagtgagcagcagggagcaatgt cttgacttgtaagccccttagcaaggctggttcatttgtttattaaaagcaggtgtgggtgaatttatgcaaatgagtatgcaaactagtgg aacagcagaaggattgaatggatacaccaaaaataaccacaactgtttaagggaaaagggtccataataaatgtggggaacaaaaaa caaataaatgtgattttttta SEQ ID NO: 8 - mouse PNPLA3 (367 aa; NCBI Ref. Seq. No. XP_006520409.1)
MEILMDLVRKARSRNIGTLHPFFNINKCIRDGLQESLPDNVHQVISGKVHISLTRVSD

GENVLVSEFHSKDEVVDALVCSCFIPLFSGLIPPSFRGERYVDGGVSDNVPVLDAKTT

ITVSPFYGEHDICPKVKSTNFFHVNITNLSLRLCTGNLQLLTRALFPSDVKVMGELCY

QGYLDAFRFLEENGICNGPQRSLSLSLVAPEACLENGKLVGDKVPVSLCFTDENIWET

LSPELSTALSEAIKDREGYLSKVCNLLPVRILSYIMLPCSLPVESAIAAVHRLVTWLPDI

QDDIQWLQWATSQVCARMTMCLLPSTSMRFLGQSQFLGLHCIKGLKTKGKAQLSLQ

HASSARTTARFGAQAVQTF

SEQ ID NO: 9 - DsiRNA 1 passenger (sense) strand
UCUGCAGGUCCUCUCAGAUCUUGUG

SEQ ID NO: 10 - DsiRNA 1 guide (antisense) strand
CACAAGAUCUGAGAGGACCUGCAGAGU

SEQ ID NO: 11 - DsiRNA 2 passenger (sense) strand
AGGUCCUCUCAGAUCUUGUGCGGAA

SEQ ID NO: 12 - DsiRNA 2 guide (antisense) strand
UUCCGCACAAGAUCUGAGAGGACCUGC

SEQ ID NO: 13 - DsiRNA 3 passenger (sense) strand
AUUGGCAUCUUCCAUCCAUCCUUCA

SEQ ID NO: 14 - DsiRNA 3 guide (antisense) strand
UGAAGGAUGGAUGGAAGAUGCCAAUGU

-continued

SEQ ID NO: 15 - DsiRNA 4 passenger (sense) strand
AUCUUCCAUCCAUCCUUCAACUUAA

SEQ ID NO: 16 - DsiRNA 4 guide (antisense) strand
UUAAGUUGAAGGAUGGAUGGAAGAUGC

SEQ ID NO: 17 - DsiRNA 5 passenger (sense) strand
UCUUCCAUCCAUCCUUCAACUUAAG

SEQ ID NO: 18 - DsiRNA 5 guide (antisense) strand
CUUAAGUUGAAGGAUGGAUGGAAGAUG

SEQ ID NO: 19 - DsiRNA 6 passenger (sense) strand
CCAGAGUGUCUGAUGGGGAAAACGU

SEQ ID NO: 20 - DsiRNA 6 guide (antisense) strand
ACGUUUUCCCCAUCAGACACUCUGGUA

SEQ ID NO: 21 - DsiRNA 7 passenger (sense) strand
GAGUGUCUGAUGGGGAAAACGUUCU

SEQ ID NO: 22 - DsiRNA 7 guide (antisense) strand
AGAACGUUUUCCCCAUCAGACACUCUG

SEQ ID NO: 23 - DsiRNA 8 passenger (sense) strand
AUGGGGAAAACGUUCUGGUGUCUGA

SEQ ID NO: 24 - DsiRNA 8 guide (antisense) strand
UCAGACACCAGAACGUUUUCCCCAUCA

SEQ ID NO: 25 - DsiRNA 9 passenger (sense) strand
GGGGAAAACGUUCUGGUGUCUGACU

SEQ ID NO: 26 - DsiRNA 9 guide (antisense) strand
AGUCAGACACCAGAACGUUUUCCCCAU

SEQ ID NO: 27 - DsiRNA 10 passenger (sense) strand
GGGAAAACGUUCUGGUGUCUGACUU

SEQ ID NO: 28 - DsiRNA 10 guide (antisense) strand
AAGUCAGACACCAGAACGUUUUCCCCA

SEQ ID NO: 29 - DsiRNA 11 passenger (sense) strand
GGAAAACGUUCUGGUGUCUGACUUU

SEQ ID NO: 30 - DsiRNA 11 guide (antisense) strand
AAAGUCAGACACCAGAACGUUUUCCCC

SEQ ID NO: 31 - DsiRNA 12 passenger (sense) strand
GAAAACGUUCUGGUGUCUGACUUUC

SEQ ID NO: 32 - DsiRNA 12 guide (antisense) strand
GAAAGUCAGACACCAGAACGUUUUCCC

SEQ ID NO: 33 - DsiRNA 13 passenger (sense) strand
AAAACGUUCUGGUGUCUGACUUUCG

SEQ ID NO: 34 - DsiRNA 13 guide (antisense) strand
CGAAAGUCAGACACCAGAACGUUUUCC

SEQ ID NO: 35 - DsiRNA 14 passenger (sense) strand
AAACGUUCUGGUGUCUGACUUUCGG

SEQ ID NO: 36 - DsiRNA 14 guide (antisense) strand
CCGAAAGUCAGACACCAGAACGUUUUC

SEQ ID NO: 37 - DsiRNA 15 passenger (sense) strand
AACGUUCUGGUGUCUGACUUUCGGU

SEQ ID NO: 38 - DsiRNA 15 guide (antisense) strand
ACCGAAAGUCAGACACCAGAACGUUUU

SEQ ID NO: 39 - DsiRNA 16 passenger (sense) strand
ACGUUCUGGUGUCUGACUUUCGGUC

SEQ ID NO: 40 - DsiRNA 16 guide (antisense) strand
GACCGAAAGUCAGACACCAGAACGUUU

SEQ ID NO: 41 - DsiRNA 17 passenger (sense) strand
GUUCUGGUGUCUGACUUUCGGUCCA

-continued

SEQ ID NO: 42 - DsiRNA 17 guide (antisense) strand
UGGACCGAAAGUCAGACACCAGAACGU

SEQ ID NO: 43 - DsiRNA 18 passenger (sense) strand
GACGAAGUCGUGGAUGCCUUGGUAU

SEQ ID NO: 44 - DsiRNA 18 guide (antisense) strand
AUACCAAGGCAUCCACGACUUCGUCUU

SEQ ID NO: 45 - DsiRNA 19 passenger (sense) strand
ACGAAGUCGUGGAUGCCUUGGUAUG

SEQ ID NO: 46 - DsiRNA 19 guide (antisense) strand
CAUACCAAGGCAUCCACGACUUCGUCU

SEQ ID NO: 47 - DsiRNA 20 passenger (sense) strand
CGAAGUCGUGGAUGCCUUGGUAUGU

SEQ ID NO: 48 - DsiRNA 20 guide (antisense) strand
ACAUACCAAGGCAUCCACGACUUCGUC

SEQ ID NO: 49 - DsiRNA 21 passenger (sense) strand
CAGAGGCGUGCGAUAUGUGGAUGGA

SEQ ID NO: 50 - DsiRNA 21 guide (antisense) strand
UCCAUCCACAUAUCGCACGCCUCUGAA

SEQ ID NO: 51 - DsiRNA 22 passenger (sense) strand
GCGAUAUGUGGAUGGAGGAGUGAGU

SEQ ID NO: 52 - DsiRNA 22 guide (antisense) strand
ACUCACUCCUCCAUCCACAUAUCGCAC

SEQ ID NO: 53 - DsiRNA 23 passenger (sense) strand
GAUGGAGGAGUGAGUGACAACGUAC

SEQ ID NO: 54 - DsiRNA 23 guide (antisense) strand
GUACGUUGUCACUCACUCCUCCAUCCA

SEQ ID NO: 55 - DsiRNA 24 passenger (sense) strand
GAGGAGUGAGUGACAACGUACCCUU

SEQ ID NO: 56 - DsiRNA 24 guide (antisense) strand
AAGGGUACGUUGUCACUCACUCCUCCA

SEQ ID NO: 57 - DsiRNA 25 passenger (sense) strand
GAGUGAGUGACAACGUACCCUUCAU

SEQ ID NO: 58 - DsiRNA 25 guide (antisense) strand
AUGAAGGGUACGUUGUCACUCACUCCU

SEQ ID NO: 59 - DsiRNA 26 passenger (sense) strand
AGUGAGUGACAACGUACCCUUCAUU

SEQ ID NO: 60 - DsiRNA 26 guide (antisense) strand
AAUGAAGGGUACGUUGUCACUCACUCC

SEQ ID NO: 61 - DsiRNA 27 passenger (sense) strand
GUGAGUGACAACGUACCCUUCAUUG

SEQ ID NO: 62 - DsiRNA 27 guide (antisense) strand
CAAUGAAGGGUACGUUGUCACUCACUC

SEQ ID NO: 63 - DsiRNA 28 passenger (sense) strand
UGAGUGACAACGUACCCUUCAUUGA

SEQ ID NO: 64 - DsiRNA 28 guide (antisense) strand
UCAAUGAAGGGUACGUUGUCACUCACU

SEQ ID NO: 65 - DsiRNA 29 passenger (sense) strand
GAGUGACAACGUACCCUUCAUUGAU

SEQ ID NO: 66 - DsiRNA 29 guide (antisense) strand
AUCAAUGAAGGGUACGUUGUCACUCAC

SEQ ID NO: 67 - DsiRNA 30 passenger (sense) strand
AGUGACAACGUACCCUUCAUUGAUG

SEQ ID NO: 68 - DsiRNA 30 guide (antisense) strand
CAUCAAUGAAGGGUACGUUGUCACUCA

-continued

SEQ ID NO: 69 - DsiRNA 31 passenger (sense) strand
GUGACAACGUACCCUUCAUUGAUGC

SEQ ID NO: 70 - DsiRNA 31 guide (antisense) strand
GCAUCAAUGAAGGGUACGUUGUCACUC

SEQ ID NO: 71 - DsiRNA 32 passenger (sense) strand
UGACAACGUACCCUUCAUUGAUGCC

SEQ ID NO: 72 - DsiRNA 32 guide (antisense) strand
GGCAUCAAUGAAGGGUACGUUGUCACU

SEQ ID NO: 73 - DsiRNA 33 passenger (sense) strand
GACAACGUACCCUUCAUUGAUGCCA

SEQ ID NO: 74 - DsiRNA 33 guide (antisense) strand
UGGCAUCAAUGAAGGGUACGUUGUCAC

SEQ ID NO: 75 - DsiRNA 34 passenger (sense) strand
CAACGUACCCUUCAUUGAUGCCAAA

SEQ ID NO: 76 - DsiRNA 34 guide (antisense) strand
UUUGGCAUCAAUGAAGGGUACGUUGUC

SEQ ID NO: 77 - DsiRNA 35 passenger (sense) strand
AACGUACCCUUCAUUGAUGCCAAAA

SEQ ID NO: 78 - DsiRNA 35 guide (antisense) strand
UUUUGGCAUCAAUGAAGGGUACGUUGU

SEQ ID NO: 79 - DsiRNA 36 passenger (sense) strand
ACGUACCCUUCAUUGAUGCCAAAAC

SEQ ID NO: 80 - DsiRNA 36 guide (antisense) strand
GUUUUGGCAUCAAUGAAGGGUACGUUG

SEQ ID NO: 81 - DsiRNA 37 passenger (sense) strand
CGUACCCUUCAUUGAUGCCAAAACA

SEQ ID NO: 82 - DsiRNA 37 guide (antisense) strand
UGUUUUGGCAUCAAUGAAGGGUACGUU

SEQ ID NO: 83 - DsiRNA 38 passenger (sense) strand
UACCCUUCAUUGAUGCCAAAACAAC

SEQ ID NO: 84 - DsiRNA 38 guide (antisense) strand
GUUGUUUUGGCAUCAAUGAAGGGUACG

SEQ ID NO: 85 - DsiRNA 39 passenger (sense) strand
UUGAUGCCAAAACAACCAUCACCGU

SEQ ID NO: 86 - DsiRNA 39 guide (antisense) strand
ACGGUGAUGGUUGUUUUGGCAUCAAUG

SEQ ID NO: 87 - DsiRNA 40 passenger (sense) strand
GAUGCCAAAACAACCAUCACCGUGU

SEQ ID NO: 88 - DsiRNA 40 guide (antisense) strand
ACACGGUGAUGGUUGUUUUGGCAUCAA

SEQ ID NO: 89 - DsiRNA 41 passenger (sense) strand
AUGGGGAGUACGACAUCUGCCCUAA

SEQ ID NO: 90 - DsiRNA 41 guide (antisense) strand
UUAGGGCAGAUGUCGUACUCCCCAUAG

SEQ ID NO: 91 - DsiRNA 42 passenger (sense) strand
GUACGACAUCUGCCCUAAAGUCAAG

SEQ ID NO: 92 - DsiRNA 42 guide (antisense) strand
CUUGACUUUAGGGCAGAUGUCGUACUC

SEQ ID NO: 93 - DsiRNA 43 passenger (sense) strand
GACAUCUGCCCUAAAGUCAAGUCCA

SEQ ID NO: 94 - DsiRNA 43 guide (antisense) strand
UGGACUUGACUUUAGGGCAGAUGUCGU

SEQ ID NO: 95 - DsiRNA 44 passenger (sense) strand
ACAUCUGCCCUAAAGUCAAGUCCAC

-continued

SEQ ID NO: 96 - DsiRNA 44 guide (sense) strand
GUGGACUUGACUUUAGGGCAGAUGUCG

SEQ ID NO: 97 - DsiRNA 45 passenger (sense) strand
GUCAAGUCCACGAACUUUCUUCAUG

SEQ ID NO: 98 - DsiRNA 45 guide (antisense) strand
CAUGAAGAAAGUUCGUGGACUUGACUU

SEQ ID NO: 99 - DsiRNA 46 passenger (sense) strand
UCAAGUCCACGAACUUUCUUCAUGU

SEQ ID NO: 100 - DsiRNA 46 guide (antisense) strand
ACAUGAAGAAAGUUCGUGGACUUGACU

SEQ ID NO: 101 - DsiRNA 47 passenger (sense) strand
CAAGUCCACGAACUUUCUUCAUGUG

SEQ ID NO: 102 - DsiRNA 47 guide (antisense) strand
CACAUGAAGAAAGUUCGUGGACUUGAC

SEQ ID NO: 103 - DsiRNA 48 passenger (sense) strand
GUCCACGAACUUUCUUCAUGUGGAC

SEQ ID NO: 104 - DsiRNA 48 guide (antisense) strand
GUCCACAUGAAGAAAGUUCGUGGACUU

SEQ ID NO: 105 - DsiRNA 49 passenger (sense) strand
CCACGAACUUUCUUCAUGUGGACAU

SEQ ID NO: 106 - DsiRNA 49 guide (antisense) strand
AUGUCCACAUGAAGAAAGUUCGUGGAC

SEQ ID NO: 107 - DsiRNA 50 passenger (sense) strand
CACGAACUUUCUUCAUGUGGACAUC

SEQ ID NO: 108 - DsiRNA 50 guide (antisense) strand
GAUGUCCACAUGAAGAAAGUUCGUGGA

SEQ ID NO: 109 - DsiRNA 51 passenger (sense) strand
ACGAACUUUCUUCAUGUGGACAUCA

SEQ ID NO: 110 - DsiRNA 51 guide (antisense) strand
UGAUGUCCACAUGAAGAAAGUUCGUGG

SEQ ID NO: 111 - DsiRNA 52 passenger (sense) strand
CGAACUUUCUUCAUGUGGACAUCAC

SEQ ID NO: 112 - DsiRNA 52 guide (antisense) strand
GUGAUGUCCACAUGAAGAAAGUUCGUG

SEQ ID NO: 113 - DsiRNA 53 passenger (sense) strand
GAACUUUCUUCAUGUGGACAUCACC

SEQ ID NO: 114 - DsiRNA 53 guide (antisense) strand
GGUGAUGUCCACAUGAAGAAAGUUCGU

SEQ ID NO: 115 - DsiRNA 54 passenger (sense) strand
AACUUUCUUCAUGUGGACAUCACCA

SEQ ID NO: 116 - DsiRNA 54 guide (antisense) strand
UGGUGAUGUCCACAUGAAGAAAGUUCG

SEQ ID NO: 117 - DsiRNA 55 passenger (sense) strand
ACUUUCUUCAUGUGGACAUCACCAA

SEQ ID NO: 118 - DsiRNA 55 guide (antisense) strand
UUGGUGAUGUCCACAUGAAGAAAGUUC

SEQ ID NO: 119 - DsiRNA 56 passenger (sense) strand
CUUUCUUCAUGUGGACAUCACCAAG

SEQ ID NO: 120 - DsiRNA 56 guide (antisense) strand
CUUGGUGAUGUCCACAUGAAGAAAGUU

SEQ ID NO: 121 - DsiRNA 57 passenger (sense) strand
UUUCUUCAUGUGGACAUCACCAAGC

SEQ ID NO: 122 - DsiRNA 57 guide (antisense) strand
GCUUGGUGAUGUCCACAUGAAGAAAGU

-continued

SEQ ID NO: 123 - DsiRNA 58 passenger (sense) strand
UUCUUCAUGUGGACAUCACCAAGCU

SEQ ID NO: 124 - DsiRNA 58 guide (antisense) strand
AGCUUGGUGAUGUCCACAUGAAGAAAG

SEQ ID NO: 125 - DsiRNA 59 passenger (sense) strand
CUUCAUGUGGACAUCACCAAGCUCA

SEQ ID NO: 126 - DsiRNA 59 guide (antisense) strand
UGAGCUUGGUGAUGUCCACAUGAAGAA

SEQ ID NO: 127 - DsiRNA 60 passenger (sense) strand
UUCAUGUGGACAUCACCAAGCUCAG

SEQ ID NO: 128 - DsiRNA 60 guide (antisense) strand
CUGAGCUUGGUGAUGUCCACAUGAAGA

SEQ ID NO: 129 - DsiRNA 61 passenger (sense) strand
UCAUGUGGACAUCACCAAGCUCAGU

SEQ ID NO: 130 - DsiRNA 61 guide (antisense) strand
ACUGAGCUUGGUGAUGUCCACAUGAAG

SEQ ID NO: 131 - DsiRNA 62 passenger (sense) strand
CAUGUGGACAUCACCAAGCUCAGUC

SEQ ID NO: 132 - DsiRNA 62 guide (antisense) strand
GACUGAGCUUGGUGAUGUCCACAUGAA

SEQ ID NO: 133 - DsiRNA 63 passenger (sense) strand
AUGUGGACAUCACCAAGCUCAGUCU

SEQ ID NO: 134 - DsiRNA 63 guide (antisense) strand
AGACUGAGCUUGGUGAUGUCCACAUGA

SEQ ID NO: 135 - DsiRNA 64 passenger (sense) strand
UGUGGACAUCACCAAGCUCAGUCUA

SEQ ID NO: 136 - DsiRNA 64 guide (antisense) strand
UAGACUGAGCUUGGUGAUGUCCACAUG

SEQ ID NO: 137 - DsiRNA 65 passenger (sense) strand
GUGGACAUCACCAAGCUCAGUCUAC

SEQ ID NO: 138 - DsiRNA 65 guide (antisense) strand
GUAGACUGAGCUUGGUGAUGUCCACAU

SEQ ID NO: 139 - DsiRNA 66 passenger (sense) strand
UGGACAUCACCAAGCUCAGUCUACG

SEQ ID NO: 140 - DsiRNA 66 guide (antisense) strand
CGUAGACUGAGCUUGGUGAUGUCCACA

SEQ ID NO: 141 - DsiRNA 67 passenger (sense) strand
AGCUUUUGUCCCCCCGGAUCUCAAG

SEQ ID NO: 142 - DsiRNA 67 guide (antisense) strand
CUUGAGAUCCGGGGGGACAAAAGCUCU

SEQ ID NO: 143 - DsiRNA 68 passenger (sense) strand
AAGGUGCUGGGAGAGAUAUGCCUUC

SEQ ID NO: 144 - DsiRNA 68 guide (antisense) strand
GAAGGCAUAUCUCUCCCAGCACCUUGA

SEQ ID NO: 145 - DsiRNA 69 passenger (sense) strand
GGGAGAGAUAUGCCUUCGAGGAUAU

SEQ ID NO: 146 - DsiRNA 69 guide (antisense) strand
AUAUCCUCGAAGGCAUAUCUCUCCCAG

SEQ ID NO: 147 - DsiRNA 70 passenger (sense) strand
GGAGAGAUAUGCCUUCGAGGAUAUU

SEQ ID NO: 148 - DsiRNA 70 guide (antisense) strand
AAUAUCCUCGAAGGCAUAUCUCUCCCA

SEQ ID NO: 149 - DsiRNA 71 passenger (sense) strand
AGAGAUAUGCCUUCGAGGAUAUUUG

-continued

SEQ ID NO: 150 - DsiRNA 71 guide (antisense) strand
CAAAUAUCCUCGAAGGCAUAUCUCUCC

SEQ ID NO: 151 - DsiRNA 72 passenger (sense) strand
GAGAUAUGCCUUCGAGGAUAUUUGG

SEQ ID NO: 152 - DsiRNA 72 guide (antisense) strand
CCAAAUAUCCUCGAAGGCAUAUCUCUC

SEQ ID NO: 153 - DsiRNA 73 passenger (sense) strand
AGAUAUGCCUUCGAGGAUAUUUGGA

SEQ ID NO: 154 - DsiRNA 73 guide (antisense) strand
UCCAAAUAUCCUCGAAGGCAUAUCUCU

SEQ ID NO: 155 - DsiRNA 74 passenger (sense) strand
GAUAUGCCUUCGAGGAUAUUUGGAU

SEQ ID NO: 156 - DsiRNA 74 guide (antisense) strand
AUCCAAAUAUCCUCGAAGGCAUAUCUC

SEQ ID NO: 157 - DsiRNA 75 passenger (sense) strand
AUAUGCCUUCGAGGAUAUUUGGAUG

SEQ ID NO: 158 - DsiRNA 75 guide (antisense) strand
CAUCCAAAUAUCCUCGAAGGCAUAUCU

SEQ ID NO: 159 - DsiRNA 76 passenger (sense) strand
AUGCCUUCGAGGAUAUUUGGAUGCA

SEQ ID NO: 160 - DsiRNA 76 guide (antisense) strand
UGCAUCCAAAUAUCCUCGAAGGCAUAU

SEQ ID NO: 161 - DsiRNA 77 passenger (sense) strand
UGCCUUCGAGGAUAUUUGGAUGCAU

SEQ ID NO: 162 - DsiRNA 77 guide (antisense) strand
AUGCAUCCAAAUAUCCUCGAAGGCAUA

SEQ ID NO: 163 - DsiRNA 78 passenger (sense) strand
GCCUUCGAGGAUAUUUGGAUGCAUU

SEQ ID NO: 164 - DsiRNA 78 guide (antisense) strand
AAUGCAUCCAAAUAUCCUCGAAGGCAU

SEQ ID NO: 165 - DsiRNA 79 passenger (sense) strand
UCAGGUUCUUGGAAGAGAAGGGCAU

SEQ ID NO: 166 - DsiRNA 79 guide (antisense) strand
AUGCCCUUCUCUUCCAAGAACCUGAAU

SEQ ID NO: 167 - DsiRNA 80 passenger (sense) strand
CAGGUUCUUGGAAGAGAAGGGCAUC

SEQ ID NO: 168 - DsiRNA 80 guide (antisense) strand
GAUGCCCUUCUCUUCCAAGAACCUGAA

SEQ ID NO: 169 - DsiRNA 81 passenger (sense) strand
AGGUUCUUGGAAGAGAAGGGCAUCU

SEQ ID NO: 170 - DsiRNA 81 guide (antisense) strand
AGAUGCCCUUCUCUUCCAAGAACCUGA

SEQ ID NO: 171 - DsiRNA 82 passenger (sense) strand
GGUUCUUGGAAGAGAAGGGCAUCUG

SEQ ID NO: 172 - DsiRNA 82 guide (antisense) strand
CAGAUGCCCUUCUCUUCCAAGAACCUG

SEQ ID NO: 173 - DsiRNA 83 passenger (sense) strand
UGGAAGAGAAGGGCAUCUGCAACAG

SEQ ID NO: 174 - DsiRNA 83 guide (antisense) strand
CUGUUGCAGAUGCCCUUCUCUUCCAAG

SEQ ID NO: 175 - DsiRNA 84 passenger (sense) strand
UGAAGUCAUCCUCAGAAGGGAUGGA

SEQ ID NO: 176 - DsiRNA 84 guide (antisense) strand
UCCAUCCCUUCUGAGGAUGACUUCAGG

-continued

SEQ ID NO: 177 - DsiRNA 85 passenger (sense) strand
GAAGUCAUCCUCAGAAGGGAUGGAU

SEQ ID NO: 178 - DsiRNA 85 guide (antisense) strand
AUCCAUCCCUUCUGAGGAUGACUUCAG

SEQ ID NO: 179 - DsiRNA 86 passenger (sense) strand
AAGUCAUCCUCAGAAGGGAUGGAUC

SEQ ID NO: 180 - DsiRNA 86 guide (antisense) strand
GAUCCAUCCCUUCUGAGGAUGACUUCA

SEQ ID NO: 181 - DsiRNA 87 passenger (sense) strand
GUCAUCCUCAGAAGGGAUGGAUCCU

SEQ ID NO: 182 - DsiRNA 87 guide (antisense) strand
AGGAUCCAUCCCUUCUGAGGAUGACUU

SEQ ID NO: 183 - DsiRNA 88 passenger (sense) strand
CAUCCUCAGAAGGGAUGGAUCCUGA

SEQ ID NO: 184 - DsiRNA 88 guide (antisense) strand
UCAGGAUCCAUCCCUUCUGAGGAUGAC

SEQ ID NO: 185 - DsiRNA 89 passenger (sense) strand
AUCCUCAGAAGGGAUGGAUCCUGAG

SEQ ID NO: 186 - DsiRNA 89 guide (antisense) strand)
CUCAGGAUCCAUCCCUUCUGAGGAUGA SEQ ID NO: 187 - DsiRNA 90 passenger (sense) strand
CUAGACCACCUGCGUCUCAGCAUCC SEQ ID NO: 188 - DsiRNA 90 guide (antisense) strand
GGAUGCUGAGACGCAGGUGGUCUAGCA SEQ ID NO: 189 - DsiRNA 91 passenger (sense) strand
AGUGAAGAAAUGAAAGACAAAGGUG SEQ ID NO: 190 - DsiRNA 91 guide (antisense) strand
CACCUUUGUCUUUCAUUUCUUCACUCA SEQ ID NO: 191 - DsiRNA 92 passenger (sense) strand
GUGAAGAAAUGAAAGACAAAGGUGG SEQ ID NO: 192 - DsiRNA 92 guide (antisense) strand
CCACCUUUGUCUUUCAUUUCUUCACUC SEQ ID NO: 193 - DsiRNA 93 passenger (sense) strand
UGAAGAAAUGAAAGACAAAGGUGGA SEQ ID NO: 194 - DsiRNA 93 guide (antisense) strand
UCCACCUUUGUCUUUCAUUUCUUCACU SEQ ID NO: 195 - DsiRNA 94 passenger (sense) strand
GAAGAAAUGAAAGACAAAGGUGGAU SEQ ID NO: 196 - DsiRNA 94 guide (antisense) strand
AUCCACCUUUGUCUUUCAUUUCUUCAC SEQ ID NO: 197 - DsiRNA 95 passenger (sense) strand
AAGAAAUGAAAGACAAAGGUGGAUA SEQ ID NO: 198 - DsiRNA 95 guide (antisense) strand
UAUCCACCUUUGUCUUUCAUUUCUUCA SEQ ID NO: 199 - DsiRNA 96 passenger (sense) strand
AGAAAUGAAAGACAAAGGUGGAUAC SEQ ID NO: 200 - DsiRNA 96 guide (antisense) strand
GUAUCCACCUUUGUCUUUCAUUUCUUC SEQ ID NO: 201 - DsiRNA 97 passenger (sense) strand
GAAAUGAAAGACAAAGGUGGAUACA SEQ ID NO: 202 - DsiRNA 97 guide (antisense) strand
UGUAUCCACCUUUGUCUUUCAUUUCUU SEQ ID NO: 203 - DsiRNA 98 passenger (sense) strand
AAAUGAAAGACAAAGGUGGAUACAU -continued SEQ ID NO: 204 - DsiRNA 98 guide (antisense) strand
AUGUAUCCACCUUUGUCUUUCAUUUCU SEQ ID NO: 205 - DsiRNA 99 passenger (sense) strand
AAUGAAAGACAAAGGUGGAUACAUG SEQ ID NO: 206 - DsiRNA 99 guide (antisense) strand
CAUGUAUCCACCUUUGUCUUUCAUUUC SEQ ID NO: 207 - DsiRNA 100 passenger (sense) strand
AUGAAAGACAAAGGUGGAUACAUGA SEQ ID NO: 208 - DsiRNA 100 guide (antisense) strand
UCAUGUAUCCACCUUUGUCUUUCAUUU SEQ ID NO: 209 - DsiRNA 101 passenger (sense) strand
UGAAAGACAAAGGUGGAUACAUGAG SEQ ID NO: 210 - DsiRNA 101 guide (antisense) strand
CUCAUGUAUCCACCUUUGUCUUUCAUU SEQ ID NO: 211 - DsiRNA 102 passenger (sense) strand
GAAAGACAAAGGUGGAUACAUGAGC SEQ ID NO: 212 - DsiRNA 102 guide (antisense) strand
GCUCAUGUAUCCACCUUUGUCUUUCAU SEQ ID NO: 213 - DsiRNA 103 passenger (sense) strand
AAGACAAAGGUGGAUACAUGAGCAA SEQ ID NO: 214 - DsiRNA 103 guide (antisense) strand
UUGCUCAUGUAUCCACCUUUGUCUUUC SEQ ID NO: 215 - DsiRNA 104 passenger (sense) strand
AGACAAAGGUGGAUACAUGAGCAAG SEQ ID NO: 216 - DsiRNA 104 guide (antisense) strand
CUUGCUCAUGUAUCCACCUUUGUCUUU SEQ ID NO: 217 - DsiRNA 105 passenger (sense) strand
GACAAAGGUGGAUACAUGAGCAAGA SEQ ID NO: 218 - DsiRNA 105 guide (antisense) strand
UCUUGCUCAUGUAUCCACCUUUGUCUU SEQ ID NO: 219 - DsiRNA 106 passenger (sense) strand
ACAAAGGUGGAUACAUGAGCAAGAU SEQ ID NO: 220 - DsiRNA 106 guide (antisense) strand
AUCUUGCUCAUGUAUCCACCUUUGUCU SEQ ID NO: 221 - DsiRNA 107 passenger (sense) strand
AAGGUGGAUACAUGAGCAAGAUUUG SEQ ID NO: 222 - DsiRNA 107 guide (antisense) strand
CAAAUCUUGCUCAUGUAUCCACCUUUG SEQ ID NO: 223 - DsiRNA 108 passenger (sense) strand
AGGUGGAUACAUGAGCAAGAUUUGC SEQ ID NO: 224 - DsiRNA 108 guide (antisense) strand
GCAAAUCUUGCUCAUGUAUCCACCUUU SEQ ID NO: 225 - DsiRNA 109 passenger (sense) strand
UGGAUACAUGAGCAAGAUUUGCAAC SEQ ID NO: 226 - DsiRNA 109 guide (antisense) strand
GUUGCAAAUCUUGCUCAUGUAUCCACC SEQ ID NO: 227 - DsiRNA 110 passenger (sense) strand
GGAUACAUGAGCAAGAUUUGCAACU SEQ ID NO: 228 - DsiRNA 110 guide (antisense) strand
AGUUGCAAAUCUUGCUCAUGUAUCCAC SEQ ID NO: 229 - DsiRNA 111 passenger (sense) strand
GAUACAUGAGCAAGAUUUGCAACUU SEQ ID NO: 230 - DsiRNA 111 guide (antisense) strand
AAGUUGCAAAUCUUGCUCAUGUAUCCA -continued SEQ ID NO: 231 - DsiRNA 112 passenger (sense) strand
AUACAUGAGCAAGAUUUGCAACUUG SEQ ID NO: 232 -DsiRNA 112 guide (antisense) strand
CAAGUUGCAAAUCUUGCUCAUGUAUCC SEQ ID NO: 233 - DsiRNA 113 passenger (sense) strand
UACAUGAGCAAGAUUUGCAACUUGC SEQ ID NO: 234 - DsiRNA 113 guide (antisense) strand
GCAAGUUGCAAAUCUUGCUCAUGUAUC SEQ ID NO: 235 - DsiRNA 114 passenger (sense) strand
ACAUGAGCAAGAUUUGCAACUUGCU SEQ ID NO: 236 - DsiRNA 114 guide (antisense) strand
AGCAAGUUGCAAAUCUUGCUCAUGUAU SEQ ID NO: 237 - DsiRNA 115 passenger (sense) strand
CAUGAGCAAGAUUUGCAACUUGCUA SEQ ID NO: 238 - DsiRNA 115 guide (antisense) strand
UAGCAAGUUGCAAAUCUUGCUCAUGUA SEQ ID NO: 239: DsiRNA 116 passenger (sense) strand
AUGAGCAAGAUUUGCAACUUGCUAC SEQ ID NO: 240 - DsiRNA 116 guide (antisense) strand
GUAGCAAGUUGCAAAUCUUGCUCAUGU SEQ ID NO: 241 - DsiRNA 117 passenger (sense) strand
UGAGCAAGAUUUGCAACUUGCUACC SEQ ID NO: 242 - DsiRNA 117 guide (antisense) strand
GGUAGCAAGUUGCAAAUCUUGCUCAUG SEQ ID NO: 243 - DsiRNA 118 passenger (sense) strand
GAGCAAGAUUUGCAACUUGCUACCC SEQ ID NO: 244 - DsiRNA 118 guide (antisense) strand
GGGUAGCAAGUUGCAAAUCUUGCUCAU SEQ ID NO: 245 - DsiRNA 119 passenger (sense) strand
AGCAAGAUUUGCAACUUGCUACCCA SEQ ID NO: 246 - DsiRNA 119 guide (antisense) strand
UGGGUAGCAAGUUGCAAAUCUUGCUCA SEQ ID NO: 247 - DsiRNA 120 passenger (sense) strand
GCAAGAUUUGCAACUUGCUACCCAU SEQ ID NO: 248 - DsiRNA 120 guide (antisense) strand
AUGGGUAGCAAGUUGCAAAUCUUGCUC SEQ ID NO: 249 - DsiRNA 121 passenger (sense) strand
CAAGAUUUGCAACUUGCUACCCAUU SEQ ID NO: 250 - DsiRNA 121 guide (antisense) strand
AAUGGGUAGCAAGUUGCAAAUCUUGCU SEQ ID NO: 251 - DsiRNA 122 passenger (sense) strand
AAGAUUUGCAACUUGCUACCCAUUA SEQ ID NO: 252 - DsiRNA 122 guide (antisense) strand
UAAUGGGUAGCAAGUUGCAAAUCUUGC SEQ ID NO: 253 - DsiRNA 123 passenger (sense) strand
AGAUUUGCAACUUGCUACCCAUUAG SEQ ID NO: 254 - DsiRNA 123 guide (antisense) strand
CUAAUGGGUAGCAAGUUGCAAAUCUUG SEQ ID NO: 255 - DsiRNA 124 passenger (sense) strand
GAUUUGCAACUUGCUACCCAUUAGG SEQ ID NO: 256 - DsiRNA 124 guide (antisense) strand
CCUAAUGGGUAGCAAGUUGCAAAUCUU SEQ ID NO: 257 - DsiRNA 125 passenger (sense) strand
AUUUGCAACUUGCUACCCAUUAGGA -continued SEQ ID NO: 258 - DsiRNA 125 guide (antisense) strand
UCCUAAUGGGUAGCAAGUUGCAAAUCU SEQ ID NO: 259 - DsiRNA 126 passenger (sense) strand
UUUGCAACUUGCUACCCAUUAGGAU SEQ ID NO: 260 - DsiRNA 126 guide (antisense) strand
AUCCUAAUGGGUAGCAAGUUGCAAAUC SEQ ID NO: 261 - DsiRNA 127 passenger (sense) strand
UUGCAACUUGCUACCCAUUAGGAUA SEQ ID NO: 262 - DsiRNA 127 guide (antisense) strand
UAUCCUAAUGGGUAGCAAGUUGCAAAU SEQ ID NO: 263 - DsiRNA 128 passenger (sense) strand
UGCAACUUGCUACCCAUUAGGAUAA SEQ ID NO: 264 - DsiRNA 128 guide (antisense) strand
UUAUCCUAAUGGGUAGCAAGUUGCAAA SEQ ID NO: 265 - DsiRNA 129 - passenger (sense) strand
GCAACUUGCUACCCAUUAGGAUAAU SEQ ID NO: 266 - DsiRNA 129 guide (antisense) strand
AUUAUCCUAAUGGGUAGCAAGUUGCAA SEQ ID NO: 267 - DsiRNA 130 passenger (sense) strand
CAACUUGCUACCCAUUAGGAUAAUG SEQ ID NO: 268 - DsiRNA 130 guide (antisense) strand
CAUUAUCCUAAUGGGUAGCAAGUUGCA SEQ ID NO: 269 - DsiRNA 131 passenger (sense) strand
CUUGCUACCCAUUAGGAUAAUGUCU SEQ ID NO: 270 - DsiRNA 131 guide (antisense) strand
AGACAUUAUCCUAAUGGGUAGCAAGUU SEQ ID NO: 271 - DsiRNA 132 passenger (sense) strand
UUGCUACCCAUUAGGAUAAUGUCUU SEQ ID NO: 272 - DsiRNA 132 guide (antisense) strand
AAGACAUUAUCCUAAUGGGUAGCAAGU SEQ ID NO: 273 - DsiRNA 133 passenger (sense) strand
UGCUACCCAUUAGGAUAAUGUCUUA SEQ ID NO: 274 - DsiRNA 133 guide (antisense) strand
UAAGACAUUAUCCUAAUGGGUAGCAAG SEQ ID NO: 275 - DsiRNA 134 passenger (sense) strand
AUUAGGAUAAUGUCUUAUGUAAUGC SEQ ID NO: 276 - DsiRNA 134 guide (antisense) strand
GCAUUACAUAAGACAUUAUCCUAAUGG SEQ ID NO: 277 - DsiRNA 135 passenger (sense) strand
UUAGGAUAAUGUCUUAUGUAAUGCU SEQ ID NO: 278 - DsiRNA 135 guide (antisense) strand
AGCAUUACAUAAGACAUUAUCCUAAUG SEQ ID NO: 279 - DsiRNA 136 passenger (sense) strand
CUGUGGAAUCUGCCAUUGCGAUUGU SEQ ID NO: 280 - DsiRNA 136 guide (antisense) strand
ACAAUCGCAAUGGCAGAUUCCACAGGC SEQ ID NO: 281 - DsiRNA 137 passenger (sense) strand
GGAAUCUGCCAUUGCGAUUGUCCAG SEQ ID NO: 282 - DsiRNA 137 guide (antisense) strand
CUGGACAAUCGCAAUGGCAGAUUCCAC SEQ ID NO: 283 - DsiRNA 138 passenger (sense) strand
GAAUCUGCCAUUGCGAUUGUCCAGA SEQ ID NO: 284 - DsiRNA 138 guide (antisense) strand
UCUGGACAAUCGCAAUGGCAGAUUCCA -continued SEQ ID NO: 285 - DsiRNA 139 passenger (sense) strand
AAUCUGCCAUUGCGAUUGUCCAGAG SEQ ID NO: 286 - DsiRNA 139 guide (antisense) strand
CUCUGGACAAUCGCAAUGGCAGAUUCC SEQ ID NO: 287 - DsiRNA 140 passenger (sense) strand
AUCUGCCAUUGCGAUUGUCCAGAGA SEQ ID NO: 288 - DsiRNA 140 guide (antisense) strand
UCUCUGGACAAUCGCAAUGGCAGAUUC SEQ ID NO: 289 - DsiRNA 141 passenger (sense) strand
CCAUUGCGAUUGUCCAGAGACUGGU SEQ ID NO: 290 - DsiRNA 141 guide (antisense) strand
ACCAGUCUCUGGACAAUCGCAAUGGCA SEQ ID NO: 291 - DsiRNA 142 passenger (sense) strand
CAUUGCGAUUGUCCAGAGACUGGUG SEQ ID NO: 292 - DsiRNA 142 guide (antisense) strand
CACCAGUCUCUGGACAAUCGCAAUGGC SEQ ID NO: 293 - DsiRNA 143 passenger (sense) strand
AUUGCGAUUGUCCAGAGACUGGUGA SEQ ID NO: 294 - DsiRNA 143 guide (antisense) strand
UCACCAGUCUCUGGACAAUCGCAAUGG SEQ ID NO: 295 - DsiRNA 144 passenger (sense) strand
UUGCGAUUGUCCAGAGACUGGUGAC SEQ ID NO: 296 - DsiRNA 144 guide (antisense) strand
GUCACCAGUCUCUGGACAAUCGCAAUG SEQ ID NO: 297 - DsiRNA 145 passenger (sense) strand
UGCGAUUGUCCAGAGACUGGUGACA SEQ ID NO: 298 - DsiRNA 145 guide (antisense) strand
UGUCACCAGUCUCUGGACAAUCGCAAU SEQ ID NO: 299 - DsiRNA 146 passenger (sense) strand
GCGAUUGUCCAGAGACUGGUGACAU SEQ ID NO: 300 - DsiRNA 146 guide (antisense) strand
AUGUCACCAGUCUCUGGACAAUCGCAA SEQ ID NO: 301 - DsiRNA 147 passenger (sense) strand
CGAUUGUCCAGAGACUGGUGACAUG SEQ ID NO: 302 - DsiRNA 147 guide (antisense) strand
CAUGUCACCAGUCUCUGGACAAUCGCA SEQ ID NO: 303 - DsiRNA 148 passenger (sense)
AUUGUCCAGAGACUGGUGACAUGGC SEQ ID NO: 304 - DsiRNA 148 guide (antisense) strand
GCCAUGUCACCAGUCUCUGGACAAUCG SEQ ID NO: 305 - DsiRNA 149 passenger (sense) strand
GUCCAGAGACUGGUGACAUGGCUUC SEQ ID NO: 306 - DsiRNA 149 guide (antisense) strand
GAAGCCAUGUCACCAGUCUCUGGACAA SEQ ID NO: 307 - DsiRNA 150 passenger (sense) strand
CCAGAGACUGGUGACAUGGCUUCCA SEQ ID NO: 308 - DsiRNA 150 guide (antisense) strand
UGGAAGCCAUGUCACCAGUCUCUGGAC SEQ ID NO: 309 - DsiRNA 151 passenger (sense)
CAGAGACUGGUGACAUGGCUUCCAG SEQ ID NO: 310 - DsiRNA 151 guide (antisense) strand
CUGGAAGCCAUGUCACCAGUCUCUGGA SEQ ID NO: 311 - DsiRNA 152 passenger (sense) strand
AGAGACUGGUGACAUGGCUUCCAGA -continued SEQ ID NO: 312 - DsiRNA 152 guide (antisense) strand
UCUGGAAGCCAUGUCACCAGUCUCUGG SEQ ID NO: 313 - DsiRNA 153 passenger (sense) strand
GAGACUGGUGACAUGGCUUCCAGAU SEQ ID NO: 314 - DsiRNA 153 guide (antisense) strand
AUCUGGAAGCCAUGUCACCAGUCUCUG SEQ ID NO: 315 - DsiRNA 154 passenger (sense) strand
AGACUGGUGACAUGGCUUCCAGAUA SEQ ID NO: 316 - DsiRNA 154 guide (antisense) strand
UAUCUGGAAGCCAUGUCACCAGUCUCU SEQ ID NO: 317 - DsiRNA 155 passenger (sense) strand
GACUGGUGACAUGGCUUCCAGAUAU SEQ ID NO: 318 - DsiRNA 155 guide (antisense) strand
AUAUCUGGAAGCCAUGUCACCAGUCUC SEQ ID NO: 319 - DsiRNA 156 passenger (sense) strand
ACUGGUGACAUGGCUUCCAGAUAUG SEQ ID NO: 320 - DsiRNA 156 guide (antisense) strand
CAUAUCUGGAAGCCAUGUCACCAGUCU SEQ ID NO: 321 - DsiRNA 157 passenger (sense) strand
CUGGUGACAUGGCUUCCAGAUAUGC SEQ ID NO: 322 - DsiRNA 157 guide (antisense) strand
GCAUAUCUGGAAGCCAUGUCACCAGUC SEQ ID NO: 323 - DsiRNA 158 passenger (sense) strand
GACAUGGCUUCCAGAUAUGCCCGAC SEQ ID NO: 324 - DsiRNA 158 guide (antisense) strand
GUCGGGCAUAUCUGGAAGCCAUGUCAC SEQ ID NO: 325 - DsiRNA 159 passenger (sense) strand
CAUGGCUUCCAGAUAUGCCCGACGA SEQ ID NO: 326 - DsiRNA 159 guide (antisense) strand
UCGUCGGGCAUAUCUGGAAGCCAUGUC SEQ ID NO: 327 - DsiRNA 160 passenger (sense) strand
CAGAUAUGCCCGACGAUGUCCUGUG SEQ ID NO: 328 - DsiRNA 160 guide (antisense) strand
CACAGGACAUCGUCGGGCAUAUCUGGA SEQ ID NO: 329 - DsiRNA 161 passenger (sense) strand
CUCACAGGUGUUCACUCGAGUGCUG SEQ ID NO: 330 - DsiRNA 161 guide (antisense) strand
CAGCACUCGAGUGAACACCUGUGAGGU SEQ ID NO: 331 - DsiRNA 162 passenger (sense) strand
CACUCGAGUGCUGAUGUGUCUGCUC SEQ ID NO: 332 - DsiRNA 162 guide (antisense) strand
GAGCAGACACAUCAGCACUCGAGUGAA SEQ ID NO: 333 - DsiRNA 163 passenger (sense) strand
CUCGAGUGCUGAUGUGUCUGCUCCC SEQ ID NO: 334 - DsiRNA 163 guide (antisense) strand
GGGAGCAGACACAUCAGCACUCGAGUG SEQ ID NO: 335 - DsiRNA 164 passenger (sense) strand
CCCAAAUGCCAGUGAGCAGCCAACA SEQ ID NO: 336 - DsiRNA 164 guide (antisense) strand
UGUUGGCUGCUCACUGGCAUUUGGGAC SEQ ID NO: 337 - DsiRNA 165 passenger (sense) strand
UCAGGUCCAGCCUGAACUUCUUCUU SEQ ID NO: 338 - DsiRNA 165 guide (antisense) strand
AAGAAGAAGUUCAGGCUGGACCUGAGG -continued SEQ ID NO: 339 - DsiRNA 166 passenger (sense) strand
CAGGUCCAGCCUGAACUUCUUCUUG SEQ ID NO: 340 - DsiRNA 166 guide (antisense) strand
CAAGAAGAAGUUCAGGCUGGACCUGAG SEQ ID NO: 341 - DsiRNA 167 passenger (sense) strand
AGGUCCAGCCUGAACUUCUUCUUGG SEQ ID NO: 342 - DsiRNA 167 guide (antisense) strand
CCAAGAAGAAGUUCAGGCUGGACCUGA SEQ ID NO: 343 - DsiRNA 168 passenger (sense) strand
CAAUAAAGUACCUGCUGGUGCUGAG SEQ ID NO: 344 - DsiRNA 168 guide (antisense) strand
CUCAGCACCAGCAGGUACUUUAUUGCC SEQ ID NO: 345 - DsiRNA 169 passenger (sense) strand
AAUAAAGUACCUGCUGGUGCUGAGG SEQ ID NO: 346 - DsiRNA 169 guide (antisense) strand
CCUCAGCACCAGCAGGUACUUUAUUGC SEQ ID NO: 347 - DsiRNA 170 passenger (sense) strand
AUAAAGUACCUGCUGGUGCUGAGGG SEQ ID NO: 348 - DsiRNA 170 guide (antisense) strand
CCCUCAGCACCAGCAGGUACUUUAUUG SEQ ID NO: 349 - DsiRNA 171 passenger (sense) strand
CUCUCCACCUUUCCCAGUUUUUCAC SEQ ID NO: 350 - DsiRNA 171 guide (antisense) strand
GUGAAAAACUGGGAAAGGUGGAGAGCC SEQ ID NO: 351 - DsiRNA 172 passenger (sense) strand
CUCCACCUUUCCCAGUUUUUCACUA SEQ ID NO: 352 - DsiRNA 172 guide (antisense) strand
UAGUGAAAAACUGGGAAAGGUGGAGAG SEQ ID NO: 353 - DsiRNA 173 passenger (sense) strand
UCCACCUUUCCCAGUUUUUCACUAG SEQ ID NO: 354 - DsiRNA 173 guide (antisense) strand
CUAGUGAAAAACUGGGAAAGGUGGAGA SEQ ID NO: 355 - DsiRNA 174 passenger (sense) strand
CCACCUUUCCCAGUUUUUCACUAGA SEQ ID NO: 356 - DsiRNA 174 guide (antisense) strand
UCUAGUGAAAAACUGGGAAAGGUGGAG SEQ ID NO: 357 - DsiRNA 175 passenger (sense) strand
CACCUUUCCCAGUUUUUCACUAGAG SEQ ID NO: 358 - DsiRNA 175 guide (antisense) strand
CUCUAGUGAAAAACUGGGAAAGGUGGA SEQ ID NO: 359 - DsiRNA 176 passenger (sense) strand
ACCUUUCCCAGUUUUUCACUAGAGA SEQ ID NO: 360 - DsiRNA 176 guide (antisense) strand
UCUCUAGUGAAAAACUGGGAAAGGUGG SEQ ID NO: 361 - DsiRNA 177 passenger (sense) strand
CCUUUCCCAGUUUUUCACUAGAGAA SEQ ID NO: 362 - DsiRNA 177 guide (antisense) strand
UUCUCUAGUGAAAAACUGGGAAAGGUG SEQ ID NO: 363 - DsiRNA 178 passenger (sense) strand
AGUUUUUCACUAGAGAAGAGUCUGU SEQ ID NO: 364 - DsiRNA 178 guide (antisense) strand
ACAGACUCUUCUCUAGUGAAAAACUGG SEQ ID NO: 365 - DsiRNA 179 passenger (sense) strand
UCUAGCAGAUUCUUUCAGAGGUGCU -continued SEQ ID NO: 366 - DsiRNA 179 guide (antisense) strand
AGCACCUCUGAAAGAAUCUGCUAGACU SEQ ID NO: 367 - DsiRNA 180 passenger (sense) strand
AGCAGAUUCUUUCAGAGGUGCUAAA SEQ ID NO: 368 - DsiRNA 180 guide (antisense) strand
UUUAGCACCUCUGAAAGAAUCUGCUAG SEQ ID NO: 369 - DsiRNA 181 passenger (sense) strand
GCAGAUUCUUUCAGAGGUGCUAAAG SEQ ID NO: 370 - DsiRNA 181 guide (antisense) strand
CUUUAGCACCUCUGAAAGAAUCUGCUA SEQ ID NO: 371 - DsiRNA 182 passenger (sense) strand
CAGAUUCUUUCAGAGGUGCUAAAGU SEQ ID NO: 372 - DsiRNA 182 guide (antisense) strand
ACUUUAGCACCUCUGAAAGAAUCUGCU SEQ ID NO: 373 - DsiRNA 183 passenger (sense) strand
AGAUUCUUUCAGAGGUGCUAAAGUU SEQ ID NO: 374 - DsiRNA 183 guide (antisense) strand
AACUUUAGCACCUCUGAAAGAAUCUGC SEQ ID NO: 375 - DsiRNA 184 passenger (sense) strand
GAUUCUUUCAGAGGUGCUAAAGUUU SEQ ID NO: 376 - DsiRNA 184 guide (antisense) strand
AAACUUUAGCACCUCUGAAAGAAUCUG SEQ ID NO: 377 - DsiRNA 185 passenger (sense) strand
AUUCUUUCAGAGGUGCUAAAGUUUC SEQ ID NO: 378 - DsiRNA 185 guide (antisense) strand
GAAACUUUAGCACCUCUGAAAGAAUCU SEQ ID NO: 379 - DsiRNA 186 passenger (sense) strand
AGGUGCUAAAGUUUCCCAUCUUUGU SEQ ID NO: 380 - DsiRNA 186 guide (antisense) strand
ACAAAGAUGGGAAACUUUAGCACCUCU SEQ ID NO: 381 - DsiRNA 187 passenger (sense) strand
GGUGCUAAAGUUUCCCAUCUUUGUG SEQ ID NO: 382 - DsiRNA 187 guide (antisense) strand
CACAAAGAUGGGAAACUUUAGCACCUC SEQ ID NO: 383 - DsiRNA 188 passenger (sense) strand
GUGCUAAAGUUUCCCAUCUUUGUGC SEQ ID NO: 384 - DsiRNA 188 guide (antisense) strand
GCACAAAGAUGGGAAACUUUAGCACCU SEQ ID NO: 385 - DsiRNA 189 passenger (sense) strand
GCUAAAGUUUCCCAUCUUUGUGCAG SEQ ID NO: 386 - DsiRNA 189 guide (antisense) strand
CUGCACAAAGAUGGGAAACUUUAGCAC SEQ ID NO: 387 - DsiRNA 190 passenger (sense) strand
CUAAAGUUUCCCAUCUUUGUGCAGC SEQ ID NO: 388 - DsiRNA 190 guide (antisense) strand
GCUGCACAAAGAUGGGAAACUUUAGCA SEQ ID NO: 389 - DsiRNA 191 passenger (sense) strand
UAAAGUUUCCCAUCUUUGUGCAGCU SEQ ID NO: 390 - DsiRNA 191 guide (antisense) strand
AGCUGCACAAAGAUGGGAAACUUUAGC SEQ ID NO: 391 - DsiRNA 192 passenger (sense) strand
AAAGUUUCCCAUCUUUGUGCAGCUA SEQ ID NO: 392 - DsiRNA 192 guide (antisense) strand
UAGCUGCACAAAGAUGGGAAACUUUAG -continued SEQ ID NO: 393 - DsiRNA 193 passenger (sense) strand
AAGUUUCCCAUCUUUGUGCAGCUAC SEQ ID NO: 394 - DsiRNA 193 guide (antisense) strand
GUAGCUGCACAAAGAUGGGAAACUUUA SEQ ID NO: 395 - DsiRNA 194 passenger (sense) strand
AGUUUCCCAUCUUUGUGCAGCUACC SEQ ID NO: 396 - DsiRNA 194 guide (antisense) strand
GGUAGCUGCACAAAGAUGGGAAACUUU SEQ ID NO: 397 - DsiRNA 195 passenger (sense) strand
GUUUCCCAUCUUUGUGCAGCUACCU SEQ ID NO: 398 - DsiRNA 195 guide (antisense) strand
AGGUAGCUGCACAAAGAUGGGAAACUU SEQ ID NO: 399 - DsiRNA 196 passenger (sense) strand
AUCUUUGUGCAGCUACCUCCGCAUU SEQ ID NO: 400 - DsiRNA 196 guide (antisense) strand
AAUGCGGAGGUAGCUGCACAAAGAUGG SEQ ID NO: 401 - DsiRNA 197 passenger (sense) strand
GUGCAGCUACCUCCGCAUUGCUGUG SEQ ID NO: 402 - DsiRNA 197 guide (antisense) strand
CACAGCAAUGCGGAGGUAGCUGCACAA SEQ ID NO: 403 - DsiRNA 198 passenger (sense) strand
CCAGCCUCUGAGCUGAGUUGGUUUU SEQ ID NO: 404 - DsiRNA 198 guide (antisense) strand
AAAACCAACUCAGCUCAGAGGCUGGGA SEQ ID NO: 405 - DsiRNA 199 passenger (sense) strand
CAGCCUCUGAGCUGAGUUGGUUUUA SEQ ID NO: 406 - DsiRNA 199 guide (antisense) strand
UAAAACCAACUCAGCUCAGAGGCUGGG SEQ ID NO: 407 - DsiRNA 200 passenger (sense) strand
AGCCUCUGAGCUGAGUUGGUUUUAU SEQ ID NO: 408 - DsiRNA 200 guide (antisense) strand
AUAAAACCAACUCAGCUCAGAGGCUGG SEQ ID NO: 409 - DsiRNA 201 passenger (sense) strand
GCCUCUGAGCUGAGUUGGUUUUAUG SEQ ID NO: 410 - DsiRNA 201 guide (antisense) strand
CAUAAAACCAACUCAGCUCAGAGGCUG SEQ ID NO: 411 - DsiRNA 202 passenger (sense) strand
CCUCUGAGCUGAGUUGGUUUUAUGA SEQ ID NO: 412 - DsiRNA 202 guide (antisense) strand
UCAUAAAACCAACUCAGCUCAGAGGCU SEQ ID NO: 413 - DsiRNA 203 passenger (sense) strand
CUCUGAGCUGAGUUGGUUUUAUGAA SEQ ID NO: 414 - DsiRNA 203 guide (antisense) strand
UUCAUAAAACCAACUCAGCUCAGAGGC SEQ ID NO: 415 - DsiRNA 204 passenger (sense) strand
UCUGAGCUGAGUUGGUUUUAUGAAA SEQ ID NO: 416 - DsiRNA 204 guide (antisense) strand
UUUCAUAAAACCAACUCAGCUCAGAGG SEQ ID NO: 417 - DsiRNA 205 passenger (sense) strand
UGAGCUGAGUUGGUUUUAUGAAAAG SEQ ID NO: 418 - DsiRNA 205 guide (antisense) strand
CUUUUCAUAAAACCAACUCAGCUCAGA SEQ ID NO: 419 - DsiRNA 206 passenger (sense) strand
UGAGUUGGUUUUAUGAAAAGCUAGG -continued SEQ ID NO: 420 - DsiRNA 206 guide (antisense) strand
CCUAGCUUUUCAUAAAACCAACUCAGC SEQ ID NO: 421 - DsiRNA 207 passenger (sense) strand
GAGUUGGUUUUAUGAAAAGCUAGGA SEQ ID NO: 422 - DsiRNA 207 guide (antisense) strand
UCCUAGCUUUUCAUAAAACCAACUCAG SEQ ID NO: 423 - DsiRNA 208 passenger (sense) strand
UUGGUUUUAUGAAAAGCUAGGAAGC SEQ ID NO: 424 - DsiRNA 208 guide (antisense) strand
GCUUCCUAGCUUUUCAUAAAACCAACU SEQ ID NO: 425 - DsiRNA 209 passenger (sense) strand
UGGUUUUAUGAAAAGCUAGGAAGCA SEQ ID NO: 426 - DsiRNA 209 guide (antisense) strand
UGCUUCCUAGCUUUUCAUAAAACCAAC SEQ ID NO: 427 - DsiRNA 210 passenger (sense) strand
GGUUUUAUGAAAAGCUAGGAAGCAA SEQ ID NO: 428 - DsiRNA 210 guide (antisense) strand
UUGCUUCCUAGCUUUUCAUAAAACCAA SEQ ID NO: 429 - DsiRNA 211 passenger (sense) strand
UUUUAUGAAAAGCUAGGAAGCAACC SEQ ID NO: 430 - DsiRNA 211 guide (antisense) strand
GGUUGCUUCCUAGCUUUUCAUAAAACC SEQ ID NO: 431 - DsiRNA 212 passenger (sense) strand
UUAUGAAAAGCUAGGAAGCAACCUU SEQ ID NO: 432 - DsiRNA 212 guide (antisense) strand
AAGGUUGCUUCCUAGCUUUUCAUAAAA SEQ ID NO: 433 - DsiRNA 213 passenger (sense) strand
UAUGAAAAGCUAGGAAGCAACCUUU SEQ ID NO: 434 - DsiRNA 213 guide (antisense) strand
AAAGGUUGCUUCCUAGCUUUUCAUAAA SEQ ID NO: 435 - DsiRNA 214 passenger (sense) strand
AUGAAAAGCUAGGAAGCAACCUUUC SEQ ID NO: 436 - DsiRNA 214 guide (antisense) strand
GAAAGGUUGCUUCCUAGCUUUUCAUAA SEQ ID NO: 437 - DsiRNA 215 passenger (sense) strand
CCAGCACUUAACUCUAAUACAUCAG SEQ ID NO: 438 - DsiRNA 215 guide (antisense) strand
CUGAUGUAUUAGAGUUAAGUGCUGGAC SEQ ID NO: 439 - DsiRNA 216 passenger (sense) strand
CAGCACUUAACUCUAAUACAUCAGC SEQ ID NO: 440 - DsiRNA 216 guide (antisense) strand
GCUGAUGUAUUAGAGUUAAGUGCUGGA SEQ ID NO: 441 - DsiRNA 217 passenger (sense) strand
UAAUACAUCAGCAUGCGUUAAUUCA SEQ ID NO: 442 - DsiRNA 217 guide (antisense) strand
UGAAUUAACGCAUGCUGAUGUAUUAGA SEQ ID NO: 443 - DsiRNA 218 passenger (sense) strand
AAUACAUCAGCAUGCGUUAAUUCAG SEQ ID NO: 444 - DsiRNA 218 guide (antisense) strand
CUGAAUUAACGCAUGCUGAUGUAUUAG SEQ ID NO: 445 - DsiRNA 219 passenger (sense) strand
AGCAUGCGUUAAUUCAGCUGGUUGG SEQ ID NO: 446 - DsiRNA 219 guide (antisense) strand
CCAACCAGCUGAAUUAACGCAUGCUGA -continued SEQ ID NO: 447 - DsiRNA 220 passenger (sense) strand
GCAUGCGUUAAUUCAGCUGGUUGGG SEQ ID NO: 448 - DsiRNA 220 guide (antisense) strand
CCCAACCAGCUGAAUUAACGCAUGCUG SEQ ID NO: 449 - DsiRNA 221 passenger (sense) strand
UGCGUUAAUUCAGCUGGUUGGGAAA SEQ ID NO: 450 - DsiRNA 221 guide (antisense) strand
UUUCCCAACCAGCUGAAUUAACGCAUG SEQ ID NO: 451 - DsiRNA 222 passenger (sense) strand
GCGUUAAUUCAGCUGGUUGGGAAAU SEQ ID NO: 452 - DsiRNA 222 guide (antisense) strand
AUUUCCCAACCAGCUGAAUUAACGCAU SEQ ID NO: 453 - DsiRNA 223 passenger (sense) strand
CGUUAAUUCAGCUGGUUGGGAAAUG SEQ ID NO: 454 - DsiRNA 223 guide (antisense) strand
CAUUUCCCAACCAGCUGAAUUAACGCA SEQ ID NO: 455 - DsiRNA 224 passenger (sense) strand
GUUAAUUCAGCUGGUUGGGAAAUGA SEQ ID NO: 456 - DsiRNA 224 guide (antisense) strand
UCAUUUCCCAACCAGCUGAAUUAACGC SEQ ID NO: 457 - DsiRNA 225 passenger (sense) strand
UUAAUUCAGCUGGUUGGGAAAUGAC SEQ ID NO: 458 - DsiRNA 225 guide (antisense) strand
GUCAUUUCCCAACCAGCUGAAUUAACG SEQ ID NO: 459 - DsiRNA 226 passenger (sense) strand
UAAUUCAGCUGGUUGGGAAAUGACA SEQ ID NO: 460 - DsiRNA 226 guide (antisense) strand
UGUCAUUUCCCAACCAGCUGAAUUAAC SEQ ID NO: 461 - DsiRNA 227 passenger (sense) strand
AUUCAGCUGGUUGGGAAAUGACACC SEQ ID NO: 462 - DsiRNA 227 guide (antisense) strand
GGUGUCAUUUCCCAACCAGCUGAAUUA SEQ ID NO: 463 - DsiRNA 228 passenger (sense) strand
UUCAGCUGGUUGGGAAAUGACACCA SEQ ID NO: 464 - DsiRNA 228 guide (antisense) strand
UGGUGUCAUUUCCCAACCAGCUGAAUU SEQ ID NO: 465 - DsiRNA 229 passenger (sense) strand
UCAGCUGGUUGGGAAAUGACACCAG SEQ ID NO: 466 - DsiRNA 229 guide (antisense) strand
CUGGUGUCAUUUCCCAACCAGCUGAAU SEQ ID NO: 467 - DsiRNA 230 passenger (sense) strand
CAGCUGGUUGGGAAAUGACACCAGG SEQ ID NO: 468 - DsiRNA 230 guide (antisense) strand
CCUGGUGUCAUUUCCCAACCAGCUGAA SEQ ID NO: 469 - DsiRNA 231 passenger (sense) strand
AGCUGGUUGGGAAAUGACACCAGGA SEQ ID NO: 470 - DsiRNA 231 guide (antisense) strand
UCCUGGUGUCAUUUCCCAACCAGCUGA SEQ ID NO: 471 - DsiRNA 232 passenger (sense) strand
GCUGGUUGGGAAAUGACACCAGGAA SEQ ID NO: 472 - DsiRNA 232 guide (antisense) strand
UUCCUGGUGUCAUUUCCCAACCAGCUG SEQ ID NO: 473 - DsiRNA 233 passenger (sense) strand
GCAGAGGGUCCCUUACUGACUGUUU -continued SEQ ID NO: 474 - DsiRNA 233 guide (antisense) strand
AAACAGUCAGUAAGGGACCCUCUGCAC SEQ ID NO: 475 - DsiRNA 234 passenger (sense) strand
CAGAGGGUCCCUUACUGACUGUUUC SEQ ID NO: 476 - DsiRNA 234 guide (antisense) strand
GAAACAGUCAGUAAGGGACCCUCUGCA SEQ ID NO: 477 - DsiRNA 235 passenger (sense) strand
AGAGGGUCCCUUACUGACUGUUUCG SEQ ID NO: 478 - DsiRNA 235 guide (antisense) strand
CGAAACAGUCAGUAAGGGACCCUCUGC SEQ ID NO: 479 - DsiRNA 236 passenger (sense) strand
CCUAUUAAUGGUCAGACUGUUCCAG SEQ ID NO: 480 - DsiRNA 236 guide (antisense) strand
CUGGAACAGUCUGACCAUUAAUAGGGC SEQ ID NO: 481 - DsiRNA 237 passenger (sense) strand
CUAUUAAUGGUCAGACUGUUCCAGC SEQ ID NO: 482 - DsiRNA 237 guide (antisense) strand
GCUGGAACAGUCUGACCAUUAAUAGGG SEQ ID NO: 483 - DsiRNA 238 passenger (sense) strand
UAUUAAUGGUCAGACUGUUCCAGCA SEQ ID NO: 484 - DsiRNA 238 guide (antisense) strand
UGCUGGAACAGUCUGACCAUUAAUAGG SEQ ID NO: 485 - DsiRNA 239 passenger (sense) strand
AUUAAUGGUCAGACUGUUCCAGCAU SEQ ID NO: 486 - DsiRNA 239 guide (antisense) strand
AUGCUGGAACAGUCUGACCAUUAAUAG SEQ ID NO: 487 - DsiRNA 240 passenger (sense) strand
UUAAUGGUCAGACUGUUCCAGCAUG SEQ ID NO: 488 - DsiRNA 240 guide (antisense) strand
CAUGCUGGAACAGUCUGACCAUUAAUA SEQ ID NO: 489 - DsiRNA 241 passenger (sense) strand
UAAUGGUCAGACUGUUCCAGCAUGA SEQ ID NO: 490 - DsiRNA 241 guide (antisense) strand
UCAUGCUGGAACAGUCUGACCAUUAAU SEQ ID NO: 491 - DsiRNA 242 passenger (sense) strand
AAUGGUCAGACUGUUCCAGCAUGAG SEQ ID NO: 492 - DsiRNA 242 guide (antisense) strand
CUCAUGCUGGAACAGUCUGACCAUUAA SEQ ID NO: 493 - DsiRNA 243 passenger (sense) strand
AGAACGACACUGCCUGUCAGGUGGU SEQ ID NO: 494 - DsiRNA 243 guide (antisense) strand
ACCACCUGACAGGCAGUGUCGUUCUUG SEQ ID NO: 495 - DsiRNA 244 passenger (sense) strand
CGACACUGCCUGUCAGGUGGUCUGC SEQ ID NO: 496 - DsiRNA 244 guide (antisense) strand
GCAGACCACCUGACAGGCAGUGUCGUU SEQ ID NO: 497 - DsiRNA 245 passenger (sense) strand
AACCUUGACUACUAAAAACGUCUCC SEQ ID NO: 498 - DsiRNA 245 guide (antisense) strand
GGAGACGUUUUUAGUAGUCAAGGUUAU SEQ ID NO: 499 - DsiRNA 246 passenger (sense) strand
UUUAGAACACCUUUUUCACCUAACU SEQ ID NO: 500 - DsiRNA 246 guide (antisense) strand
AGUUAGGUGAAAAAGGUGUUCUAAAAU -continued SEQ ID NO: 501 - DsiRNA 247 passenger (sense) strand
UUAGAACACCUUUUUCACCUAACUA SEQ ID NO: 502 - DsiRNA 247 guide (antisense) strand
UAGUUAGGUGAAAAAGGUGUUCUAAAA SEQ ID NO: 503 - DsiRNA 248 passenger (sense) strand
UAGAACACCUUUUUCACCUAACUAA SEQ ID NO: 504 - DsiRNA 248 guide (antisense) strand
UUAGUUAGGUGAAAAAGGUGUUCUAAA SEQ ID NO: 505 - DsiRNA 249 passenger (sense) strand
AGAACACCUUUUUCACCUAACUAAA SEQ ID NO: 506 - DsiRNA 249 guide (antisense) strand
UUUAGUUAGGUGAAAAAGGUGUUCUAA SEQ ID NO: 507 - DsiRNA 250 passenger (sense) strand
GAACACCUUUUUCACCUAACUAAAA SEQ ID NO: 508 - DsiRNA 250 guide (antisense) strand
UUUUAGUUAGGUGAAAAAGGUGUUCUA SEQ ID NO: 509 - DsiRNA 251 passenger (sense) strand
AACACCUUUUUCACCUAACUAAAAU SEQ ID NO: 510 - DsiRNA 251 guide (antisense) strand
AUUUUAGUUAGGUGAAAAAGGUGUUCU SEQ ID NO: 511 - DsiRNA 252 passenger (sense) strand
ACACCUUUUUCACCUAACUAAAAUA SEQ ID NO: 512 - DsiRNA 252 guide (antisense) strand
UAUUUUAGUUAGGUGAAAAAGGUGUUC SEQ ID NO: 513 - DsiRNA 253 passenger (sense) strand
CACCUUUUUCACCUAACUAAAAUAA SEQ ID NO: 514 - DsiRNA 253 guide (antisense) strand
UUAUUUUAGUUAGGUGAAAAAGGUGUU SEQ ID NO: 515 - DsiRNA 254 passenger (sense) strand
ACCUUUUUCACCUAACUAAAAUAAU SEQ ID NO: 516 - DsiRNA 254 guide (antisense) strand
AUUAUUUUAGUUAGGUGAAAAAGGUGU SEQ ID NO: 517 - DsiRNA 255 passenger (sense) strand
CUUUUUCACCUAACUAAAAUAAUGU SEQ ID NO: 518 - DsiRNA 255 guide (antisense) strand
ACAUUAUUUUAGUUAGGUGAAAAAGGU SEQ ID NO: 519 - DsiRNA 256 passenger (sense) strand
UUUUCACCUAACUAAAAUAAUGUUU SEQ ID NO: 520 - DsiRNA 256 guide (antisense) strand
AAACAUUAUUUUAGUUAGGUGAAAAAG SEQ ID NO: 521 - DsiRNA 257 passenger (sense) strand
UUCACCUAACUAAAAUAAUGUUUAA SEQ ID NO: 522 - DsiRNA 257 guide (antisense) strand
UUAAACAUUAUUUUAGUUAGGUGAAAA SEQ ID NO: 523 - DsiRNA 258 passenger (sense) strand
UCACCUAACUAAAAUAAUGUUUAAA SEQ ID NO: 524 - DsiRNA 258 guide (antisense) strand
UUUAAACAUUAUUUUAGUUAGGUGAAA SEQ ID NO: 525 - DsiRNA 259 passenger (sense) strand
CACCUAACUAAAAUAAUGUUUAAAG SEQ ID NO: 526 - DsiRNA 259 guide (antisense) strand
CUUUAAACAUUAUUUUAGUUAGGUGAA SEQ ID NO: 527 - DsiRNA 260 passenger (sense) strand
ACCUAACUAAAAUAAUGUUUAAAGA -continued SEQ ID NO: 528 - DsiRNA 260 guide (antisense) strand
UCUUUAAACAUUAUUUUAGUUAGGUGA SEQ ID NO: 529 - DsiRNA 261 passenger (sense) strand
CCUAACUAAAAUAAUGUUUAAAGAG SEQ ID NO: 530 - DsiRNA 261 guide (antisense) strand
CUCUUUAAACAUUAUUUUAGUUAGGUG SEQ ID NO: 531 - DsiRNA 262 passenger (sense) strand
CUAACUAAAAUAAUGUUUAAAGAGU SEQ ID NO: 532 - DsiRNA 262 guide (antisense) strand
ACUCUUUAAACAUUAUUUUAGUUAGGU SEQ ID NO: 533 - DsiRNA 263 passenger (sense) strand
UAACUAAAAUAAUGUUUAAAGAGUU SEQ ID NO: 534 - DsiRNA 263 guide (antisense) strand
AACUCUUUAAACAUUAUUUUAGUUAGG SEQ ID NO: 535 - DsiRNA 264 passenger (sense) strand
AACUAAAAUAAUGUUUAAAGAGUUU SEQ ID NO: 536 - DsiRNA 264 guide (antisense) strand
AAACUCUUUAAACAUUAUUUUAGUUAG SEQ ID NO: 537 - DsiRNA 265 passenger (sense) strand
ACUAAAAUAAUGUUUAAAGAGUUUU SEQ ID NO: 538 - DsiRNA 265 guide (antisense) strand
AAAACUCUUUAAACAUUAUUUUAGUUA SEQ ID NO: 539 - DsiRNA 266 passenger (sense) strand
CUAAAAUAAUGUUUAAAGAGUUUUG SEQ ID NO: 540 - DsiRNA 266 guide (antisense) strand
CAAAACUCUUUAAACAUUAUUUUAGUU SEQ ID NO: 541 - DsiRNA 267 passenger (sense) strand
UAAAAUAAUGUUUAAAGAGUUUUGU SEQ ID NO: 542 - DsiRNA 267 guide (antisense) strand
ACAAAACUCUUUAAACAUUAUUUUAGU SEQ ID NO: 543 - DsiRNA 268 passenger (sense) strand
AAGAGUUUUGUAUAAAAAUGUAAGG SEQ ID NO: 544 - DsiRNA 268 guide (antisense) strand
CCUUACAUUUUUAUACAAAACUCUUUA SEQ ID NO: 545 - DsiRNA 269 passenger (sense) strand
GUUUUGUAUAAAAAUGUAAGGAAGC SEQ ID NO: 546 - DsiRNA 269 guide (antisense) strand
GCUUCCUUACAUUUUUAUACAAAACUC SEQ ID NO: 547 - DsiRNA 270 passenger (sense) strand
UUUUGUAUAAAAAUGUAAGGAAGCG SEQ ID NO: 548 - DsiRNA 270 guide (antisense) strand
CGCUUCCUUACAUUUUUAUACAAAACU SEQ ID NO: 549 - DsiRNA 271 passenger (sense) strand
UUUGUAUAAAAAUGUAAGGAAGCGU SEQ ID NO: 550 - DsiRNA 271 guide (antisense) strand
ACGCUUCCUUACAUUUUUAUACAAAAC SEQ ID NO: 551 - DsiRNA 272 passenger (sense) strand
UUGUAUAAAAAUGUAAGGAAGCGUU SEQ ID NO: 552 - DsiRNA 272 guide (antisense) strand
AACGCUUCCUUACAUUUUUAUACAAAA SEQ ID NO: 553 - DsiRNA 273 passenger (sense) strand
UGUAUAAAAAUGUAAGGAAGCGUUG SEQ ID NO: 554 - DsiRNA 273 guide (antisense) strand
CAACGCUUCCUUACAUUUUUAUACAAA -continued SEQ ID NO: 555 - DsiRNA 274 passenger (sense) strand
GUAUAAAAAUGUAAGGAAGCGUUGU SEQ ID NO: 556 - DsiRNA 274 guide (antisense) strand
ACAACGCUUCCUUACAUUUUUAUACAA SEQ ID NO: 557 - DsiRNA 275 passenger (sense) strand
AUGUAAGGAAGCGUUGUUACCUGUU SEQ ID NO: 558 - DsiRNA 275 guide (antisense) strand
AACAGGUAACAACGCUUCCUUACAUUU SEQ ID NO: 559 - DsiRNA 276 passenger (sense) strand
UUUUGUAUUAUGUGAAUCAGUGAGA SEQ ID NO: 560 - DsiRNA 276 guide (antisense) strand
UCUCACUGAUUCACAUAAUACAAAAUU SEQ ID NO: 561 - DsiRNA 277 passenger (sense) strand
UUUGUAUUAUGUGAAUCAGUGAGAU SEQ ID NO: 562 - DsiRNA 277 guide (antisense) strand
AUCUCACUGAUUCACAUAAUACAAAAU SEQ ID NO: 563 - DsiRNA 278 passenger (sense) strand
UUGUAUUAUGUGAAUCAGUGAGAUG SEQ ID NO: 564 - DsiRNA 278 guide (antisense) strand
CAUCUCACUGAUUCACAUAAUACAAAA SEQ ID NO: 565 - DsiRNA 279 passenger (sense) strand
UGUAUUAUGUGAAUCAGUGAGAUGU SEQ ID NO: 566 - DsiRNA 279 guide (antisense) strand
ACAUCUCACUGAUUCACAUAAUACAAA SEQ ID NO: 567 - DsiRNA 280 passenger (sense) strand
GUAUUAUGUGAAUCAGUGAGAUGUU SEQ ID NO: 568 - DsiRNA 280 guide (antisense) strand
AACAUCUCACUGAUUCACAUAAUACAA SEQ ID NO: 569 - DsiRNA 281 passenger (sense) strand
UAUUAUGUGAAUCAGUGAGAUGUUA SEQ ID NO: 570 - DsiRNA 281 guide (antisense) strand
UAACAUCUCACUGAUUCACAUAAUACA SEQ ID NO: 571 - DsiRNA 282 passenger (sense) strand
AUUAUGUGAAUCAGUGAGAUGUUAG SEQ ID NO: 572 - DsiRNA 282 guide (antisense) strand
CUAACAUCUCACUGAUUCACAUAAUAC SEQ ID NO: 573 - DsiRNA 283 passenger (sense) strand
UUAUGUGAAUCAGUGAGAUGUUAGU SEQ ID NO: 574 - DsiRNA 283 guide (antisense) strand
ACUAACAUCUCACUGAUUCACAUAAUA SEQ ID NO: 575 - DsiRNA 284 passenger (sense) strand
UAUGUGAAUCAGUGAGAUGUUAGUA SEQ ID NO: 576 - DsiRNA 284 guide (antisense) strand
UACUAACAUCUCACUGAUUCACAUAAU SEQ ID NO: 577 - DsiRNA 285 passenger (sense) strand
AUGUGAAUCAGUGAGAUGUUAGUAG SEQ ID NO: 578 - DsiRNA 285 guide (antisense) strand
CUACUAACAUCUCACUGAUUCACAUAA SEQ ID NO: 579 - DsiRNA 286 passenger (sense) strand
UGUGAAUCAGUGAGAUGUUAGUAGA SEQ ID NO: 580 - DsiRNA 286 guide (antisense) strand
UCUACUAACAUCUCACUGAUUCACAUA SEQ ID NO: 581 - DsiRNA 287 passenger (sense) strand
GUGAAUCAGUGAGAUGUUAGUAGAA -continued SEQ ID NO: 582 - DsiRNA 287 guide (antisense) strand
UUCUACUAACAUCUCACUGAUUCACAU SEQ ID NO: 583 - DsiRNA 288 passenger (sense) strand
GUGAGAUGUUAGUAGAAUAAGCCUU SEQ ID NO: 584 - DsiRNA 288 guide (antisense) strand
AAGGCUUAUUCUACUAACAUCUCACUG SEQ ID NO: 585 - DsiRNA 289 passenger (sense) strand
UUUUCUAUUUAUGCAUUUGAGUACA SEQ ID NO: 586 - DsiRNA 289 guide (antisense) strand
UGUACUCAAAUGCAUAAAUAGAAAAAA SEQ ID NO: 587 - DsiRNA 290 passenger (sense) strand
UUUCUAUUUAUGCAUUUGAGUACAG SEQ ID NO: 588 - DsiRNA 290 guide (antisense) strand
CUGUACUCAAAUGCAUAAAUAGAAAAA SEQ ID NO: 589 - DsiRNA 291 passenger (sense) strand
UUCUAUUUAUGCAUUUGAGUACAGT SEQ ID NO: 590 - DsiRNA 291 guide (antisense) strand
ACUGUACUCAAAUGCAUAAAUAGAAAA SEQ ID NO: 591 - DsiRNA 292 passenger (sense) strand
CUAUUUAUGCAUUUGAGUACAGUAC SEQ ID NO: 592 - DsiRNA 292 guide (antisense) strand
GUACUGUACUCAAAUGCAUAAAUAGAA SEQ ID NO: 593 - DsiRNA 293 passenger (sense) strand
UGCUCAAACUGUUAAAUGUUGGAAA SEQ ID NO: 594 - DsiRNA 293 guide (antisense) strand
UUUCCAACAUUUAACAGUUUGAGCACA SEQ ID NO: - DsiRNA 294 passenger (sense) strand
GCUCAAACUGUUAAAUGUUGGAAAA 595

SEQ ID NO: 596 - DsiRNA 294 guide (antisense) strand
UUUUCCAACAUUUAACAGUUUGAGCAC SEQ ID NO: 597 - DsiRNA 295 passenger (sense) strand
CUCAAACUGUUAAAUGUUGGAAAAG SEQ ID NO: 598 - DsiRNA 295 guide (antisense) strand
CUUUUCCAACAUUUAACAGUUUGAGCA SEQ ID NO: 599 - DsiRNA 296 passenger (sense) strand
UCAAACUGUUAAAUGUUGGAAAAGA SEQ ID NO: 600 - DsiRNA 296 guide (antisense) strand
UCUUUUCCAACAUUUAACAGUUUGAGC SEQ ID NO: 601 - DsiRNA 297 passenger (sense) strand
CAAACUGUUAAAUGUUGGAAAAGAA SEQ ID NO: 602 - DsiRNA 297 guide (antisense) strand
UUCUUUUCCAACAUUUAACAGUUUGAG SEQ ID NO: 603 - DsiRNA 298 passenger (sense) strand
AAACUGUUAAAUGUUGGAAAAGAAA SEQ ID NO: 604 - DsiRNA 298 guide (antisense) strand
UUUCUUUUCCAACAUUUAACAGUUUGA SEQ ID NO: 605 - DsiRNA 299 passenger (sense) strand
AACUGUUAAAUGUUGGAAAAGAAAG SEQ ID NO: 606 - DsiRNA 299 guide (antisense) strand
CUUUCUUUUCCAACAUUUAACAGUUUG SEQ ID NO: 607 - DsiRNA 300 passenger (sense) strand
ACUGUUAAAUGUUGGAAAAGAAAGA SEQ ID NO: 608 - DsiRNA 300 guide (antisense) strand
UCUUUCUUUUCCAACAUUUAACAGUUU -continued SEQ ID NO: 609 - DsiRNA 301 passenger (sense) strand
CUGUUAAAUGUUGGAAAAGAAAGAT SEQ ID NO: 610 - DsiRNA 301 guide (antisense) strand
AUCUUUCUUUUCCAACAUUUAACAGUU SEQ ID NO: 611 - DsiRNA 302 passenger (sense) strand
UGUUAAAUGUUGGAAAAGAAAGATA SEQ ID NO: 612 - DsiRNA 302 guide (antisense) strand
UAUCUUUCUUUUCCAACAUUUAACAGU SEQ ID NO: 613 - DsiRNA 303 passenger (sense) strand
GUUAAAUGUUGGAAAAGAAAGAUAC SEQ ID NO: 614 - DsiRNA 303 guide (antisense) strand
GUAUCUUUCUUUUCCAACAUUUAACAG SEQ ID NO: 615 - DsiRNA 304 passenger (sense) strand
UUAAAUGUUGGAAAAGAAAGAUACA SEQ ID NO: 616 - DsiRNA 304 guide (antisense) strand
UGUAUCUUUCUUUUCCAACAUUUAACA SEQ ID NO: 617 - DsiRNA 305 passenger (sense) strand
UAAAUGUUGGAAAAGAAAGAUACAA SEQ ID NO: 618 - DsiRNA 305 guide (antisense) strand
UUGUAUCUUUCUUUUCCAACAUUUAAC SEQ ID NO: 619 - DsiRNA 306 passenger (sense) strand
GCACUUGACUGAGAAGACAGACCCT SEQ ID NO: 620 - DsiRNA 306 guide (antisense) strand
AGGGUCUGUCUUCUCAGUCAAGUGCUU SEQ ID NO: 621 - DsiRNA 307 passenger (sense) strand
GAGAAAAGAGGCUACUUGUGAAAAT SEQ ID NO: 622 - DsiRNA 307 guide (antisense) strand
AUUUUCACAAGUAGCCUCUUUUCUCAA SEQ ID NO: 623 - DsiRNA 308 passenger (sense) strand
AGAAAAGAGGCUACUUGUGAAAATA SEQ ID NO: 624 - DsiRNA 308 guide (antisense) strand
UAUUUUCACAAGUAGCCUCUUUUCUCA SEQ ID NO: 625 - DsiRNA 309 passenger (sense) strand
GAAAAGAGGCUACUUGUGAAAAUAA SEQ ID NO: 626 - DsiRNA 309 guide (antisense) strand
UUAUUUUCACAAGUAGCCUCUUUUCUC SEQ ID NO: 627 - DsiRNA 310 passenger (sense) strand
AAAAGAGGCUACUUGUGAAAAUAAT SEQ ID NO: 628 - DsiRNA 310 guide (antisense) strand
AUUAUUUUCACAAGUAGCCUCUUUUCU SEQ ID NO: 629 - DsiRNA 311 passenger (sense) strand
AAAGAGGCUACUUGUGAAAAUAATG SEQ ID NO: 630 - DsiRNA 311 guide (antisense) strand
CAUUAUUUUCACAAGUAGCCUCUUUUC SEQ ID NO: 631 - DsiRNA 312 passenger (sense) strand
AAGAGGCUACUUGUGAAAAUAAUGA SEQ ID NO: 632 - DsiRNA 312 guide (antisense) strand
UCAUUAUUUUCACAAGUAGCCUCUUUU SEQ ID NO: 633 - DsiRNA 313 passenger (sense) strand
AGAGGCUACUUGUGAAAAUAAUGAG SEQ ID NO: 634 - DsiRNA 313 guide (antisense) strand
CUCAUUAUUUUCACAAGUAGCCUCUUU SEQ ID NO: 635 - DsiRNA 314 passenger (sense) strand
GAGGCUACUUGUGAAAAUAAUGAGC -continued SEQ ID NO: 636 - DsiRNA 314 guide (antisense) strand
GCUCAUUAUUUUCACAAGUAGCCUCUU SEQ ID NO: 637 - DsiRNA 315 passenger (sense) strand
GGCUACUUGUGAAAAUAAUGAGCCC SEQ ID NO: 638 - DsiRNA 315 guide (antisense) strand
GGGCUCAUUAUUUUCACAAGUAGCCUC SEQ ID NO: 639 - DsiRNA 316 passenger (sense) strand
CUACUUGUGAAAAUAAUGAGCCCCC SEQ ID NO: 640 - DsiRNA 316 guide (antisense) strand
GGGGGCUCAUUAUUUUCACAAGUAGCC SEQ ID NO: 641 - DsiRNA 317 passenger (sense) strand
UGAACCUGCCUUCUUACAUCUUGAG SEQ ID NO: 642 - DsiRNA 317 guide (antisense) strand
CUCAAGAUGUAAGAAGGCAGGUUCAAA SEQ ID NO: 643 - DsiRNA 318 passenger (sense) strand
AAAGUUACAAGUUUCUUUUCCCAAG SEQ ID NO: 644 - DsiRNA 318 guide (antisense) strand
CUUGGGAAAAGAAACUUGUAACUUUCC SEQ ID NO: 645 - DsiRNA 319 passenger (sense) strand
AAGUUACAAGUUUCUUUUCCCAAGT SEQ ID NO: 646 - DsiRNA 319 guide (antisense) strand
ACUUGGGAAAAGAAACUUGUAACUUUC SEQ ID NO: 647 - DsiRNA 320 passenger (sense) strand
AGUUACAAGUUUCUUUUCCCAAGTT SEQ ID NO: 648 - DsiRNA 320 guide (antisense) strand
AACUUGGGAAAAGAAACUUGUAACUUU SEQ ID NO: 649 - DsiRNA 321 passenger (sense) strand
AGUUUCUUUUCCCAAGUUUCCCAGT SEQ ID NO: 650 - DsiRNA 321 guide (antisense) strand
ACUGGGAAACUUGGGAAAAGAAACUUG SEQ ID NO: 651 - DsiRNA 322 passenger (sense) strand
CAACAGUAUUUUCUAAUAACCAGTA SEQ ID NO: 652 - DsiRNA 322 guide (antisense) strand
UACUGGUUAUUAGAAAAUACUGUUGGC SEQ ID NO: 653 - DsiRNA 323 passenger (sense) strand
AACAGUAUUUUCUAAUAACCAGUAT SEQ ID NO: 654 - DsiRNA 323 guide (antisense) strand
AUACUGGUUAUUAGAAAAUACUGUUGG SEQ ID NO: 655 - DsiRNA 324 passenger (sense) strand
ACAGUAUUUUCUAAUAACCAGUATA SEQ ID NO: 656 - DsiRNA 324 guide (antisense) strand
UAUACUGGUUAUUAGAAAAUACUGUUG SEQ ID NO: 657 - DsiRNA 325 passenger (sense) strand
CAGUAUUUUCUAAUAACCAGUAUAT SEQ ID NO: 658 - DsiRNA 325 guide (antisense) strand
AUAUACUGGUUAUUAGAAAAUACUGUU SEQ ID NO: 659 - DsiRNA 326 passenger (sense) strand
UUGUGAUUGUUAUCAGGAAAAAATA SEQ ID NO: 660 - DsiRNA 326 guide (antisense) strand
UAUUUUUUCCUGAUAACAAUCACAAUA SEQ ID NO: 661 - DsiRNA 327 passenger (sense) strand
UGUGAUUGUUAUCAGGAAAAAAUAT SEQ ID NO: 662 - DsiRNA 327 guide (antisense) strand
AUAUUUUUUCCUGAUAACAAUCACAAU -continued SEQ ID NO: 663 - DsiRNA 328 passenger (sense) strand
GUGAUUGUUAUCAGGAAAAAAUATA SEQ ID NO: 664 - DsiRNA 328 guide (antisense) strand
UAUAUUUUUUCCUGAUAACAAUCACAA SEQ ID NO: 665 - DsiRNA 329 passenger (sense) strand
UGAUUGUUAUCAGGAAAAAAUAUAT SEQ ID NO: 666 - DsiRNA 329 guide (antisense) strand
AUAUAUUUUUUCCUGAUAACAAUCACA SEQ ID NO: 667 - DsiRNA 330 passenger (sense) strand
GAUUGUUAUCAGGAAAAAAUAUATT SEQ ID NO: 668 - DsiRNA 330 guide (antisense) strand
AAUAUAUUUUUUCCUGAUAACAAUCAC SEQ ID NO: 669 - DsiRNA 331 passenger (sense) strand
AUUGUUAUCAGGAAAAAAUAUAUTA SEQ ID NO: 670 - DsiRNA 331 guide (antisense) strand
UAAUAUAUUUUUUCCUGAUAACAAUCA SEQ ID NO: 671 - DsiRNA 332 passenger (sense) strand
UUGUUAUCAGGAAAAAAUAUAUUAA SEQ ID NO: 672 - DsiRNA 332 guide (antisense) strand
UUAAUAUAUUUUUUCCUGAUAACAAUC SEQ ID NO: 673 - DsiRNA 333 passenger (sense) strand
UGUUAUCAGGAAAAAAUAUAUUAAA SEQ ID NO: 674 - DsiRNA 333 guide (antisense) strand
UUUAAUAUAUUUUUUCCUGAUAACAAU SEQ ID NO: 675 - DsiRNA 334 passenger (sense) strand
GUUAUCAGGAAAAAAUAUAUUAAAT SEQ ID NO: 676 - DsiRNA 334 guide (antisense) strand
AUUUAAUAUAUUUUUUCCUGAUAACAA SEQ ID NO: 677 - DsiRNA 335 passenger (sense) strand
UUAUCAGGAAAAAAUAUAUUAAATG SEQ ID NO: 678 - DsiRNA 335 guide (antisense) strand
CAUUUAAUAUAUUUUUUCCUGAUAACA SEQ ID NO: 679 - DsiRNA 336 passenger (sense) strand
UAUCAGGAAAAAAUAUAUUAAAUGG SEQ ID NO: 680 - DsiRNA 336 guide (antisense) strand
CCAUUUAAUAUAUUUUUUCCUGAUAAC SEQ ID NO: 681 - DsiRNA 337 passenger (sense) strand
AUCAGGAAAAAAUAUAUUAAAUGGC SEQ ID NO: 682 - DsiRNA 337 guide (antisense) strand
GCCAUUUAAUAUAUUUUUUCCUGAUAA SEQ ID NO: 683 - DsiRNA 338 passenger (sense) strand
AGGAAAAAAUAUAUUAAAUGGCUGA SEQ ID NO: 684 - DsiRNA 338 guide (antisense) strand
UCAGCCAUUUAAUAUAUUUUUUCCUGA SEQ ID NO: 685 - DsiRNA 339 passenger (sense) strand
GGAAAAAAUAUAUUAAAUGGCUGAT SEQ ID NO: 686 - DsiRNA 339 guide (antisense) strand
AUCAGCCAUUUAAUAUAUUUUUUCCUG SEQ ID NO: 687 - DsiRNA 340 passenger (sense) strand
GAAAAAAUAUAUUAAAUGGCUGATA SEQ ID NO: 688 - DsiRNA 340 guide (antisense) strand
UAUCAGCCAUUUAAUAUAUUUUUUCCU SEQ ID NO: 689 - DsiRNA 341 passenger (sense) strand
AAAAAAUAUAUUAAAUGGCUGAUAG -continued SEQ ID NO: 690 - DsiRNA 341 guide (antisense) strand
CUAUCAGCCAUUUAAUAUAUUUUUUCC SEQ ID NO: 691 - DsiRNA 342 passenger (sense) strand
UAUUUUCUUUCUGCUUUUAAAAATT SEQ ID NO: 692 - DsiRNA 342 guide (antisense) strand
AAUUUUUAAAAGCAGAAAGAAAAUACG SEQ ID NO: 693 - DsiRNA 343 passenger (sense) strand
AUUUUCUUUCUGCUUUUAAAAAUTA SEQ ID NO: 694 - DsiRNA 343 guide (antisense) strand
UAAUUUUUAAAAGCAGAAAGAAAAUAC SEQ ID NO: 695 - DsiRNA 344 passenger (sense) strand
UCUUUCUGCUUUUAAAAAUUAUUCA SEQ ID NO: 696 - DsiRNA 344 guide (antisense) strand
UGAAUAAUUUUUAAAAGCAGAAAGAAA SEQ ID NO: 697 - DsiRNA 345 passenger (sense) strand
CUUUCUGCUUUUAAAAAUUAUUCAG SEQ ID NO: 698 - DsiRNA 345 guide (antisense) strand
CUGAAUAAUUUUUAAAAGCAGAAAGAA SEQ ID NO: 699 - DsiRNA 346 passenger (sense) strand
UUUCUGCUUUUAAAAAUUAUUCAGG SEQ ID NO: 700 - DsiRNA 346 guide (antisense) strand
CCUGAAUAAUUUUUAAAAGCAGAAAGA SEQ ID NO: 701 - DsiRNA 347 passenger (sense) strand
CUACUAAAAACACAAAAAUUAGCCA SEQ ID NO: 702 - DsiRNA 347 guide (antisense) strand
UGGCUAAUUUUUGUGUUUUUAGUAGAG SEQ ID NO: 703 - DsiRNA 348 passenger (sense) strand
CAAGAUAAGGAAAUCAGGAAGUGTA SEQ ID NO: 704 - DsiRNA 348 guide (antisense) strand
UACACUUCCUGAUUUCCUUAUCUUGAU SEQ ID NO: 705 - DsiRNA 349 passenger (sense) strand
AAGAUAAGGAAAUCAGGAAGUGUAA SEQ ID NO: 706 - DsiRNA 349 guide (antisense) strand
UUACACUUCCUGAUUUCCUUAUCUUGA SEQ ID NO: 707 - DsiRNA 350 passenger (sense) strand
AGAUAAGGAAAUCAGGAAGUGUAAT SEQ ID NO: 708 - DsiRNA 350 guide (antisense) strand
AUUACACUUCCUGAUUUCCUUAUCUUG SEQ ID NO: 709 - DsiRNA 351 passenger (sense) strand
GAUAAGGAAAUCAGGAAGUGUAATA SEQ ID NO: 710 - DsiRNA 351 guide (antisense) strand
UAUUACACUUCCUGAUUUCCUUAUCUU SEQ ID NO: 711 - DsiRNA 352 passenger (sense) strand
AUAAGGAAAUCAGGAAGUGUAAUAT SEQ ID NO: 712 - DsiRNA 352 guide (antisense) strand
AUAUUACACUUCCUGAUUUCCUUAUCU SEQ ID NO: 713 - DsiRNA 353 passenger (sense) strand
UAAGGAAAUCAGGAAGUGUAAUATT SEQ ID NO: 714 - DsiRNA 353 guide (antisense) strand
AAUAUUACACUUCCUGAUUUCCUUAUC SEQ ID NO: 715 - DsiRNA 354 passenger (sense) strand
AAGGAAAUCAGGAAGUGUAAUAUTC SEQ ID NO: 716 - DsiRNA 354 guide (antisense) strand
GAAUAUUACACUUCCUGAUUUCCUUAU -continued SEQ ID NO: 717 - DsiRNA 355 passenger (sense) strand
AGGAAAUCAGGAAGUGUAAUAUUCT SEQ ID NO: 718 - DsiRNA 355 guide (antisense) strand
AGAAUAUUACACUUCCUGAUUUCCUUA SEQ ID NO: 719 - DsiRNA 356 passenger (sense) strand
GGAAAUCAGGAAGUGUAAUAUUCTT SEQ ID NO: 720 - DsiRNA 356 guide (antisense) strand
AAGAAUAUUACACUUCCUGAUUUCCUU SEQ ID NO: 721 - DsiRNA 357 passenger (sense) strand
GAAAUCAGGAAGUGUAAUAUUCUTA SEQ ID NO: 722 - DsiRNA 357 guide (antisense) strand
UAAGAAUAUUACACUUCCUGAUUUCCU SEQ ID NO: 723 - DsiRNA 358 passenger (sense) strand
CUAUGAAUGCAUUCUUAUUUCUUCT SEQ ID NO: 724 - DsiRNA 358 guide (antisense) strand
AGAAGAAAUAAGAAUGCAUUCAUAGGC SEQ ID NO: 725 - DsiRNA 359 passenger (sense) strand
UAUGAAUGCAUUCUUAUUUCUUCTT SEQ ID NO: 726 - DsiRNA 359 guide (antisense) strand
AAGAAGAAAUAAGAAUGCAUUCAUAGG SEQ ID NO: 727 - DsiRNA 360 passenger (sense) strand
CUACCACACCCAGCUAGUUUUUUTT SEQ ID NO: 728 - DsiRNA 360 guide (antisense) strand
AAAAAAAACUAGCUGGGUGUGGUAGUG SEQ ID NO: 729 - DsiRNA 361 passenger (sense) strand
CCACACCCAGCUAGUUUUUUUUUGT SEQ ID NO: 730 - DsiRNA 361 guide (antisense) strand
ACAAAAAAAAACUAGCUGGGUGUGGUA SEQ ID NO: 731 - DsiRNA 362 passenger (sense) strand
CACACCCAGCUAGUUUUUUUUUGTA SEQ ID NO: 732 - DsiRNA 362 guide (antisense) strand
UACAAAAAAAAACUAGCUGGGUGUGGU SEQ ID NO: 733 - DsiRNA 363 passenger (sense) strand
GCUAGGAUUACAGGUGUGAGCUACC SEQ ID NO: 734 - DsiRNA 363 guide (antisense) strand
GGUAGCUCACACCUGUAAUCCUAGCAC SEQ ID NO: 735 - DsiRNA 364 passenger (sense) strand
CUAGGAUUACAGGUGUGAGCUACCA SEQ ID NO: 736 - DsiRNA 364 guide (antisense) strand
UGGUAGCUCACACCUGUAAUCCUAGCA SEQ ID NO: 737 - DsiRNA 365 passenger (sense) strand
CCAUGCCUGGUCCAACAUUCUUCAT SEQ ID NO: 738 - DsiRNA 365 guide (antisense) strand
AUGAAGAAUGUUGGACCAGGCAUGGUA SEQ ID NO: 739 - DsiRNA 366 passenger (sense) strand
UGCAGAGUAUGAGCCUGAUUUUGTT SEQ ID NO: 740 - DsiRNA 366 guide (antisense) strand
AACAAAAUCAGGCUCAUACUCUGCACU SEQ ID NO: 741 - DsiRNA 367 passenger (sense) strand
GCAGAGUAUGAGCCUGAUUUUGUTT SEQ ID NO: 742 - DsiRNA 367 guide (antisense) strand
AAACAAAAUCAGGCUCAUACUCUGCAC SEQ ID NO: 743 - DsiRNA 368 passenger (sense) strand
CAGAGUAUGAGCCUGAUUUUGUUTA -continued SEQ ID NO: 744 - DsiRNA 368 guide (antisense) strand
UAAACAAAAUCAGGCUCAUACUCUGCA SEQ ID NO: 745 - DsiRNA 369 passenger (sense) strand
AGAGUAUGAGCCUGAUUUUGUUUAA SEQ ID NO: 746 - DsiRNA 369 guide (antisense) strand
UUAAACAAAAUCAGGCUCAUACUCUGC SEQ ID NO: 747 - DsiRNA 370 passenger (sense) strand
GAGUAUGAGCCUGAUUUUGUUUAAA SEQ ID NO: 748 - DsiRNA 370 guide (antisense) strand
UUUAAACAAAAUCAGGCUCAUACUCUG SEQ ID NO: 749 - DsiRNA 371 passenger (sense)
GGGUGAAACCCCAUCUCUACUAAAA SEQ ID NO: 750 - DsiRNA 371 guide (antisense) strand
UUUUAGUAGAGAUGGGGUUUCACCCAG SEQ ID NO: 751 - DsiRNA 372 passenger (sense) strand
GUGAAACCCCAUCUCUACUAAAAAA SEQ ID NO: 752 - DsiRNA 372 guide (antisense) strand
UUUUUUAGUAGAGAUGGGGUUUCACCC SEQ ID NO: 753 - DsiRNA 373 passenger (sense) strand
UGAAACCCCAUCUCUACUAAAAAAT SEQ ID NO: 754 - DsiRNA 373 guide (antisense) strand
AUUUUUUAGUAGAGAUGGGGUUUCACC SEQ ID NO: 755 - DsiRNA 374 passenger (sense) strand
GAAACCCCAUCUCUACUAAAAAATG SEQ ID NO: 756 - DsiRNA 374 guide (antisense) strand
CAUUUUUUAGUAGAGAUGGGGUUUCAC SEQ ID NO: 757 - DsiRNA 375 guide (antisense) strand
AAACCCCAUCUCUACUAAAAAAUGC SEQ ID NO: 758 - DsiRNA 375 guide (antisense) strand
GCAUUUUUUAGUAGAGAUGGGGUUUCA SEQ ID NO: 759 - DsiRNA 376 passenger (sense) strand
AACCCCAUCUCUACUAAAAAAUGCA SEQ ID NO: 760 - DsiRNA 376 guide (antisense) strand
UGCAUUUUUUAGUAGAGAUGGGGUUUC SEQ ID NO: 761 - DsiRNA 377 passenger (sense) strand
CCCAUCUCUACUAAAAAAUGCAAAA SEQ ID NO: 762 - DsiRNA 377 guide (antisense) strand
UUUUGCAUUUUUUAGUAGAGAUGGGGU SEQ ID NO: 763 - DsiRNA 378 passenger (sense) strand
AUCAAAACCCUUAUGGCAGACUGTT SEQ ID NO: 764 - DsiRNA 378 guide (antisense) strand
AACAGUCUGCCAUAAGGGUUUUGAUAU SEQ ID NO: 765 - DsiRNA 379 passenger (sense) strand
UAUUUUAUUUGUCGUGCUUAUAUGT SEQ ID NO: 766 - DsiRNA 379 guide (antisense) strand
ACAUAUAAGCACGACAAAUAAAAUACA SEQ ID NO: 767 - DsiRNA 380 passenger (sense) strand
GUGUUGCCCAAGUUUCUAUGGUGAA SEQ ID NO: 768 - DsiRNA 380 guide (antisense) strand
UUCACCAUAGAAACUUGGGCAACACAU SEQ ID NO: 769 - DsiRNA 381 passenger (sense) strand
GCCCAAGUUUCUAUGGUGAACGGTA SEQ ID NO: 770 - DsiRNA 381 guide (antisense) strand
UACCGUUCACCAUAGAAACUUGGGCAA -continued SEQ ID NO: 771 - DsiRNA 382 passenger (sense) strand
CCCAAGUUUCUAUGGUGAACGGUAT SEQ ID NO: 772 - DsiRNA 382 guide (antisense) strand
AUACCGUUCACCAUAGAAACUUGGGCA SEQ ID NO: 773 - DsiRNA 383 passenger (sense) strand
ACUUUCAGCAUGAGAAAAUAACUCC SEQ ID NO: 774 - DsiRNA 383 guide (antisense) strand
GGAGUUAUUUUCUCAUGCUGAAAGUGA SEQ ID NO: 775 - DsiRNA 384 passenger (sense) strand
CUUUCAGCAUGAGAAAAUAACUCCT SEQ ID NO: 776 - DsiRNA 384 guide (antisense) strand
AGGAGUUAUUUUCUCAUGCUGAAAGUG SEQ ID NO: 777 -PNPLA3 oligonucleotide 1 passenger (sense) strand
UGAGUGACAACGUACCCUUAGCAGCCGAAAGGCUGC SEQ ID NO: 778 - PNPLA3 oligonucleotide 1 guide (antisense) strand
UAAGGGUACGUUGUCACUCAGG SEQ ID NO: 779 - PNPLA3 oligonucleotide 2 passenger (sense) strand
GAGUGACAACGUACCCUUCAGCAGCCGAAAGGCUGC SEQ ID NO: 780 - PNPLA3 oligonucleotide 2 guide (antisense) strand
UGAAGGGUACGUUGUCACUCGG SEQ ID NO: 781 - PNPLA3 oligonucleotide 3 passenger (sense) strand
AGUGACAACGUACCCUUCAAGCAGCCGAAAGGCUGC SEQ ID NO: 782 - PNPLA3 oligonucleotide 3 guide (antisense) strand
UUGAAGGGUACGUUGUCACUGG SEQ ID NO: 783 - PNPLA3 oligonucleotide 4 passenger (sense) strand
UGACAACGUACCCUUCAUUAGCAGCCGAAAGGCUGC SEQ ID NO: 784 - PNPLA3 oligonucleotide 4 guide (antisense) strand
UAAUGAAGGGUACGUUGUCAGG SEQ ID NO: 785 - PNPLA3 oligonucleotide 5 passenger (sense) strand
GACAACGUACCCUUCAUUGAGCAGCCGAAAGGCUGC SEQ ID NO: 786 - PNPLA3 oligonucleotide 5 guide (antisense) strand
UCAAUGAAGGGUACGUUGUCGG SEQ ID NO: 787 - PNPLA3 oligonucleotide 6 passenger (sense) strand
CAACGUACCCUUCAUUGAUAGCAGCCGAAAGGCUGC SEQ ID NO: 788 - PNPLA3 oligonucleotide 6 guide (antisense) strand
UAUCAAUGAAGGGUACGUUGGG SEQ ID NO: 789 - PNPLA3 oligonucleotide 7 passenger (sense) strand
AACGUACCCUUCAUUGAUGAGCAGCCGAAAGGCUGC SEQ ID NO: 790 - PNPLA3 oligonucleotide 7 guide (antisense) strand
UCAUCAAUGAAGGGUACGUUGG SEQ ID NO: 791 - PNPLA3 oligonucleotide 8 passenger (sense) strand
ACGUACCCUUCAUUGAUGCAGCAGCCGAAAGGCUGC SEQ ID NO: 792 - PNPLA3 oligonucleotide 8 guide (antisense) strand
UGCAUCAAUGAAGGGUACGUGG SEQ ID NO: 793 - PNPLA3 oligonucleotide 9 passenger (sense) strand
CGUACCCUUCAUUGAUGCCAGCAGCCGAAAGGCUGC SEQ ID NO: 794 - PNPLA3 oligonucleotide 9 guide (antisense) strand
UGGCAUCAAUGAAGGGUACGGG SEQ ID NO: 795 - PNPLA3 oligonucleotide 10 passenger (sense) strand
UACCCUUCAUUGAUGCCAAAGCAGCCGAAAGGCUGC SEQ ID NO: 796 - PNPLA3 oligonucleotide 10 guide (antisense) strand
UUUGGCAUCAAUGAAGGGUAGG SEQ ID NO: 797 - PNPLA3 oligonucleotide 11 passenger (sense) strand
CACGAACUUUCUUCAUGUGAGCAGCCGAAAGGCUGC -continued SEQ ID NO: 798 - PNPLA3 oligonucleotide 11 guide (antisense) strand
UCACAUGAAGAAAGUUCGUGGG SEQ ID NO: 799 - PNPLA3 oligonucleotide 12 passenger (sense) strand
ACGAACUUUCUUCAUGUGGAGCAGCCGAAAGGCUGC SEQ ID NO: 800 - PNPLA3 oligonucleotide 12 guide (antisense) strand
UCCACAUGAAGAAAGUUCGUGG SEQ ID NO: 801 - PNPLA3 oligonucleotide 13 passenger (sense) strand
CGAACUUUCUUCAUGUGGAAGCAGCCGAAAGGCUGC SEQ ID NO: 802 - PNPLA3 oligonucleotide 13 guide (antisense) strand
UUCCACAUGAAGAAAGUUCGGG SEQ ID NO: 803 - PNPLA3 oligonucleotide 14 passenger (sense) strand
ACUUUCUUCAUGUGGACAUAGCAGCCGAAAGGCUGC SEQ ID NO: 804 - PNPLA3 oligonucleotide 14 guide (antisense) strand
UAUGUCCACAUGAAGAAAGUGG SEQ ID NO: 805 - PNPLA3 oligonucleotide 15 passenger (sense) strand
UUUCUUCAUGUGGACAUCAAGCAGCCGAAAGGCUGC SEQ ID NO: 806 - PNPLA3 oligonucleotide 15 guide (antisense) strand
UUGAUGUCCACAUGAAGAAAGG SEQ ID NO: 807 - PNPLA3 oligonucleotide 16 passenger (sense) strand
CUUCAUGUGGACAUCACCAAGCAGCCGAAAGGCUGC SEQ ID NO: 808 - PNPLA3 oligonucleotide 16 guide (antisense) strand
UUGGUGAUGUCCACAUGAAGGG SEQ ID NO: 809 - PNPLA3 oligonucleotide 17 passenger (sense) strand
AUGUGGACAUCACCAAGCUAGCAGCCGAAAGGCUGC SEQ ID NO: 810 - PNPLA3 oligonucleotide 17 guide (antisense) strand
UAGCUUGGUGAUGUCCACAUGG SEQ ID NO: 811 -PNPLA3 oligonucleotide 18 passenger (sense) strand
UGUGGACAUCACCAAGCUCAGCAGCCGAAAGGCUGC SEQ ID NO: 812 - PNPLA3 oligonucleotide 18 guide (antisense) strand
UGAGCUUGGUGAUGUCCACAGG SEQ ID NO: 813 - PNPLA3 oligonucleotide 19 passenger (sense) strand
GUGGACAUCACCAAGCUCAAGCAGCCGAAAGGCUGC SEQ ID NO: 814 - PNPLA3 oligonucleotide 19 guide (antisense) strand
UUGAGCUUGGUGAUGUCCACGG SEQ ID NO: 815 - PNPLA3 oligonucleotide 20 passenger (sense) strand
UGGACAUCACCAAGCUCAGAGCAGCCGAAAGGCUGC SEQ ID NO: 816 - PNPLA3 oligonucleotide 20 guide (antisense) strand
UCUGAGCUUGGUGAUGUCCAGG SEQ ID NO: 817 - PNPLA3 oligonucleotide 21 passenger (sense) strand
AGAUAUGCCUUCGAGGAUAAGCAGCCGAAAGGCUGC SEQ ID NO: 818 - PNPLA3 oligonucleotide 21 guide (antisense) strand
UUAUCCUCGAAGGCAUAUCUGG SEQ ID NO: 819 - PNPLA3 oligonucleotide 22 passenger (sense) strand
AUGCCUUCGAGGAUAUUUGAGCAGCCGAAAGGCUGC SEQ ID NO: 820 - PNPLA3 oligonucleotide 22 guide (antisense) strand
UCAAAUAUCCUCGAAGGCAUGG SEQ ID NO: 821 - PNPLA3 oligonucleotide 23 passenger (sense) strand
GCCUUCGAGGAUAUUUGGAAGCAGCCGAAAGGCUGC SEQ ID NO: 822 - PNPLA3 oligonucleotide 23 guide (antisense) strand
UUCCAAAUAUCCUCGAAGGCGG SEQ ID NO: 823 - PNPLA3 oligonucleotide 24 passenger (sense) strand
UGAAGUCAUCCUCAGAAGGAGCAGCCGAAAGGCUGC SEQ ID NO: 824 - PNPLA3 oligonucleotide 24 guide (antisense) strand
UCCUUCUGAGGAUGACUUCAGG -continued SEQ ID NO: 825 - PNPLA3 oligonucleotide 25 passenger (sense) strand
GAAGUCAUCCUCAGAAGGGAGCAGCCGAAAGGCUGC SEQ ID NO: 826 - PNPLA3 oligonucleotide 25 guide (antisense) strand
UCCCUUCUGAGGAUGACUUCGG SEQ ID NO: 827 - PNPLA3 oligonucleotide 26 passenger (sense) strand
AUCCUCAGAAGGGAUGGAUAGCAGCCGAAAGGCUGC SEQ ID NO: 828 - PNPLA3 oligonucleotide 26 guide (antisense) strand
UAUCCAUCCCUUCUGAGGAUGG SEQ ID NO: 829 - PNPLA3 oligonucleotide 27 passenger (sense) strand
AGUGAAGAAAUGAAAGACAAGCAGCCGAAAGGCUGC SEQ ID NO: 830 - PNPLA3 oligonucleotide 27 guide (antisense) strand
UUGUCUUUCAUUUCUUCACUGG SEQ ID NO: 831 - PNPLA3 oligonucleotide 28 passenger (sense) strand
AAGAAAUGAAAGACAAAGGAGCAGCCGAAAGGCUGC SEQ ID NO: 832 - PNPLA3 oligonucleotide 28 guide (antisense) strand
UCCUUUGUCUUUCAUUUCUUGG SEQ ID NO: 833 - PNPLA3 oligonucleotide 29 passenger (sense) strand
AGAAAUGAAAGACAAAGGUAGCAGCCGAAAGGCUGC SEQ ID NO: 834 - PNPLA3 oligonucleotide 29 guide (antisense) strand
UACCUUUGUCUUUCAUUUCUGG SEQ ID NO: 835 - PNPLA3 oligonucleotide 30 passenger (sense) strand
GAAAUGAAAGACAAAGGUGAGCAGCCGAAAGGCUGC SEQ ID NO: 836 - PNPLA3 oligonucleotide 30 guide (antisense) strand
UCACCUUUGUCUUUCAUUUCGG SEQ ID NO: 837 - PNPLA3 oligonucleotide 31 passenger (sense) strand
AAAUGAAAGACAAAGGUGGAGCAGCCGAAAGGCUGC SEQ ID NO: 838 - PNPLA3 oligonucleotide 31 guide (antisense) strand
UCCACCUUUGUCUUUCAUUUGG SEQ ID NO: 839 - PNPLA3 oligonucleotide 32 passenger (sense) strand
AAUGAAAGACAAAGGUGGAAGCAGCCGAAAGGCUGC SEQ ID NO: 840 - PNPLA3 oligonucleotide 32 guide (antisense) strand
UUCCACCUUUGUCUUUCAUUGG SEQ ID NO: 841 - PNPLA3 oligonucleotide 33 passenger (sense) strand
AUGAAAGACAAAGGUGGAUAGCAGCCGAAAGGCUGC SEQ ID NO: 842 - PNPLA3 oligonucleotide 33 guide (antisense) strand
UAUCCACCUUUGUCUUUCAUGG SEQ ID NO: 843 - PNPLA3 oligonucleotide 34 passenger (sense) strand
UGAAAGACAAAGGUGGAUAAGCAGCCGAAAGGCUGC SEQ ID NO: 844 - PNPLA3 oligonucleotide 34 guide (antisense) strand
UUAUCCACCUUUGUCUUUCAGG SEQ ID NO: 845 - PNPLA3 oligonucleotide 35 passenger (sense) strand
GAAAGACAAAGGUGGAUACAGCAGCCGAAAGGCUGC SEQ ID NO: 846 - PNPLA3 oligonucleotide 35 guide (antisense) strand
UGUAUCCACCUUUGUCUUUCGG SEQ ID NO: 847 - PNPLA3 oligonucleotide 36 passenger (sense) strand
AAGACAAAGGUGGAUACAUAGCAGCCGAAAGGCUGC SEQ ID NO: 848 - PNPLA3 oligonucleotide 36 guide (antisense) strand
UAUGUAUCCACCUUUGUCUUGG SEQ ID NO: 849 - PNPLA3 oligonucleotide 37 passenger (sense) strand
AGACAAAGGUGGAUACAUGAGCAGCCGAAAGGCUGC SEQ ID NO: 850 - PNPLA3 oligonucleotide 37 guide (antisense) strand
UCAUGUAUCCACCUUUGUCUGG SEQ ID NO: 851 - PNPLA3 oligonucleotide 38 passenger (sense) strand
GACAAAGGUGGAUACAUGAAGCAGCCGAAAGGCUGC -continued SEQ ID NO: 852 - PNPLA3 oligonucleotide 38 guide (antisense) strand
UUCAUGUAUCCACCUUUGUCGG SEQ ID NO: 853 - PNPLA3 oligonucleotide 39 passenger guide (sense) strand
ACAAAGGUGGAUACAUGAGAGCAGCCGAAAGGCUGC SEQ ID NO: 854 - PNPLA3 oligonucleotide 39 guide (antisense) strand
UCUCAUGUAUCCACCUUUGUGG SEQ ID NO: 855 - PNPLA3 oligonucleotide 40 passenger (sense) strand
AAGGUGGAUACAUGAGCAAAGCAGCCGAAAGGCUGC SEQ ID NO: 856 - PNPLA3 oligonucleotide 40 guide (antisense) strand
UUUGCUCAUGUAUCCACCUUGG SEQ ID NO: 857 - PNPLA3 oligonucleotide 41 passenger (sense) strand
AGGUGGAUACAUGAGCAAGAGCAGCCGAAAGGCUGC SEQ ID NO: 858 - PNPLA3 oligonucleotide 41 guide (antisense) strand
UCUUGCUCAUGUAUCCACCUGG SEQ ID NO: 859 - PNPLA3 oligonucleotide 42 passenger (sense) strand
UGGAUACAUGAGCAAGAUUAGCAGCCGAAAGGCUGC SEQ ID NO: 860 - PNPLA3 oligonucleotide 42 guide (antisense) strand
UAAUCUUGCUCAUGUAUCCAGG SEQ ID NO: 861 - PNPLA3 oligonucleotide 43 passenger (sense) strand
GGAUACAUGAGCAAGAUUUAGCAGCCGAAAGGCUGC SEQ ID NO: 862 - PNPLA3 oligonucleotide 43 guide (antisense) strand
UAAAUCUUGCUCAUGUAUCCGG SEQ ID NO: 863 - PNPLA3 oligonucleotide 44 passenger (sense) strand
GAUACAUGAGCAAGAUUUGAGCAGCCGAAAGGCUGC SEQ ID NO: 864 - PNPLA3 oligonucleotide 44 guide (antisense) strand
UCAAAUCUUGCUCAUGUAUCGG SEQ ID NO: 865 - PNPLA3 oligonucleotide 45 passenger (sense) strand
AUACAUGAGCAAGAUUUGCAGCAGCCGAAAGGCUGC SEQ ID NO: 866 - PNPLA3 oligonucleotide 45 guide (antisense) strand
UGCAAAUCUUGCUCAUGUAUGG SEQ ID NO: 867 - PNPLA3 oligonucleotide 46 passenger (sense) strand
UACAUGAGCAAGAUUUGCAAGCAGCCGAAAGGCUGC SEQ ID NO: 868 - PNPLA3 oligonucleotide 46 guide (antisense) strand
UUGCAAAUCUUGCUCAUGUAGG SEQ ID NO: 869 - PNPLA3 oligonucleotide 47 passenger (sense) strand
ACAUGAGCAAGAUUUGCAAAGCAGCCGAAAGGCUGC SEQ ID NO: 870 - PNPLA3 oligonucleotide 47 guide (antisense) strand
UUUGCAAAUCUUGCUCAUGUGG SEQ ID NO: 871 - PNPLA3 oligonucleotide 48 passenger (sense) strand
UGAGCAAGAUUUGCAACUUAGCAGCCGAAAGGCUGC SEQ ID NO: 872 - PNPLA3 oligonucleotide 48 guide (antisense) strand
UAAGUUGCAAAUCUUGCUCAGG SEQ ID NO: 873 - PNPLA3 oligonucleotide 49 passenger (sense) strand
GAGCAAGAUUUGCAACUUGAGCAGCCGAAAGGCUGC SEQ ID NO: 874 - PNPLA3 oligonucleotide 49 guide (antisense) strand
UCAAGUUGCAAAUCUUGCUCGG SEQ ID NO: 875 - PNPLA3 oligonucleotide 50 passenger (sense) strand
AGCAAGAUUUGCAACUUGCAGCAGCCGAAAGGCUGC SEQ ID NO: 876 - PNPLA3 oligonucleotide 50 guide (antisense) strand
UGCAAGUUGCAAAUCUUGCUGG SEQ ID NO: 877 - PNPLA3 oligonucleotide 51 passenger (sense) strand
GCAAGAUUUGCAACUUGCUAGCAGCCGAAAGGCUGC SEQ ID NO: 878 - PNPLA3 oligonucleotide 51 guide (antisense) strand
UAGCAAGUUGCAAAUCUUGCGG -continued SEQ ID NO: 879 - PNPLA3 oligonucleotide 52 passenger (sense) strand
CAAGAUUUGCAACUUGCUAAGCAGCCGAAAGGCUGC SEQ ID NO: 880 - PNPLA3 oligonucleotide 52 guide (antisense) strand
UUAGCAAGUUGCAAAUCUUGGG SEQ ID NO: 881 - PNPLA3 oligonucleotide 53 passenger (sense) strand
AAGAUUUGCAACUUGCUACAGCAGCCGAAAGGCUGC SEQ ID NO: 882 - PNPLA3 oligonucleotide 53 guide (antisense) strand
UGUAGCAAGUUGCAAAUCUUGG SEQ ID NO: 883 - PNPLA3 oligonucleotide 54 passenger (sense) strand
AGAUUUGCAACUUGCUACCAGCAGCCGAAAGGCUGC SEQ ID NO: 884 - PNPLA3 oligonucleotide 54 guide (antisense) strand
UGGUAGCAAGUUGCAAAUCUGG SEQ ID NO: 885 - PNPLA3 oligonucleotide 55 passenger (sense) strand
AUUUGCAACUUGCUACCCAAGCAGCCGAAAGGCUGC SEQ ID NO: 886 - PNPLA3 oligonucleotide 55 guide (antisense) strand
UUGGGUAGCAAGUUGCAAAUGG SEQ ID NO: 887 - PNPLA3 oligonucleotide 56 passenger (sense) strand
UUGCAACUUGCUACCCAUUAGCAGCCGAAAGGCUGC SEQ ID NO: 888 - PNPLA3 oligonucleotide 56 guide (antisense) strand
UAAUGGGUAGCAAGUUGCAAGG SEQ ID NO: 889 - PNPLA3 oligonucleotide 57 passenger (sense) strand
UGCAACUUGCUACCCAUUAAGCAGCCGAAAGGCUGC SEQ ID NO: 890 - PNPLA3 oligonucleotide 57 guide (antisense) strand
UUAAUGGGUAGCAAGUUGCAGG SEQ ID NO: 891 - PNPLA3 oligonucleotide 58 passenger (sense) strand
GCAACUUGCUACCCAUUAGAGCAGCCGAAAGGCUGC SEQ ID NO: 892 - PNPLA3 oligonucleotide 58 guide (antisense) strand
UCUAAUGGGUAGCAAGUUGCGG SEQ ID NO: 893 - PNPLA3 oligonucleotide 59 passenger (sense) strand
CAACUUGCUACCCAUUAGGAGCAGCCGAAAGGCUGC SEQ ID NO: 894 - PNPLA3 oligonucleotide 59 guide (antisense) strand
UCCUAAUGGGUAGCAAGUUGGG SEQ ID NO: 895 - PNPLA3 oligonucleotide 60 passenger (sense) strand
CUUGCUACCCAUUAGGAUAAGCAGCCGAAAGGCUGC SEQ ID NO: 896 - PNPLA3 oligonucleotide 60 guide (antisense) strand
UUAUCCUAAUGGGUAGCAAGGG SEQ ID NO: 897 - PNPLA3 oligonucleotide 61 passenger (sense) strand
UGCUACCCAUUAGGAUAAUAGCAGCCGAAAGGCUGC SEQ ID NO: 898 - PNPLA3 oligonucleotide 61 guide (antisense) strand
UAUUAUCCUAAUGGGUAGCAGG SEQ ID NO: 899 - PNPLA3 oligonucleotide 62 passenger (sense) strand
AUUAGGAUAAUGUCUUAUGAGCAGCCGAAAGGCUGC SEQ ID NO: 900 - PNPLA3 oligonucleotide 62 guide (antisense) strand
UCAUAAGACAUUAUCCUAAUGG SEQ ID NO: 901 - PNPLA3 oligonucleotide 63 passenger (sense) strand
UUAGGAUAAUGUCUUAUGUAGCAGCCGAAAGGCUGC SEQ ID NO: 902 - PNPLA3 oligonucleotide 63 guide (antisense) strand
UACAUAAGACAUUAUCCUAAGG SEQ ID NO: 903 - PNPLA3 oligonucleotide 64 passenger (sense) strand
UGCGAUUGUCCAGAGACUGAGCAGCCGAAAGGCUGC SEQ ID NO: 904 - PNPLA3 oligonucleotide 64 guide (antisense) strand
UCAGUCUCUGGACAAUCGCAGG SEQ ID NO: 905 - PNPLA3 oligonucleotide 65 passenger (sense) strand
CGAUUGUCCAGAGACUGGUAGCAGCCGAAAGGCUGC -continued SEQ ID NO: 906 - PNPLA3 oligonucleotide 65 guide (antisense) strand
UACCAGUCUCUGGACAAUCGGG SEQ ID NO: 907 - PNPLA3 oligonucleotide 66 passenger (sense) strand
GUCCAGAGACUGGUGACAUAGCAGCCGAAAGGCUGC SEQ ID NO: 908 - PNPLA3 oligonucleotide 66 guide (antisense) strand
UAUGUCACCAGUCUCUGGACGG SEQ ID NO: 909 - PNPLA3 oligonucleotide 67 passenger (sense) strand
AGAGACUGGUGACAUGGCUAGCAGCCGAAAGGCUGC SEQ ID NO: 910 - PNPLA3 oligonucleotide 67 guide (antisense) strand
UAGCCAUGUCACCAGUCUCUGG SEQ ID NO: 911 - PNPLA3 oligonucleotide 68 passenger (sense) strand
ACUGGUGACAUGGCUUCCAAGCAGCCGAAAGGCUGC SEQ ID NO: 912 - PNPLA3 oligonucleotide 68 guide (antisense) strand
UUGGAAGCCAUGUCACCAGUGG SEQ ID NO: 913 - PNPLA3 oligonucleotide 69 passenger (sense) strand
CUCCACCUUUCCCAGUUUUAGCAGCCGAAAGGCUGC SEQ ID NO: 914 - PNPLA3 oligonucleotide 69 guide (antisense) strand
UAAAACUGGGAAAGGUGGAGGG SEQ ID NO: 915 - PNPLA3 oligonucleotide 70 passenger (sense) strand
CACCUUUCCCAGUUUUUCAAGCAGCCGAAAGGCUGC SEQ ID NO: 916 - PNPLA3 oligonucleotide 70 guide (antisense) strand
UUGAAAAACUGGGAAAGGUGGG SEQ ID NO: 917 - PNPLA3 oligonucleotide 71 passenger (sense) strand
AGUUUUUCACUAGAGAAGAAGCAGCCGAAAGGCUGC SEQ ID NO: 918 - PNPLA3 oligonucleotide 71 guide (antisense) strand
UUCUUCUCUAGUGAAAAACUGG SEQ ID NO: 919 - PNPLA3 oligonucleotide 72 passenger (sense) strand
AGCAGAUUCUUUCAGAGGUAGCAGCCGAAAGGCUGC SEQ ID NO: 920 - PNPLA3 oligonucleotide 72 guide (antisense) strand
UACCUCUGAAAGAAUCUGCUGG SEQ ID NO: 921 - PNPLA3 oligonucleotide 73 passenger (sense) strand
GCAGAUUCUUUCAGAGGUGAGCAGCCGAAAGGCUGC SEQ ID NO: 922 - PNPLA3 oligonucleotide 73 guide (antisense) strand
UCACCUCUGAAAGAAUCUGCGG SEQ ID NO: 923 - PNPLA3 oligonucleotide 74 passenger (sense) strand
AGAUUCUUUCAGAGGUGCUAGCAGCCGAAAGGCUGC SEQ ID NO: 924 - PNPLA3 oligonucleotide 74 guide (antisense) strand
UAGCACCUCUGAAAGAAUCUGG SEQ ID NO: 925 - PNPLA3 oligonucleotide 75 passenger (sense) strand
AGGUGCUAAAGUUUCCCAUAGCAGCCGAAAGGCUGC SEQ ID NO: 926 - PNPLA3 oligonucleotide 75 guide (antisense) strand
UAUGGGAAACUUUAGCACCUGG SEQ ID NO: 927 - PNPLA3 oligonucleotide 76 passenger (sense) strand
AAAGUUUCCCAUCUUUGUGAGCAGCCGAAAGGCUGC SEQ ID NO: 928 - PNPLA3 oligonucleotide 76 guide (antisense) strand
UCACAAAGAUGGGAAACUUUGG SEQ ID NO: 929 - PNPLA3 oligonucleotide 77 passenger (sense) strand
AGUUUCCCAUCUUUGUGCAAGCAGCCGAAAGGCUGC SEQ ID NO: 930 - PNPLA3 oligonucleotide 77 guide (antisense) strand
UUGCACAAAGAUGGGAAACUGG SEQ ID NO: 931 - PNPLA3 oligonucleotide 78 passenger (sense) strand
AGCCUCUGAGCUGAGUUGGAGCAGCCGAAAGGCUGC SEQ ID NO: 932 - PNPLA3 oligonucleotide 78 guide (antisense) strand
UCCAACUCAGCUCAGAGGCUGG -continued SEQ ID NO: 933 - PNPLA3 oligonucleotide 79 passenger (sense) strand
GCCUCUGAGCUGAGUUGGUAGCAGCCGAAAGGCUGC SEQ ID NO: 934 - PNPLA3 oligonucleotide 79 guide (antisense) strand
UACCAACUCAGCUCAGAGGCGG SEQ ID NO: 935 - PNPLA3 oligonucleotide 80 passenger (sense) strand
CCUCUGAGCUGAGUUGGUUAGCAGCCGAAAGGCUGC SEQ ID NO: 936 - PNPLA3 oligonucleotide 80 guide (antisense) strand
UAACCAACUCAGCUCAGAGGGG SEQ ID NO: 937 - PNPLA3 oligonucleotide 81 passenger (sense) strand
CUCUGAGCUGAGUUGGUUUAGCAGCCGAAAGGCUGC SEQ ID NO: 938 - PNPLA3 oligonucleotide 81 guide (antisense) strand
UAAACCAACUCAGCUCAGAGGG SEQ ID NO: 939 - PNPLA3 oligonucleotide 82 passenger (sense) strand
UCUGAGCUGAGUUGGUUUUAGCAGCCGAAAGGCUGC SEQ ID NO: 940 - PNPLA3 oligonucleotide 82 guide (antisense) strand
UAAAACCAACUCAGCUCAGAGG SEQ ID NO: 941 - PNPLA3 oligonucleotide 83 passenger (sense) strand
UGAGCUGAGUUGGUUUUAUAGCAGCCGAAAGGCUGC SEQ ID NO: 942 - PNPLA3 oligonucleotide 83 guide (antisense) strand
UAUAAAACCAACUCAGCUCAGG SEQ ID NO: 943 - PNPLA3 oligonucleotide 84 passenger (sense) strand
UGAGUUGGUUUUAUGAAAAAGCAGCCGAAAGGCUGC SEQ ID NO: 944 - PNPLA3 oligonucleotide 84 guide (antisense) strand
UUUUUCAUAAAACCAACUCAGG SEQ ID NO: 945 - PNPLA3 oligonucleotide 85 passenger (sense) strand
GAGUUGGUUUUAUGAAAAGAGCAGCCGAAAGGCUGC SEQ ID NO: 946 - PNPLA3 oligonucleotide 85 guide (antisense) strand
UCUUUUCAUAAAACCAACUCGG SEQ ID NO: 947 - PNPLA3 oligonucleotide 86 passenger (sense) strand
UUGGUUUUAUGAAAAGCUAAGCAGCCGAAAGGCUGC SEQ ID NO: 948 - PNPLA3 oligonucleotide 86 guide (antisense) strand
UUAGCUUUUCAUAAAACCAAGG SEQ ID NO: 949 - PNPLA3 oligonucleotide 87 passenger (sense) strand
UGGUUUUAUGAAAAGCUAGAGCAGCCGAAAGGCUGC SEQ ID NO: 950 - PNPLA3 oligonucleotide 87 guide (antisense) strand
UCUAGCUUUUCAUAAAACCAGG SEQ ID NO: 951 - PNPLA3 oligonucleotide 88 passenger (sense) strand
GGUUUUAUGAAAAGCUAGGAGCAGCCGAAAGGCUGC SEQ ID NO: 952 - PNPLA3 oligonucleotide 88 guide (antisense) strand
UCCUAGCUUUUCAUAAAACCGG SEQ ID NO: 953 - PNPLA3 oligonucleotide 89 passenger (sense) strand
UUUUAUGAAAAGCUAGGAAAGCAGCCGAAAGGCUGC SEQ ID NO: 954 - PNPLA3 oligonucleotide 89 guide (antisense) strand
UUUCCUAGCUUUUCAUAAAAGG SEQ ID NO: 955 - PNPLA3 oligonucleotide 90 passenger (sense) strand
UAUGAAAAGCUAGGAAGCAAGCAGCCGAAAGGCUGC SEQ ID NO: 956 - PNPLA3 oligonucleotide 90 guide (antisense) strand
UUGCUUCCUAGCUUUUCAUAGG SEQ ID NO: 957 - PNPLA3 oligonucleotide 91 passenger (sense) strand
AUGAAAAGCUAGGAAGCAAAGCAGCCGAAAGGCUGC SEQ ID NO: 958 - PNPLA3 oligonucleotide 91 guide (antisense) strand
UUUGCUUCCUAGCUUUUCAUGG SEQ ID NO: 959 - PNPLA3 oligonucleotide 92 passenger (sense) strand
CCAGCACUUAACUCUAAUAAGCAGCCGAAAGGCUGC -continued SEQ ID NO: 960 - PNPLA3 oligonucleotide 92 guide (antisense) strand
UUAUUAGAGUUAAGUGCUGGGG SEQ ID NO: 961 - PNPLA3 oligonucleotide 93 passenger (sense) strand
CAGCACUUAACUCUAAUACAGCAGCCGAAAGGCUGC SEQ ID NO: 962 - PNPLA3 oligonucleotide 93 guide (antisense) strand
UGUAUUAGAGUUAAGUGCUGGG SEQ ID NO: 963 - PNPLA3 oligonucleotide 94 passenger (sense) strand
UAAUACAUCAGCAUGCGUUAGCAGCCGAAAGGCUGC SEQ ID NO: 964 - PNPLA3 oligonucleotide 94 guide (antisense) strand
UAACGCAUGCUGAUGUAUUAGG SEQ ID NO: 965 - PNPLA3 oligonucleotide 95 passenger (sense) strand
AAUACAUCAGCAUGCGUUAAGCAGCCGAAAGGCUGC SEQ ID NO: 966 - PNPLA3 oligonucleotide 95 guide (antisense) strand
UUAACGCAUGCUGAUGUAUUGG SEQ ID NO: 967 - PNPLA3 oligonucleotide 96 passenger (sense) strand
UGCGUUAAUUCAGCUGGUUAGCAGCCGAAAGGCUGC SEQ ID NO: 968 - PNPLA3 oligonucleotide 96 guide (antisense) strand
UAACCAGCUGAAUUAACGCAGG SEQ ID NO: 969 - PNPLA3 oligonucleotide 97 passenger (sense) strand
GCGUUAAUUCAGCUGGUUGAGCAGCCGAAAGGCUGC SEQ ID NO: 970 - PNPLA3 oligonucleotide 97 guide (antisense) strand
UCAACCAGCUGAAUUAACGCGG SEQ ID NO: 971 - PNPLA3 oligonucleotide 98 passenger (sense) strand
CGUUAAUUCAGCUGGUUGGAGCAGCCGAAAGGCUGC SEQ ID NO: 972 - PNPLA3 oligonucleotide 98 guide (antisense) strand
UCCAACCAGCUGAAUUAACGGG SEQ ID NO: 973 - PNPLA3 oligonucleotide 99 passenger (sense) strand
UUAAUUCAGCUGGUUGGGAAGCAGCCGAAAGGCUGC SEQ ID NO: 974 - PNPLA3 oligonucleotide 99 guide (antisense) strand
UUCCCAACCAGCUGAAUUAAGG SEQ ID NO: 975 - PNPLA3 oligonucleotide 100 passenger (sense) strand
UAAUUCAGCUGGUUGGGAAAGCAGCCGAAAGGCUGC SEQ ID NO: 976 - PNPLA3 oligonucleotide 100 guide (antisense) strand
UUUCCCAACCAGCUGAAUUAGG SEQ ID NO: 977 - PNPLA3 oligonucleotide 101 passenger (sense) strand
GCAGAGGGUCCCUUACUGAAGCAGCCGAAAGGCUGC SEQ ID NO: 978 - PNPLA3 oligonucleotide 101 guide (antisense) strand
UUCAGUAAGGGACCCUCUGCGG SEQ ID NO: 979 - PNPLA3 oligonucleotide 102 passenger (sense) strand
CUAUUAAUGGUCAGACUGUAGCAGCCGAAAGGCUGC SEQ ID NO: 980 - PNPLA3 oligonucleotide 102 guide (antisense) strand
UACAGUCUGACCAUUAAUAGGG SEQ ID NO: 981 - PNPLA3 oligonucleotide 103 passenger (sense) strand
UAUUAAUGGUCAGACUGUUAGCAGCCGAAAGGCUGC SEQ ID NO: 982 - PNPLA3 oligonucleotide 103 guide (antisense) strand
UAACAGUCUGACCAUUAAUAGG SEQ ID NO: 983 - PNPLA3 oligonucleotide 104 passenger (sense) strand
AUUAAUGGUCAGACUGUUCAGCAGCCGAAAGGCUGC SEQ ID NO: 984 - PNPLA3 oligonucleotide 104 guide (antisense) strand
UGAACAGUCUGACCAUUAAUGG SEQ ID NO: 985 - PNPLA3 oligonucleotide 105 passenger (sense) strand
UUAAUGGUCAGACUGUUCCAGCAGCCGAAAGGCUGC SEQ ID NO: 986 - PNPLA3 oligonucleotide 105 guide (antisense) strand
UGGAACAGUCUGACCAUUAAGG -continued SEQ ID NO: 987 - PNPLA3 oligonucleotide 106 passenger (sense) strand
UAAUGGUCAGACUGUUCCAAGCAGCCGAAAGGCUGC SEQ ID NO: 988 - PNPLA3 oligonucleotide 106 guide (antisense) strand
UUGGAACAGUCUGACCAUUAGG SEQ ID NO: 989 - PNPLA3 oligonucleotide 107 passenger (sense) strand
AAUGGUCAGACUGUUCCAGAGCAGCCGAAAGGCUGC SEQ ID NO: 990 - PNPLA3 oligonucleotide 107 guide (antisense) strand
UCUGGAACAGUCUGACCAUUGG SEQ ID NO: 991 - PNPLA3 oligonucleotide 108 passenger (sense) strand
AGAACACCUUUUUCACCUAAGCAGCCGAAAGGCUGC SEQ ID NO: 992 - PNPLA3 oligonucleotide 108 guide (antisense) strand
UUAGGUGAAAAAGGUGUUCUGG SEQ ID NO: 993 - PNPLA3 oligonucleotide 109 passenger (sense) strand
GAACACCUUUUUCACCUAAAGCAGCCGAAAGGCUGC SEQ ID NO: 994 - PNPLA3 oligonucleotide 109 guide (antisense) strand
UUUAGGUGAAAAAGGUGUUCGG SEQ ID NO: 995 - PNPLA3 oligonucleotide 110 passenger (sense) strand
AACACCUUUUUCACCUAACAGCAGCCGAAAGGCUGC SEQ ID NO: 996 - PNPLA3 oligonucleotide 110 guide (antisense) strand
UGUUAGGUGAAAAAGGUGUUGG SEQ ID NO: 997 - PNPLA3 oligonucleotide 111 passenger (sense) strand
ACACCUUUUUCACCUAACUAGCAGCCGAAAGGCUGC SEQ ID NO: 998 - PNPLA3 oligonucleotide 111 guide (antisense) strand
UAGUUAGGUGAAAAAGGUGUGG SEQ ID NO: 999 - PNPLA3 oligonucleotide 112 passenger (sense) strand
CACCUUUUUCACCUAACUAAGCAGCCGAAAGGCUGC SEQ ID NO: 1000 - PNPLA3 oligonucleotide 112 guide (antisense) strand
UUAGUUAGGUGAAAAAGGUGGG SEQ ID NO: 1001 - PNPLA3 oligonucleotide 113 passenger (sense) strand
ACCUUUUUCACCUAACUAAAGCAGCCGAAAGGCUGC SEQ ID NO: 1002 - PNPLA3 oligonucleotide 113 guide (antisense) strand
UUUAGUUAGGUGAAAAAGGUGG SEQ ID NO: 1003 - PNPLA3 oligonucleotide 114 passenger (sense) strand
CUUUUUCACCUAACUAAAAAGCAGCCGAAAGGCUGC SEQ ID NO: 1004 - PNPLA3 oligonucleotide 114 guide (antisense) strand
UUUUUAGUUAGGUGAAAAAGGG SEQ ID NO: 1005 - PNPLA3 oligonucleotide 115 passenger (sense) strand
UUUUCACCUAACUAAAAUAAGCAGCCGAAAGGCUGC SEQ ID NO: 1006 - PNPLA3 oligonucleotide 115 guide (antisense) strand
UUAUUUUAGUUAGGUGAAAAGG SEQ ID NO: 1007 - PNPLA3 oligonucleotide 116 passenger (sense) strand
UUCACCUAACUAAAAUAAUAGCAGCCGAAAGGCUGC SEQ ID NO: 1008 - PNPLA3 oligonucleotide 116 guide (antisense) strand
UAUUAUUUUAGUUAGGUGAAGG SEQ ID NO: 1009 - PNPLA3 oligonucleotide 117 passenger (sense) strand
UCACCUAACUAAAAUAAUGAGCAGCCGAAAGGCUGC SEQ ID NO: 1010 - PNPLA3 oligonucleotide 117 guide (antisense) strand
UCAUUAUUUUAGUUAGGUGAGG SEQ ID NO: 1011 -PNPLA3 oligonucleotide 118 passenger (sense) strand
CACCUAACUAAAAUAAUGUAGCAGCCGAAAGGCUGC SEQ ID NO: 1012 - PNPLA3 oligonucleotide 118 guide (antisense) strand
UACAUUAUUUUAGUUAGGUGGG SEQ ID NO: 1013 - PNPLA3 oligonucleotide 119 passenger (sense) strand
ACCUAACUAAAAUAAUGUUAGCAGCCGAAAGGCUGC -continued SEQ ID NO: 1014 - PNPLA3 oligonucleotide 119 guide (antisense) strand
UAACAUUAUUUUAGUUAGGUGG SEQ ID NO: 1015 - PNPLA3 oligonucleotide 120 passenger (sense) strand
CCUAACUAAAAUAAUGUUUAGCAGCCGAAAGGCUGC SEQ ID NO: 1016 - PNPLA3 oligonucleotide 120 guide (antisense) strand
UAAACAUUAUUUUAGUUAGGGG SEQ ID NO: 1017 - PNPLA3 oligonucleotide 121 passenger (sense) strand
CUAACUAAAAUAAUGUUUAAGCAGCCGAAAGGCUGC SEQ ID NO: 1018 - PNPLA3 oligonucleotide 121 guide (antisense) strand
UUAAACAUUAUUUUAGUUAGGG SEQ ID NO: 1019 - PNPLA3 oligonucleotide 122 passenger (sense) strand
UAACUAAAAUAAUGUUUAAAGCAGCCGAAAGGCUGC SEQ ID NO: 1020 - PNPLA3 oligonucleotide 122 guide (antisense) strand
UUUAAACAUUAUUUUAGUUAGG SEQ ID NO: 1021 - PNPLA3 oligonucleotide 123 passenger (sense) strand
AACUAAAAUAAUGUUUAAAAGCAGCCGAAAGGCUGC SEQ ID NO: 1022 - PNPLA3 oligonucleotide 123 guide (antisense) strand
UUUUAAACAUUAUUUUAGUUGG SEQ ID NO: 1023 - PNPLA3 oligonucleotide 124 passenger (sense) strand
ACUAAAAUAAUGUUUAAAGAGCAGCCGAAAGGCUGC SEQ ID NO: 1024 - PNPLA3 oligonucleotide 124 guide (antisense) strand
UCUUUAAACAUUAUUUUAGUGG SEQ ID NO: 1025 - PNPLA3 oligonucleotide 125 passenger (sense) strand
CUAAAAUAAUGUUUAAAGAAGCAGCCGAAAGGCUGC SEQ ID NO: 1026 - PNPLA3 oligonucleotide 125 guide (antisense) strand
UUCUUUAAACAUUAUUUUAGGG SEQ ID NO: 1027 - PNPLA3 oligonucleotide 126 passenger (sense) strand
UAAAAUAAUGUUUAAAGAGAGCAGCCGAAAGGCUGC SEQ ID NO: 1028 - PNPLA3 oligonucleotide 126 guide (antisense) strand
UCUCUUUAAACAUUAUUUUAGG SEQ ID NO: 1029 - PNPLA3 oligonucleotide 127 passenger (sense) strand
AAGAGUUUUGUAUAAAAAUAGCAGCCGAAAGGCUGC SEQ ID NO: 1030 - PNPLA3 oligonucleotide 127 guide (antisense) strand
UAUUUUUAUACAAAACUCUUGG SEQ ID NO: 1031 - PNPLA3 oligonucleotide 128 passenger (sense) strand
GUUUUGUAUAAAAAUGUAAAGCAGCCGAAAGGCUGC SEQ ID NO: 1032 - PNPLA3 oligonucleotide 128 guide (antisense) strand
UUUACAUUUUUAUACAAAACGG SEQ ID NO: 1033 - PNPLA3 oligonucleotide 129 passenger (sense) strand
UUGUAUAAAAAUGUAAGGAAGCAGCCGAAAGGCUGC SEQ ID NO: 1034 - PNPLA3 oligonucleotide 129 guide (antisense) strand
UUCCUUACAUUUUUAUACAAGG SEQ ID NO: 1035 - PNPLA3 oligonucleotide 130 passenger (sense) strand
UGUAUAAAAAUGUAAGGAAAGCAGCCGAAAGGCUGC SEQ ID NO: 1036 - PNPLA3 oligonucleotide 130 guide (antisense) strand
UUUCCUUACAUUUUUAUACAGG SEQ ID NO: 1037 - PNPLA3 oligonucleotide 131 passenger (sense) strand
GUAUAAAAAUGUAAGGAAGAGCAGCCGAAAGGCUGC SEQ ID NO: 1038 - PNPLA3 oligonucleotide 131 guide (antisense) strand
UCUUCCUUACAUUUUUAUACGG SEQ ID NO: 1039 - PNPLA3 oligonucleotide 132 passenger (sense) strand
AUGUAAGGAAGCGUUGUUAAGCAGCCGAAAGGCUGC SEQ ID NO: 1040 - PNPLA3 oligonucleotide 132 guide (antisense) strand
UUAACAACGCUUCCUUACAUGG -continued SEQ ID NO: 1041 - PNPLA3 oligonucleotide 133 passenger (sense) strand
UUUUGUAUUAUGUGAAUCAAGCAGCCGAAAGGCUGC SEQ ID NO: 1042 - PNPLA3 oligonucleotide 133 guide (antisense) strand
UUGAUUCACAUAAUACAAAAGG SEQ ID NO: 1043 - PNPLA3 oligonucleotide 134 passenger (sense) strand
UUUGUAUUAUGUGAAUCAGAGCAGCCGAAAGGCUGC SEQ ID NO: 1044 - PNPLA3 oligonucleotide 134 guide (antisense) strand
UCUGAUUCACAUAAUACAAAGG SEQ ID NO: 1045 - PNPLA3 oligonucleotide 135 passenger (sense) strand
UUGUAUUAUGUGAAUCAGUAGCAGCCGAAAGGCUGC SEQ ID NO: 1046 - PNPLA3 oligonucleotide 135 guide (antisense) strand
UACUGAUUCACAUAAUACAAGG SEQ ID NO: 1047 - PNPLA3 oligonucleotide 136 passenger (sense) strand
GUAUUAUGUGAAUCAGUGAAGCAGCCGAAAGGCUGC SEQ ID NO: 1048 - PNPLA3 oligonucleotide 136 guide (antisense) strand
UUCACUGAUUCACAUAAUACGG SEQ ID NO: 1049 - PNPLA3 oligonucleotide 137 passenger (sense) strand
UAUUAUGUGAAUCAGUGAGAGCAGCCGAAAGGCUGC SEQ ID NO: 1050 - PNPLA3 oligonucleotide 137 guide (antisense) strand
UCUCACUGAUUCACAUAAUAGG SEQ ID NO: 1051 - PNPLA3 oligonucleotide 138 passenger (sense) strand
AUUAUGUGAAUCAGUGAGAAGCAGCCGAAAGGCUGC SEQ ID NO: 1052 - PNPLA3 oligonucleotide 138 guide (antisense) strand
UUCUCACUGAUUCACAUAAUGG SEQ ID NO: 1053 - PNPLA3 oligonucleotide 139 passenger (sense) strand
UUAUGUGAAUCAGUGAGAUAGCAGCCGAAAGGCUGC SEQ ID NO: 1054 - PNPLA3 oligonucleotide 139 guide (antisense) strand
UAUCUCACUGAUUCACAUAAGG SEQ ID NO: 1055 - PNPLA3 oligonucleotide 140 passenger (sense) strand
UAUGUGAAUCAGUGAGAUGAGCAGCCGAAAGGCUGC SEQ ID NO: 1056 - PNPLA3 oligonucleotide 140 guide (antisense) strand
UCAUCUCACUGAUUCACAUAGG SEQ ID NO: 1057 - PNPLA3 oligonucleotide 141 passenger (sense) strand
AUGUGAAUCAGUGAGAUGUAGCAGCCGAAAGGCUGC SEQ ID NO: 1058 - PNPLA3 oligonucleotide 141 guide (antisense) strand
UACAUCUCACUGAUUCACAUGG SEQ ID NO: 1059 - PNPLA3 oligonucleotide 142 passenger (sense) strand
UGUGAAUCAGUGAGAUGUUAGCAGCCGAAAGGCUGC SEQ ID NO: 1060 - PNPLA3 oligonucleotide 142 guide (antisense) strand
UAACAUCUCACUGAUUCACAGG SEQ ID NO: 1061 - PNPLA3 oligonucleotide 143 passenger (sense) strand
GUGAAUCAGUGAGAUGUUAAGCAGCCGAAAGGCUGC SEQ ID NO: 1062 - PNPLA3 oligonucleotide 143 guide (antisense) strand
UUAACAUCUCACUGAUUCACGG SEQ ID NO: 1063 - PNPLA3 oligonucleotide 144 passenger (sense) strand
GUGAGAUGUUAGUAGAAUAAGCAGCCGAAAGGCUGC SEQ ID NO: 1064 - PNPLA3 oligonucleotide 144 guide (antisense) strand
UUAUUCUACUAACAUCUCACGG SEQ ID NO: 1065 - PNPLA3 oligonucleotide 145 passenger (sense) strand
UUUCUAUUUAUGCAUUUGAAGCAGCCGAAAGGCUGC SEQ ID NO: 1066 - PNPLA3 oligonucleotide 145 guide (antisense) strand
UUCAAAUGCAUAAAUAGAAAGG SEQ ID NO: 1067 - PNPLA3 oligonucleotide 146 passenger (sense) strand
CUAUUUAUGCAUUUGAGUAAGCAGCCGAAAGGCUGC -continued SEQ ID NO: 1068 - PNPLA3 oligonucleotide 146 guide (antisense) strand
UUACUCAAAUGCAUAAAUAGGG SEQ ID NO: 1069 - PNPLA3 oligonucleotide 147 passenger (sense) strand
UGCUCAAACUGUUAAAUGUAGCAGCCGAAAGGCUGC SEQ ID NO: 1070 - PNPLA3 oligonucleotide 147 guide (antisense) strand
UACAUUUAACAGUUUGAGCAGG SEQ ID NO: 1071 - PNPLA3 oligonucleotide 148 passenger (sense) strand
GCUCAAACUGUUAAAUGUUAGCAGCCGAAAGGCUGC SEQ ID NO: 1072 - PNPLA3 oligonucleotide 148 guide (antisense) strand
UAACAUUUAACAGUUUGAGCGG SEQ ID NO: 1073 - PNPLA3 oligonucleotide 149 passenger (sense) strand
CUCAAACUGUUAAAUGUUGAGCAGCCGAAAGGCUGC SEQ ID NO: 1074 - PNPLA3 oligonucleotide 149 guide (antisense) strand
UCAACAUUUAACAGUUUGAGGG SEQ ID NO: 1075 - PNPLA3 oligonucleotide 150 passenger (sense) strand
UCAAACUGUUAAAUGUUGGAGCAGCCGAAAGGCUGC SEQ ID NO: 1076 - PNPLA3 oligonucleotide 150 guide (antisense) strand
UCCAACAUUUAACAGUUUGAGG SEQ ID NO: 1077 - PNPLA3 oligonucleotide 151 passenger (sense) strand
CAAACUGUUAAAUGUUGGAAGCAGCCGAAAGGCUGC SEQ ID NO: 1078 - PNPLA3 oligonucleotide 151 guide (antisense) strand
UUCCAACAUUUAACAGUUUGGG SEQ ID NO: 1079 - PNPLA3 oligonucleotide 152 passenger (sense) strand
AAACUGUUAAAUGUUGGAAAGCAGCCGAAAGGCUGC SEQ ID NO: 1080 - PNPLA3 oligonucleotide 152 guide (antisense) strand
UUUCCAACAUUUAACAGUUUGG SEQ ID NO: 1081 - PNPLA3 oligonucleotide 153 passenger (sense) strand
AACUGUUAAAUGUUGGAAAAGCAGCCGAAAGGCUGC SEQ ID NO: 1082 - PNPLA3 oligonucleotide 153 guide (antisense) strand
UUUUCCAACAUUUAACAGUUGG SEQ ID NO: 1083 - PNPLA3 oligonucleotide 154 passenger (sense) strand
UGUUAAAUGUUGGAAAAGAAGCAGCCGAAAGGCUGC SEQ ID NO: 1084 - PNPLA3 oligonucleotide 154 guide (antisense) strand
UUCUUUUCCAACAUUUAACAGG SEQ ID NO: 1085 - PNPLA3 oligonucleotide 155 passenger (sense) strand
GUUAAAUGUUGGAAAAGAAAGCAGCCGAAAGGCUGC SEQ ID NO: 1086 - PNPLA3 oligonucleotide 155 guide (antisense) strand
UUUCUUUUCCAACAUUUAACGG SEQ ID NO: 1087 - PNPLA3 oligonucleotide 156 passenger (sense) strand
UUAAAUGUUGGAAAAGAAAAGCAGCCGAAAGGCUGC SEQ ID NO: 1088 - PNPLA3 oligonucleotide 156 guide (antisense) strand
UUUUCUUUUCCAACAUUUAAGG SEQ ID NO: 1089 - PNPLA3 oligonucleotide 157 passenger (sense) strand
UAAAUGUUGGAAAAGAAAGAGCAGCCGAAAGGCUGC SEQ ID NO: 1090 - PNPLA3 oligonucleotide 157 guide (antisense) strand
UCUUUCUUUUCCAACAUUUAGG SEQ ID NO: 1091 - PNPLA3 oligonucleotide 158 passenger (sense) strand
AGAAAAGAGGCUACUUGUGAGCAGCCGAAAGGCUGC SEQ ID NO: 1092 - PNPLA3 oligonucleotide 158 guide (antisense) strand
UCACAAGUAGCCUCUUUUCUGG SEQ ID NO: 1093 - PNPLA3 oligonucleotide 159 passenger (sense) strand
GAAAAGAGGCUACUUGUGAAGCAGCCGAAAGGCUGC SEQ ID NO: 1094 - PNPLA3 oligonucleotide 159 guide (antisense) strand
UUCACAAGUAGCCUCUUUUCGG -continued SEQ ID NO: 1095 - PNPLA3 oligonucleotide 160 passenger (sense) strand
AAAAGAGGCUACUUGUGAAAGCAGCCGAAAGGCUGC SEQ ID NO: 1096 - PNPLA3 oligonucleotide 160 guide (antisense) strand
UUUCACAAGUAGCCUCUUUUGG SEQ ID NO: 1097 - PNPLA3 oligonucleotide 161 passenger (sense) strand
AGAGGCUACUUGUGAAAAUAGCAGCCGAAAGGCUGC SEQ ID NO: 1098 - PNPLA3 oligonucleotide 161 guide (antisense) strand
UAUUUUCACAAGUAGCCUCUGG SEQ ID NO: 1099 - PNPLA3 oligonucleotide 162 passenger (sense) strand
GAGGCUACUUGUGAAAAUAAGCAGCCGAAAGGCUGC SEQ ID NO: 1100 - PNPLA3 oligonucleotide 162 guide (antisense) strand
UUAUUUUCACAAGUAGCCUCGG SEQ ID NO: 1101 - PNPLA3 oligonucleotide 163 passenger (sense) strand
AAAGUUACAAGUUUCUUUUAGCAGCCGAAAGGCUGC SEQ ID NO: 1102 - PNPLA3 oligonucleotide 163 guide (antisense) strand
UAAAAGAAACUUGUAACUUUGG SEQ ID NO: 1103 - PNPLA3 oligonucleotide 164 passenger (sense) strand
CAACAGUAUUUUCUAAUAAAGCAGCCGAAAGGCUGC SEQ ID NO: 1104 - PNPLA3 oligonucleotide 164 guide (antisense) strand
UUUAUUAGAAAAUACUGUUGGG SEQ ID NO: 1105 - PNPLA3 oligonucleotide 165 passenger (sense) strand
AACAGUAUUUUCUAAUAACAGCAGCCGAAAGGCUGC SEQ ID NO: 1106 - PNPLA3 oligonucleotide 165 guide (antisense) strand
UGUUAUUAGAAAAUACUGUUGG SEQ ID NO: 1107 - PNPLA3 oligonucleotide 166 passenger (sense) strand
ACAGUAUUUUCUAAUAACCAGCAGCCGAAAGGCUGC SEQ ID NO: 1108 - PNPLA3 oligonucleotide 166 guide (antisense) strand
UGGUUAUUAGAAAAUACUGUGG SEQ ID NO: 1109 - PNPLA3 oligonucleotide 167 passenger (sense) strand
CAGUAUUUUCUAAUAACCAAGCAGCCGAAAGGCUGC SEQ ID NO: 1110 - PNPLA3 oligonucleotide 167 guide (antisense) strand
UUGGUUAUUAGAAAAUACUGGG SEQ ID NO: 1111 - PNPLA3 oligonucleotide 168 passenger (sense) strand
UUGUGAUUGUUAUCAGGAAAGCAGCCGAAAGGCUGC SEQ ID NO: 1112 - PNPLA3 oligonucleotide 168 guide (antisense) strand
UUUCCUGAUAACAAUCACAAGG SEQ ID NO: 1113 - PNPLA3 oligonucleotide 169 passenger (sense) strand
UGUGAUUGUUAUCAGGAAAAGCAGCCGAAAGGCUGC SEQ ID NO: 1114 - PNPLA3 oligonucleotide 169 guide (antisense) strand
UUUUCCUGAUAACAAUCACAGG SEQ ID NO: 1115 - PNPLA3 oligonucleotide 170 passenger (sense) strand
GUGAUUGUUAUCAGGAAAAAGCAGCCGAAAGGCUGC SEQ ID NO: 1116 - PNPLA3 oligonucleotide 170 guide (antisense) strand
UUUUUCCUGAUAACAAUCACGG SEQ ID NO: 1117 - PNPLA3 oligonucleotide 171 passenger (sense) strand
UGAUUGUUAUCAGGAAAAAAGCAGCCGAAAGGCUGC SEQ ID NO: 1118 - PNPLA3 oligonucleotide 171 guide (antisense) strand
UUUUUUCCUGAUAACAAUCAGG SEQ ID NO: 1119 - PNPLA3 oligonucleotide 172 passenger (sense) strand
GAUUGUUAUCAGGAAAAAAAGCAGCCGAAAGGCUGC SEQ ID NO: 1120 - PNPLA3 oligonucleotide 172 guide (antisense) strand
UUUUUUUCCUGAUAACAAUCGG SEQ ID NO: 1121 - PNPLA3 oligonucleotide 173 passenger (sense) strand
AUUGUUAUCAGGAAAAAAUAGCAGCCGAAAGGCUGC -continued SEQ ID NO: 1122 - PNPLA3 oligonucleotide 173 guide (antisense) strand
UAUUUUUUCCUGAUAACAAUGG SEQ ID NO: 1123 - PNPLA3 oligonucleotide 174 passenger (sense) strand
UUGUUAUCAGGAAAAAAUAAGCAGCCGAAAGGCUGC SEQ ID NO: 1124 - PNPLA3 oligonucleotide 174 guide (antisense) strand
UUAUUUUUUCCUGAUAACAAGG SEQ ID NO: 1125 - PNPLA3 oligonucleotide 175 passenger (sense) strand
UGUUAUCAGGAAAAAAUAUAGCAGCCGAAAGGCUGC SEQ ID NO: 1126 - PNPLA3 oligonucleotide 175 guide (antisense) strand
UAUAUUUUUUCCUGAUAACAGG SEQ ID NO: 1127 - PNPLA3 oligonucleotide 176 passenger (sense) strand
GUUAUCAGGAAAAAAUAUAAGCAGCCGAAAGGCUGC SEQ ID NO: 1128 - PNPLA3 oligonucleotide 176 guide (antisense) strand
UUAUAUUUUUUCCUGAUAACGG SEQ ID NO: 1129 - PNPLA3 oligonucleotide 177 passenger (sense) strand
UUAUCAGGAAAAAAUAUAUAGCAGCCGAAAGGCUGC SEQ ID NO: 1130 - PNPLA3 oligonucleotide 177 guide (antisense) strand
UAUAUAUUUUUUCCUGAUAAGG SEQ ID NO: 1131 - PNPLA3 oligonucleotide 178 passenger (sense) strand
AGGAAAAAAUAUAUUAAAUAGCAGCCGAAAGGCUGC SEQ ID NO: 1132 - PNPLA3 oligonucleotide 178 guide (antisense) strand
UAUUUAAUAUAUUUUUUCCUGG SEQ ID NO: 1133 - PNPLA3 oligonucleotide 179 passenger (sense) strand
GGAAAAAAUAUAUUAAAUGAGCAGCCGAAAGGCUGC SEQ ID NO: 1134 - PNPLA3 oligonucleotide 179 guide (antisense) strand
UCAUUUAAUAUAUUUUUUCCGG SEQ ID NO: 1135 - PNPLA3 oligonucleotide 180 passenger (sense) strand
GAAAAAAUAUAUUAAAUGGAGCAGCCGAAAGGCUGC SEQ ID NO: 1136 - PNPLA3 oligonucleotide 180 guide (antisense) strand
UCCAUUUAAUAUAUUUUUUCGG SEQ ID NO: 1137 - PNPLA3 oligonucleotide 181 passenger (sense) strand
AUUUUCUUUCUGCUUUUAAAGCAGCCGAAAGGCUGC SEQ ID NO: 1138 - PNPLA3 oligonucleotide 181 guide (antisense) strand
UUUAAAAGCAGAAAGAAAAUGG SEQ ID NO: 1139 - PNPLA3 oligonucleotide 182 passenger (sense) strand
UCUUUCUGCUUUUAAAAAUAGCAGCCGAAAGGCUGC SEQ ID NO: 1140 - PNPLA3 oligonucleotide 182 guide (antisense) strand
UAUUUUUAAAAGCAGAAAGAGG SEQ ID NO: 1141 - PNPLA3 oligonucleotide 183 passenger (sense) strand
UAAGGAAAUCAGGAAGUGUAGCAGCCGAAAGGCUGC SEQ ID NO: 1142 - PNPLA3 oligonucleotide 183 guide (antisense) strand
UACACUUCCUGAUUUCCUUAGG SEQ ID NO: 1143 - PNPLA3 oligonucleotide 184 passenger (sense) strand
AAGGAAAUCAGGAAGUGUAAGCAGCCGAAAGGCUGC SEQ ID NO: 1144 - PNPLA3 oligonucleotide 184 guide (antisense) strand
UUACACUUCCUGAUUUCCUUGG SEQ ID NO: 1145 - PNPLA3 oligonucleotide 185 passenger (sense) strand
GGAAAUCAGGAAGUGUAAUAGCAGCCGAAAGGCUGC SEQ ID NO: 1146 - PNPLA3 oligonucleotide 185 guide (antisense) strand
UAUUACACUUCCUGAUUUCCGG SEQ ID NO: 1147 - PNPLA3 oligonucleotide 186 passenger (sense) strand
CCACACCCAGCUAGUUUUUAGCAGCCGAAAGGCUGC SEQ ID NO: 1148 - PNPLA3 oligonucleotide 186 guide (antisense) strand
UAAAAACUAGCUGGGUGUGGGG -continued SEQ ID NO: 1149 - PNPLA3 oligonucleotide 187 passenger (sense) strand
CACACCCAGCUAGUUUUUUAGCAGCCGAAAGGCUGC SEQ ID NO: 1150 - PNPLA3 oligonucleotide 187 guide (antisense) strand
UAAAAAACUAGCUGGGUGUGGG SEQ ID NO: 1151 - PNPLA3 oligonucleotide 188 passenger (sense) strand
CUAGGAUUACAGGUGUGAGAGCAGCCGAAAGGCUGC SEQ ID NO: 1152 - PNPLA3 oligonucleotide 188 guide (antisense) strand
UCUCACACCUGUAAUCCUAGGG SEQ ID NO: 1153 - PNPLA3 oligonucleotide 189 passenger (sense) strand
AGAGUAUGAGCCUGAUUUUAGCAGCCGAAAGGCUGC SEQ ID NO: 1154 - PNPLA3 oligonucleotide 189 guide (antisense) strand
UAAAAUCAGGCUCAUACUCUGG SEQ ID NO: 1155 - PNPLA3 oligonucleotide 190 passenger (sense) strand
GAGUAUGAGCCUGAUUUUGAGCAGCCGAAAGGCUGC SEQ ID NO: 1156 - PNPLA3 oligonucleotide 190 guide (antisense) strand
UCAAAAUCAGGCUCAUACUCGG SEQ ID NO: 1157 - PNPLA3 oligonucleotide 191 passenger (sense) strand
CCCAUCUCUACUAAAAAAUAGCAGCCGAAAGGCUGC SEQ ID NO: 1158 - PNPLA3 oligonucleotide 191 guide (antisense) strand
UAUUUUUUAGUAGAGAUGGGGG SEQ ID NO: 1159 - PNPLA3 oligonucleotide 192 passenger (sense) strand
ACUUUCAGCAUGAGAAAAUAGCAGCCGAAAGGCUGC SEQ ID NO: 1160 - PNPLA3 oligonucleotide 192 guide (antisense) strand
UAUUUUCUCAUGCUGAAAGUGG SEQ ID NO: 1161 - PNPLA3 oligonucleotide 193 passenger (sense) strand
CUGAGCUGAGUUGGUUUUAGCAGCCGAAAGGCUGC SEQ ID NO: 1162 - PNPLA3 oligonucleotide 193 guide (antisense) strand
UUAAAACCAACUCAGCUCAGGG SEQ ID NO: 1163 - PNPLA3 oligonucleotide 194 passenger (sense) strand
GCUGAGUUGGUUUUAUGAAAGCAGCCGAAAGGCUGC SEQ ID NO: 1164 - PNPLA3 oligonucleotide 194 guide (sense) strand
UUUCAUAAAACCAACUCAGCGG SEQ ID NO: 1165 - PNPLA3 control passenger (sense) strand
CUGUUGAAUUUUGUAUUAUA SEQ ID NO: 1166 - PNPLA3 control guide (antisense) strand
UAUAAUACAAAAUUCAACAGGG SEQ ID NO: 1167 - Target Sequence 1
CAACGTACCCTTCATTGAT SEQ ID NO: 1168 - Target Sequence 2
TGAAAGACAAAGGTGGATA SEQ ID NO: 1169 - Target Sequence 3
TACATGAGCAAGATTTGCA SEQ ID NO: 1170 - Target Sequence 4
TGAGCAAGATTTGCAACTT SEQ ID NO: 1171 - Target Sequence 5
CTCTGAGCTGAGTTGGTTT SEQ ID NO: 1172 - Target Sequence 6
CTTTTTCACCTAACTAAAA SEQ ID NO: 1173 - Target Sequence 7
TTCACCTAACTAAAATAAT SEQ ID NO: 1174 - Target Sequence 8
CTAACTAAAATAATGTTTA SEQ ID NO: 1175 - Target Sequence 9
CTGAGCTGAGTTGGTTTTA -continued SEQ ID NO: 1176 - Target Sequence 10
GCTGAGTTGGTTTTATGAA SEQ ID NO: 1177 - Artificial Sequence
GCAGCCGAAAGGCUGC

TABLE A

| No. | SEQ ID NO. and Mod. Pattern | DP Number | Modified Oligonucleotide |
|---|---|---|---|
| 1 | 1170 SM1224/ ASM1508 | DP17736P: DP17735G | [mCs][mC][fC][mA][mU][mU][mA][fG][fG][fA][mU][fA][fA][mU][mG][mU][fC][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1178) [MePhosphonate-4O-mUs][fAs][fAs][mG][fA][mC][fA][fU][mU][fA][mU][fC][mC][fU][mA][fA][mU][mG][fG][mGs][mGs][mG] (SEQ ID NO: 1179) |
| 2 | 0643 SM1405/ ASM2028 | DP17919P: DP17918G | [mAs][mC][mA][mA][mC][mG][mU][fA][fC][fC][fC][mU][mU][mC][mA][mU][mU][mG][mA][mA][mG][mC][mA][mG][mC][mC][mG][ademA-GalNAc][ademA-GalNAc][ademA-GalNAc][mG][mG][mC][mU][mG][mC] (SEQ ID NO: 1180) [MePhosphonate-4O-mUs][fUs][fCs][fA][fA][mU][fG][mA][mA][fG][mG][mG][mU][fA][mC][mG][mU][mU][mG][mUs][mGs][mG] (SEQ ID NO: 1181) |
| 3 | 1110 SM1405/ ASM2028 | DP17921P: DP17920G | [mGs][mC][mA][mC][mU][mG][mA][fG][fU][fG][fA][mA][mG][mA][mA][mA][mU][mG][mA][mA][mG][mC][mA][mG][mC][mC][mG][ademA-GalNAc][ademA-GalNAc][ademA-GalNAc][mG][mG][mC][mU][mG][mC] (SEQ ID NO: 1182) [MePhosphonate-4O-mUs][fUs][fCs][fA][fU][mU][fU][mC][mU][fU][mC][mA][mC][fU][mC][mA][mG][mU][mG][mCs][mGs][mG] (SEQ ID NO: 1183) |
| 4 | 1162 SM1405/ ASM2028 | DP17923P: DP17922G | [mAs][mC][mU][mU][mG][mC][mU][fA][fC][fC][fC][mA][mU][mU][mA][mG][mG][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1184) [MePhosphonate-4O-mUs][fAs][fUs][fC][fC][mU][fA][mA][mU][fG][mG][mG][mU][fA][mG][mC][mA][mA][mG][mUs][mGs][mG] (SEQ ID NO: 1185) |
| 5 | 1170 SM1405/ ASM2028 | DP17925P: DP17924G | [mCs][mC][mC][mA][mU][mU][mA][fG][fG][fA][fU][mA][mA][mU][mG][mU][mC][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1186) [MePhosphonate-4O-mUs][fAs][fAs][fG][fA][mC][fA][mU][mU][fA][mU][mC][mC][fU][mA][mA][mU][mG][mG][mGs][mGs][mG] (SEQ ID NO: 1187) |
| 6 | 1699 SM1405/ ASM2028 | DP17927P: DP17926G | [mCs][mU][mG][mA][mG][mC][mU][fG][fA][fG][fU][mU][mG][mG][mU][mU][mU][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1188) [MePhosphonate-4O-mUs][fUs][fAs][fA][fA][mA][fC][mC][mA][fA][mC][mU][mC][fA][mG][mC][mU][mC][mA][mGs][mGs][mG] (SEQ ID NO: 1189) |
| 7 | 1703 SM1405/ ASM2028 | DP17929P: DP17928G | [mGs][mC][mU][mG][mA][mG][mU][fU][fG][fG][fU][mU][mU][mU][mA][mU][mG][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1190) [MePhosphonate-4O-mUs][fUs][fUs][fC][fA][mU][fA][mA][mA][fA][mC][mC][mA][fA][mC][mU][mC][mA][mG][mCs][mGs][mG] (SEQ ID NO: 1191) |
| 8 | 1708 SM1405/ ASM2028 | DP17931P: DP17930G | [mGs][mU][mU][mG][mG][mU][mU][fU][fU][fA][fU][mG][mA][mA][mA][mA][mG][mC][mU][mA][mG][mC][mA][mG][mC][mC][mG][ademA-GalNAc][ademA-GalNAc][ademA-GalNAc][mG][mG][mC][mU][mG][mC] (SEQ ID NO: 1192) [MePhosphonate-4O-mUs][fAs][fGs][fC][fU][mU][fU][mU][mC][fA][mU][mA][mA][fA][mA][mC][mC][mA][mA][mCs][mGs][mG] (SEQ ID NO: 1193) |

TABLE A-continued

| No. | SEQ ID NO. and Mod. Pattern | DP Number | Modified Oligonucleotide |
|---|---|---|---|
| 9 | 2104 SM1405/ ASM2028 | DP17933P: DP17932G | [mGs][mG][mU][mA][mA][mC][mA][fA][fG][fA][fU][mG][mA][mU][mA][mA][mU][mC][mU][mA][mG][mC][mA][mG][mC][mC][mG][ademA-GalNAc][ademA-GalNAc][ademA-GalNAc][mG][mG][mC][mU][mG][mC] (SEQ ID NO: 1194) [MePhosphonate-4O-mUs][fAs][fGs][fA][fU][mU][fA][mU][mC][fA][mU][mC][mU][fU][mG][mU][mU][mA][mC][mCs][mGs][mG] (SEQ ID NO: 1195) |
| 10 | 2143 SM1405/ ASM2028 | DP17935P: DP17934G | [mUs][mU][mU][mC][mA][mC][mC][fU][fA][fA][fC][mU][mA][mA][mA][mA][mU][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1196) [MePhosphonate-4O-mUs][fUs][fUs][fA][fU][mU][fU][mU][mA][fG][mU][mU][mA][fG][mG][mU][mG][mA][mA][mAs][mGs][mG] (SEQ ID NO: 1197) |
| 11 | 2155 SM1405/ ASM2028 | DP17937P: DP17936G | [mAs][mA][mA][mA][mU][mA][mA][fU][fG][fU][fU][mU][mA][mA][mA][mG][mA][mG][mU][mA][mG][mC][mA][mG][mC][mC][mG][ademA-GalNAc][ademA-GalNAc][ademA-GalNAc][mG][mG][mC][mU][mG][mC] (SEQ ID NO: 1198) [MePhosphonate-4O-mUs][fAs][fCs][fU][fC][mU][fU][mU][mA][fA][mA][mC][mA][fU][mU][mA][mU][mU][mU][mUs][mGs][mG] (SEQ ID NO: 1199) |
| 12 | 2156 SM1405/ ASM2028 | DP17939P: DP17938G | [mAs][mA][mA][mU][mA][mA][mU][fG][fU][fU][fU][mA][mA][mA][mG][mA][mG][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1200) [MePhosphonate-4O-mUs][fAs][fAs][fC][fU][mC][fU][mU][mU][fA][mA][mA][mC][fA][mU][mU][mA][mU][mU][mUs][mGs][mG] (SEQ ID NO: 1201) |
| 13 | 2157 SM1405/ ASM2028 | DP17941P: DP17940G | [mAs][mA][mU][mA][mA][mU][mG][fU][fU][fU][fA][mA][mA][mG][mA][mG][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1202) [MePhosphonate-4O-mUs][fAs][fAs][fA][fC][mU][fC][mU][mU][fU][mA][mA][mA][fC][mA][mU][mU][mA][mU][mUs][mGs][mG] (SEQ ID NO: 1203) |
| 14 | 2163 SM1405/ ASM2028 | DP17943P: DP17942G | [mGs][mU][mU][mU][mA][mA][mA][fG][fA][fG][fU][mU][mU][mU][mG][mU][mA][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1204) [MePhosphonate-4O-mUs][fUs][fAs][fU][fA][mC][fA][mA][mA][fA][mC][mU][mC][fU][mU][mU][mA][mA][mA][mCs][mGs][mG] (SEQ ID NO: 1205) |
| 15 | 2165 SM1405/ ASM2028 | DP17945P: DP17944G | [mUs][mU][mA][mA][mA][mG][mA][fG][fU][fU][fU][mU][mG][mU][mA][mU][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1206) [MePhosphonate-4O-mUs][fUs][fUs][fU][fA][mU][fA][mC][mA][fA][mA][mA][mC][fU][mC][mU][mU][mU][mA][mAs][mGs][mG] (SEQ ID NO: 1207) |
| 16 | 2170 SM1405/ ASM2028 | DP17947P: DP17946G | [mGs][mA][mG][mU][mU][mU][mU][fG][fU][fA][fU][mA][mA][mA][mA][mA][mU][mG][mU][mA][mG][mC][mA][mG][mC][mC][mG][ademA-GalNAc][ademA-GalNAc][ademA-GalNAc][mG][mG][mC][mU][mG][mC] (SEQ ID NO: 1208) [MePhosphonate-4O-mUs][fAs][fCs][fA][fU][mU][fU][mU][mU][fA][mU][mA][mC][fA][mA][mA][mA][mC][mU][mCs][mGs][mG] (SEQ ID NO: 1209) |
| 17 | 2195 SM1405/ ASM2028 | DP17949P: DP17948G | [mGs][mC][mG][mU][mU][mG][mU][fU][fA][fC][fC][mU][mG][mU][mU][mG][mA][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1210) [MePhosphonate-4O-mUs][fAs][fUs][fU][fC][mA][fA][mC][mA][fG][mG][mU][mA][fA][mC][mA][mA][mC][mG][mCs][mGs][mG] (SEQ ID NO: 1211) |

TABLE A-continued

| No. | SEQ ID NO. and Mod. Pattern | DP Number | Modified Oligonucleotide |
|---|---|---|---|
| 18 | 2200 SM1405/ ASM2028 | DP17951P: DP17950G | [mGs][mU][mU][mA][mC][mC][mU][fG][fU][fU][fG][mA][mA] U[m][mU][mU][mU][mG][mU][mA][mG][mC][mA][mG][mC][mC] [mG][ademA-GalNAc][ademA-GalNAc][ademA-GalNAc][mG][mG][mC][mU][mG][mC] (SEQ ID NO: 1212) [MePhosphonate-40-mUs][fAs][fCs][fA][fA][mA][fA][mU][mU][fC][mA][mA][mC][fA] [mG][mG][mU][mA][mA][mCs][mGs][mG] (SEQ ID NO: 1213) |
| 19 | 2204 SM1405/ ASM2028 | DP17953P: DP17952G | [mCs][mC][mU][mG][mU][mU][mG][fA][fA][fU][fU][mU][mU] [mG][mU][mA][mU][mU][mA][mA][mG][mC][mA][mG][mC][mC] [mG][ademA-GalNAc][ademA-GalNAc][ademA-GalNAc][mG][mG][mC][mU][mG][mC] (SEQ ID NO: 1214) [MePhosphonate-40-mUs][fUs][fAs][fA][fU][mA][fC][mA][mA][fA][mA][mU][mU][fC] [mA][mA][mC][mA][mG][mGs][mGs][mG] (SEQ ID NO: 1215) |
| 20 | 2205 SM1405/ ASM2028 | DP17955P: DP17954G | [mCs][mU][mG][mU][mU][mG][mA][fA][fU][fU][fU][mU][mG] [mU][mA][mU][mU][mA][mU][mA][mG][mC][mA][mG][mC][mC] [mG][ademA-GalNAc][ademA-GalNAc][ademA-GalNAc][mG][mG][mC][mU][mG][mC] (SEQ ID NO: 1216) [MePhosphonate-40-mUs][fAs][fUs][fA][fA][mU][fA][mC][mA][fA][mA][mA][mU][fU] [mC][mA][mA][mC][mA][mGs][mGs][mG] (SEQ ID NO: 1217) |
| 21 | 2210 SM1405/ ASM2028 | DP17957P: DP17956G | [mGs][mA][mA][mU][mU][mU][mU][fG][fU][fA][fU][mU][mA] [mU][mG][mU][mG][mA][mA][mA][mG][mC][mA][mG][mC][mC] [mG][ademA-GalNAc][ademA-GalNAc][ademA-GalNAc][mG][mG][mC][mU][mG][mC] (SEQ ID NO: 1218) [MePhosphonate-40-mUs][fUs][fUs][fC][fA][mC][fA][mU][mA][fA][mU][mA][mC][fA] [mA][mA][mA][mU][mU][mCs][mGs][mG] (SEQ ID NO: 1219) |

TABLE B

| SEQ ID NO. and Mod. Pattern | DP Number | Modified Oligonucleotide |
|---|---|---|
| 0644 SM1405/ ASM2028 | DP18056P: DP18055G | [mCs][mA][mA][mC][mG][mU][mA][fC][fC][fC][fU][mU][mC][mA] [mU][mU][mG][mA][mU][mA][mG][mC][mA][mG][mC][mC][mG] [ademA-GalNAc][ademA-GalNAc][ademA-GalNAc][mG][mG][mC][mU][mG][mC] (SEQ ID NO: 1220) [MePhosphonate-40-mUs][fAs][fUs][fC][fA][mA][fU][mG][mA][fA][mG][mG][mG][fU] [mA][mC][mG][mU][mU][mGs][mGs][mG] (SEQ ID NO: 1221) |
| 0745 SM1405/ ASM2028 | DP18084P: DP18083G | [mUs][mG][mG][mA][mC][mA][mU][fC][fA][fC][fC][mA][mA][mG] [mC][mU][mC][mA][mG][mA][mG][mC][mA][mG][mC][mC][mG] [ademA-GalNAc][ademA-GalNAc][ademA-GalNAc][mG][mG][mC][mU][mG][mC] (SEQ ID NO: 1222) [MePhosphonate-40-mUs][fCs][fUs][fG][fA][mG][fC][mU][mU][fG][mG][mU][mG][fA] [mU][mG][mU][mC][mC][mAs][mGs][mG] (SEQ ID NO: 1223) |
| 1126 SM1405/ ASM2028 | DP18112P: 8DP1111G | [mUs][mG][mA][mA][mA][mG][mA][fC][fA][fA][fA][mG][mG][mU] [mG][mG][mA][mU][mA][mA][mG][mC][mA][mG][mC][mC][mG] [ademA-GalNAc][ademA-GalNAc][ademA-GalNAc][mG][mG][mC][mU][mG][mC] (SEQ ID NO: 1224) [MePhosphonate-40-mUs][fUs][fAs][fU][fC][mC][fA][mC][mC][fU][mU][mU][mG][fU] [mC][mU][mU][mU][mC][mAs][mGs][mG] (SEQ ID NO: 1225) |
| 1129 SM1405/ ASM2028 | DP18116P: DP18115G | [mAs][mA][mG][mA][mC][mA][mA][fA][fG][fG][fU][mG][mG][mA] [mU][mA][mC][mA][mU][mA][mG][mC][mA][mG][mC][mC][mG] [ademA-GalNAc][ademA-GalNAc][ademA-GalNAc][mG][mG][mC][mU][mG][mC] (SEQ ID NO: 1226) [MePhosphonate-40-mUs][fAs][fUs][fG][fU][mA][fU][mC][mC][fA][mC][mC][mU][fU] [mU][mG][mU][mC][mU][mUs][mGs][mG] (SEQ ID NO: 1227) |

TABLE B-continued

| SEQ ID NO. and Mod. Pattern | DP Number | Modified Oligonucleotide |
|---|---|---|
| 1130 SM1405/ ASM2028 | DP18118P: DP18117G | [mAs][mG][mA][mC][mA][mA][mA][fG][fG][fU][fG][mG][mA][mU][mA][mC][mA][mU][mG][mA][mG][mC][mA][mG][mC][mC][mG][ademA-GalNAc][ademA-GalNAc][ademA-GalNAc][mG][mG][mC][mU][mG][mC] (SEQ ID NO: 1228) [MePhosphonate-4O-mUs][fCs][fAs][fU][fG][mU][fA][mU][mC][fC][mA][mC][mC][fU][mU][mU][mG][mU][mC][mUs][mGs][mG] (SEQ ID NO: 1229) |
| 1143 SM1405/ ASM2028 | DP18136P: DP18135G | [mUs][mA][mC][mA][mU][mG][mA][fG][fC][fA][fA][mG][mA][mU][mU][mU][mG][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 1230) [MePhosphonate-4O-mUs][fUs][fGs][fC][fA][mA][fA][mU][mC][fU][mU][mG][mC][fU][mC][mA][mU][mG][mU][mAs][mGs][mG] (SEQ ID NO: 1231) |
| 1147 SM1405/ ASM2028 | DP18140P: DP18139G | [mUs][mG][mA][mG][mC][mA][mA][fG][fA][fU][fU][mU][mG][mC][mA][mA][mC][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1232) [MePhosphonate-4O-mUs][fAs][fAs][fG][fU][mU][fG][mC][mA][fA][mA][mU][mC][fU][mU][mG][mC][mU][mC][mAs][mGs][mG] (SEQ ID NO: 1233) |
| 1152 SM1405/ ASM2028 | DP18150P: DP18149G | [mAs][mA][mG][mA][mU][mU][mU][fG][fC][fA][fA][mC][mU][mU][mG][mC][mU][mA][mC][mA][mG][mC][mA][mG][mC][mC][mG][ademA-GalNAc][ademA-GalNAc][ademA-GalNAc][mG][mG][mC][mU][mG][mC] (SEQ ID NO: 1234) [MePhosphonate-4O-mUs][fGs][fUs][fA][fG][mC][fA][mA][mG][fU][mU][mG][mC][fA][mA][mA][mU][mC][mU][mUs][mGs][mG] (SEQ ID NO: 1235) |
| 1229 SM1405/ ASM2028 | DP18172P: DP18171G | [mUs][mG][mC][mG][mA][mU][mU][fG][fU][fC][fC][mA][mG][mA][mG][mA][mC][mU][mG][mA][mG][mC][mA][mG][mC][mC][mG][ademA-GalNAc][ademA-GalNAc][ademA-GalNAc][mG][mG][mC][mU][mG][mC] (SEQ ID NO: 1236) [MePhosphonate-4O-mUs][fCs][fAs][fG][fU][mC][fU][mC][mU][fG][mG][mA][mC][fA][mA][mU][mC][mG][mC][mAs][mGs][mG] (SEQ ID NO: 1237) |
| 2142 SM1405/ ASM2028 | DP18274P: DP18273G | [mUs][mU][mU][mU][mC][mA][mC][fC][fU][fA][fA][mC][mU][mA][mA][mA][mA][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1238) [MePhosphonate-4O-mUs][fUs][fAs][fU][fU][mU][fU][mA][mG][fU][mU][mA][mG][fG][mU][mG][mA][mA][mA][mAs][mGs][mG] (SEQ ID NO: 1239) |
| 1698 SM1405/ ASM2028 | DP18208P: DP18207G | [mUs][mC][mU][mG][mA][mG][mC][fU][fG][fA][fG][mU][mU][mG][mG][mU][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1240) [MePhosphonate-4O-mUs][fAs][fAs][fA][fA][mC][fC][mA][mA][fC][mU][mC][mA][fG][mC][mU][mC][mA][mG][mAs][mGs][mG] (SEQ ID NO: 1241) |
| 2138 SM1405/ ASM2028 | DP18270P: 8DP1269G | [mAs][mC][mC][mU][mU][mU][mU][fU][fC][fA][fC][mC][mU][mA][mA][mC][mU][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1242) [MePhosphonate-4O-mUs][fUs][fUs][fA][fG][mU][fU][mA][mG][fG][mU][mG][mA][fA][mA][mA][mA][mG][mG][mUs][mGs][mG] (SEQ ID NO: 1243) |
| 2140 SM1405/ ASM2028 | DP18272P: DP18271G | [mCs][mU][mU][mU][mU][mU][mC][fA][fC][fC][fU][mA][mA][mC][mU][mA][mA][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1244) [MePhosphonate-4O-mUs][fUs][fUs][fU][fU][mA][fG][mU][mU][fA][mG][mG][mU][fG][mA][mA][mA][mA][mA][mGs][mGs][mG] (SEQ ID NO: 1245) |

TABLE B-continued

| SEQ ID NO. and Mod. Pattern | DP Number | Modified Oligonucleotide |
|---|---|---|
| 2144 SM1405/ ASM2028 | DP18276P: DP18275G | [mUs][mU][mC][mA][mC][mC][mU][fA][fA][fC][fU][mA][mA][mA][mA][mU][mA][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1246) [MePhosphonate-4O-mUs][fAs][fUs][fU][fA][mU][fU][mU][mU][fA][mG][mU][mU][fA][mG][mG][mU][mG][mA][mAs][mGs][mG] (SEQ ID NO: 1247) |
| 2146 SM1405/ ASM2028 | DP18280P: DP18279G | [mCs][mA][mC][mC][mU][mA][mA][fC][fU][fA][fA][mA][mA][mU][mA][mA][mU][mG][mU][mA][mG][mC][mA][mG][mC][mC][mG][ademA-GalNAc][ademA-GalNAc][ademA-GalNAc][mG][mG][mC][mU][mG][mC] (SEQ ID NO: 1248) [MePhosphonate-4O-mUs][fAs][fCs][fA][fU][mU][fA][mU][mU][fU][mU][mA][mG][fU][mU][mA][mG][mG][mU][mGs][mGs][mG] (SEQ ID NO: 1249) |
| 2149 SM1405/ ASM2028 | DP18286P: DP18285G | [mCs][mU][mA][mA][mC][mU][mA][fA][fA][fA][fU][mA][mA][mU][mG][mU][mU][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1250) [MePhosphonate-4O-mUs][fUs][fAs][fA][fA][mC][fA][mU][mU][fA][mU][mU][mU][fU][mA][mG][mU][mU][mA][mGs][mGs][mG] (SEQ ID NO: 1251) |
| 2137 SM1405/ ASM2028 | DP18268P: 8DP1267G | [mCs][mA][mC][mC][mU][mU][mU][fU][fU][fC][fA][mC][mC][mU][mA][mA][mC][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1252) [MePhosphonate-4O-mUs][fUs][fAs][fG][fU][mU][fA][mG][mG][fU][mG][mA][mA][fA][mA][mA][mG][mG][mU][mGs][mGs][mG] (SEQ ID NO: 1253) |
| 2205 SM1405/ ASM2028 | DP17955P: DP17954G | [mCs][mU][mG][mU][mU][mG][mA][fA][fU][fU][fU][mU][mG][mU][mA][mU][mU][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1216) [MePhosphonate-4O-mUs][fAs][fUs][fA][fA][mU][fA][mC][mA][fA][mA][mA][mU][fU][mC][mA][mA][mC][mA][mGs][mGs][mG] (SEQ ID NO: 1217) |

TABLE C

| SEQ ID NO. and Mod. Pattern | DP Number | Modified Oligonucleotide |
|---|---|---|
| 1697 SM1405/ ASM2028 | DP18206P: DP18205G | [mCs][mU][mC][mU][mG][mA][mG][fC][fU][fG][fA][mG][mU][mU][mG][mG][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1254) [MePhosphonate-4O-mUs][fAs][fAs][fA][fC][mC][fA][mA][mC][fU][mC][mA][mG][fC][mU][mC][mA][mG][mA][mGs][mGs][mG] (SEQ ID NO: 1255) |
| 1614 SM1405/ ASM2028 | DP18194P: DP18193G | [mAs][mG][mG][mU][mG][mC][mU][fA][fA][fA][fG][mU][mU][mU][mC][mC][mC][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1256) [MePhosphonate-4O-mUs][fAs][fUs][fG][fG][mG][fA][mA][mA][fC][mU][mU][mU][fA][mG][mC][mA][mC][mC][mUs][mGs][mG] (SEQ ID NO: 1257) |
| 2176 SM1405/ ASM2028 | DP18304P: DP18303G | [mUs][mG][mU][mA][mU][mA][mA][fA][fA][fA][fU][mG][mU][mA][mA][mG][mG][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1258) [MePhosphonate-4O-mUs][fUs][fUs][fC][fC][mU][fU][mA][mC][fA][mU][mU][mU][fU][mU][mA][mU][mA][mC][mAs][mGs][mG] (SEQ ID NO: 1259) |

TABLE C-continued

| SEQ ID NO. and Mod. Pattern | DP Number | Modified Oligonucleotide |
|---|---|---|
| 2222 SM1405/ ASM2028 | DP18326P: DP18325G | [mAs][mU][mG][mU][mG][mA][mA][fU][fC][fA][fG][mU][mG][mA][mG][mA][mU][mG][mU][mA][mG][mC][mA][mG][mC][mC][mG][ademA-GalNAc][ademA-GalNAc][ademA-GalNAc][mG][mG][mC][mU][mG][mC] (SEQ ID NO: 1260) [MePhosphonate-4O-mUs][fAs][fCs][fA][fU][mC][fU][mC][mA][fC][mU][mG][mA][fU][mU][mC][mA][mC][mA][mUs][mGs][mG] (SEQ ID NO: 1261) |
| 1173 SM1405/ ASM2028 | DP18168P: DP18167G | [mAs][mU][mU][mA][mG][mG][mA][fU][fA][fA][fU][mG][mU][mC][mU][mU][mA][mU][mG][mA][mG][mC][mA][mG][mC][mC][mG][ademA-GalNAc][ademA-GalNAc][ademA-GalNAc][mG][mG][mC][mU][mG][mC] (SEQ ID NO: 1262) [MePhosphonate-4O-mUs][fCs][fAs][fU][fA][mA][fG][mA][mC][fA][mU][mU][mA][fU][mC][mC][mU][mA][mA][mUs][mGs][mG] (SEQ ID NO: 1263) |
| 2136 SM1405/ ASM2028 | DP18266P: DP18265G | [mAs][mC][mA][mC][mC][mU][mU][fU][fU][fU][fC][mA][mC][mC][mU][mA][mA][mC][mU][mA][mG][mC][mA][mG][mC][mC][mG][ademA-GalNAc][ademA-GalNAc][ademA-GalNAc][mG][mG][mC][mU][mG][mC] (SEQ ID NO: 1264) [MePhosphonate-4O-mUs][fAs][fGs][fU][fU][mA][fG][mG][mU][fG][mA][mA][mA][fA][mA][mG][mG][mU][mG][mUs][mGs][mG] (SEQ ID NO: 1265) |
| 0637 SM1405/ ASM2028 | DP18046P: DP18045G | [mUs][mG][mA][mG][mU][mG][mA][fC][fA][fA][fC][mG][mU][mA][mC][mC][mC][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1266) [MePhosphonate-4O-mUs][fAs][fAs][fG][fG][mG][fU][mA][mC][fG][mU][mU][mG][fU][mC][mA][mC][mU][mC][mAs][mGs][mG] (SEQ ID NO: 1267) |
| 1116 SM1405/ ASM2028 | DP18098P: DP18097G | [mAs][mG][mU][mG][mA][mA][mG][fA][fA][fA][fU][mG][mA][mA][mA][mG][mA][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 1268) [MePhosphonate-4O-mUs][fUs][fGs][fU][fC][mU][fU][mU][mC][fA][mU][mU][mU][fC][mU][mU][mC][mA][mC][mUs][mGs][mG] (SEQ ID NO: 1269) |
| 0923 SM1405/ ASM2028 | DP18096P: DP18095G | [mAs][mU][mC][mC][mU][mC][mA][fG][fA][fA][fG][mG][mG][mA][mU][mG][mG][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1270) [MePhosphonate-4O-mUs][fAs][fUs][fC][fC][mA][fU][mC][mC][fC][mU][mU][mC][fU][mG][mA][mG][mG][mA][mUs][mGs][mG] (SEQ ID NO: 1271) |
| 0641 SM1405/ ASM2028 | DP18052P: DP18051G | [mUs][mG][mA][mC][mA][mA][mC][fG][fU][fA][fC][mC][mC][mU][mU][mC][mA][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1272) [MePhosphonate-4O-mUs][fAs][fAs][fU][fG][mA][fA][mG][mG][fG][mU][mA][mC][fG][mU][mU][mG][mU][mC][mAs][mGs][mG] (SEQ ID NO: 1273) |
| 1136 SM1405/ ASM2028 | DP18126P: DP18125G | [mAs][mG][mG][mU][mG][mG][mA][fU][fA][fC][fA][mU][mG][mA][mG][mC][mA][mA][mG][mA][mG][mC][mA][mG][mC][mC][mG][ademA-GalNAc][ademA-GalNAc][ademA-GalNAc][mG][mG][mC][mU][mG][mC] (SEQ ID NO: 1274) [MePhosphonate-4O-mUs][fCs][fUs][fU][fG][mC][fU][mC][mA][fU][mG][mU][mA][fU][mC][mC][mA][mC][mC][mUs][mGs][mG] (SEQ ID NO: 1275) |

TABLE C-continued

| SEQ ID NO. and Mod. Pattern | DP Number | Modified Oligonucleotide |
|---|---|---|
| 1158 SM1405/ ASM2028 | DP18158P: DP18157G | [mUs][mG][mC][mA][mA][mC][mU][fU][fG][fC][fU][mA][mC][mC][mC][mA][mU][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1276) [MePhosphonate-4O-mUs][fUs][fAs][fA][fU][mG][fG][mG][mU][fA][mG][mC][mA][fA][mG][mU][mU][mG][mC][mAs][mGs][mG] (SEQ ID NO: 1277) |
| 1151 SM1405/ ASM2028 | DP18148P: DP18147G | [mCs][mA][mA][mG][mA][mU][mU][fU][fG][fC][fA][mA][mC][mU][mU][mG][mC][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1278) [MePhosphonate-4O-mUs][fUs][fAs][fG][fC][mA][fA][mG][mU][fU][mG][mC][mA][fA][mA][mU][mC][mU][mU][mGs][mGs][mG] (SEQ ID NO: 1279) |
| 1541 SM1405/ ASM2028 | DP18184P: DP18183G | [mCs][mA][mC][mC][mU][mU][mU][fC][fC][fC][fA][mG][mU][mU][mU][mU][mU][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 1280) [MePhosphonate-4O-mUs][fUs][fGs][fA][fA][mA][fA][mA][mC][fU][mG][mG][mG][fA][mA][mA][mG][mG][mU][mGs][mGs][mG] (SEQ ID NO: 1281) |
| 1157 SM1405/ ASM2028 | DP18156P: DP18155G | [mUs][mU][mG][mC][mA][mA][mC][fU][fU][fG][fC][mU][mA][mC][mC][mC][mA][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1282) [MePhosphonate-4O-mUs][fAs][fAs][fU][fG][mG][fG][mU][mA][fG][mC][mA][mA][fG][mU][mU][mG][mC][mA][mAs][mGs][mG] (SEQ ID NO: 1283) |
| 1163 SM1405/ ASM2028 | DP18164P: DP18163G | [mCs][mU][mU][mG][mC][mU][mA][fC][fC][fC][fA][mU][mU][mA][mG][mG][mA][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1284) [MePhosphonate-4O-mUs][fUs][fAs][fU][fC][mC][fU][mA][mA][fU][mG][mG][mG][fU][mA][mG][mC][mA][mA][mGs][mGs][mG] (SEQ ID NO: 1285) |
| 1125 SM1405/ ASM2028 | DP18110P: DP18109G | [mAs][mU][mG][mA][mA][mA][mG][fA][fC][fA][fA][mA][mG][mG][mU][mG][mG][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1286) [MePhosphonate-4O-mUs][fAs][fUs][fC][fC][mA][fC][mC][mU][fU][mU][mG][mU][fC][mU][mU][mU][mC][mA][mUs][mGs][mG] (SEQ ID NO: 1287) |
| 2205 SM1405/ ASM2028 | DP17955P: DP17954G | [mCs][mU][mG][mU][mU][mG][mA][fA][fU][fU][fU][mU][mG][mU][mA][mU][mU][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1216) [MePhosphonate-4O-mUs][fAs][fUs][fA][fA][mU][fA][mC][mA][fA][mA][mA][mU][fU][mC][mA][mA][mC][mA][mGs][mGs][mG] (SEQ ID NO: 1217) |

TABLE D

| SEQID NO. and Mod. Pattern | DP Number | Modified Oligonucleotide |
|---|---|---|
| 0639 SM1405/ ASM2028 | DP18050P: DP18049G | [mAs][mG][mU][mG][mA][mC][mA][fA][fC][fG][fU][mA][mC][mC][mC][mU][mU][mC][mA][mA][mG][mC][mA][mG][mC][mC][mG][ademA-GalNAc][ademA-GalNAc][ademA- |

TABLE D-continued

| SEQID NO. and Mod. Pattern | DP Number | Modified Oligonucleotide |
|---|---|---|
| | | GalNAc][mG][mG][mC][mU][mG][mC] (SEQ ID NO: 1288) [MePhosphonate-4O-mUs][fUs][fGs][fA][fA][mG][fG][mG][mU][fA][mC][mG][mU][fU][mG][mU][mC][mA][mC][mUs][mGs][mG] (SEQ ID NO: 1289) |
| 0644 SM1405/ ASM2028 | DP18056P: DP18055G | [mCs][mA][mA][mC][mG][mU][mA][fC][fC][fC][fU][mU][mC][mA][mU][mU][mG][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1220) [MePhosphonate-4O-mUs][fAs][fUs][fC][fA][mA][fU][mG][mA][fA][mG][mG][mG][fU][mA][mC][mG][mU][mU][mGs][mGs][mG] (SEQ ID NO: 1221) |
| 0729 SM1405/ ASM2028 | DP18068P: DP18067G | [mAs][mC][mG][mA][mA][mC][mU][fU][fU][fC][fU][mU][mC][mA][mU][mG][mU][mG][mG][mA][mG][mC][mA][mG][mC][mC][mG][ademA-GalNAc][ademA-GalNAc][ademA-GalNAc][mG][mG][mC][mU][mG][mC] (SEQ ID NO: 1290) [MePhosphonate-4O-mUs][fCs][fCs][fA][fC][mA][fU][mG][mA][fA][mG][mA][mA][fA][mG][mU][mU][mC][mG][mUs][mGs][mG] (SEQ ID NO: 1291) |
| 0735 SM1405/ ASM2028 | DP18074P: DP18073G | [mUs][mU][mU][mC][mU][mU][mC][fA][fU][fG][fU][mG][mG][mA][mC][mA][mU][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 1292) [MePhosphonate-4O-mUs][fUs][fGs][fA][fU][mG][fU][mC][mC][fA][mC][mA][mU][fG][mA][mA][mG][mA][mA][mAs][mGs][mG] (SEQ ID NO: 1293) |
| 0743 SM1405/ ASM2028 | DP18080P: DP18079G | [mUs][mG][mU][mG][mG][mA][mC][fA][fU][fC][fA][mC][mC][mA][mA][mG][mC][mU][mC][mA][mG][mC][mA][mG][mC][mC][mG][ademA-GalNAc][ademA-GalNAc][ademA-GalNAc][mG][mG][mC][mU][mG][mC] (SEQ ID NO: 1294) [MePhosphonate-4O-mUs][fGs][fAs][fG][fC][mU][fU][mG][mG][fU][mG][mA][mU][fG][mU][mC][mC][mA][mC][mAs][mGs][mG] (SEQ ID NO: 1295) |
| 0744 SM1405/ SM2028A | DP18082P: DP18081G | [mGs][mU][mG][mG][mA][mC][mA][fU][fC][fA][fC][mC][mA][mA][mG][mC][mU][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 1296) [MePhosphonate-4O-mUs][fUs][fGs][fA][fG][mC][fU][mU][mG][fG][mU][mG][mA][fU][mG][mU][mC][mC][mA][mCs][mGs][mG] (SEQ ID NO: 1297) |
| 0838 SM1405/ ASM2028 | DP18086P: DP18085G | [mAs][mG][mA][mU][mA][mU][mG][fC][fC][fU][fU][mC][mG][mA][mG][mG][mA][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1298) [MePhosphonate-4O-mUs][fUs][fAs][fU][fC][mC][fU][mC][mG][fA][mA][mG][mG][fC][mA][mU][mA][mU][mC][mUs][mGs][mG] (SEQ ID NO: 1299) |
| 1126 SM1405/ ASM2028 | DP18112P: DP18111G | [mUs][mG][mA][mA][mA][mG][mA][fC][fA][fA][fA][mG][mG][mU][mG][mG][mA][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1224) [MePhosphonate-4O-mUs][fUs][fAs][fU][fC][mC][fA][mC][mC][fU][mU][mU][mG][fU][mC][mU][mU][mU][mC][mAs][mGs][mG] (SEQ ID NO: 1225) |

TABLE D-continued

| SEQID NO. and Mod. Pattern | DP Number | Modified Oligonucleotide |
|---|---|---|
| 1143 SM1405/ ASM2028 | DP18136P: DP18135G | [mUs][mA][mC][mA][mU][mG][mA][fG][fC][fA][fA][mG][mA][mU][mU][mU][mG][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 1230) [MePhosphonate-4O-mUs][fUs][fGs][fC][fA][mA][fA][mU][mC][fU][mU][mG][mC][fU][mC][mA][mU][mG][mU][mAs][mGs][mG] (SEQ ID NO: 1231) |
| 1147 SM1405/ ASM2028 | DP18140P: DP18139G | [mUs][mG][mA][mG][mC][mA][mA][fG][fA][fU][fU][mU][mG][mC][mA][mA][mC][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1232) [MePhosphonate-4O-mUs][fAs][fAs][fG][fU][mU][fG][mC][mA][fA][mA][mU][mC][fU][mU][mG][mC][mU][mC][mAs][mGs][mG] (SEQ ID NO: 1233) |
| 1152 SM1405/ ASM2028 | DP18150P: DP18149G | [mAs][mA][mG][mA][mU][mU][mU][fG][fC][fA][fA][mC][mU][mU][mG][mC][mU][mA][mC][mA][mG][mC][mA][mG][mC][mC][mG][ademA-GalNAc][ademA-GalNAc][ademA-GalNAc][mG][mG][mC][mU][mG][mC] (SEQ ID NO: 1234) [MePhosphonate-4O-mUs][fGs][fUs][fA][fG][mC][fA][mA][mG][fU][mU][mG][mC][fA][mA][mA][mU][mC][mU][mUs][mGs][mG] (SEQ ID NO: 1235) |
| 1173 SM1405/ ASM2028 | DP18168P: DP18167G | [mAs][mU][mU][mA][mG][mG][mA][fU][fA][fA][fU][mG][mU][mC][mU][mU][mA][mU][mG][mA][mG][mC][mA][mG][mC][mC][mG][ademA-GalNAc][ademA-GalNAc][ademA-GalNAc][mG][mG][mC][mU][mG][mC] (SEQ ID NO: 1262) [MePhosphonate-4O-mUs][fCs][fAs][fU][fA][mA][fG][mA][mC][fA][mU][mU][mA][fU][mC][mC][mU][mA][mA][mUs][mGs][mG] (SEQ ID NO: 1263) |
| 1697 SM1405/ ASM2028 | DP18206P: DP18205G | [mCs][mU][mC][mU][mG][mA][mG][fC][fU][fG][fA][mG][mU][mU][mG][mG][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1254) [MePhosphonate-4O-mUs][fAs][fAs][fA][fC][mC][fA][mA][mC][fU][mC][mA][mG][fC][mU][mC][mA][mG][mA][mGs][mGs][mG] (SEQ ID NO: 1255) |
| 1699 SM1405/ ASM2028 | DP17927P: DP17926G | [mCs][mU][mG][mA][mG][mC][mU][fG][fA][fG][fU][mU][mG][mG][mU][mU][mU][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1188) [MePhosphonate-4O-mUs][fUs][fAs][fA][fA][mA][fC][mC][mA][fA][mC][mU][mC][fA][mG][mC][mU][mC][mA][mGs][mGs][mG] (SEQ ID NO: 1189) |
| 1703 SM1405/ ASM2028 | DP17929P: DP17928G | [mGs][mC][mU][mG][mA][mG][mU][fU][fG][fG][fU][mU][mU][mU][mA][mU][mG][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1190) [MePhosphonate-4O-mUs][fUs][fUs][fC][fA][mU][fA][mA][mA][fA][mC][mC][mA][fA][mC][mU][mC][mA][mG][mCs][mGs][mG] (SEQ ID NO: 1191) |
| 2140 SM1405/ ASM2028 | DP18272P: DP18271G | [mCs][mU][mU][mU][mU][mU][mC][fA][fC][fC][fU][mA][mA][mC][mU][mA][mA][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 1244) [MePhosphonate-4O-mUs][fUs][fUs][fU][fU][mA][fG][mU][mU][fA][mG][mG][mU][fG][mA][mA][mA][mA][mA][mGs][mGs][mG] (SEQ ID NO: 1245) |

TABLE D-continued

| SEQID NO. and Mod. Pattern | DP Number | Modified Oligonucleotide |
|---|---|---|
| 2144 SM1405/ ASM2028 | DP18276P: DP18275G | [mUs][mU][mC][mA][mC][mC][mU][fA][fA][fC][fU][mA][mA][mA][mA][mU][mA][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1246) [MePhosphonate-4O-mUs][fAs][fUs][fU][fA][mU][fU][mU][mU][fA][mG][mU][mU][fA][mG][mG][mU][mG][mA][mAs][mGs][mG] (SEQ ID NO: 1247) |
| 2149 SM1405/ ASM2028 | DP18286P: DP18285G | [mCs][mU][mA][mA][mC][mU][mA][fA][fA][fA][fU][mA][mA][mU][mG][mU][mU][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1250) [MePhosphonate-4O-mUs][fUs][fAs][fA][fA][mC][fA][mU][mU][fA][mU][mU][mU][fU][mA][mG][mU][mU][mA][mGs][mGs][mG] (SEQ ID NO: 1251) |
| 2156 SM1405/ ASM2028 | DP17939P: DP17938G | [mAs][mA][mA][mU][mA][mA][mU][fG][fU][fU][fU][mA][mA][mA][mG][mA][mG][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 1200) [MePhosphonate-4O-mUs][fAs][fAs][fC][fU][mC][fU][mU][mU][fA][mA][mA][mC][fA][mU][mU][mA][mU][mU][mUs][mGs][mG] (SEQ ID NO: 1201) |
| 2195 SM1405/ ASM2028 | DP17949P: DP17948G | [mGs][mC][mG][mU][mU][mG][mU][fU][fA][fC][fC][mU][mG][mU][mU][mG][mA][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1300) [MePhosphonate-4O-mUs][fAs][fUs][fU][fC][mA][fA][mC][mA][fG][mG][mU][mA][fA][mC][mA][mA][mC][mG][mCs][mGs][mG] (SEQ ID NO: 1301) |
| 2205 SM1405/ ASM2028 | DP17955P: DP17954G | [mCs][mU][mG][mU][mU][mG][mA][fA][fU][fU][fU][mU][mG][mU][mA][mU][mU][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 1216) [MePhosphonate-4O-mUs][fAs][fUs][fA][fA][mU][fA][mC][mA][fA][mA][mA][mU][fU][mC][mA][mA][mC][mA][mGs][mGs][mG] (SEQ ID NO: 1217) |

The invention claimed is:

1. An RNAi oligonucleotide for reducing patatin-like phospholipase domain-containing protein 3 (PNPLA3) expression, the oligonucleotide comprising a sense strand and an antisense strand, wherein the sense strand and the antisense strand form a duplex region, wherein the sense strand is: [mCs][mU][mA][mA][mC][mU][mA][fA][fA][fA][fU][mA][mA][mU][mG][mU][mU][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 1250), wherein nucleotides at positions 1, 2, 3, 4, 5, 6, 7, 12, 13, 14, 15, 16, 17, 18, 19, 20, 21, 22, 23, 24, 25, 26, 27, 31, 32, 33, 34, 35, and 36 are modified with 2'-O-methyl; nucleotides at positions 8, 9, 10, and 11 are modified with 2'-fluoro; the internucleotide linkage between nucleotides at positions 1 and 2 is a phosphorothioate linkage; and nucleotides at positions 28, 29, and 30 are modified with adem-GalNAc; and the antisense strand is: [MePhosphonate-4O-mUs][fUs][fAs][fA][fA][mC][fA][mU][mU][fA][mU][mU][mU][fU][mA][mG][mU][mU][mA][m Gs][mGs][mG] (SEQ ID NO: 1251), wherein nucleotides at positions 1, 6, 8, 9, 11, 12, 13, 15, 16, 17, 18, 19, 20, 21, and 22 are modified with 2'-O-methyl; nucleotides at positions 2, 3, 4, 5, 7, 10, and 14 are modified with 2'-fluoro; the internucleotide linkages between nucleotides at positions 1 and 2, positions 2 and 3, positions 3 and 4, positions 20 and 21, and positions 21 and 22 are phosphorothioate linkages; and nucleotide at position 1 is a 4'-phosphate analog comprising 5'-methoxyphosphonate-4'-oxy.

2. A pharmaceutical composition comprising the RNAi oligonucleotide of claim 1, and a pharmaceutically acceptable carrier, delivery agent or excipient.

3. The pharmaceutical composition of claim 2, wherein the carrier comprises phosphate buffered saline.

* * * * *

SEQUENCE LISTING

<160> NUMBER OF SEQ ID NOS: 1303

<210> SEQ ID NO 1
<211> LENGTH: 2753
<212> TYPE: DNA
<213> ORGANISM: Homo sapiens

<400> SEQUENCE: 1
agagagcgct tgcgggcgcc gggcggagct gctgcggatc aggacccgag ccgattcccg 60
atcccgaccc agatcctaac ccgcgccccc gccccgccgc cgccgccatg tacgacgcag 120
agcgcggctg gagcttgtcc ttcgcgggct gcggcttcct gggcttctac cacgtcgggg 180
cgacccgctg cctgagcgag cacgccccgc acctcctccg cgacgcgcgc atgttgttcg 240
gcgcttcggc cggggcgttg cactgcgtcg gcgtcctctc cggtatcccg ctggagcaga 300
ctctgcaggt cctctcagat cttgtgcgga aggccaggag tcggaacatt ggcatcttcc 360
atccatcctt caacttaagc aagttcctcc gacagggtct ctgcaaatgc ctcccggcca 420

-continued

```
atgtccacca gctcatctcc ggcaaaatag gcatctctct taccagagtg tctgatgggg    480
aaaacgttct ggtgtctgac tttcggtcca aagacgaagt cgtggatgcc ttggtatgtt    540
cctgcttcat ccccttctac agtggcctta tccctccttc cttcagaggc gtgcgatatg    600
tggatggagg agtgagtgac aacgtaccct tcattgatgc caaaacaacc atcaccgtgt    660
ccccttcta tggggagtac gacatctgcc ctaaagtcaa gtccacgaac tttcttcatg    720
tggacatcac caagctcagt ctacgcctct gcacagggaa cctctacctt ctctcgagag    780
cttttgtccc cccggatctc aaggtgctgg gagagatatg ccttcgagga tatttggatg    840
cattcaggtt cttggaagag aagggcatct gcaacaggcc ccagccaggc ctgaagtcat    900
cctcagaagg gatggatcct gaggtcgcca tgcccagctg ggcaaacatg agtctggatt    960
cttccccgga gtcggctgcc ttggctgtga ggctggaggg agatgagctg ctagaccacc   1020
tgcgtctcag catcctgccc tgggatgaga gcatcctgga caccctctcg cccaggctcg   1080
ctacagcact gagtgaagaa atgaaagaca aaggtggata catgagcaag atttgcaact   1140
tgctacccat taggataatg tcttatgtaa tgctgccctg taccctgcct gtggaatctg   1200
ccattgcgat tgtccagaga ctggtgacat ggcttccaga tatgcccgac gatgtcctgt   1260
ggttgcagtg ggtgacctca caggtgttca ctcgagtgct gatgtgtctg ctccccgcct   1320
ccaggtccca aatgccagtg agcagccaac aggcctcccc atgcacacct gagcaggact   1380
ggccctgctg gactccctgc tcccccaagg gctgtccagc agagaccaaa gcagaggcca   1440
ccccgcggtc catcctcagg tccagcctga acttcttctt gggcaataaa gtacctgctg   1500
gtgctgaggg gctctccacc tttcccagtt tttcactaga gaagagtctg tgagtcactt   1560
gaggaggcga gtctagcaga ttctttcaga ggtgctaaag tttcccatct ttgtgcagct   1620
acctccgcat tgctgtgtag tgacccctgc ctgtgacgtg gaggatccca gcctctgagc   1680
tgagttggtt ttatgaaaag ctaggaagca acctttcgcc tgtgcagcgg tccagcactt   1740
aactctaata catcagcatg cgttaattca gctggttggg aaatgacacc aggaagccca   1800
gtgcagaggg tcccttactg actgtttcgt ggccctatta atggtcagac tgttccagca   1860
tgaggttctt agaatgacag gtgtttggat gggtgggggc cttgtgatgg ggggtaggct   1920
ggcccatgtg tgatcttgtg gggtggaggg aagagaatag catgatccca cttccccatg   1980
ctgtgggaag ggtgcagtt cgtccccaag aacgacactg cctgtcaggt ggtctgcaaa   2040
gatgataacc ttgactacta aaaacgtctc catggcgggg gtaacaagat gataatctac   2100
ttaattttag aacacctttt tcacctaact aaaataatgt ttaaagagtt ttgtataaaa   2160
atgtaaggaa gcgttgttac ctgttgaatt ttgtattatg tgaatcagtg agatgttagt   2220
agaataagcc ttaaaaaaaa aaaaatcggt tgggtgcagt ggcacacggc tgtaatccca   2280
gcactttggg aggccaaggt tggcagatca cctgaggtca ggagttcaag accagtctgg   2340
ccaacatagc aaaaccctgt ctctactaaa aatacaaaaa ttatctgggc atggtggtgc   2400
atgcctgtaa tcccagctat tcggaaggct gaggcaggag aatcacttga acccaggagg   2460
cggaggttgc ggtgagctga gattgcacca tttcattcca gcctgggcaa catgagtgaa   2520
agtctgactc aaaaaaaaaa aatttaaaaa acaaaaataat ctagtgtgca gggcattcac   2580
ctcagccccc caggcaggag ccaagcacag caggagcttc cgcctcctct ccactggagc   2640
acacaacttg aacctggctt attttctgca gggaccagcc ccacatggtc agtgagtttc   2700
tccccatgtg tggcgatgag agagtgtaga aataaagaca caagacaaag aga          2753
```

<210> SEQ ID NO 2
<211> LENGTH: 481
<212> TYPE: PRT
<213> ORGANISM: Homo sapiens

<400> SEQUENCE: 2

```
Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125

Val Ser Asp Phe Arg Ser Lys Asp Glu Val Val Asp Ala Leu Val Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
        355                 360                 365

Val Gln Arg Leu Val Thr Trp Leu Pro Asp Met Pro Asp Asp Val Leu
    370                 375                 380
```

```
Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Thr Pro Cys Ser
            420                 425                 430

Pro Lys Gly Cys Pro Ala Glu Thr Lys Ala Glu Ala Thr Pro Arg Ser
        435                 440                 445

Ile Leu Arg Ser Ser Leu Asn Phe Phe Leu Gly Asn Lys Val Pro Ala
    450                 455                 460

Gly Ala Glu Gly Leu Ser Thr Phe Pro Ser Phe Ser Leu Glu Lys Ser
465                 470                 475                 480

Leu


<210> SEQ ID NO 3
<211> LENGTH: 2753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

agagagcgct tgcgggcgcc gggcggagct gctgcggatc aggacccgag ccgattcccg     60

atcccgaccc agatcctaac ccgcgccccc gccccgccgc cgccgccatg tacgacgcag    120

agcgcggctg gagcttgtcc ttcgcgggct gcggcttcct gggcttctac cacgtcgggg    180

cgacccgctg cctgagcgag cacgccccgc acctcctccg cgacgcgcgc atgttgttcg    240

gcgcttcggc cggggcgttg cactgcgtcg gcgtcctctc cggtatcccg ctggagcaga    300

ctctgcaggt cctctcagat cttgtgcgga aggccaggag tcggaacatt ggcatcttcc    360

atccatcctt caacttaagc aagttcctcc gacagggtct ctgcaaatgc ctcccggcca    420

atgtccacca gctcatctcc ggcaaaatag gcatctctct taccagagtg tctgatgggg    480

aaaacgttct ggtgtctgac tttcggtcca aagacgaagt cgtggatgcc ttggtatgtt    540

cctgcttcat gcccttctac agtggcctta tccctccttc cttcagaggc gtgcgatatg    600

tggatggagg agtgagtgac aacgtaccct tcattgatgc caaaacaacc atcaccgtgt    660

ccccctteta tggggagtac gacatctgcc ctaaagtcaa gtccacgaac tttcttcatg    720

tggacatcac caagctcagt ctacgcctct gcacagggaa cctctacctt ctctcgagag    780

cttttgtccc cccggatctc aaggtgctgg gagagatatg ccttcgagga tatttggatg    840

cattcaggtt cttggaagag aagggcatct gcaacaggcc ccagccaggc ctgaagtcat    900

cctcagaagg gatggatcct gaggtcgcca tgcccagctg ggcaaacatg agtctggatt    960

cttccccgga gtcggctgcc ttggctgtga ggctggaggg agatgagctg ctagaccacc   1020

tgcgtctcag catcctgccc tgggatgaga gcatcctgga caccctctcg cccaggctcg   1080

ctacagcact gagtgaagaa atgaaagaca aaggtggata catgagcaag atttgcaact   1140

tgctacccat taggataatg tcttatgtaa tgctgccctg taccctgcct gtggaatctg   1200

ccattgcgat tgtccagaga ctggtgacat ggcttccaga tatgcccgac gatgtcctgt   1260

ggttgcagtg ggtgacctca caggtgttca ctcgagtgct gatgtgtctg ctccccgcct   1320

ccaggtccca aatgccagtg agcagccaac aggcctcccc atgcacacct gagcaggact   1380

ggccctgctg gactccctgc tcccccaagg gctgtccagc agagaccaaa gcagaggcca   1440
```

-continued

```
ccccgcggtc catcctcagg tccagcctga acttcttctt gggcaataaa gtacctgctg   1500
gtgctgaggg gctctccacc tttcccagtt tttcactaga gaagagtctg tgagtcactt   1560
gaggaggcga gtctagcaga ttctttcaga ggtgctaaag tttcccatct ttgtgcagct   1620
acctccgcat tgctgtgtag tgacccctgc ctgtgacgtg gaggatccca gcctctgagc   1680
tgagttggtt ttatgaaaag ctaggaagca acctttcgcc tgtgcagcgg tccagcactt   1740
aactctaata catcagcatg cgttaattca gctggttggg aaatgacacc aggaagccca   1800
gtgcagaggg tcccttactg actgtttcgt ggccctatta atggtcagac tgttccagca   1860
tgaggttctt agaatgacag gtgtttggat gggtgggggc cttgtgatgg ggggtaggct   1920
ggcccatgtg tgatcttgtg gggtggaggg aagagaatag catgatccca cttccccatg   1980
ctgtgggaag gggtgcagtt cgtccccaag aacgacactg cctgtcaggt ggtctgcaaa   2040
gatgataacc ttgactacta aaaacgtctc catggcgggg gtaacaagat gataatctac   2100
ttaattttag aacacctttt tcacctaact aaaataatgt ttaaagagtt ttgtataaaa   2160
atgtaaggaa gcgttgttac ctgttgaatt ttgtattatg tgaatcagtg agatgttagt   2220
agaataagcc ttaaaaaaaa aaaaatcggt tgggtgcagt ggcacacggc tgtaatccca   2280
gcactttggg aggccaaggt tggcagatca cctgaggtca ggagttcaag accagtctgg   2340
ccaacatagc aaaaccctgt ctctactaaa aatacaaaaa ttatctgggc atggtggtgc   2400
atgcctgtaa tcccagctat tcggaaggct gaggcaggag aatcacttga acccaggagg   2460
cggaggttgc ggtgagctga gattgcacca tttcattcca gcctgggcaa catgagtgaa   2520
agtctgactc aaaaaaaaaa aatttaaaaa acaaaataat ctagtgtgca gggcattcac   2580
ctcagccccc caggcaggag ccaagcacag caggagcttc cgcctcctct ccactggagc   2640
acacaacttg aacctggctt attttctgca gggaccagcc ccacatggtc agtgagtttc   2700
tccccatgtg tggcgatgag agagtgtaga aataaagaca caagacaaag aga          2753
```

<210> SEQ ID NO 4
<211> LENGTH: 481
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Leu Ser Lys Phe Leu Arg Gln
                85                  90                  95

Gly Leu Cys Lys Cys Leu Pro Ala Asn Val His Gln Leu Ile Ser Gly
            100                 105                 110

Lys Ile Gly Ile Ser Leu Thr Arg Val Ser Asp Gly Glu Asn Val Leu
        115                 120                 125
```

```
Val Ser Asp Phe Arg Ser Lys Asp Glu Val Val Asp Ala Leu Val Cys
    130                 135                 140

Ser Cys Phe Met Pro Phe Tyr Ser Gly Leu Ile Pro Pro Ser Phe Arg
145                 150                 155                 160

Gly Val Arg Tyr Val Asp Gly Gly Val Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Arg Pro Gln Pro Gly Leu Lys Ser Ser Ser Glu Gly Met Asp Pro Glu
            260                 265                 270

Val Ala Met Pro Ser Trp Ala Asn Met Ser Leu Asp Ser Ser Pro Glu
        275                 280                 285

Ser Ala Ala Leu Ala Val Arg Leu Glu Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Arg Leu Ala Thr Ala Leu Ser Glu Glu Met Lys Asp Lys Gly
                325                 330                 335

Gly Tyr Met Ser Lys Ile Cys Asn Leu Leu Pro Ile Arg Ile Met Ser
            340                 345                 350

Tyr Val Met Leu Pro Cys Thr Leu Pro Val Glu Ser Ala Ile Ala Ile
        355                 360                 365

Val Gln Arg Leu Val Thr Trp Leu Pro Asp Met Pro Asp Asp Val Leu
    370                 375                 380

Trp Leu Gln Trp Val Thr Ser Gln Val Phe Thr Arg Val Leu Met Cys
385                 390                 395                 400

Leu Leu Pro Ala Ser Arg Ser Gln Met Pro Val Ser Ser Gln Gln Ala
                405                 410                 415

Ser Pro Cys Thr Pro Glu Gln Asp Trp Pro Cys Trp Thr Pro Cys Ser
            420                 425                 430

Pro Lys Gly Cys Pro Ala Glu Thr Lys Ala Glu Ala Thr Pro Arg Ser
        435                 440                 445

Ile Leu Arg Ser Ser Leu Asn Phe Phe Leu Gly Asn Lys Val Pro Ala
    450                 455                 460

Gly Ala Glu Gly Leu Ser Thr Phe Pro Ser Phe Ser Leu Glu Lys Ser
465                 470                 475                 480

Leu


<210> SEQ ID NO 5
<211> LENGTH: 2291
<212> TYPE: DNA
<213> ORGANISM: Macaca fascicularis

<400> SEQUENCE: 5

cgagggaggc ggggcggacg tcgcgcgtgg aaagcccggg cggagacgcg gcggctgggt      60

cacgagcgct tgcgggcgcc cggcggagct gctgcggatc aggacccgag ccgatccccg     120
```

atcccgactc cgatccggat ccgcgccccc gcccccgccc cgccatgtac gacgccgagc 180
gcggctggag cttgtccttc gcgggctgcg gcttcctggg cttctaccac gtcggggcga 240
cccggtgcct gagcgagcac gccccgcacc tcctccgcga cgcgcgcatg ttgttcggcg 300
cctcggccgg ggcgttgcac tgcgtcggcg tcctctccgg gatcccgctg gagcagactc 360
tgcaggtcct ctcagatctt gtccggaagg ccaggagtcg gaacattggt atcttccatc 420
catccttcaa cataggcaag ttcctccgac aggatctcta caaatacctc ccggccaatg 480
tccaccagct catctctggc aaaatatgcg tctcactcac cagagtgtct gatggggaaa 540
acgttctggt gtctgacttt cagtccaaag acgaagtcgt ggatgccttg atttgttcct 600
gcttcatccc tttctacagt ggccttatcc ctccttcctt cagaggcgtg cgatatgtgg 660
atggaggagc gagtgacaac gtacccttca ttgatgccaa gacaaccatc accgtgtcgc 720
ccttctatgg ggagtacgac atctgcccta aagtcaagtc caccaacttt cttcatgtgg 780
acatcaccaa gctcagccta cgcctctgca cagggaacct ctaccttctc tcaagagcgt 840
ttgtcccccc ggatctcaag gtgctgggag agatatgcct tcgaggatat ttggacgcgt 900
tcaggttctt ggaagagaag ggcatctgca acaagcccca gcggggtctg aagtcatcct 960
cagaagggat ggattctgag gtcactgcgc ccggctggga aaacacaagt ctggattctt 1020
ccccggagcc ggctgccttg gctatgaggc tggatggaga tgagctgcta gaccacctgc 1080
gtctcagcat cctgccctgg gatgagagca tcctggacac cctgtcgccc gagctcgcta 1140
cagtgagtga agcaatgaaa gacaaaggtg gatacatgag caagatttgc aacttgctac 1200
ccattaggat aatatcttat gtgatgctgc cctgtaccct gcctgtggag tctgccattg 1260
cgattgtcca gagactggtg acatggcttc cagatatgcc cgacgatgtg cagtggctgc 1320
agtgggtgac ctcacaggtc ttcactcgag cgctgatgtg tctgcttccc gcctccaggt 1380
cccaaatgcc agtgagcagc gaacaggcct ccccatgcaa accggagcag gactggcact 1440
gctggactcc ctgctccccc gaggactgtc ctgcagaggc caaagcagag gctaccccac 1500
ggtccatcct caggtccagc ctgaacttct tctggggcaa taaagtacct gctggtgctg 1560
aggggctctc cacctttccc agtttttcac tggagaagaa tttgtgagtc atttgaggag 1620
gcgagtctag gagattcttt cagaggtgct aaagcttccc atctttgtgc agctacctcc 1680
gcattgccgt gtagtgaccc ctgcctgtga cgtggaggat cccagcctct gagctgagtt 1740
ggttttatga aaagctagga agcaatgttt ggtctgtgca gcagtccagc acttaagtct 1800
aatacgtcag catgcgttag ttcagctggt tgggaaatga caccgggaag cctagcgcag 1860
agggtccctt actgactatt tcatggtcct attaatggtc agactgttcc agtgtgaggt 1920
tcttagaatg actagtgttt ggatgggtgg gggccttgtg gtggggggtg ggctggccta 1980
tgtgtgatct tgtggggtgg aaggaagaga gtagcacaat cccacctccc catgccgtgg 2040
gaaggggtgc acttggttcc caagaaggac actgcctgtc aggtggcctg caaatataat 2100
aaccttgaca actaaaaacc tctccatggg ggtgggaggt accaagataa taaccgattt 2160
acattttaga gcaccttttt cacctaacta aaataatgtt taaagagttt tatataaaaa 2220
tgtaaggaag agttgttatc tgttgaattt tgtattatat gaatcagtga gatgttaata 2280
gaataagcct t 2291

<210> SEQ ID NO 6
<211> LENGTH: 480
<212> TYPE: PRT

<213> ORGANISM: Macaca fascicularis

<400> SEQUENCE: 6

```
Met Tyr Asp Ala Glu Arg Gly Trp Ser Leu Ser Phe Ala Gly Cys Gly
1               5                   10                  15

Phe Leu Gly Phe Tyr His Val Gly Ala Thr Arg Cys Leu Ser Glu His
            20                  25                  30

Ala Pro His Leu Leu Arg Asp Ala Arg Met Leu Phe Gly Ala Ser Ala
        35                  40                  45

Gly Ala Leu His Cys Val Gly Val Leu Ser Gly Ile Pro Leu Glu Gln
    50                  55                  60

Thr Leu Gln Val Leu Ser Asp Leu Val Arg Lys Ala Arg Ser Arg Asn
65                  70                  75                  80

Ile Gly Ile Phe His Pro Ser Phe Asn Ile Gly Lys Phe Leu Arg Gln
                85                  90                  95

Asp Leu Tyr Lys Tyr Leu Pro Ala Asn Val His Gln Leu Ile Ser Gly
            100                 105                 110

Lys Ile Cys Val Ser Leu Thr Arg Val Ser Asp Gly Glu Asn Val Leu
        115                 120                 125

Val Ser Asp Phe Gln Ser Lys Asp Glu Val Val Asp Ala Leu Ile Cys
    130                 135                 140

Ser Cys Phe Ile Pro Phe Tyr Ser Gly Leu Ile Pro Pro Ser Phe Arg
145                 150                 155                 160

Gly Val Arg Tyr Val Asp Gly Gly Ala Ser Asp Asn Val Pro Phe Ile
                165                 170                 175

Asp Ala Lys Thr Thr Ile Thr Val Ser Pro Phe Tyr Gly Glu Tyr Asp
            180                 185                 190

Ile Cys Pro Lys Val Lys Ser Thr Asn Phe Leu His Val Asp Ile Thr
        195                 200                 205

Lys Leu Ser Leu Arg Leu Cys Thr Gly Asn Leu Tyr Leu Leu Ser Arg
    210                 215                 220

Ala Phe Val Pro Pro Asp Leu Lys Val Leu Gly Glu Ile Cys Leu Arg
225                 230                 235                 240

Gly Tyr Leu Asp Ala Phe Arg Phe Leu Glu Glu Lys Gly Ile Cys Asn
                245                 250                 255

Lys Pro Gln Arg Gly Leu Lys Ser Ser Ser Glu Gly Met Asp Ser Glu
            260                 265                 270

Val Thr Ala Pro Gly Trp Glu Asn Thr Ser Leu Asp Ser Ser Pro Glu
        275                 280                 285

Pro Ala Ala Leu Ala Met Arg Leu Asp Gly Asp Glu Leu Leu Asp His
    290                 295                 300

Leu Arg Leu Ser Ile Leu Pro Trp Asp Glu Ser Ile Leu Asp Thr Leu
305                 310                 315                 320

Ser Pro Glu Leu Ala Thr Val Ser Glu Ala Met Lys Asp Lys Gly Gly
                325                 330                 335

Tyr Met Ser Lys Ile Cys Asn Leu Leu Pro Ile Arg Ile Ile Ser Tyr
            340                 345                 350

Val Met Leu Pro Cys Thr Leu Pro Val Glu Ser Ala Ile Ala Ile Val
        355                 360                 365

Gln Arg Leu Val Thr Trp Leu Pro Asp Met Pro Asp Asp Val Gln Trp
    370                 375                 380

Leu Gln Trp Val Thr Ser Gln Val Phe Thr Arg Ala Leu Met Cys Leu
385                 390                 395                 400
```

-continued

```
Leu Pro Ala Ser Arg Ser Gln Met Pro Val Ser Ser Glu Gln Ala Ser
                405                 410                 415

Pro Cys Lys Pro Glu Gln Asp Trp His Cys Trp Thr Pro Cys Ser Pro
            420                 425                 430

Glu Asp Cys Pro Ala Glu Ala Lys Ala Glu Ala Thr Pro Arg Ser Ile
        435                 440                 445

Leu Arg Ser Ser Leu Asn Phe Phe Trp Gly Asn Lys Val Pro Ala Gly
    450                 455                 460

Ala Glu Gly Leu Ser Thr Phe Pro Ser Phe Ser Leu Glu Lys Asn Leu
465                 470                 475                 480
```

<210> SEQ ID NO 7
<211> LENGTH: 4675
<212> TYPE: DNA
<213> ORGANISM: Mus musculus

<400> SEQUENCE: 7

```
cacccgaaga cagcttaggc ggctgcggct ctttaagctc agagcagcaa caccgggagc     60

agagctgaac tgcagcgccg cccggagctt caagcaccat gtatgaccca gagcgccgct    120

ggagcctgtc gtttgcaggc tgcggcttcc tgggcttcta ccacgtcggg gctacgctat    180

gtctgagcga gcgcgccccg cacctcctcc gcgatgcgcg cactttcttt ggctgctcgg    240

ccggtgcact gcacgcggtc accttcgtgt gcagtctccc tctcggtgcg tccacggcca    300

ctacccaggc cccgcgtgcg gggaggggtt gctacacctg ggaatcggt aacactttcc    360

ggggtgcccg aagaaacctg tccggagagc tctcatcctt cccggtgccg ttgagcactc    420

agctggagac cctgggcctg tcacctggcg tgggatttcc cggggccggc tggagcagac    480

gcgctccgag catcttcttc ctgacccgct ctggcgccct ggtcctgtca gctgggtcat    540

ccctgagcag cagggaacga cgcaggtttg ccgggtcctc tggtccctga gccgcagaag    600

gccgtataat ggagatcctc atggacctcg tgcggaaagc caggagccgc aacatcggca    660

ccctccaccc gttcttcaac attaacaagt gcatcagaga cgggctccag gagagcctcc    720

cagacaatgt ccaccaggtc atttctggca aggttcacat ctcactcacc agggtgtcgg    780

atggggagaa cgtgctggtg tctgagttcc attccaaaga cgaagtcgtg gatgccctgg    840

tgtgttcctg cttcattccc ctcttctctg gcctaatccc tccttccttc cgaggcgagc    900

ggtacgtgga cggaggagtg agcgacaacg tccctgtgct ggatgccaaa accaccatca    960

cggtgtcacc tttctacggt gagcatgaca tctgccccaa agtcaagtcc accaacttct   1020

tccacgtgaa tatcaccaac ctcagcctcc gcctctgcac tgggaacctc caacttctga   1080

ccagagcgct cttcccgtct gatgtgaagg tgatgggaga gctgtgctat caagggtacc   1140

tggacgcctt ccggttcctg gaggagaatg gcatctgtaa cgggccacag cgcagcctga   1200

gtctgtcctt ggtggcgcca gaagcctgct tggaaaatgg caaacttgtg ggagacaagg   1260

tgccagtcag cctatgcttt acagatgaga acatctggga gacactgtcc cccgagctca   1320

gcacagctct gagtgaagcg attaaggaca gggagggcta cctgagcaaa gtctgcaacc   1380

tcctgcccgt caggatcctg tcctacatca tgctgccctg cagtctgccc gtggagtcgg   1440

ctatcgctgc agtccacagg ctggtgacat ggctccctga tatccaggat gatatccagt   1500

ggctacaatg ggcgacatcc caggtttgtg cccgaatgac gatgtgcctg ctcccctcta   1560

ccagcatgag attcctggga caatcccaat tccttggcct ccattgtatc aaagggctga   1620

aaaccaaagg gaaggcacag ctgtctcttc agcatgcctc ttctgccaga accactgcaa   1680
```

```
ggtttggtgc tcaggctgtg caaacattct agcaatgttt gactcagtgt caagcaggtg   1740
acaaggaaca tggtgctgtg tggggggaac ccatggccca ggtgagggct tattggtggg   1800
tgaagctgtg ggtgttcagg tggtggagaa ggccttaagg gatgggactg acacctcagc   1860
actgaaggca ggaggaagct gtggctctgg gttgcacccc tgcctggctc caccctctct   1920
ggcatctgta gaagttacag ctggttcttc ctctcagccc catgctccca gaaataagac   1980
tcagacccaa attatagtta caaatacctt ggccatatag ctaggctctt ctcagactag   2040
ctcataactt aactcattaa ttttaacctc catcctgcca catggctggt ggcctgtgct   2100
caggtaccat gagtccagct cttcacatct ttccggatga atcttccata attctttctg   2160
cctcctggat gttccacctt ctattccacc ttttcctata ggccatggtt ttgtttttgt   2220
tttttttttc caaatttaat ttaattaatt aatttattta tttttggttt ttcgagacag   2280
ggtttctctg tatcgccctg gctgtcctgg aactcactat gtaagccagg ctggcctcaa   2340
actcagaaat ccgcctgcct ctgcctcctg agtgctggga ttaaaggcgt gcgcaaccat   2400
gcccggtgtg gttttttttt ttttttaatt gacaggtgga tgcatctata taatccataa   2460
catattctct ctacaggtat ctattaggtt ttgggtgagg tgtggagttc tagggaactc   2520
tgagagaaat tcctggggag taagtggttt atcaagttga ttggaggagt ttttaatgct   2580
atggacagac agacagaagg acaacagcat agtcggggct accagggagt tcaggccccg   2640
gcatcggaga tagaagcagg atggggtctt tgaagagatt ctgagcccac acagcagagg   2700
agggactctc tctttagagc ttttgaggat gagggaggtt gactgcaaga gcctacagcc   2760
aggctcgagg caggcagggg gtggggagca ggatgtaaac cccttcgatg ctgacagact   2820
cacttctggg gtaaaatatt atgagatgcc tgtcagtgtc tgtgaagaga cctgagcaga   2880
gtctggattc tgacatcaat catgttctta caatactgaa gacctgagag cctgcaatct   2940
tggtttgtaa attgctggtc tccgtgcttc cagtgaactt ggacattctt ctcatggttg   3000
gtccaggaga ggccaaagct gagggcaccc tgccttccac ccccagtcca gcttgacctt   3060
ttatctggag caacagtgtc tagatgatgg gtgggtgagg ggtgctatac tgtctgtccc   3120
tctgggaagg gttctgttac ttttggaggc agctaggaag tttctctgtg cagctgcccc   3180
ctggtgctgt gtggtgacct cattgcctgt gaccccagga tcacaggatc tgggctaaag   3240
tggtagtcca tagaaaccaa agacaatgat ttggtgttta gaaagctact cttggtctgg   3300
gtgaagtctg gtgcttaagg gctatcacaa agagcgtgtc aaaccatctc tcagcctgtg   3360
agtcagtggg gagcccaagg gcatcagtgt ttggaaactg gaatccaaac cgggcaatct   3420
cggaaggaaa ctgtttagga attgtgatgg gacgggccgt ggctgtctct gaaaagggcc   3480
tgccagataa cttattactt ttaaggacac ctttggctct tactaattta taaagcattt   3540
tatataaaca caccagggag tgcatggtga actacacgta tgatcagtta agtggggcta   3600
gaattaggta gggagagcat cggacctctg cctcctcaac ctcaacttgc ttgctttctc   3660
cactggctcc aaatctttgt atagtcatca gccatgacca cctctctccc tccccatcta   3720
ctaccagcag cgttaatggg aataagtacc cacttctctc aggtgtacta tacagctgtg   3780
ggtgtggtgt gtgtttcctg taattcacac tttagaaagg aaacaagcaa acaaaagaaa   3840
ccaggtgctg cccatactcc taagtgtaga cagtgaaggt gtgtgtctcc catgcctgag   3900
tctcctggag gcctagtgag ctccaggttc atgcaagcac atcaggagga atcatataat   3960
ctcagcacgg ttgatccaga tgggataaga aaggactctg ggagagagaa tgtggttcta   4020
gagacaaagt gtctaggcta cacagaagat aagactgtcc caaggaaaga aaagaaacca   4080
```

```
ggaactaggg tgcagctcag ttgtcagagg acttctctag gcttgaagcc cagagtccaa   4140

tctcagcacc ttataaactg tggagtgaca ggcagtgaca tcggcctgta atcccaacac   4200

tcaagcagta gaggcaagag gatcataagt tcaaggtctt ccttggctat ttagggagtt   4260

ggaggttagc tctggctaca tgagaccctg tctcaaaaaa aaaaaaaaaa aaaagtagaa   4320

acttctgcct tgctttgagc tgccccttc tggacgtttc tcatcagtag agaatattcc   4380

tgccacccta tcagacaaaa ctcccactgg tttggagtct ctccattctc aggaacacct   4440

caggagtcag acagtgagca gcagggagca atgtcttgac ttgtaagccc cttagcaagg   4500

ctggttcatt tgtttattaa aagcaggtgt gggtgaattt atgcaaatga gtatgcaaac   4560

tagtggaaca gcagaaggat tgaatggata caccaaaaat aaccacaact gtttaaggga   4620

aaagggtcca taataaatgt ggggaacaaa aaacaaataa atgtgatttt tttta        4675
```

```
<210> SEQ ID NO 8
<211> LENGTH: 367
<212> TYPE: PRT
<213> ORGANISM: Mus musculus

<400> SEQUENCE: 8

Met Glu Ile Leu Met Asp Leu Val Arg Lys Ala Arg Ser Arg Asn Ile
1               5                   10                  15

Gly Thr Leu His Pro Phe Phe Asn Ile Asn Lys Cys Ile Arg Asp Gly
            20                  25                  30

Leu Gln Glu Ser Leu Pro Asp Asn Val His Gln Val Ile Ser Gly Lys
        35                  40                  45

Val His Ile Ser Leu Thr Arg Val Ser Asp Gly Glu Asn Val Leu Val
    50                  55                  60

Ser Glu Phe His Ser Lys Asp Glu Val Val Asp Ala Leu Val Cys Ser
65                  70                  75                  80

Cys Phe Ile Pro Leu Phe Ser Gly Leu Ile Pro Pro Ser Phe Arg Gly
                85                  90                  95

Glu Arg Tyr Val Asp Gly Gly Val Ser Asp Asn Val Pro Val Leu Asp
            100                 105                 110

Ala Lys Thr Thr Ile Thr Val Ser Pro Phe Tyr Gly Glu His Asp Ile
        115                 120                 125

Cys Pro Lys Val Lys Ser Thr Asn Phe Phe His Val Asn Ile Thr Asn
    130                 135                 140

Leu Ser Leu Arg Leu Cys Thr Gly Asn Leu Gln Leu Leu Thr Arg Ala
145                 150                 155                 160

Leu Phe Pro Ser Asp Val Lys Val Met Gly Glu Leu Cys Tyr Gln Gly
                165                 170                 175

Tyr Leu Asp Ala Phe Arg Phe Leu Glu Glu Asn Gly Ile Cys Asn Gly
            180                 185                 190

Pro Gln Arg Ser Leu Ser Leu Ser Leu Val Ala Pro Glu Ala Cys Leu
        195                 200                 205

Glu Asn Gly Lys Leu Val Gly Asp Lys Val Pro Val Ser Leu Cys Phe
    210                 215                 220

Thr Asp Glu Asn Ile Trp Glu Thr Leu Ser Pro Glu Leu Ser Thr Ala
225                 230                 235                 240

Leu Ser Glu Ala Ile Lys Asp Arg Glu Gly Tyr Leu Ser Lys Val Cys
                245                 250                 255

Asn Leu Leu Pro Val Arg Ile Leu Ser Tyr Ile Met Leu Pro Cys Ser
            260                 265                 270
```

```
Leu Pro Val Glu Ser Ala Ile Ala Ala Val His Arg Leu Val Thr Trp
        275                 280                 285

Leu Pro Asp Ile Gln Asp Asp Ile Gln Trp Leu Gln Trp Ala Thr Ser
    290                 295                 300

Gln Val Cys Ala Arg Met Thr Met Cys Leu Leu Pro Ser Thr Ser Met
305                 310                 315                 320

Arg Phe Leu Gly Gln Ser Gln Phe Leu Gly Leu His Cys Ile Lys Gly
                325                 330                 335

Leu Lys Thr Lys Gly Lys Ala Gln Leu Ser Leu Gln His Ala Ser Ser
            340                 345                 350

Ala Arg Thr Thr Ala Arg Phe Gly Ala Gln Ala Val Gln Thr Phe
        355                 360                 365


<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9

ucugcagguc cucucagauc uugug                                           25


<210> SEQ ID NO 10
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10

cacaagaucu gagaggaccu gcagagu                                         27


<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11

agguccucuc agaucuugug cggaa                                           25


<210> SEQ ID NO 12
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12

uuccgcacaa gaucugagag gaccugc                                         27


<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 13
auuggcaucu uccauccauc cuuca 25

<210> SEQ ID NO 14
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
ugaaggaugg auggaagaug ccaaugu 27

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 15
aucuuccauc cauccuucaa cuuaa 25

<210> SEQ ID NO 16
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 16
uuaaguugaa ggauggaugg aagaugc 27

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 17
ucuuccaucc auccuucaac uuaag 25

<210> SEQ ID NO 18
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 18
cuuaaguuga aggauggaug gaagaug 27

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 19
ccagagugug ugauggggaa aacgu 25

<210> SEQ ID NO 20
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
acguuuuccc caucagacac ucuggua 27

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 21
gagugucuga uggggaaaac guucu 25

<210> SEQ ID NO 22
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 22
agaacguuuu ccccaucaga cacucug 27

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 23
auggggaaaa cguucuggug ucuga 25

<210> SEQ ID NO 24
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 24
ucagacacca gaacguuuuc cccauca 27

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25

```
ggggaaaacg uucugguguc ugacu                                            25

<210> SEQ ID NO 26
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26

agucagacac cagaacguuu uccccau                                          27

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27

gggaaaacgu ucuggugucu gacuu                                            25

<210> SEQ ID NO 28
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28

aagucagaca ccagaacguu uucccca                                          27

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29

ggaaaacguu cuggugucug acuuu                                            25

<210> SEQ ID NO 30
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30

aaagucagac accagaacgu uuucccc                                          27

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
```

gaaaacguuc uggugucuga cuuuc 25

<210> SEQ ID NO 32
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 32
gaaagucaga caccagaacg uuuuccc 27

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 33
aaaacguucu ggugucugac uuucg 25

<210> SEQ ID NO 34
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 34
cgaaagucag acaccagaac guuuucc 27

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 35
aaacguucug gugucugacu uucgg 25

<210> SEQ ID NO 36
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 36
ccgaaaguca gacaccagaa cguuuuc 27

<210> SEQ ID NO 37
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 37
aacguucugg ugucugacuu ucggu 25

<210> SEQ ID NO 38
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 38
accgaaaguc agacaccaga acguuuu 27

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 39
acguucuggu gucugacuuu cgguc 25

<210> SEQ ID NO 40
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
gaccgaaagu cagacaccag aacguuu 27

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 41
guucuggugu cugacuuucg gucca 25

<210> SEQ ID NO 42
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 42
uggaccgaaa gucagacacc agaacgu 27

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 43
gacgaagucg uggaugccuu gguau 25

<210> SEQ ID NO 44
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 44
auaccaaggc auccacgacu ucgucuu 27

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 45
acgaagucgu ggaugccuug guaug 25

<210> SEQ ID NO 46
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 46
cauaccaagg cauccacgac uucgucu 27

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 47
cgaagucgug gaugccuugg uaugu 25

<210> SEQ ID NO 48
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 48
acauaccaag gcauccacga cuucguc 27

<210> SEQ ID NO 49
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 49
cagaggcgug cgauaugugg augga 25

-continued

<210> SEQ ID NO 50
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 50
uccauccaca uaucgcacgc cucugaa 27

<210> SEQ ID NO 51
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 51
gcgauaugug gauggaggag ugagu 25

<210> SEQ ID NO 52
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 52
acucacuccu ccauccacau aucgcac 27

<210> SEQ ID NO 53
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 53
gauggaggag ugagugacaa cguac 25

<210> SEQ ID NO 54
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 54
guacguuguc acucacuccu ccaucca 27

<210> SEQ ID NO 55
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
gaggagugag ugacaacgua cccuu 25

<210> SEQ ID NO 56

<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
aaggguacgu ugucacucac uccucca 27

<210> SEQ ID NO 57
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
gagugaguga caacguaccc uucau 25

<210> SEQ ID NO 58
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
augaagggua cguugucacu cacuccu 27

<210> SEQ ID NO 59
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 59
agugagugac aacguacccu ucauu 25

<210> SEQ ID NO 60
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 60
aaugaagggu acguugucac ucacucc 27

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 61
gugagugaca acguacccuu cauug 25

<210> SEQ ID NO 62
<211> LENGTH: 27

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 62
caaugaaggg uacguuguca cucacuc 27

<210> SEQ ID NO 63
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 63
ugagugacaa cguacccuuc auuga 25

<210> SEQ ID NO 64
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 64
ucaaugaagg guacguuguc acucacu 27

<210> SEQ ID NO 65
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 65
gagugacaac guacccuuca uugau 25

<210> SEQ ID NO 66
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 66
aucaaugaag gguacguugu cacucac 27

<210> SEQ ID NO 67
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 67
agugacaacg uacccuucau ugaug 25

<210> SEQ ID NO 68
<211> LENGTH: 27
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 68
caucaaugaa ggguacguug ucacuca 27

<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gugacaacgu acccuucauu gaugc 25

<210> SEQ ID NO 70
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gcaucaauga aggguacguu gucacuc 27

<210> SEQ ID NO 71
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ugacaacgua cccuucauug augcc 25

<210> SEQ ID NO 72
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ggcaucaaug aaggguacgu ugucacu 27

<210> SEQ ID NO 73
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gacaacguac ccuucauuga ugcca 25

<210> SEQ ID NO 74
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uggcaucaau gaaggguacg uugucac 27

<210> SEQ ID NO 75
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
caacguaccc uucauugaug ccaaa 25

<210> SEQ ID NO 76
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuuggcauca augaagggua cguuguc 27

<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
aacguacccu ucauugaugc caaaa 25

<210> SEQ ID NO 78
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uuuuggcauc aaugaagggu acguugu 27

<210> SEQ ID NO 79
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
acguacccuu cauugaugcc aaaac 25

<210> SEQ ID NO 80
<211> LENGTH: 27
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 80
guuuuggcau caaugaaggg uacguug 27

<210> SEQ ID NO 81
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 81
cguacccuuc auugaugcca aaaca 25

<210> SEQ ID NO 82
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 82
uguuuuggca ucaaugaagg guacguu 27

<210> SEQ ID NO 83
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 83
uacccuucau ugaugccaaa acaac 25

<210> SEQ ID NO 84
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 84
guuguuuugg caucaaugaa ggguacg 27

<210> SEQ ID NO 85
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 85
uugaugccaa aacaaccauc accgu 25

<210> SEQ ID NO 86
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 86
acggugaugg uuguuuuggc aucaaug 27

<210> SEQ ID NO 87
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 87
gaugccaaaa caaccaucac cgugu 25

<210> SEQ ID NO 88
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 88
acacggugau gguuguuuug gcaucaa 27

<210> SEQ ID NO 89
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 89
auggggagua cgacaucugc ccuaa 25

<210> SEQ ID NO 90
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 90
uuagggcaga ugucguacuc cccauag 27

<210> SEQ ID NO 91
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 91
guacgacauc ugcccuaaag ucaag 25

<210> SEQ ID NO 92
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 92
cuugacuuua gggcagaugu cguacuc 27

<210> SEQ ID NO 93
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 93
gacaucugcc cuaaagucaa gucca 25

<210> SEQ ID NO 94
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 94
uggacuugac uuuagggcag augucgu 27

<210> SEQ ID NO 95
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 95
acaucugccc uaaagucaag uccac 25

<210> SEQ ID NO 96
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 96
guggacuuga cuuuagggca gaugucg 27

<210> SEQ ID NO 97
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 97
gucaagucca cgaacuuucu ucaug 25

<210> SEQ ID NO 98
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 98
caugaagaaa guucguggac uugacuu 27

<210> SEQ ID NO 99
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 99
ucaaguccac gaacuuucuu caugu 25

<210> SEQ ID NO 100
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 100
acaugaagaa aguucgugga cuugacu 27

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 101
caaguccacg aacuuucuuc augug 25

<210> SEQ ID NO 102
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 102
cacaugaaga aaguucgugg acuugac 27

<210> SEQ ID NO 103
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 103
guccacgaac uuucuucaug uggac 25

<210> SEQ ID NO 104
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 104
guccacauga agaaaguucg uggacuu 27

<210> SEQ ID NO 105
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 105
ccacgaacuu ucuucaugug gacau 25

<210> SEQ ID NO 106
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 106
auguccacau gaagaaaguu cguggac 27

<210> SEQ ID NO 107
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 107
cacgaacuuu cuucaugugg acauc 25

<210> SEQ ID NO 108
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 108
gauguccaca ugaagaaagu ucgugga 27

<210> SEQ ID NO 109
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 109
acgaacuuuc uucaugugga cauca 25

<210> SEQ ID NO 110
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 110
ugauguccac augaagaaag uucgugg 27

<210> SEQ ID NO 111
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 111
cgaacuuucu ucauguggac aucac 25

<210> SEQ ID NO 112
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 112
gugaugucca caugaagaaa guucgug 27

<210> SEQ ID NO 113
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 113
gaacuuucuu cauguggaca ucacc 25

<210> SEQ ID NO 114
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 114
ggugaugucc acaugaagaa aguucgu 27

<210> SEQ ID NO 115
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115
aacuuucuuc auguggacau cacca 25

<210> SEQ ID NO 116
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
uggugauguc cacaugaaga aaguucg 27

<210> SEQ ID NO 117
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
acuuucuuca uguggacauc accaa 25

<210> SEQ ID NO 118
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
uuggugaugu ccacaugaag aaaguuc 27

<210> SEQ ID NO 119
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 119
cuuucuucau guggacauca ccaag 25

<210> SEQ ID NO 120
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120
cuuggugaug uccacaugaa gaaaguu 27

<210> SEQ ID NO 121
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 121
uuucuucaug uggacaucac caagc 25

<210> SEQ ID NO 122
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 122
gcuuggugau guccacauga agaaagu 27

<210> SEQ ID NO 123
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 123
uucuucaugu ggacaucacc aagcu 25

<210> SEQ ID NO 124
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 124
agcuugguga uguccacaug aagaaag 27

<210> SEQ ID NO 125
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 125
cuucaugugg acaucaccaa gcuca 25

<210> SEQ ID NO 126
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 126
ugagcuuggu gauguccaca ugaagaa 27

<210> SEQ ID NO 127
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 127
uucaugugga caucaccaag cucag 25

<210> SEQ ID NO 128
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 128
cugagcuugg ugauguccac augaaga 27

<210> SEQ ID NO 129
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 129
ucauguggac aucaccaagc ucagu 25

<210> SEQ ID NO 130
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 130
acugagcuug gugaugucca caugaag 27

<210> SEQ ID NO 131
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 131
cauguggaca ucaccaagcu caguc 25

<210> SEQ ID NO 132
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 132
gacugagcuu ggugaugucc acaugaa 27

<210> SEQ ID NO 133
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 133
auguggacau caccaagcuc agucu 25

<210> SEQ ID NO 134
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 134
agacugagcu uggugauguc cacauga 27

<210> SEQ ID NO 135

-continued

<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 135
uguggacauc accaagcuca gucua 25

<210> SEQ ID NO 136
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 136
uagacugagc uuggugaugu ccacaug 27

<210> SEQ ID NO 137
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 137
guggacauca ccaagcucag ucuac 25

<210> SEQ ID NO 138
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 138
guagacugag cuuggugaug uccacau 27

<210> SEQ ID NO 139
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 139
uggacaucac caagcucagu cuacg 25

<210> SEQ ID NO 140
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 140
cguagacuga gcuuggugau guccaca 27

<210> SEQ ID NO 141
<211> LENGTH: 25

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 141
agcuuuuguc cccccggauc ucaag 25

<210> SEQ ID NO 142
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 142
cuugagaucc gggggacaa aagcucu 27

<210> SEQ ID NO 143
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 143
aaggugcugg gagagauaug ccuuc 25

<210> SEQ ID NO 144
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 144
gaaggcauau cucucccagc accuuga 27

<210> SEQ ID NO 145
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 145
gggagagaua ugccuucgag gauau 25

<210> SEQ ID NO 146
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 146
auauccucga aggcauaucu cucccag 27

<210> SEQ ID NO 147
<211> LENGTH: 25
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 147
ggagagauau gccuucgagg auauu 25

<210> SEQ ID NO 148
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 148
aauauccucg aaggcauauc ucuccca 27

<210> SEQ ID NO 149
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 149
agagauaugc cuucgaggau auuug 25

<210> SEQ ID NO 150
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 150
caaauauccu cgaaggcaua ucucucc 27

<210> SEQ ID NO 151
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 151
gagauaugcc uucgaggaua uuugg 25

<210> SEQ ID NO 152
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 152
ccaaauaucc ucgaaggcau aucucuc 27

<210> SEQ ID NO 153
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 153
agauaugccu ucgaggauau uugga 25

<210> SEQ ID NO 154
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
uccaaauauc cucgaaggca uaucucu 27

<210> SEQ ID NO 155
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 155
gauaugccuu cgaggauauu uggau 25

<210> SEQ ID NO 156
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
auccaaauau ccucgaaggc auaucuc 27

<210> SEQ ID NO 157
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 157
auaugccuuc gaggauauuu ggaug 25

<210> SEQ ID NO 158
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 158
cauccaaaua uccucgaagg cauaucu 27

<210> SEQ ID NO 159
<211> LENGTH: 25
<212> TYPE: RNA
<213> ORGANISM: Artificial Sequence
<220> FEATURE:

-continued

<223> OTHER INFORMATION: Description of Artificial Sequence: Synthetic
oligonucleotide

<400> SEQUENCE: 159
augccuucga ggauauuugg augca 25

<210> SEQ ID NO 160
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 160
ugcauccaaa uauccucgaa ggcauau 27

<210> SEQ ID NO 161
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 161
ugccuucgag gauauuugga ugcau 25

<210> SEQ ID NO 162
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 162
augcauccaa auauccucga aggcaua 27

<210> SEQ ID NO 163
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 163
gccuucgagg auauuuggau gcauu 25

<210> SEQ ID NO 164
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 164
aaugcaucca aauauccucg aaggcau 27

<210> SEQ ID NO 165
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 165
ucagguucuu ggaagagaag ggcau 25

<210> SEQ ID NO 166
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 166
augcccuucu cuuccaagaa ccugaau 27

<210> SEQ ID NO 167
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 167
cagguucuug gaagagaagg gcauc 25

<210> SEQ ID NO 168
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 168
gaugcccuuc ucuuccaaga accugaa 27

<210> SEQ ID NO 169
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 169
agguucuugg aagagaaggg caucu 25

<210> SEQ ID NO 170
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 170
agaugcccuu cucuuccaag aaccuga 27

<210> SEQ ID NO 171
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 171
gguucuugga agagaagggc aucug 25

<210> SEQ ID NO 172
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 172
cagaugcccu ucucuuccaa gaaccug 27

<210> SEQ ID NO 173
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 173
uggaagagaa gggcaucugc aacag 25

<210> SEQ ID NO 174
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 174
cuguugcaga ugcccuucuc uuccaag 27

<210> SEQ ID NO 175
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 175
ugaagucauc cucagaaggg augga 25

<210> SEQ ID NO 176
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 176
uccaucccuu cugaggauga cuucagg 27

<210> SEQ ID NO 177
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 177
gaagucaucc ucagaaggga uggau 25

<210> SEQ ID NO 178
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 178
auccaucccu ucugaggaug acuucag 27

<210> SEQ ID NO 179
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 179
aagucauccu cagaagggau ggauc 25

<210> SEQ ID NO 180
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 180
gauccauccc uucugaggau gacuuca 27

<210> SEQ ID NO 181
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 181
gucauccuca gaagggaugg auccu 25

<210> SEQ ID NO 182
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 182
aggauccauc ccuucugagg augacuu 27

<210> SEQ ID NO 183
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 183
cauccucaga agggauggau ccuga 25

<210> SEQ ID NO 184
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 184
ucaggaucca ucccuucuga ggaugac 27

<210> SEQ ID NO 185
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 185
auccucagaa gggauggauc cugag 25

<210> SEQ ID NO 186
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 186
cucaggaucc aucccuucug aggauga 27

<210> SEQ ID NO 187
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 187
cuagaccacc ugcgucucag caucc 25

<210> SEQ ID NO 188
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 188
ggaugcugag acgcaggugg ucuagca 27

<210> SEQ ID NO 189
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 189
agugaagaaa ugaaagacaa aggug 25

<210> SEQ ID NO 190
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 190
caccuuuguc uuucauuucu ucacuca 27

<210> SEQ ID NO 191
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 191
gugaagaaau gaaagacaaa ggugg 25

<210> SEQ ID NO 192
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 192
ccaccuuugu cuuucauuuc uucacuc 27

<210> SEQ ID NO 193
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 193
ugaagaaaug aaagacaaag gugga 25

<210> SEQ ID NO 194
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 194
uccaccuuug ucuuucauuu cuucacu 27

<210> SEQ ID NO 195
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 195
gaagaaauga aagacaaagg uggau 25

<210> SEQ ID NO 196
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 196
auccaccuuu gucuuucauu ucuucac 27

<210> SEQ ID NO 197
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 197
aagaaaugaa agacaaaggu ggaua 25

<210> SEQ ID NO 198
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 198
uauccaccuu ugucuuucau uucuuca 27

<210> SEQ ID NO 199
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 199
agaaaugaaa gacaaaggug gauac 25

<210> SEQ ID NO 200
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 200
guauccaccu uugucuuuca uuucuuc 27

<210> SEQ ID NO 201
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 201
gaaaugaaag acaaaggugg auaca 25

<210> SEQ ID NO 202
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 202
uguauccacc uuugucuuuc auuucuu 27

<210> SEQ ID NO 203
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 203
aaaugaaaga caaaggugga uacau 25

<210> SEQ ID NO 204
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 204
auguauccac cuuugucuuu cauuucu 27

<210> SEQ ID NO 205
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 205
aaugaaagac aaagguggau acaug 25

<210> SEQ ID NO 206
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 206
cauguaucca ccuuugucuu ucauuuc 27

<210> SEQ ID NO 207
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 207
augaaagaca aagguggaua cauga 25

-continued

<210> SEQ ID NO 208
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 208
ucauguaucc accuuugucu uucauuu 27

<210> SEQ ID NO 209
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 209
ugaaagacaa agguggauac augag 25

<210> SEQ ID NO 210
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 210
cucauguauc caccuuuguc uuucauu 27

<210> SEQ ID NO 211
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 211
gaaagacaaa gguggauaca ugagc 25

<210> SEQ ID NO 212
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 212
gcucauguau ccaccuuugu cuuucau 27

<210> SEQ ID NO 213
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 213
aagacaaagg uggauacaug agcaa 25

<210> SEQ ID NO 214

<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 214
uugcucaugu auccaccuuu gucuuuc 27

<210> SEQ ID NO 215
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 215
agacaaaggu ggauacauga gcaag 25

<210> SEQ ID NO 216
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 216
cuugcucaug uauccaccuu ugucuuu 27

<210> SEQ ID NO 217
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 217
gacaaaggug gauacaugag caaga 25

<210> SEQ ID NO 218
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 218
ucuugcucau guauccaccu uugucuu 27

<210> SEQ ID NO 219
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 219
acaaaggugg auacaugagc aagau 25

<210> SEQ ID NO 220
<211> LENGTH: 27

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 220
aucuugcuca uguauccacc uuugucu 27

<210> SEQ ID NO 221
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 221
aagguggaua caugagcaag auuug 25

<210> SEQ ID NO 222
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 222
caaaucuugc ucauguaucc accuuug 27

<210> SEQ ID NO 223
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 223
agguggauac augagcaaga uuugc 25

<210> SEQ ID NO 224
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 224
gcaaaucuug cucauguauc caccuuu 27

<210> SEQ ID NO 225
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 225
uggauacaug agcaagauuu gcaac 25

<210> SEQ ID NO 226
<211> LENGTH: 27
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 226
guugcaaauc uugcucaugu auccacc 27

<210> SEQ ID NO 227
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 227
ggauacauga gcaagauuug caacu 25

<210> SEQ ID NO 228
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 228
aguugcaaau cuugcucaug uauccac 27

<210> SEQ ID NO 229
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 229
gauacaugag caagauuugc aacuu 25

<210> SEQ ID NO 230
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 230
aaguugcaaa ucuugcucau guaucca 27

<210> SEQ ID NO 231
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 231
auacaugagc aagauuugca acuug 25

<210> SEQ ID NO 232
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 232
caaguugcaa aucuugcuca uguaucc 27

<210> SEQ ID NO 233
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 233
uacaugagca agauuugcaa cuugc 25

<210> SEQ ID NO 234
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 234
gcaaguugca aaucuugcuc auguauc 27

<210> SEQ ID NO 235
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 235
acaugagcaa gauuugcaac uugcu 25

<210> SEQ ID NO 236
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 236
agcaaguugc aaaucuugcu cauguau 27

<210> SEQ ID NO 237
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 237
caugagcaag auuugcaacu ugcua 25

<210> SEQ ID NO 238
<211> LENGTH: 27
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 238
uagcaaguug caaaucuugc ucaugua 27

<210> SEQ ID NO 239
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
augagcaaga uuugcaacuu gcuac 25

<210> SEQ ID NO 240
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
guagcaaguu gcaaaucuug cucaugu 27

<210> SEQ ID NO 241
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ugagcaagau uugcaacuug cuacc 25

<210> SEQ ID NO 242
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gguagcaagu ugcaaaucuu gcucaug 27

<210> SEQ ID NO 243
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
gagcaagauu ugcaacuugc uaccc 25

<210> SEQ ID NO 244
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 244
ggguagcaag uugcaaaucu ugcucau        27

<210> SEQ ID NO 245
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
agcaagauuu gcaacuugcu accca        25

<210> SEQ ID NO 246
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
uggguagcaa guugcaaauc uugcuca        27

<210> SEQ ID NO 247
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
gcaagauuug caacuugcua cccau        25

<210> SEQ ID NO 248
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
auggguagca aguugcaaau cuugcuc        27

<210> SEQ ID NO 249
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
caagauuugc aacuugcuac ccauu        25

<210> SEQ ID NO 250
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
aauggguagc aaguugcaaa ucuugcu 27

<210> SEQ ID NO 251
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 251
aagauuugca acuugcuacc cauua 25

<210> SEQ ID NO 252
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 252 uaaugggua g caaguugcaa aucuugc 27

<210> SEQ ID NO 253
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 253
agauuugcaa cuugcuaccc auuag 25

<210> SEQ ID NO 254
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 254
cuaaugggua gcaaguugca aaucuug 27

<210> SEQ ID NO 255
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 255
gauuugcaac uugcuaccca uuagg 25

<210> SEQ ID NO 256
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 256
ccuaaugggu agcaaguugc aaaucuu 27

<210> SEQ ID NO 257
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 257
auuugcaacu ugcuacccau uagga 25

<210> SEQ ID NO 258
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 258
uccuaauggg uagcaaguug caaaucu 27

<210> SEQ ID NO 259
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 259
uuugcaacuu gcuacccauu aggau 25

<210> SEQ ID NO 260
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 260
auccuaaugg guagcaaguu gcaaauc 27

<210> SEQ ID NO 261
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 261
uugcaacuug cuacccauua ggaua 25

<210> SEQ ID NO 262
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 262
uauccuaaug gguagcaagu ugcaaau 27

<210> SEQ ID NO 263
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 263
ugcaacuugc uacccauuag gauaa 25

<210> SEQ ID NO 264
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 264
uuauccuaau ggguagcaag uugcaaa 27

<210> SEQ ID NO 265
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 265
gcaacuugcu acccauuagg auaau 25

<210> SEQ ID NO 266
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 266
auuauccuaa uggguagcaa guugcaa 27

<210> SEQ ID NO 267
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 267
caacuugcua cccauuagga uaaug 25

<210> SEQ ID NO 268
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 268
cauuauccua auggguagca aguugca 27

<210> SEQ ID NO 269
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 269
cuugcuaccc auuaggauaa ugucu 25

<210> SEQ ID NO 270
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 270
agacauuauc cuaaugggua gcaaguu 27

<210> SEQ ID NO 271
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 271
uugcuaccca uuaggauaau gucuu 25

<210> SEQ ID NO 272
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 272
aagacauuau ccuaaugggu agcaagu 27

<210> SEQ ID NO 273
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 273
ugcuacccau uaggauaaug ucuua 25

<210> SEQ ID NO 274
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 274
uaagacauua uccuaauggg uagcaag 27

<210> SEQ ID NO 275
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 275
auuaggauaa ugucuuaugu aaugc 25

<210> SEQ ID NO 276
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 276
gcauuacaua agacauuauc cuaaugg 27

<210> SEQ ID NO 277
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 277
uuaggauaau gucuuaugua augcu 25

<210> SEQ ID NO 278
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 278
agcauuacau aagacauuau ccuaaug 27

<210> SEQ ID NO 279
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 279
cuguggaauc ugccauugcg auugu 25

<210> SEQ ID NO 280
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 280
acaaucgcaa uggcagauuc cacaggc 27

<210> SEQ ID NO 281
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ggaaucugcc auugcgauug uccag 25

<210> SEQ ID NO 282
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
cuggacaauc gcaauggcag auuccac 27

<210> SEQ ID NO 283
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
gaaucugcca uugcgauugu ccaga 25

<210> SEQ ID NO 284
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
ucuggacaau cgcaauggca gauucca 27

<210> SEQ ID NO 285
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
aaucugccau ugcgauuguc cagag 25

<210> SEQ ID NO 286
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
cucuggacaa ucgcaauggc agauucc 27

<210> SEQ ID NO 287
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 287
aucugccauu gcgauugucc agaga 25

<210> SEQ ID NO 288
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 288
ucucuggaca aucgcaaugg cagauuc 27

<210> SEQ ID NO 289
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 289
ccauugcgau uguccagaga cuggu 25

<210> SEQ ID NO 290
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 290
accagucucu ggacaaucgc aauggca 27

<210> SEQ ID NO 291
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 291
cauugcgauu guccagagac uggug 25

<210> SEQ ID NO 292
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 292
caccagucuc uggacaaucg caauggc 27

<210> SEQ ID NO 293

<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 293
auugcgauug uccagagacu gguga 25

<210> SEQ ID NO 294
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 294
ucaccagucu cuggacaauc gcaaugg 27

<210> SEQ ID NO 295
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 295
uugcgauugu ccagagacug gugac 25

<210> SEQ ID NO 296
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 296
gucaccaguc ucuggacaau cgcaaug 27

<210> SEQ ID NO 297
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 297
ugcgauuguc cagagacugg ugaca 25

<210> SEQ ID NO 298
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 298
ugucaccagu cucuggacaa ucgcaau 27

<210> SEQ ID NO 299
<211> LENGTH: 25

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 299
gcgauugucc agagacuggu gacau 25

<210> SEQ ID NO 300
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 300
augucaccag ucucuggaca aucgcaa 27

<210> SEQ ID NO 301
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 301
cgauugucca gagacuggug acaug 25

<210> SEQ ID NO 302
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 302
caugucacca gucucuggac aaucgca 27

<210> SEQ ID NO 303
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 303
auuguccaga gacuggugac auggc 25

<210> SEQ ID NO 304
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 304
gccaugucac cagucucugg acaaucg 27

<210> SEQ ID NO 305
<211> LENGTH: 25
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 305
guccagagac uggugacaug gcuuc 25

<210> SEQ ID NO 306
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 306
gaagccaugu caccagucuc uggacaa 27

<210> SEQ ID NO 307
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 307
ccagagacug gugacauggc uucca 25

<210> SEQ ID NO 308
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 308
uggaagccau gucaccaguc ucuggac 27

<210> SEQ ID NO 309
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 309
cagagacugg ugacauggcu uccag 25

<210> SEQ ID NO 310
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 310
cuggaagcca ugucaccagu cucugga 27

<210> SEQ ID NO 311
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 311
agagacuggu gacauggcuu ccaga 25

<210> SEQ ID NO 312
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 312
ucuggaagcc augucaccag ucucugg 27

<210> SEQ ID NO 313
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 313
gagacuggug acauggcuuc cagau 25

<210> SEQ ID NO 314
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 314
aucuggaagc caugucacca gucucug 27

<210> SEQ ID NO 315
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 315
agacugguga cauggcuucc agaua 25

<210> SEQ ID NO 316
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 316
uaucuggaag ccaugucacc agucucu 27

<210> SEQ ID NO 317
<211> LENGTH: 25
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 317
gacuggugac auggcuucca gauau 25

<210> SEQ ID NO 318
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
auaucuggaa gccaugucac cagucuc 27

<210> SEQ ID NO 319
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
acuggugaca uggcuuccag auaug 25

<210> SEQ ID NO 320
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cauaucugga agccauguca ccagucu 27

<210> SEQ ID NO 321
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
cuggugacau ggcuuccaga uaugc 25

<210> SEQ ID NO 322
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
gcauaucugg aagccauguc accaguc 27

<210> SEQ ID NO 323
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 323
gacauggcuu ccagauaugc ccgac 25

<210> SEQ ID NO 324
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 324
gucgggcaua ucuggaagcc augucac 27

<210> SEQ ID NO 325
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325
cauggcuucc agauaugccc gacga 25

<210> SEQ ID NO 326
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326
ucgucgggca uaucuggaag ccauguc 27

<210> SEQ ID NO 327
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 327
cagauaugcc cgacgauguc cugug 25

<210> SEQ ID NO 328
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 328
cacaggacau cgucgggcau aucugga 27

<210> SEQ ID NO 329
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 329
cucacaggug uucacucgag ugcug 25

<210> SEQ ID NO 330
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 330
cagcacucga gugaacaccu gugaggu 27

<210> SEQ ID NO 331
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 331
cacucgagug cugauguguc ugcuc 25

<210> SEQ ID NO 332
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 332
gagcagacac aucagcacuc gagugaa 27

<210> SEQ ID NO 333
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 333
cucgagugcu gaugugucug cuccc 25

<210> SEQ ID NO 334
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 334
gggagcagac acaucagcac ucgagug 27

<210> SEQ ID NO 335
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 335
cccaaaugcc agugagcagc caaca 25

<210> SEQ ID NO 336
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 336
uguuggcugc ucacuggcau uugggac 27

<210> SEQ ID NO 337
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 337
ucagguccag ccugaacuuc uucuu 25

<210> SEQ ID NO 338
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 338
aagaagaagu ucaggcugga ccugagg 27

<210> SEQ ID NO 339
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 339
cagguccagc cugaacuucu ucuug 25

<210> SEQ ID NO 340
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 340
caagaagaag uucaggcugg accugag 27

<210> SEQ ID NO 341
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 341

```
agguccagcc ugaacuucuu cuugg                                            25
```

<210> SEQ ID NO 342
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342

```
ccaagaagaa guucaggcug gaccuga                                          27
```

<210> SEQ ID NO 343
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343

```
caauaaagua ccugcuggug cugag                                            25
```

<210> SEQ ID NO 344
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344

```
cucagcacca gcagguacuu uauugcc                                          27
```

<210> SEQ ID NO 345
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345

```
aauaaaguac cugcuggugc ugagg                                            25
```

<210> SEQ ID NO 346
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346

```
ccucagcacc agcagguacu uuauugc                                          27
```

<210> SEQ ID NO 347
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
auaaaguacc ugcuggugcu gaggg 25

<210> SEQ ID NO 348
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 348
cccucagcac cagcagguac uuuauug 27

<210> SEQ ID NO 349
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 349
cucuccaccu uucccaguuu uucac 25

<210> SEQ ID NO 350
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 350
gugaaaaacu gggaaaggug gagagcc 27

<210> SEQ ID NO 351
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 351
cuccaccuuu cccaguuuuu cacua 25

<210> SEQ ID NO 352
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 352
uagugaaaaa cugggaaagg uggagag 27

<210> SEQ ID NO 353
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 353
uccaccuuuc ccaguuuuuc acuag 25

<210> SEQ ID NO 354
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 354
cuagugaaaa acugggaaag guggaga 27

<210> SEQ ID NO 355
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 355
ccaccuuucc caguuuuuca cuaga 25

<210> SEQ ID NO 356
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 356
ucuagugaaa aacugggaaa gguggag 27

<210> SEQ ID NO 357
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 357
caccuuuccc aguuuuucac uagag 25

<210> SEQ ID NO 358
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 358
cucuagugaa aaacugggaa aggugga 27

<210> SEQ ID NO 359
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 359
accuuuccca guuuuucacu agaga 25

<210> SEQ ID NO 360
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 360
ucucuaguga aaaacuggga aaggugg 27

<210> SEQ ID NO 361
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 361
ccuuucccag uuuuucacua gagaa 25

<210> SEQ ID NO 362
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 362
uucucuagug aaaaacuggg aaaggug 27

<210> SEQ ID NO 363
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 363
aguuuuucac uagagaagag ucugu 25

<210> SEQ ID NO 364
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 364
acagacucuu cucuagugaa aaacugg 27

<210> SEQ ID NO 365
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 365
ucuagcagau ucuuucagag gugcu 25

<210> SEQ ID NO 366
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 366
agcaccucug aaagaaucug cuagacu 27

<210> SEQ ID NO 367
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 367
agcagauucu uucagaggug cuaaa 25

<210> SEQ ID NO 368
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 368
uuuagcaccu cugaaagaau cugcuag 27

<210> SEQ ID NO 369
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 369
gcagauucuu ucagaggugc uaaag 25

<210> SEQ ID NO 370
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 370
cuuuagcacc ucugaaagaa ucugcua 27

<210> SEQ ID NO 371
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 371
cagauucuuu cagaggugcu aaagu 25

<210> SEQ ID NO 372

<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 372
acuuuagcac cucugaaaga aucugcu 27

<210> SEQ ID NO 373
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 373
agauucuuuc agaggugcua aaguu 25

<210> SEQ ID NO 374
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 374
aacuuuagca ccucugaaag aaucugc 27

<210> SEQ ID NO 375
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 375
gauucuuuca gaggugcuaa aguuu 25

<210> SEQ ID NO 376
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 376
aaacuuuagc accucugaaa gaaucug 27

<210> SEQ ID NO 377
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
auucuuucag aggugcuaaa guuuc 25

<210> SEQ ID NO 378
<211> LENGTH: 27

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 378
gaaacuuuag caccucugaa agaaucu 27

<210> SEQ ID NO 379
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 379
aggugcuaaa guuucccauc uuugu 25

<210> SEQ ID NO 380
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 380
acaaagaugg gaaacuuuag caccucu 27

<210> SEQ ID NO 381
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 381
ggugcuaaag uuucccaucu uugug 25

<210> SEQ ID NO 382
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 382
cacaaagaug ggaaacuuua gcaccuc 27

<210> SEQ ID NO 383
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383
gugcuaaagu uucccaucuu ugugc 25

<210> SEQ ID NO 384
<211> LENGTH: 27
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 384
gcacaaagau gggaaacuuu agcaccu 27

<210> SEQ ID NO 385
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 385
gcuaaaguuu cccaucuuug ugcag 25

<210> SEQ ID NO 386
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386
cugcacaaag augggaaacu uuagcac 27

<210> SEQ ID NO 387
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 387
cuaaaguuuc ccaucuuugu gcagc 25

<210> SEQ ID NO 388
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388
gcugcacaaa gaugggaaac uuuagca 27

<210> SEQ ID NO 389
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 389
uaaaguuucc caucuuugug cagcu 25

<210> SEQ ID NO 390
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390
agcugcacaa agaugggaaa cuuuagc 27

<210> SEQ ID NO 391
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
aaaguuuccc aucuuugugc agcua 25

<210> SEQ ID NO 392
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 392
uagcugcaca aagaugggaa acuuuag 27

<210> SEQ ID NO 393
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 393
aaguuuccca ucuuugugca gcuac 25

<210> SEQ ID NO 394
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 394
guagcugcac aaagauggga aacuuua 27

<210> SEQ ID NO 395
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 395
aguuucccau cuuugugcag cuacc 25

<210> SEQ ID NO 396
<211> LENGTH: 27
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 396
gguagcugca caaagauggg aaacuuu 27

<210> SEQ ID NO 397
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 397
guuucccauc uuugugcagc uaccu 25

<210> SEQ ID NO 398
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 398
agguagcugc acaaagaugg gaaacuu 27

<210> SEQ ID NO 399
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 399
aucuuugugc agcuaccucc gcauu 25

<210> SEQ ID NO 400
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 400
aaugcggagg uagcugcaca aagaugg 27

<210> SEQ ID NO 401
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 401
gugcagcuac cuccgcauug cugug 25

<210> SEQ ID NO 402
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 402
cacagcaaug cggagguagc ugcacaa 27

<210> SEQ ID NO 403
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 403
ccagccucug agcugaguug guuuu 25

<210> SEQ ID NO 404
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 404
aaaaccaacu cagcucagag gcuggga 27

<210> SEQ ID NO 405
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 405
cagccucuga gcugaguugg uuuua 25

<210> SEQ ID NO 406
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 406
uaaaaccaac ucagcucaga ggcuggg 27

<210> SEQ ID NO 407
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 407
agccucugag cugaguuggu uuuau 25

<210> SEQ ID NO 408
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 408
auaaaaccaa cucagcucag aggcugg 27

<210> SEQ ID NO 409
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 409
gccucugagc ugaguugguu uuaug 25

<210> SEQ ID NO 410
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 410
cauaaaacca acucagcuca gaggcug 27

<210> SEQ ID NO 411
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 411
ccucugagcu gaguugguuu uauga 25

<210> SEQ ID NO 412
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 412
ucauaaaacc aacucagcuc agaggcu 27

<210> SEQ ID NO 413
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 413
cucugagcug aguugguuuu augaa 25

<210> SEQ ID NO 414
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 414
uucauaaaac caacucagcu cagaggc 27

<210> SEQ ID NO 415
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 415
ucugagcuga guugguuuua ugaaa 25

<210> SEQ ID NO 416
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 416
uuucauaaaa ccaacucagc ucagagg 27

<210> SEQ ID NO 417
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 417
ugagcugagu ugguuuuaug aaaag 25

<210> SEQ ID NO 418
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 418
cuuuucauaa aaccaacuca gcucaga 27

<210> SEQ ID NO 419
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 419
ugaguugguu uuaugaaaag cuagg 25

<210> SEQ ID NO 420
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 420
ccuagcuuuu cauaaaacca acucagc 27

<210> SEQ ID NO 421
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 421
gaguugguuu uaugaaaagc uagga 25

<210> SEQ ID NO 422
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 422
uccuagcuuu ucauaaaacc aacucag 27

<210> SEQ ID NO 423
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 423
uugguuuuau gaaaagcuag gaagc 25

<210> SEQ ID NO 424
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 424
gcuuccuagc uuuucauaaa accaacu 27

<210> SEQ ID NO 425
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 425
ugguuuuaug aaaagcuagg aagca 25

<210> SEQ ID NO 426
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 426
ugcuuccuag cuuuucauaa aaccaac 27

<210> SEQ ID NO 427
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 427
gguuuuauga aaagcuagga agcaa 25

<210> SEQ ID NO 428
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 428
uugcuuccua gcuuuucaua aaaccaa 27

<210> SEQ ID NO 429
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 429
uuuuaugaaa agcuaggaag caacc 25

<210> SEQ ID NO 430
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 430
gguugcuucc uagcuuuuca uaaaacc 27

<210> SEQ ID NO 431
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 431
uuaugaaaag cuaggaagca accuu 25

<210> SEQ ID NO 432
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 432
aagguugcuu ccuagcuuuu cauaaaa 27

<210> SEQ ID NO 433
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 433
uaugaaaagc uaggaagcaa ccuuu 25

<210> SEQ ID NO 434
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 434
aaagguugcu uccuagcuuu ucauaaa 27

<210> SEQ ID NO 435
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 435
augaaaagcu aggaagcaac cuuuc 25

<210> SEQ ID NO 436
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 436
gaaagguugc uuccuagcuu uucauaa 27

<210> SEQ ID NO 437
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 437
ccagcacuua acucuaauac aucag 25

<210> SEQ ID NO 438
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 438
cugauguauu agaguuaagu gcuggac 27

<210> SEQ ID NO 439
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 439
cagcacuuaa cucuaauaca ucagc 25

<210> SEQ ID NO 440
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 440
gcugauguau uagaguuaag ugcugga 27

<210> SEQ ID NO 441
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 441
uaauacauca gcaugcguua auuca 25

<210> SEQ ID NO 442
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 442
ugaauuaacg caugcugaug uauuaga 27

<210> SEQ ID NO 443
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 443
aauacaucag caugcguuaa uucag 25

<210> SEQ ID NO 444
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 444
cugaauuaac gcaugcugau guauuag 27

<210> SEQ ID NO 445
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 445
agcaugcguu aauucagcug guugg 25

<210> SEQ ID NO 446
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 446
ccaaccagcu gaauuaacgc augcuga 27

<210> SEQ ID NO 447
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 447
gcaugcguua auucagcugg uuggg 25

<210> SEQ ID NO 448
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 448
cccaaccagc ugaauuaacg caugcug 27

<210> SEQ ID NO 449
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 449
ugcguuaauu cagcugguug ggaaa 25

<210> SEQ ID NO 450
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 450
uuucccaacc agcugaauua acgcaug 27

<210> SEQ ID NO 451

<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 451
gcguuaauuc agcugguugg gaaau 25

<210> SEQ ID NO 452
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 452
auuucccaac cagcugaauu aacgcau 27

<210> SEQ ID NO 453
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 453
cguuaauuca gcugguuggg aaaug 25

<210> SEQ ID NO 454
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 454
cauuucccaa ccagcugaau uaacgca 27

<210> SEQ ID NO 455
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 455
guuaauucag cugguuggga aauga 25

<210> SEQ ID NO 456
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 456
ucauuuccca accagcugaa uuaacgc 27

<210> SEQ ID NO 457
<211> LENGTH: 25

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 457
uuaauucagc ugguugggaa augac 25

<210> SEQ ID NO 458
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 458
gucauuuccc aaccagcuga auuaacg 27

<210> SEQ ID NO 459
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 459
uaauucagcu gguugggaaa ugaca 25

<210> SEQ ID NO 460
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 460
ugucauuucc caaccagcug aauuaac 27

<210> SEQ ID NO 461
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 461
auucagcugg uugggaaaug acacc 25

<210> SEQ ID NO 462
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 462
ggugucauuu cccaaccagc ugaauua 27

<210> SEQ ID NO 463
<211> LENGTH: 25
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 463
uucagcuggu ugggaaauga cacca 25

<210> SEQ ID NO 464
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 464
uggugucauu ucccaaccag cugaauu 27

<210> SEQ ID NO 465
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465
ucagcugguu gggaaaugac accag 25

<210> SEQ ID NO 466
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 466
cuggugucau uucccaacca gcugaau 27

<210> SEQ ID NO 467
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467
cagcugguug ggaaaugaca ccagg 25

<210> SEQ ID NO 468
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 468
ccugguguca uuucccaacc agcugaa 27

<210> SEQ ID NO 469
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469
agcugguugg gaaaugacac cagga 25

<210> SEQ ID NO 470
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 470 uccuggugucc auuucccaac cagcuga 27

<210> SEQ ID NO 471
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 471
gcugguuggg aaaugacacc aggaa 25

<210> SEQ ID NO 472
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 472
uuccuggugu cauuucccaa ccagcug 27

<210> SEQ ID NO 473
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 473
gcagaggguc ccuuacugac uguuu 25

<210> SEQ ID NO 474
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 474
aaacagucag uaagggaccc ucugcac 27

<210> SEQ ID NO 475
<211> LENGTH: 25
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 475
cagagggucc cuuacugacu guuuc 25

<210> SEQ ID NO 476
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 476
gaaacaguca guaagggacc cucugca 27

<210> SEQ ID NO 477
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 477
agaggguccc uuacugacug uuucg 25

<210> SEQ ID NO 478
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 478
cgaaacaguc aguaagggac ccucugc 27

<210> SEQ ID NO 479
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 479
ccuauuaaug gucagacugu uccag 25

<210> SEQ ID NO 480
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 480
cuggaacagu cugaccauua auagggc 27

<210> SEQ ID NO 481
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 481
cuauuaaugg ucagacuguu ccagc 25

<210> SEQ ID NO 482
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 482
gcuggaacag ucugaccauu aauaggg 27

<210> SEQ ID NO 483
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 483
uauuaauggu cagacuguuc cagca 25

<210> SEQ ID NO 484
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 484
ugcuggaaca gucugaccau uaauagg 27

<210> SEQ ID NO 485
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 485
auuaaugguc agacuguucc agcau 25

<210> SEQ ID NO 486
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 486
augcuggaac agucugacca uuaauag 27

<210> SEQ ID NO 487
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 487
uuaaugguca gacuguucca gcaug 25

<210> SEQ ID NO 488
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 488
caugcuggaa cagucugacc auuaaua 27

<210> SEQ ID NO 489
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 489
uaauggucag acuguuccag cauga 25

<210> SEQ ID NO 490
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 490
ucaugcugga acagucugac cauuaau 27

<210> SEQ ID NO 491
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 491
aauggucaga cuguuccagc augag 25

<210> SEQ ID NO 492
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 492
cucaugcugg aacagucuga ccauuaa 27

<210> SEQ ID NO 493
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 493
agaacgacac ugccugucag guggu 25

<210> SEQ ID NO 494
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 494
accaccugac aggcaguguc guucuug 27

<210> SEQ ID NO 495
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 495
cgacacugcc ugucaggugg ucugc 25

<210> SEQ ID NO 496
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 496
gcagaccacc ugacaggcag ugucguu 27

<210> SEQ ID NO 497
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 497
aaccuugacu acuaaaaacg ucucc 25

<210> SEQ ID NO 498
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 498
ggagacguuu uuaguaguca agguuau 27

<210> SEQ ID NO 499
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 499
uuuagaacac cuuuuucacc uaacu 25

<210> SEQ ID NO 500
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 500
aguuaggaga aaaaggaguu cuaaaau 27

<210> SEQ ID NO 501
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 501
uuagaacacc uuuuucaccu aacua 25

<210> SEQ ID NO 502
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 502
uaguuaggug aaaaaggugu ucuaaaa 27

<210> SEQ ID NO 503
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 503
uagaacaccu uuuucaccua acuaa 25

<210> SEQ ID NO 504
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 504
uuaguuaggu gaaaaaggug uucuaaa 27

<210> SEQ ID NO 505
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 505
agaacaccuu uuucaccuaa cuaaa 25

<210> SEQ ID NO 506
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 506
uuuaguuagg ugaaaaaggu guucuaa 27

<210> SEQ ID NO 507
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 507
gaacaccuuu uucaccuaac uaaaa 25

<210> SEQ ID NO 508
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 508
uuuuaguuag gugaaaaagg uguucua 27

<210> SEQ ID NO 509
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 509
aacaccuuuu ucaccuaacu aaaau 25

<210> SEQ ID NO 510
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 510
auuuuaguua ggugaaaaag guguucu 27

<210> SEQ ID NO 511
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 511
acaccuuuuu caccuaacua aaaua 25

<210> SEQ ID NO 512
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 512
uauuuuaguu aggugaaaaa gguguuc 27

<210> SEQ ID NO 513
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 513
caccuuuuuc accuaacuaa aauaa 25

<210> SEQ ID NO 514
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 514
uuauuuuagu uaggugaaaa agguguu 27

<210> SEQ ID NO 515
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 515
accuuuuuca ccuaacuaaa auaau 25

<210> SEQ ID NO 516
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 516
auuauuuuag uuaggugaaa aaggugu 27

<210> SEQ ID NO 517
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 517
cuuuuucacc uaacuaaaau aaugu 25

<210> SEQ ID NO 518
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 518
acauuauuuu aguuagguga aaaaggu 27

<210> SEQ ID NO 519
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 519
uuuucaccua acuaaaauaa uguuu 25

<210> SEQ ID NO 520
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 520
aaacauuauu uuaguuaggu gaaaaag 27

<210> SEQ ID NO 521
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 521
uucaccuaac uaaaauaaug uuuaa 25

<210> SEQ ID NO 522
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 522
uuaaacauua uuuuaguuag gugaaaa 27

<210> SEQ ID NO 523
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 523
ucaccuaacu aaaauaaugu uuaaa 25

```
<210> SEQ ID NO 524
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524

uuuaaacauu auuuuaguua ggugaaa                                           27

<210> SEQ ID NO 525
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525

caccuaacua aaauaauguu uaaag                                             25

<210> SEQ ID NO 526
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526

cuuuaaacau uauuuuaguu aggugaa                                           27

<210> SEQ ID NO 527
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527

accuaacuaa aauaauguuu aaaga                                             25

<210> SEQ ID NO 528
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528

ucuuuaaaca uuauuuuagu uagguga                                           27

<210> SEQ ID NO 529
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529

ccuaacuaaa auaauguuua aagag                                             25

<210> SEQ ID NO 530
```

<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 530
cucuuuaaac auuauuuuag uuaggug 27

<210> SEQ ID NO 531
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 531
cuaacuaaaa uaauguuuaa agagu 25

<210> SEQ ID NO 532
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 532
acucuuuaaa cauuauuuua guuaggu 27

<210> SEQ ID NO 533
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 533
uaacuaaaau aauguuuaaa gaguu 25

<210> SEQ ID NO 534
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 534
aacucuuuaa acauuauuuu aguuagg 27

<210> SEQ ID NO 535
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 535
aacuaaaaua auguuuaaag aguuu 25

<210> SEQ ID NO 536
<211> LENGTH: 27

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 536
aaacucuuua aacauuauuu uaguuag 27

<210> SEQ ID NO 537
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 537
acuaaaauaa uguuuaaaga guuuu 25

<210> SEQ ID NO 538
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 538
aaaacucuuu aaacauuauu uuaguua 27

<210> SEQ ID NO 539
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 539
cuaaaauaau guuuaaagag uuuug 25

<210> SEQ ID NO 540
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 540
caaaacucuu uaaacauuau uuuaguu 27

<210> SEQ ID NO 541
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 541
uaaaauaaug uuuaaagagu uuugu 25

<210> SEQ ID NO 542
<211> LENGTH: 27
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 542
acaaaacucu uuaaacauua uuuuagu 27

<210> SEQ ID NO 543
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 543
aagaguuuug uauaaaaaug uaagg 25

<210> SEQ ID NO 544
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 544
ccuuacauuu uuauacaaaa cucuuua 27

<210> SEQ ID NO 545
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 545
guuuuguaua aaaauguaag gaagc 25

<210> SEQ ID NO 546
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 546
gcuuccuuac auuuuuauac aaaacuc 27

<210> SEQ ID NO 547
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 547
uuuuguauaa aaauguaagg aagcg 25

<210> SEQ ID NO 548
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 548
cgcuuccuua cauuuuuaua caaaacu 27

<210> SEQ ID NO 549
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 549
uuuguauaaa aauguaagga agcgu 25

<210> SEQ ID NO 550
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 550
acgcuuccuu acauuuuuau acaaaac 27

<210> SEQ ID NO 551
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 551
uuguauaaaa auguaaggaa gcguu 25

<210> SEQ ID NO 552
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 552
aacgcuuccu uacauuuuua uacaaaa 27

<210> SEQ ID NO 553
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 553
uguauaaaaa uguaaggaag cguug 25

<210> SEQ ID NO 554
<211> LENGTH: 27
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 554
caacgcuucc uuacauuuuu auacaaa 27

<210> SEQ ID NO 555
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 555
guauaaaaau guaaggaagc guugu 25

<210> SEQ ID NO 556
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 556
acaacgcuuc cuuacauuuu uauacaa 27

<210> SEQ ID NO 557
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 557
auguaaggaa gcguuguuac cuguu 25

<210> SEQ ID NO 558
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 558
aacagguaac aacgcuuccu uacauuu 27

<210> SEQ ID NO 559
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 559
uuuuguauua ugugaaucag ugaga 25

<210> SEQ ID NO 560
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 560
ucucacugau ucacauaaua caaaauu 27

<210> SEQ ID NO 561
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 561
uuuguauuau gugaaucagu gagau 25

<210> SEQ ID NO 562
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 562
aucucacuga uucacauaau acaaaau 27

<210> SEQ ID NO 563
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 563
uuguauuaug ugaaucagug agaug 25

<210> SEQ ID NO 564
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564
caucucacug auucacauaa uacaaaa 27

<210> SEQ ID NO 565
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 565
uguauuaugu gaaucaguga gaugu 25

<210> SEQ ID NO 566
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 566
acaucucacu gauucacaua auacaaa 27

<210> SEQ ID NO 567
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 567
guauuaugug aaucagugag auguu 25

<210> SEQ ID NO 568
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 568
aacaucucac ugauucacau aauacaa 27

<210> SEQ ID NO 569
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 569
uauuauguga aucagugaga uguua 25

<210> SEQ ID NO 570
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 570
uaacaucuca cugauucaca uaauaca 27

<210> SEQ ID NO 571
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 571
auuaugugaa ucagugagau guuag 25

<210> SEQ ID NO 572
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 572
cuaacaucuc acugauucac auaauac 27

<210> SEQ ID NO 573
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 573
uuaugugaau cagugagaug uuagu 25

<210> SEQ ID NO 574
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 574
acuaacaucu cacugauuca cauaaua 27

<210> SEQ ID NO 575
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 575
uaugugaauc agugagaugu uagua 25

<210> SEQ ID NO 576
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 576
uacuaacauc ucacugauuc acauaau 27

<210> SEQ ID NO 577
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 577
augugaauca gugagauguu aguag 25

<210> SEQ ID NO 578
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 578
cuacuaacau cucacugauu cacauaa 27

<210> SEQ ID NO 579
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 579
ugugaaucag ugagauguua guaga 25

<210> SEQ ID NO 580
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 580
ucuacuaaca ucucacugau ucacaua 27

<210> SEQ ID NO 581
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 581
gugaaucagu gagauguuag uagaa 25

<210> SEQ ID NO 582
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 582
uucuacuaac aucucacuga uucacau 27

<210> SEQ ID NO 583
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 583
gugagauguu aguagaauaa gccuu 25

<210> SEQ ID NO 584
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 584
aaggcuuauu cuacuaacau cucacug 27

<210> SEQ ID NO 585
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 585
uuuucuauuu augcauuuga guaca 25

<210> SEQ ID NO 586
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 586
uguacucaaa ugcauaaaua gaaaaaa 27

<210> SEQ ID NO 587
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 587
uuucuauuua ugcauuugag uacag 25

<210> SEQ ID NO 588
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 588
cuguacucaa augcauaaau agaaaaa 27

<210> SEQ ID NO 589
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 589
uucuauuuau gcauuugagu acagt 25

<210> SEQ ID NO 590
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 590
acuguacuca aaugcauaaa uagaaaa 27

<210> SEQ ID NO 591
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 591
cuauuuaugc auuugaguac aguac 25

<210> SEQ ID NO 592
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 592
guacuguacu caaaugcaua aauagaa 27

<210> SEQ ID NO 593
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 593
ugcucaaacu guuaaauguu ggaaa 25

<210> SEQ ID NO 594
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 594
uuuccaacau uuaacaguuu gagcaca 27

<210> SEQ ID NO 595
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 595
gcucaaacug uuaaauguug gaaaa 25

<210> SEQ ID NO 596
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 596
uuuuccaaca uuuaacaguu ugagcac 27

<210> SEQ ID NO 597
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 597
cucaaacugu uaaauguugg aaaag 25

<210> SEQ ID NO 598
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 598
cuuuuccaac auuuaacagu uugagca 27

<210> SEQ ID NO 599
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 599
ucaaacuguu aaauguugga aaaga 25

<210> SEQ ID NO 600
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 600
ucuuuuccaa cauuuaacag uuugagc 27

<210> SEQ ID NO 601
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 601
caaacuguua aauguuggaa aagaa 25

<210> SEQ ID NO 602
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 602
uucuuuucca acauuuaaca guuugag 27

<210> SEQ ID NO 603
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 603
aaacuguuaa auguuggaaa agaaa 25

<210> SEQ ID NO 604
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 604
uuucuuuucc aacauuuaac aguuuga 27

<210> SEQ ID NO 605
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 605
aacuguuaaa uguuggaaaa gaaag 25

<210> SEQ ID NO 606
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 606
cuuucuuuuc caacauuuaa caguuug 27

<210> SEQ ID NO 607
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 607
acuguuaaau guuggaaaag aaaga 25

<210> SEQ ID NO 608
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 608
ucuuucuuuu ccaacauuua acaguuu 27

<210> SEQ ID NO 609
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 609
cuguuaaaug uuggaaaaga aagat 25

<210> SEQ ID NO 610
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 610
aucuuucuuu uccaacauuu aacaguu 27

<210> SEQ ID NO 611
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 611
uguuaaaugu uggaaaagaa agata 25

<210> SEQ ID NO 612
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 612
uaucuuucuu uuccaacauu uaacagu 27

<210> SEQ ID NO 613
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 613
guuaaauguu ggaaaagaaa gauac 25

<210> SEQ ID NO 614
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 614
guaucuuucu uuuccaacau uuaacag 27

<210> SEQ ID NO 615
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 615 uuaaaauguug gaaaagaaag auaca 25

<210> SEQ ID NO 616
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 616
uguaucuuuc uuuuccaaca uuuaaca 27

<210> SEQ ID NO 617
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 617
uaaauguugg aaaagaaaga uacaa 25

<210> SEQ ID NO 618
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 618
uuguaucuuu cuuuuccaac auuuaac 27

<210> SEQ ID NO 619
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 619
gcacuugacu gagaagacag accct 25

<210> SEQ ID NO 620
<211> LENGTH: 27
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 620

agggucuguc uucucaguca agugcuu                                          27


<210> SEQ ID NO 621
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621

gagaaaagag gcuacuugug aaaat                                            25


<210> SEQ ID NO 622
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622

auuuucacaa guagccucuu uucucaa                                          27


<210> SEQ ID NO 623
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623

agaaaagagg cuacuuguga aaata                                            25


<210> SEQ ID NO 624
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624

uauuuucaca aguagccucu uuucuca                                          27


<210> SEQ ID NO 625
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625

gaaaagaggc uacuugugaa aauaa                                            25
```

<210> SEQ ID NO 626
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
uuauuuucac aaguagccuc uuuucuc 27

<210> SEQ ID NO 627
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 627
aaaagaggcu acuugugaaa auaat 25

<210> SEQ ID NO 628
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
auuauuuuca caaguagccu cuuuucu 27

<210> SEQ ID NO 629
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 629
aaagaggcua cuugugaaaa uaatg 25

<210> SEQ ID NO 630
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
cauuauuuuc acaaguagcc ucuuuuc 27

<210> SEQ ID NO 631
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
aagaggcuac uugugaaaau aauga 25

<210> SEQ ID NO 632
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 632
ucauuauuuu cacaaguagc cucuuuu 27

<210> SEQ ID NO 633
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 633
agaggcuacu ugugaaaaua augag 25

<210> SEQ ID NO 634
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 634
cucauuauuu ucacaaguag ccucuuu 27

<210> SEQ ID NO 635
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 635
gaggcuacuu gugaaaauaa ugagc 25

<210> SEQ ID NO 636
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 636
gcucauuauu uucacaagua gccucuu 27

<210> SEQ ID NO 637
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 637
ggcuacuugu gaaaauaaug agccc 25

<210> SEQ ID NO 638
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 638
gggcucauua uuuucacaag uagccuc 27

<210> SEQ ID NO 639
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 639
cuacuuguga aaauaaugag ccccc 25

<210> SEQ ID NO 640
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 640
gggggcucau uauuuucaca aguagcc 27

<210> SEQ ID NO 641
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 641
ugaaccugcc uucuuacauc uugag 25

<210> SEQ ID NO 642
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 642
cucaagaugu aagaaggcag guucaaa 27

<210> SEQ ID NO 643
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 643
aaaguuacaa guuucuuuuc ccaag 25

<210> SEQ ID NO 644
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 644
cuugggaaaa gaaacuugua acuuucc 27

<210> SEQ ID NO 645
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 645
aaguuacaag uuucuuuucc caagt 25

<210> SEQ ID NO 646
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 646
acuugggaaa agaaacuugu aacuuuc 27

<210> SEQ ID NO 647
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 647
aguuacaagu uucuuuuccc aagtt 25

<210> SEQ ID NO 648
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 648
aacuugggaa aagaaacuug uaacuuu 27

<210> SEQ ID NO 649
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 649
aguuucuuuu cccaaguuuc ccagt 25

<210> SEQ ID NO 650
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 650
acugggaaac uugggaaaag aaacuug 27

<210> SEQ ID NO 651
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 651
caacaguauu uucuaauaac cagta 25

<210> SEQ ID NO 652
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 652
uacugguuau uagaaaauac uguuggc 27

<210> SEQ ID NO 653
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 653
aacaguauuu ucuaauaacc aguat 25

<210> SEQ ID NO 654
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 654
auacugguua uuagaaaaua cuguugg 27

<210> SEQ ID NO 655
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 655
acaguauuuu cuaauaacca guata 25

<210> SEQ ID NO 656
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 656
uauacugguu auuagaaaau acuguug 27

<210> SEQ ID NO 657
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 657
caguauuuuc uaauaaccag uauat 25

<210> SEQ ID NO 658
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 658
auauacuggu uauuagaaaa uacuguu 27

<210> SEQ ID NO 659
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 659
uugugauugu uaucaggaaa aaata 25

<210> SEQ ID NO 660

<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 660
uauuuuuucc ugauaacaau cacaaua 27

<210> SEQ ID NO 661
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 661
ugugauuguu aucaggaaaa aauat 25

<210> SEQ ID NO 662
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 662
auauuuuuuc cugauaacaa ucacaau 27

<210> SEQ ID NO 663
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 663
gugauuguua ucaggaaaaa auata 25

<210> SEQ ID NO 664
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 664
uauauuuuuu ccugauaaca aucacaa 27

<210> SEQ ID NO 665
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 665
ugauuguuau caggaaaaaa uauat 25

<210> SEQ ID NO 666
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 666
auauauuuuu uccugauaac aaucaca 27

<210> SEQ ID NO 667
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 667
gauuguuauc aggaaaaaau auatt 25

<210> SEQ ID NO 668
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 668
aauauauuuu uuccugauaa caaucac 27

<210> SEQ ID NO 669
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 669
auuguuauca ggaaaaaaua uauta 25

<210> SEQ ID NO 670
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 670
uaauauauuu uuuccugaua acaauca 27

<210> SEQ ID NO 671

<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 671
uuguuaucag gaaaaaauau auuaa 25

<210> SEQ ID NO 672
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 672
uuaauauauu uuuuccugau aacaauc 27

<210> SEQ ID NO 673
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 673
uguuaucagg aaaaaauaua uuaaa 25

<210> SEQ ID NO 674
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 674
uuuaauauau uuuuuccuga uaacaau 27

<210> SEQ ID NO 675
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 675
guuaucagga aaaaauauau uaaat 25

<210> SEQ ID NO 676
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 676
auuuaauaua uuuuuuccug auaacaa 27

<210> SEQ ID NO 677
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 677
uuaucaggaa aaaauauauu aaatg 25

<210> SEQ ID NO 678
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 678
cauuuaauau auuuuuuccu gauaaca 27

<210> SEQ ID NO 679
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 679
uaucaggaaa aaauauauua aaugg 25

<210> SEQ ID NO 680
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 680
ccauuuaaua uauuuuuucc ugauaac 27

<210> SEQ ID NO 681
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 681
aucaggaaaa aauauauuaa auggc 25

<210> SEQ ID NO 682
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 682
gccauuuaau auauuuuuuc cugauaa 27

<210> SEQ ID NO 683
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 683
aggaaaaaau auauuaaaug gcuga 25

<210> SEQ ID NO 684
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 684
ucagccauuu aauauauuuu uuccuga 27

<210> SEQ ID NO 685
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 685
ggaaaaaaua uauuaaaugg cugat 25

<210> SEQ ID NO 686
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 686
aucagccauu uaauauauuu uuuccug 27

<210> SEQ ID NO 687
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 687
gaaaaaauau auuaaauggc ugata 25

<210> SEQ ID NO 688
<211> LENGTH: 27
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 688
uaucagccau uuaauauauu uuuuccu 27

<210> SEQ ID NO 689
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 689
aaaaaauaua uuaaauggcu gauag 25

<210> SEQ ID NO 690
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 690
cuaucagcca uuuaauauau uuuuucc 27

<210> SEQ ID NO 691
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 691
uauuuucuuu cugcuuuuaa aaatt 25

<210> SEQ ID NO 692
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 692
aauuuuuaaa agcagaaaga aaauacg 27

<210> SEQ ID NO 693
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 693
auuuucuuuc ugcuuuuaaa aauta 25

<210> SEQ ID NO 694
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 694
uaauuuuuaa aagcagaaag aaaauac 27

<210> SEQ ID NO 695
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 695
ucuuucugcu uuuaaaaauu auuca 25

<210> SEQ ID NO 696
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 696
ugaauaauuu uuaaaagcag aaagaaa 27

<210> SEQ ID NO 697
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 697
cuuucugcuu uuaaaaauua uucag 25

<210> SEQ ID NO 698
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 698
cugaauaauu uuuaaaagca gaaagaa 27

<210> SEQ ID NO 699
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 699
uuucugcuuu uaaaaauuau ucagg 25

<210> SEQ ID NO 700

<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 700
ccugaauaau uuuuaaaagc agaaaga 27

<210> SEQ ID NO 701
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 701
cuacuaaaaa cacaaaaauu agcca 25

<210> SEQ ID NO 702
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 702
uggcuaauuu uuguguuuuu aguagag 27

<210> SEQ ID NO 703
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 703
caagauaagg aaaucaggaa gugta 25

<210> SEQ ID NO 704
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 704
uacacuuccu gauuuccuua ucuugau 27

<210> SEQ ID NO 705
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 705
aagauaagga aaucaggaag uguaa 25

<210> SEQ ID NO 706
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 706
uuacacuucc ugauuuccuu aucuuga 27

<210> SEQ ID NO 707
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 707
agauaaggaa aucaggaagu guaat 25

<210> SEQ ID NO 708
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 708
auuacacuuc cugauuuccu uaucuug 27

<210> SEQ ID NO 709
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 709
gauaaggaaa ucaggaagug uaata 25

<210> SEQ ID NO 710
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 710
uauuacacuu ccugauuucc uuaucuu 27

<210> SEQ ID NO 711
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 711
auaaggaaau caggaagugu aauat 25

<210> SEQ ID NO 712
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 712
auauuacacu uccugauuuc cuuaucu 27

<210> SEQ ID NO 713
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 713
uaaggaaauc aggaagugua auatt 25

<210> SEQ ID NO 714
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 714
aauauuacac uuccugauuu ccuuauc 27

<210> SEQ ID NO 715
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 715
aaggaaauca ggaaguguaa uautc 25

<210> SEQ ID NO 716
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 716
gaauauuaca cuuccugauu uccuuau 27

<210> SEQ ID NO 717
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 717
aggaaaucag gaaguguaau auuct 25

<210> SEQ ID NO 718
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 718
agaauauuac acuuccugau uuccuua 27

<210> SEQ ID NO 719
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 719
ggaaaucagg aaguguaaua uuctt 25

<210> SEQ ID NO 720
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720
aagaauauua cacuuccuga uuuccuu 27

<210> SEQ ID NO 721
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 721
gaaaucagga aguguaauau ucuta 25

<210> SEQ ID NO 722
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
uaagaauauu acacuuccug auuuccu 27

<210> SEQ ID NO 723
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 723
cuaugaaugc auucuuauuu cuuct 25

<210> SEQ ID NO 724
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
agaagaaaua agaaugcauu cauaggc 27

<210> SEQ ID NO 725
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 725
uaugaaugca uucuuauuuc uuctt 25

<210> SEQ ID NO 726
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
aagaagaaau aagaaugcau ucauagg 27

<210> SEQ ID NO 727
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 727
cuaccacacc cagcuaguuu uuutt 25

<210> SEQ ID NO 728
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 728
aaaaaaaacu agcugggugu gguagug 27

<210> SEQ ID NO 729
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 729
ccacacccag cuaguuuuuu uuugt 25

<210> SEQ ID NO 730
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 730
acaaaaaaaa acuagcuggg uguggua 27

<210> SEQ ID NO 731
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 731
cacacccagc uaguuuuuuu uugta 25

<210> SEQ ID NO 732
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 732
uacaaaaaaa aacuagcugg guguggu 27

<210> SEQ ID NO 733
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 733
gcuaggauua caggugugag cuacc 25

<210> SEQ ID NO 734
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 734
gguagcucac accuguaauc cuagcac 27

<210> SEQ ID NO 735
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 735
cuaggauuac aggugugagc uacca 25

<210> SEQ ID NO 736
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 736
ugguagcuca caccuguaau ccuagca 27

<210> SEQ ID NO 737
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 737
ccaugccugg uccaacauuc uucat 25

<210> SEQ ID NO 738
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 738
augaagaaug uuggaccagg cauggua 27

<210> SEQ ID NO 739
<211> LENGTH: 25

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 739
ugcagaguau gagccugauu uugtt 25

<210> SEQ ID NO 740
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 740
aacaaaauca ggcucauacu cugcacu 27

<210> SEQ ID NO 741
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 741
gcagaguaug agccugauuu ugutt 25

<210> SEQ ID NO 742
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 742
aaacaaaauc aggcucauac ucugcac 27

<210> SEQ ID NO 743
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 743
cagaguauga gccugauuuu guuta 25

<210> SEQ ID NO 744
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 744
uaaacaaaau caggcucaua cucugca 27

<210> SEQ ID NO 745
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 745
agaguaugag ccugauuuug uuuaa 25

<210> SEQ ID NO 746
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 746
uuaaacaaaa ucaggcucau acucugc 27

<210> SEQ ID NO 747
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 747
gaguaugagc cugauuuugu uuaaa 25

<210> SEQ ID NO 748
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 748
uuuaaacaaa aucaggcuca uacucug 27

<210> SEQ ID NO 749
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 749
gggugaaacc ccaucucuac uaaaa 25

<210> SEQ ID NO 750
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 750
uuuuaguaga gaugggguuu cacccag 27

<210> SEQ ID NO 751
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 751
gugaaacccc aucucuacua aaaaa 25

<210> SEQ ID NO 752
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 752
uuuuuuagua gagauggggu uucaccc 27

<210> SEQ ID NO 753
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 753
ugaaacccca ucucuacuaa aaaat 25

<210> SEQ ID NO 754
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 754
auuuuuuagu agagaugggg uuucacc 27

<210> SEQ ID NO 755
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 755
gaaaccccau cucuacuaaa aaatg 25

<210> SEQ ID NO 756
<211> LENGTH: 27
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 756
cauuuuuuag uagagauggg guuucac 27

<210> SEQ ID NO 757
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 757
aaaccccauc ucuacuaaaa aaugc 25

<210> SEQ ID NO 758
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 758
gcauuuuuua guagagaugg gguuuca 27

<210> SEQ ID NO 759
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 759
aaccccaucu cuacuaaaaa augca 25

<210> SEQ ID NO 760
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 760
ugcauuuuuu aguagagaug ggguuuc 27

<210> SEQ ID NO 761
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 761
cccaucucua cuaaaaaaug caaaa 25

<210> SEQ ID NO 762
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 762
uuuugcauuu uuuaguagag auggggu 27

<210> SEQ ID NO 763
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 763
aucaaaaccc uuauggcaga cugtt 25

<210> SEQ ID NO 764
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 764
aacagucugc cauaaggguu uugauau 27

<210> SEQ ID NO 765
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 765
uauuuuauuu gucgugcuua uaugt 25

<210> SEQ ID NO 766
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 766
acauauaagc acgacaaaua aaauaca 27

<210> SEQ ID NO 767
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 767
guguugccca aguuucuaug gugaa 25

-continued

<210> SEQ ID NO 768
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 768
uucaccauag aaacuugggc aacacau 27

<210> SEQ ID NO 769
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 769
gcccaaguuu cuauggugaa cggta 25

<210> SEQ ID NO 770
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 770
uaccguucac cauagaaacu ugggcaa 27

<210> SEQ ID NO 771
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 771
cccaaguuuc uauggugaac gguat 25

<210> SEQ ID NO 772
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 772
auaccguuca ccauagaaac uugggca 27

<210> SEQ ID NO 773
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 773
acuuucagca ugagaaaaua acucc 25

<210> SEQ ID NO 774
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 774
ggaguuauuu ucucaugcug aaaguga 27

<210> SEQ ID NO 775
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 775
cuuucagcau gagaaaauaa cucct 25

<210> SEQ ID NO 776
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 776
aggaguuauu uucucaugcu gaaagug 27

<210> SEQ ID NO 777
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 777
ugagugacaa cguacccuua gcagccgaaa ggcugc 36

<210> SEQ ID NO 778
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 778
uaaggguacg uugucacuca gg 22

<210> SEQ ID NO 779
<211> LENGTH: 36
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 779
gagugacaac guacccuuca gcagccgaaa ggcugc 36

<210> SEQ ID NO 780
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
ugaaggguac guugucacuc gg 22

<210> SEQ ID NO 781
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781
agugacaacg uacccuucaa gcagccgaaa ggcugc 36

<210> SEQ ID NO 782
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
uugaagggua cguugucacu gg 22

<210> SEQ ID NO 783
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
ugacaacgua cccuucauua gcagccgaaa ggcugc 36

<210> SEQ ID NO 784
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
uaaugaaggg uacguuguca gg 22

<210> SEQ ID NO 785
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 785
gacaacguac ccuucauuga gcagccgaaa ggcugc 36

<210> SEQ ID NO 786
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 786
ucaaugaagg guacguuguc gg 22

<210> SEQ ID NO 787
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 787
caacguaccc uucauugaua gcagccgaaa ggcugc 36

<210> SEQ ID NO 788
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 788
uaucaaugaa ggguacguug gg 22

<210> SEQ ID NO 789
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 789
aacguacccu ucauugauga gcagccgaaa ggcugc 36

<210> SEQ ID NO 790
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 790
ucaucaauga aggguacguu gg 22

<210> SEQ ID NO 791
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 791
acguacccuu cauugaugca gcagccgaaa ggcugc 36

<210> SEQ ID NO 792
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 792
ugcaucaaug aaggguacgu gg 22

<210> SEQ ID NO 793
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 793
cguacccuuc auugaugcca gcagccgaaa ggcugc 36

<210> SEQ ID NO 794
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 794
uggcaucaau gaaggguacg gg 22

<210> SEQ ID NO 795
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 795
uacccuucau ugaugccaaa gcagccgaaa ggcugc 36

<210> SEQ ID NO 796
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 796
uuuggcauca augaagggua gg 22

<210> SEQ ID NO 797
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 797
cacgaacuuu cuucauguga gcagccgaaa ggcugc 36

<210> SEQ ID NO 798
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 798
ucacaugaag aaaguucgug gg 22

<210> SEQ ID NO 799
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 799
acgaacuuuc uucaugugga gcagccgaaa ggcugc 36

<210> SEQ ID NO 800
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 800
uccacaugaa gaaaguucgu gg 22

<210> SEQ ID NO 801
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 801
cgaacuuucu ucauguggaa gcagccgaaa ggcugc 36

<210> SEQ ID NO 802
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 802
uuccacauga agaaaguucg gg 22

<210> SEQ ID NO 803
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 803
acuuucuuca uguggacaua gcagccgaaa ggcugc 36

<210> SEQ ID NO 804
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 804
uauguccaca ugaagaaagu gg 22

<210> SEQ ID NO 805
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 805
uuucuucaug uggacaucaa gcagccgaaa ggcugc 36

<210> SEQ ID NO 806
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 806
uugaugucca caugaagaaa gg 22

<210> SEQ ID NO 807
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 807
cuucaugugg acaucaccaa gcagccgaaa ggcugc 36

<210> SEQ ID NO 808
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 808
uuggugaugu ccacaugaag gg 22

<210> SEQ ID NO 809
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 809
auguggacau caccaagcua gcagccgaaa ggcugc 36

<210> SEQ ID NO 810
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 810
uagcuuggug auguccacau gg 22

<210> SEQ ID NO 811
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 811
uguggacauc accaagcuca gcagccgaaa ggcugc 36

<210> SEQ ID NO 812
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 812
ugagcuuggu gauguccaca gg 22

<210> SEQ ID NO 813
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 813
guggacauca ccaagcucaa gcagccgaaa ggcugc 36

<210> SEQ ID NO 814
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 814
uugagcuugg ugauguccac gg 22

<210> SEQ ID NO 815
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 815
uggacaucac caagcucaga gcagccgaaa ggcugc 36

<210> SEQ ID NO 816
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 816
ucugagcuug gugaugucca gg 22

<210> SEQ ID NO 817
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 817
agauaugccu ucgaggauaa gcagccgaaa ggcugc 36

<210> SEQ ID NO 818
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 818
uuauccucga aggcauaucu gg 22

<210> SEQ ID NO 819
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 819
augccuucga ggauauuuga gcagccgaaa ggcugc 36

<210> SEQ ID NO 820
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 820
ucaaauaucc ucgaaggcau gg 22

<210> SEQ ID NO 821
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 821
gccuucgagg auauuuggaa gcagccgaaa ggcugc 36

<210> SEQ ID NO 822
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 822
uuccaaauau ccucgaaggc gg 22

<210> SEQ ID NO 823
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 823
ugaagucauc cucagaagga gcagccgaaa ggcugc 36

<210> SEQ ID NO 824
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 824
uccuucugag gaugacuuca gg 22

<210> SEQ ID NO 825
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 825
gaagucaucc ucagaaggga gcagccgaaa ggcugc 36

<210> SEQ ID NO 826
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 826
ucccuucuga ggaugacuuc gg 22

<210> SEQ ID NO 827
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 827
auccucagaa gggauggaua gcagccgaaa ggcugc 36

<210> SEQ ID NO 828
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 828
uauccauccc uucugaggau gg 22

<210> SEQ ID NO 829
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 829
agugaagaaa ugaaagacaa gcagccgaaa ggcugc 36

<210> SEQ ID NO 830
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 830
uugucuuuca uuucuucacu gg 22

<210> SEQ ID NO 831
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 831
aagaaaugaa agacaaagga gcagccgaaa ggcugc 36

<210> SEQ ID NO 832
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 832
uccuuugucu uucauuucuu gg 22

<210> SEQ ID NO 833
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 833
agaaaugaaa gacaaaggua gcagccgaaa ggcugc 36

<210> SEQ ID NO 834

<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 834
uaccuuuguc uuucauuucu gg 22

<210> SEQ ID NO 835
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 835
gaaaugaaag acaaagguga gcagccgaaa ggcugc 36

<210> SEQ ID NO 836
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 836
ucaccuuugu cuuucauuuc gg 22

<210> SEQ ID NO 837
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 837
aaaugaaaga caaaggugga gcagccgaaa ggcugc 36

<210> SEQ ID NO 838
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 838
uccaccuuug ucuuucauuu gg 22

<210> SEQ ID NO 839
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 839
aaugaaagac aaagguggaa gcagccgaaa ggcugc 36

<210> SEQ ID NO 840
<211> LENGTH: 22

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 840
uuccaccuuu gucuuucauu gg 22

<210> SEQ ID NO 841
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 841
augaaagaca aagguggaua gcagccgaaa ggcugc 36

<210> SEQ ID NO 842
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 842
uauccaccuu ugucuuucau gg 22

<210> SEQ ID NO 843
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 843
ugaaagacaa agguggauaa gcagccgaaa ggcugc 36

<210> SEQ ID NO 844
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 844
uuauccaccu uugucuuuca gg 22

<210> SEQ ID NO 845
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 845
gaaagacaaa gguggauaca gcagccgaaa ggcugc 36

<210> SEQ ID NO 846
<211> LENGTH: 22
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 846
uguauccacc uuugucuuuc gg 22

<210> SEQ ID NO 847
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 847
aagacaaagg uggauacaua gcagccgaaa ggcugc 36

<210> SEQ ID NO 848
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 848
uauguaucca ccuuugucuu gg 22

<210> SEQ ID NO 849
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 849
agacaaaggu ggauacauga gcagccgaaa ggcugc 36

<210> SEQ ID NO 850
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 850
ucauguaucc accuuugucu gg 22

<210> SEQ ID NO 851
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 851
gacaaaggug gauacaugaa gcagccgaaa ggcugc 36

<210> SEQ ID NO 852
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 852
uucauguauc caccuuuguc gg 22

<210> SEQ ID NO 853
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 853
acaaaggugg auacaugaga gcagccgaaa ggcugc 36

<210> SEQ ID NO 854
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 854
ucucauguau ccaccuuugu gg 22

<210> SEQ ID NO 855
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 855
aagguggaua caugagcaaa gcagccgaaa ggcugc 36

<210> SEQ ID NO 856
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 856
uuugcucaug uauccaccuu gg 22

<210> SEQ ID NO 857
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 857
agguggauac augagcaaga gcagccgaaa ggcugc 36

<210> SEQ ID NO 858
<211> LENGTH: 22
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 858
ucuugcucau guauccaccu gg 22

<210> SEQ ID NO 859
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 859
uggauacaug agcaagauua gcagccgaaa ggcugc 36

<210> SEQ ID NO 860
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 860
uaaucuugcu cauguaucca gg 22

<210> SEQ ID NO 861
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 861
ggauacauga gcaagauuua gcagccgaaa ggcugc 36

<210> SEQ ID NO 862
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 862
uaaaucuugc ucauguaucc gg 22

<210> SEQ ID NO 863
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 863
gauacaugag caagauuuga gcagccgaaa ggcugc 36

<210> SEQ ID NO 864
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 864
ucaaaucuug cucauguauc gg 22

<210> SEQ ID NO 865
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 865
auacaugagc aagauuugca gcagccgaaa ggcugc 36

<210> SEQ ID NO 866
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 866
ugcaaaucuu gcucauguau gg 22

<210> SEQ ID NO 867
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 867
uacaugagca agauuugcaa gcagccgaaa ggcugc 36

<210> SEQ ID NO 868
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 868
uugcaaaucu ugcucaugua gg 22

<210> SEQ ID NO 869
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 869
acaugagcaa gauuugcaaa gcagccgaaa ggcugc 36

<210> SEQ ID NO 870
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 870
uuugcaaauc uugcucaugu gg 22

<210> SEQ ID NO 871
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 871
ugagcaagau uugcaacuua gcagccgaaa ggcugc 36

<210> SEQ ID NO 872
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 872
uaaguugcaa aucuugcuca gg 22

<210> SEQ ID NO 873
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 873
gagcaagauu ugcaacuuga gcagccgaaa ggcugc 36

<210> SEQ ID NO 874
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 874
ucaaguugca aaucuugcuc gg 22

<210> SEQ ID NO 875
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 875
agcaagauuu gcaacuugca gcagccgaaa ggcugc 36

<210> SEQ ID NO 876
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 876
ugcaaguugc aaaucuugcu gg 22

<210> SEQ ID NO 877
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 877
gcaagauuug caacuugcua gcagccgaaa ggcugc 36

<210> SEQ ID NO 878
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 878
uagcaaguug caaaucuugc gg 22

<210> SEQ ID NO 879
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 879
caagauuugc aacuugcuaa gcagccgaaa ggcugc 36

<210> SEQ ID NO 880
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 880
uuagcaaguu gcaaaucuug gg 22

<210> SEQ ID NO 881
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 881
aagauuugca acuugcuaca gcagccgaaa ggcugc 36

<210> SEQ ID NO 882
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 882
uguagcaagu ugcaaaucuu gg 22

<210> SEQ ID NO 883
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 883
agauuugcaa cuugcuacca gcagccgaaa ggcugc 36

<210> SEQ ID NO 884
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 884
ugguagcaag uugcaaaucu gg 22

<210> SEQ ID NO 885
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 885
auuugcaacu ugcuacccaa gcagccgaaa ggcugc 36

<210> SEQ ID NO 886
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 886
uuggguagca aguugcaaau gg 22

<210> SEQ ID NO 887
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 887
uugcaacuug cuacccauua gcagccgaaa ggcugc 36

<210> SEQ ID NO 888
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 888 uaaugggu ag caaguugcaa gg 22

<210> SEQ ID NO 889
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 889
ugcaacuugc uacccauuaa gcagccgaaa ggcugc 36

<210> SEQ ID NO 890
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 890
uuaaugggua gcaaguugca gg 22

<210> SEQ ID NO 891
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 891
gcaacuugcu acccauuaga gcagccgaaa ggcugc 36

<210> SEQ ID NO 892
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 892
ucuaaugggu agcaaguugc gg 22

<210> SEQ ID NO 893
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 893
caacuugcua cccauuagga gcagccgaaa ggcugc 36

<210> SEQ ID NO 894
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 894
uccuaauggg uagcaaguug gg 22

<210> SEQ ID NO 895
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 895
cuugcuaccc auuaggauaa gcagccgaaa ggcugc 36

<210> SEQ ID NO 896
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 896
uuauccuaau ggguagcaag gg 22

<210> SEQ ID NO 897
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 897
ugcuacccau uaggauaaua gcagccgaaa ggcugc 36

<210> SEQ ID NO 898
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 898
uauuauccua augggguagca gg 22

<210> SEQ ID NO 899
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 899
auuaggauaa ugucuuauga gcagccgaaa ggcugc 36

<210> SEQ ID NO 900
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 900
ucauaagaca uuauccuaau gg 22

<210> SEQ ID NO 901
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 901
uuaggauaau gucuuaugua gcagccgaaa ggcugc 36

<210> SEQ ID NO 902
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 902
uacauaagac auuauccuaa gg 22

<210> SEQ ID NO 903
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 903
ugcgauuguc cagagacuga gcagccgaaa ggcugc 36

<210> SEQ ID NO 904
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 904
ucagucucug gacaaucgca gg 22

<210> SEQ ID NO 905
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 905
cgauugucca gagacuggua gcagccgaaa ggcugc 36

<210> SEQ ID NO 906
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 906
uaccagucuc uggacaaucg gg 22

<210> SEQ ID NO 907
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 907
guccagagac uggugacaua gcagccgaaa ggcugc 36

<210> SEQ ID NO 908
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 908
uaugucacca gucucuggac gg 22

<210> SEQ ID NO 909
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 909
agagacuggu gacauggcua gcagccgaaa ggcugc 36

<210> SEQ ID NO 910
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 910
uagccauguc accagucucu gg 22

<210> SEQ ID NO 911
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 911
acuggugaca uggcuuccaa gcagccgaaa ggcugc 36

<210> SEQ ID NO 912
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 912
uuggaagcca ugucaccagu gg 22

<210> SEQ ID NO 913

<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 913
cuccaccuuu cccaguuuua gcagccgaaa ggcugc 36

<210> SEQ ID NO 914
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 914
uaaaacuggg aaagguggag gg 22

<210> SEQ ID NO 915
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 915
caccuuuccc aguuuuucaa gcagccgaaa ggcugc 36

<210> SEQ ID NO 916
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 916
uugaaaaacu gggaaaggug gg 22

<210> SEQ ID NO 917
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 917
aguuuuucac uagagaagaa gcagccgaaa ggcugc 36

<210> SEQ ID NO 918
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 918
uucuucucua gugaaaaacu gg 22

<210> SEQ ID NO 919
<211> LENGTH: 36

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 919
agcagauucu uucagaggua gcagccgaaa ggcugc 36

<210> SEQ ID NO 920
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 920
uaccucugaa agaaucugcu gg 22

<210> SEQ ID NO 921
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 921
gcagauucuu ucagagguga gcagccgaaa ggcugc 36

<210> SEQ ID NO 922
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 922
ucaccucuga aagaaucugc gg 22

<210> SEQ ID NO 923
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 923
agauucuuuc agaggugcua gcagccgaaa ggcugc 36

<210> SEQ ID NO 924
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 924
uagcaccucu gaaagaaucu gg 22

<210> SEQ ID NO 925
<211> LENGTH: 36
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 925
aggugcuaaa guuucccaua gcagccgaaa ggcugc 36

<210> SEQ ID NO 926
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 926
uaugggaaac uuuagcaccu gg 22

<210> SEQ ID NO 927
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 927
aaaguuuccc aucuuuguga gcagccgaaa ggcugc 36

<210> SEQ ID NO 928
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 928
ucacaaagau gggaaacuuu gg 22

<210> SEQ ID NO 929
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 929
aguuucccau cuuugugcaa gcagccgaaa ggcugc 36

<210> SEQ ID NO 930
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 930
uugcacaaag augggaaacu gg 22

<210> SEQ ID NO 931
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 931
agccucugag cugaguugga gcagccgaaa ggcugc 36

<210> SEQ ID NO 932
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 932
uccaacucag cucagaggcu gg 22

<210> SEQ ID NO 933
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 933
gccucugagc ugaguuggua gcagccgaaa ggcugc 36

<210> SEQ ID NO 934
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 934
uaccaacuca gcucagaggc gg 22

<210> SEQ ID NO 935
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 935
ccucugagcu gaguugguua gcagccgaaa ggcugc 36

<210> SEQ ID NO 936
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 936
uaaccaacuc agcucagagg gg 22

<210> SEQ ID NO 937
<211> LENGTH: 36
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 937
cucugagcug aguugguuua gcagccgaaa ggcugc 36

<210> SEQ ID NO 938
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 938
uaaaccaacu cagcucagag gg 22

<210> SEQ ID NO 939
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 939
ucugagcuga guugguuuua gcagccgaaa ggcugc 36

<210> SEQ ID NO 940
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 940
uaaaaccaac ucagcucaga gg 22

<210> SEQ ID NO 941
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 941
ugagcugagu ugguuuuaua gcagccgaaa ggcugc 36

<210> SEQ ID NO 942
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 942
uauaaaacca acucagcuca gg 22

<210> SEQ ID NO 943
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 943
ugaguugguu uuaugaaaaa gcagccgaaa ggcugc 36

<210> SEQ ID NO 944
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 944
uuuuucauaa aaccaacuca gg 22

<210> SEQ ID NO 945
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 945
gaguugguuu uaugaaaaga gcagccgaaa ggcugc 36

<210> SEQ ID NO 946
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 946
ucuuuucaua aaaccaacuc gg 22

<210> SEQ ID NO 947
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 947
uugguuuuau gaaaagcuaa gcagccgaaa ggcugc 36

<210> SEQ ID NO 948
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 948
uuagcuuuuc auaaaaccaa gg 22

<210> SEQ ID NO 949
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 949
ugguuuuaug aaaagcuaga gcagccgaaa ggcugc 36

<210> SEQ ID NO 950
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 950
ucuagcuuuu cauaaaacca gg 22

<210> SEQ ID NO 951
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 951
gguuuuauga aaagcuagga gcagccgaaa ggcugc 36

<210> SEQ ID NO 952
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 952
uccuagcuuu ucauaaaacc gg 22

<210> SEQ ID NO 953
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 953
uuuuaugaaa agcuaggaaa gcagccgaaa ggcugc 36

<210> SEQ ID NO 954
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 954
uuuccuagcu uuucauaaaa gg 22

<210> SEQ ID NO 955
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 955
uaugaaaagc uaggaagcaa gcagccgaaa ggcugc 36

<210> SEQ ID NO 956
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 956
uugcuuccua gcuuuucaua gg 22

<210> SEQ ID NO 957
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 957
augaaaagcu aggaagcaaa gcagccgaaa ggcugc 36

<210> SEQ ID NO 958
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 958
uuugcuuccu agcuuuucau gg 22

<210> SEQ ID NO 959
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 959
ccagcacuua acucuaauaa gcagccgaaa ggcugc 36

<210> SEQ ID NO 960
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 960
uuauuagagu uaagugcugg gg 22

<210> SEQ ID NO 961
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 961
cagcacuuaa cucuaauaca gcagccgaaa ggcugc 36

<210> SEQ ID NO 962
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 962
uguauuagag uuaagugcug gg 22

<210> SEQ ID NO 963
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 963
uaauacauca gcaugcguua gcagccgaaa ggcugc 36

<210> SEQ ID NO 964
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 964
uaacgcaugc ugauguauua gg 22

<210> SEQ ID NO 965
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 965
aauacaucag caugcguuaa gcagccgaaa ggcugc 36

<210> SEQ ID NO 966
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 966
uuaacgcaug cugauguauu gg 22

<210> SEQ ID NO 967
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 967
ugcguuaauu cagcugguua gcagccgaaa ggcugc 36

<210> SEQ ID NO 968
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 968
uaaccagcug aauuaacgca gg 22

<210> SEQ ID NO 969
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 969
gcguuaauuc agcugguuga gcagccgaaa ggcugc 36

<210> SEQ ID NO 970
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 970
ucaaccagcu gaauuaacgc gg 22

<210> SEQ ID NO 971
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 971
cguuaauuca gcugguugga gcagccgaaa ggcugc 36

<210> SEQ ID NO 972
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 972
uccaaccagc ugaauuaacg gg 22

<210> SEQ ID NO 973
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 973
uuaauucagc ugguugggaa gcagccgaaa ggcugc 36

<210> SEQ ID NO 974
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 974
uucccaacca gcugaauuaa gg 22

<210> SEQ ID NO 975
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 975
uaauucagcu gguugggaaa gcagccgaaa ggcugc 36

<210> SEQ ID NO 976
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 976
uuucccaacc agcugaauua gg 22

<210> SEQ ID NO 977
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 977
gcagaggguc ccuuacugaa gcagccgaaa ggcugc 36

<210> SEQ ID NO 978
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 978
uucaguaagg gacccucugc gg 22

<210> SEQ ID NO 979
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 979
cuauuaaugg ucagacugua gcagccgaaa ggcugc 36

<210> SEQ ID NO 980
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 980
uacagucuga ccauuaauag gg 22

<210> SEQ ID NO 981
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 981
uauuaauggu cagacuguua gcagccgaaa ggcugc 36

<210> SEQ ID NO 982
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 982
uaacagucug accauuaaua gg 22

<210> SEQ ID NO 983
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 983
auuaaugguc agacuguuca gcagccgaaa ggcugc 36

<210> SEQ ID NO 984
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 984
ugaacagucu gaccauuaau gg 22

<210> SEQ ID NO 985
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 985
uuaaugguca gacuguucca gcagccgaaa ggcugc 36

<210> SEQ ID NO 986
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 986
uggaacaguc ugaccauuaa gg 22

<210> SEQ ID NO 987
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 987
uaauggucag acuguuccaa gcagccgaaa ggcugc 36

<210> SEQ ID NO 988
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 988
uuggaacagu cugaccauua gg 22

<210> SEQ ID NO 989
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 989
aauggucaga cuguuccaga gcagccgaaa ggcugc 36

<210> SEQ ID NO 990
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 990
ucuggaacag ucugaccauu gg 22

<210> SEQ ID NO 991
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 991
agaacaccuu uuucaccuaa gcagccgaaa ggcugc 36

<210> SEQ ID NO 992

<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 992
uuaggugaaa aagguguucu gg 22

<210> SEQ ID NO 993
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 993
gaacaccuuu uucaccuaaa gcagccgaaa ggcugc 36

<210> SEQ ID NO 994
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 994
uuuaggugaa aaagguguuc gg 22

<210> SEQ ID NO 995
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 995
aacaccuuuu ucaccuaaca gcagccgaaa ggcugc 36

<210> SEQ ID NO 996
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 996
uguuagguga aaaagguguu gg 22

<210> SEQ ID NO 997
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 997
acaccuuuuu caccuaacua gcagccgaaa ggcugc 36

<210> SEQ ID NO 998
<211> LENGTH: 22

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 998
uaguuaggug aaaaaggugu gg 22

<210> SEQ ID NO 999
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 999
caccuuuuuc accuaacuaa gcagccgaaa ggcugc 36

<210> SEQ ID NO 1000
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1000
uuaguuaggu gaaaaaggug gg 22

<210> SEQ ID NO 1001
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1001
accuuuuuca ccuaacuaaa gcagccgaaa ggcugc 36

<210> SEQ ID NO 1002
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1002
uuuaguuagg ugaaaaaggu gg 22

<210> SEQ ID NO 1003
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1003
cuuuuucacc uaacuaaaaa gcagccgaaa ggcugc 36

<210> SEQ ID NO 1004
<211> LENGTH: 22
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1004
uuuuuaguua ggugaaaaag gg 22

<210> SEQ ID NO 1005
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1005
uuuucaccua acuaaaauaa gcagccgaaa ggcugc 36

<210> SEQ ID NO 1006
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1006
uuauuuuagu uaggugaaaa gg 22

<210> SEQ ID NO 1007
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1007
uucaccuaac uaaaauaaua gcagccgaaa ggcugc 36

<210> SEQ ID NO 1008
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1008
uauuauuuua guuaggugaa gg 22

<210> SEQ ID NO 1009
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1009
ucaccuaacu aaaauaauga gcagccgaaa ggcugc 36

<210> SEQ ID NO 1010
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1010
ucauuauuuu aguuagguga gg 22

<210> SEQ ID NO 1011
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1011
caccuaacua aaauaaugua gcagccgaaa ggcugc 36

<210> SEQ ID NO 1012
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1012
uacauuauuu uaguuaggug gg 22

<210> SEQ ID NO 1013
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1013
accuaacuaa aauaauguua gcagccgaaa ggcugc 36

<210> SEQ ID NO 1014
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1014
uaacauuauu uuaguuaggu gg 22

<210> SEQ ID NO 1015
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1015
ccuaacuaaa auaauguuua gcagccgaaa ggcugc 36

<210> SEQ ID NO 1016
<211> LENGTH: 22
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1016
uaaacauuau uuuaguuagg gg 22

<210> SEQ ID NO 1017
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1017
cuaacuaaaa uaauguuuaa gcagccgaaa ggcugc 36

<210> SEQ ID NO 1018
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1018
uuaaacauua uuuuaguuag gg 22

<210> SEQ ID NO 1019
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1019
uaacuaaaau aauguuuaaa gcagccgaaa ggcugc 36

<210> SEQ ID NO 1020
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1020
uuuaaacauu auuuuaguua gg 22

<210> SEQ ID NO 1021
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1021
aacuaaaaua auguuuaaaa gcagccgaaa ggcugc 36

<210> SEQ ID NO 1022
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1022
uuuuaaacau uauuuuaguu gg 22

<210> SEQ ID NO 1023
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1023
acuaaaauaa uguuuaaaga gcagccgaaa ggcugc 36

<210> SEQ ID NO 1024
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1024
ucuuuaaaca uuauuuuagu gg 22

<210> SEQ ID NO 1025
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1025
cuaaaauaau guuuaaagaa gcagccgaaa ggcugc 36

<210> SEQ ID NO 1026
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1026
uucuuuaaac auuauuuuag gg 22

<210> SEQ ID NO 1027
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1027
uaaaauaaug uuuaaagaga gcagccgaaa ggcugc 36

<210> SEQ ID NO 1028
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1028
ucucuuuaaa cauuauuuua gg 22

<210> SEQ ID NO 1029
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1029
aagaguuuug uauaaaaaua gcagccgaaa ggcugc 36

<210> SEQ ID NO 1030
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1030
uauuuuuaua caaaacucuu gg 22

<210> SEQ ID NO 1031
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1031
guuuuguaua aaaauguaaa gcagccgaaa ggcugc 36

<210> SEQ ID NO 1032
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1032
uuuacauuuu uauacaaaac gg 22

<210> SEQ ID NO 1033
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1033
uuguauaaaa auguaaggaa gcagccgaaa ggcugc 36

<210> SEQ ID NO 1034
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1034
uuccuuacau uuuuauacaa gg 22

<210> SEQ ID NO 1035
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1035
uguauaaaaa uguaaggaaa gcagccgaaa ggcugc 36

<210> SEQ ID NO 1036
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1036
uuuccuuaca uuuuuauaca gg 22

<210> SEQ ID NO 1037
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1037
guauaaaaau guaaggaaga gcagccgaaa ggcugc 36

<210> SEQ ID NO 1038
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1038
ucuuccuuac auuuuuauac gg 22

<210> SEQ ID NO 1039
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1039
auguaaggaa gcguuguuaa gcagccgaaa ggcugc 36

<210> SEQ ID NO 1040
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1040
uuaacaacgc uuccuuacau gg 22

<210> SEQ ID NO 1041
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1041
uuuuguauua ugugaaucaa gcagccgaaa ggcugc 36

<210> SEQ ID NO 1042
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1042
uugauucaca uaauacaaaa gg 22

<210> SEQ ID NO 1043
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1043
uuuguauuau gugaaucaga gcagccgaaa ggcugc 36

<210> SEQ ID NO 1044
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1044
ucugauucac auaauacaaa gg 22

<210> SEQ ID NO 1045
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1045
uuguauuaug ugaaucagua gcagccgaaa ggcugc 36

<210> SEQ ID NO 1046
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1046
uacugauuca cauaauacaa gg 22

<210> SEQ ID NO 1047
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1047
guauuaugug aaucagugaa gcagccgaaa ggcugc 36

<210> SEQ ID NO 1048
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1048
uucacugauu cacauaauac gg 22

<210> SEQ ID NO 1049
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1049
uauuauguga aucagugaga gcagccgaaa ggcugc 36

<210> SEQ ID NO 1050
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1050
ucucacugau ucacauaaua gg 22

<210> SEQ ID NO 1051
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1051
auuaugugaa ucagugagaa gcagccgaaa ggcugc 36

<210> SEQ ID NO 1052
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1052
uucucacuga uucacauaau gg 22

<210> SEQ ID NO 1053
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1053
uuaugugaau cagugagaua gcagccgaaa ggcugc 36

<210> SEQ ID NO 1054
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1054
uaucucacug auucacauaa gg 22

<210> SEQ ID NO 1055
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1055
uaugugaauc agugagauga gcagccgaaa ggcugc 36

<210> SEQ ID NO 1056
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1056
ucaucucacu gauucacaua gg 22

<210> SEQ ID NO 1057
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1057
augugaauca gugagaugua gcagccgaaa ggcugc 36

<210> SEQ ID NO 1058
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1058
uacaucucac ugauucacau gg 22

<210> SEQ ID NO 1059
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1059
ugugaaucag ugagauguua gcagccgaaa ggcugc 36

<210> SEQ ID NO 1060
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1060
uaacaucuca cugauucaca gg 22

<210> SEQ ID NO 1061
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1061
gugaaucagu gagauguuaa gcagccgaaa ggcugc 36

<210> SEQ ID NO 1062
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1062
uuaacaucuc acugauucac gg 22

<210> SEQ ID NO 1063
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1063
gugagauguu aguagaauaa gcagccgaaa ggcugc 36

<210> SEQ ID NO 1064
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1064
uuauucuacu aacaucucac gg 22

<210> SEQ ID NO 1065
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1065
uuucuauuua ugcauuugaa gcagccgaaa ggcugc 36

<210> SEQ ID NO 1066
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1066
uucaaaugca uaaauagaaa gg 22

<210> SEQ ID NO 1067
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1067
cuauuuaugc auuugaguaa gcagccgaaa ggcugc 36

<210> SEQ ID NO 1068
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1068
uuacucaaau gcauaaauag gg 22

<210> SEQ ID NO 1069
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1069
ugcucaaacu guuaaaugua gcagccgaaa ggcugc 36

<210> SEQ ID NO 1070
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1070
uacauuuaac aguuugagca gg 22

<210> SEQ ID NO 1071

<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1071
gcucaaacug uuaaauguua gcagccgaaa ggcugc 36

<210> SEQ ID NO 1072
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1072
uaacauuuaa caguuugagc gg 22

<210> SEQ ID NO 1073
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1073
cucaaacugu uaaauguuga gcagccgaaa ggcugc 36

<210> SEQ ID NO 1074
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1074
ucaacauuua acaguuugag gg 22

<210> SEQ ID NO 1075
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1075
ucaaacuguu aaauguugga gcagccgaaa ggcugc 36

<210> SEQ ID NO 1076
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1076
uccaacauuu aacaguuuga gg 22

<210> SEQ ID NO 1077
<211> LENGTH: 36

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1077
caaacuguua aauguuggaa gcagccgaaa ggcugc 36

<210> SEQ ID NO 1078
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078
uuccaacauu uaacaguuug gg 22

<210> SEQ ID NO 1079
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079
aaacuguuaa auguuggaaa gcagccgaaa ggcugc 36

<210> SEQ ID NO 1080
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1080
uuuccaacau uuaacaguuu gg 22

<210> SEQ ID NO 1081
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1081
aacuguuaaa uguuggaaaa gcagccgaaa ggcugc 36

<210> SEQ ID NO 1082
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1082
uuuuccaaca uuuaacaguu gg 22

<210> SEQ ID NO 1083
<211> LENGTH: 36
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1083
uguuaaaugu uggaaaagaa gcagccgaaa ggcugc 36

<210> SEQ ID NO 1084
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1084
uucuuuucca acauuuaaca gg 22

<210> SEQ ID NO 1085
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1085
guuaaauguu ggaaaagaaa gcagccgaaa ggcugc 36

<210> SEQ ID NO 1086
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1086
uuucuuuucc aacauuuaac gg 22

<210> SEQ ID NO 1087
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1087
uuaaauguug gaaaagaaaa gcagccgaaa ggcugc 36

<210> SEQ ID NO 1088
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1088
uuuucuuuuc caacauuuaa gg 22

<210> SEQ ID NO 1089
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1089
uaaauguugg aaaagaaaga gcagccgaaa ggcugc 36

<210> SEQ ID NO 1090
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1090
ucuuucuuuu ccaacauuua gg 22

<210> SEQ ID NO 1091
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1091
agaaaagagg cuacuuguga gcagccgaaa ggcugc 36

<210> SEQ ID NO 1092
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1092
ucacaaguag ccucuuuucu gg 22

<210> SEQ ID NO 1093
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1093
gaaaagaggc uacuugugaa gcagccgaaa ggcugc 36

<210> SEQ ID NO 1094
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1094
uucacaagua gccucuuuuc gg 22

<210> SEQ ID NO 1095
<211> LENGTH: 36
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1095
aaaagaggcu acuugugaaa gcagccgaaa ggcugc 36

<210> SEQ ID NO 1096
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1096
uuucacaagu agccucuuuu gg 22

<210> SEQ ID NO 1097
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1097
agaggcuacu ugugaaaaua gcagccgaaa ggcugc 36

<210> SEQ ID NO 1098
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1098
uauuuucaca aguagccucu gg 22

<210> SEQ ID NO 1099
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1099
gaggcuacuu gugaaaauaa gcagccgaaa ggcugc 36

<210> SEQ ID NO 1100
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1100
uuauuuucac aaguagccuc gg 22

<210> SEQ ID NO 1101
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1101
aaaguuacaa guuucuuuua gcagccgaaa ggcugc 36

<210> SEQ ID NO 1102
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1102
uaaaagaaac uuguaacuuu gg 22

<210> SEQ ID NO 1103
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1103
caacaguauu uucuaauaaa gcagccgaaa ggcugc 36

<210> SEQ ID NO 1104
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1104
uuuauuagaa aauacuguug gg 22

<210> SEQ ID NO 1105
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1105
aacaguauuu ucuaauaaca gcagccgaaa ggcugc 36

<210> SEQ ID NO 1106
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1106
uguuauuaga aaauacuguu gg 22

<210> SEQ ID NO 1107
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1107
acaguauuuu cuaauaacca gcagccgaaa ggcugc 36

<210> SEQ ID NO 1108
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1108
ugguuauuag aaaauacugu gg 22

<210> SEQ ID NO 1109
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1109
caguauuuuc uaauaaccaa gcagccgaaa ggcugc 36

<210> SEQ ID NO 1110
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1110
uugguuauua gaaaauacug gg 22

<210> SEQ ID NO 1111
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1111
uugugauugu uaucaggaaa gcagccgaaa ggcugc 36

<210> SEQ ID NO 1112
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1112
uuuccugaua acaaucacaa gg 22

<210> SEQ ID NO 1113
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1113
ugugauuguu aucaggaaaa gcagccgaaa ggcugc 36

<210> SEQ ID NO 1114
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1114
uuuuccugau aacaaucaca gg 22

<210> SEQ ID NO 1115
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1115
gugauuguua ucaggaaaaa gcagccgaaa ggcugc 36

<210> SEQ ID NO 1116
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1116
uuuuuccuga uaacaaucac gg 22

<210> SEQ ID NO 1117
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1117
ugauuguuau caggaaaaaa gcagccgaaa ggcugc 36

<210> SEQ ID NO 1118
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1118
uuuuuuccug auaacaauca gg 22

<210> SEQ ID NO 1119
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1119
gauuguuauc aggaaaaaaa gcagccgaaa ggcugc 36

<210> SEQ ID NO 1120
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1120
uuuuuuuccu gauaacaauc gg 22

<210> SEQ ID NO 1121
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1121
auuguuauca ggaaaaaaua gcagccgaaa ggcugc 36

<210> SEQ ID NO 1122
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1122
uauuuuuucc ugauaacaau gg 22

<210> SEQ ID NO 1123
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1123
uuguuaucag gaaaaaauaa gcagccgaaa ggcugc 36

<210> SEQ ID NO 1124
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1124
uuauuuuuuc cugauaacaa gg 22

<210> SEQ ID NO 1125
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1125
uguuaucagg aaaaaauaua gcagccgaaa ggcugc 36

<210> SEQ ID NO 1126
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1126
uauauuuuuu ccugauaaca gg 22

<210> SEQ ID NO 1127
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1127
guuaucagga aaaaauauaa gcagccgaaa ggcugc 36

<210> SEQ ID NO 1128
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1128
uuauauuuuu uccugauaac gg 22

<210> SEQ ID NO 1129
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1129
uuaucaggaa aaaauauaua gcagccgaaa ggcugc 36

<210> SEQ ID NO 1130
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1130
uauauauuuu uuccugauaa gg 22

<210> SEQ ID NO 1131
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1131
aggaaaaaau auauuaaaua gcagccgaaa ggcugc 36

<210> SEQ ID NO 1132
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1132
uauuuaauau auuuuuuccu gg 22

<210> SEQ ID NO 1133
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1133
ggaaaaaaua uauuaaauga gcagccgaaa ggcugc 36

<210> SEQ ID NO 1134
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1134
ucauuuaaua uauuuuuucc gg 22

<210> SEQ ID NO 1135
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1135
gaaaaaauau auuaaaugga gcagccgaaa ggcugc 36

<210> SEQ ID NO 1136
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1136
uccauuuaau auauuuuuuc gg 22

<210> SEQ ID NO 1137
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1137
auuuucuuuc ugcuuuuaaa gcagccgaaa ggcugc 36

<210> SEQ ID NO 1138
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1138
uuuaaaagca gaaagaaaau gg 22

<210> SEQ ID NO 1139
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1139
ucuuucugcu uuuaaaaaua gcagccgaaa ggcugc 36

<210> SEQ ID NO 1140
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1140
uauuuuuaaa agcagaaaga gg 22

<210> SEQ ID NO 1141
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1141
uaaggaaauc aggaagugua gcagccgaaa ggcugc 36

<210> SEQ ID NO 1142
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1142
uacacuuccu gauuuccuua gg 22

<210> SEQ ID NO 1143
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1143
aaggaaauca ggaaguguaa gcagccgaaa ggcugc 36

<210> SEQ ID NO 1144
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1144
uuacacuucc ugauuuccuu gg 22

<210> SEQ ID NO 1145
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1145
ggaaaucagg aaguguaaua gcagccgaaa ggcugc 36

<210> SEQ ID NO 1146
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1146
uauuacacuu ccugauuucc gg 22

<210> SEQ ID NO 1147
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1147
ccacacccag cuaguuuuua gcagccgaaa ggcugc 36

<210> SEQ ID NO 1148
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1148
uaaaaacuag cuggguguggg gg 22

<210> SEQ ID NO 1149
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1149
cacacccagc uaguuuuuua gcagccgaaa ggcugc 36

<210> SEQ ID NO 1150

<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1150
uaaaaaacua gcugggugug gg 22

<210> SEQ ID NO 1151
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1151
cuaggauuac aggugugaga gcagccgaaa ggcugc 36

<210> SEQ ID NO 1152
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1152
ucucacaccu guaauccuag gg 22

<210> SEQ ID NO 1153
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1153
agaguaugag ccugauuuua gcagccgaaa ggcugc 36

<210> SEQ ID NO 1154
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1154
uaaaaucagg cucauacucu gg 22

<210> SEQ ID NO 1155
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1155
gaguaugagc cugauuuuga gcagccgaaa ggcugc 36

<210> SEQ ID NO 1156
<211> LENGTH: 22

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1156
ucaaaaucag gcucauacuc gg 22

<210> SEQ ID NO 1157
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1157
cccaucucua cuaaaaaaua gcagccgaaa ggcugc 36

<210> SEQ ID NO 1158
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1158
uauuuuuuag uagagauggg gg 22

<210> SEQ ID NO 1159
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1159
acuuucagca ugagaaaaua gcagccgaaa ggcugc 36

<210> SEQ ID NO 1160
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1160
uauuuucuca ugcugaaagu gg 22

<210> SEQ ID NO 1161
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1161
cugagcugag uugguuuuag cagccgaaag gcugc 35

<210> SEQ ID NO 1162
<211> LENGTH: 22
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1162
uuaaaaccaa cucagcucag gg 22

<210> SEQ ID NO 1163
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1163
gcugaguugg uuuuaugaaa gcagccgaaa ggcugc 36

<210> SEQ ID NO 1164
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1164
uuucauaaaa ccaacucagc gg 22

<210> SEQ ID NO 1165
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1165
cuguugaauu uuguauuaua 20

<210> SEQ ID NO 1166
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1166
uauaauacaa aauucaacag gg 22

<210> SEQ ID NO 1167
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1167
caacgtaccc ttcattgat 19

<210> SEQ ID NO 1168
<211> LENGTH: 19
<212> TYPE: DNA
<213> ORGANISM: Unknown

<220> FEATURE:
<223> OTHER INFORMATION: Description of Unknown:
Target Sequence

<400> SEQUENCE: 1168
tgaaagacaa aggtggata 19

<210> SEQ ID NO 1169
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1169
tacatgagca agatttgca 19

<210> SEQ ID NO 1170
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1170
tgagcaagat ttgcaactt 19

<210> SEQ ID NO 1171
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1171
ctctgagctg agttggttt 19

<210> SEQ ID NO 1172
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1172
ctttttcacc taactaaaa 19

<210> SEQ ID NO 1173
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1173
ttcacctaac taaaataat 19

<210> SEQ ID NO 1174
<211> LENGTH: 19
<212> TYPE: DNA
<213> ORGANISM: Unknown
<220> FEATURE:

<223> OTHER INFORMATION: Description of Unknown:
Target Sequence

<400> SEQUENCE: 1174
ctaactaaaa taatgttta 19

<210> SEQ ID NO 1175
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1175
ctgagctgag ttggtttta 19

<210> SEQ ID NO 1176
<211> LENGTH: 19
<212> TYPE: DNA
<213> ORGANISM: Unknown
<220> FEATURE:
<223> OTHER INFORMATION: Description of Unknown:
Target Sequence

<400> SEQUENCE: 1176
gctgagttgg ttttatgaa 19

<210> SEQ ID NO 1177
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1177
gcagccgaaa ggcugc 16

<210> SEQ ID NO 1178
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1178
cccauuagga uaaugucuua gcagccgaaa ggcugc 36

<210> SEQ ID NO 1179
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1179
uaagacauua uccuaauggg gg 22

<210> SEQ ID NO 1180
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1180
acaacguacc cuucauugaa gcagccgaaa ggcugc 36

<210> SEQ ID NO 1181
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1181
uucaaugaag gguacguugu gg 22

<210> SEQ ID NO 1182
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1182
gcacugagug aagaaaugaa gcagccgaaa ggcugc 36

<210> SEQ ID NO 1183
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1183
uucauuucuu cacucagugc gg 22

<210> SEQ ID NO 1184
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1184
acuugcuacc cauuaggaua gcagccgaaa ggcugc 36

<210> SEQ ID NO 1185
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1185
uauccuaaug gguagcaagu gg 22

<210> SEQ ID NO 1186
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1186
cccauuagga uaaugucuua gcagccgaaa ggcugc 36

<210> SEQ ID NO 1187
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1187
uaagacauua uccuaauggg gg 22

<210> SEQ ID NO 1188
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1188
cugagcugag uugguuuuaa gcagccgaaa ggcugc 36

<210> SEQ ID NO 1189
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1189
uuaaaaccaa cucagcucag gg 22

<210> SEQ ID NO 1190
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1190
gcugaguugg uuuuaugaaa gcagccgaaa ggcugc 36

<210> SEQ ID NO 1191
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1191
uuucauaaaa ccaacucagc gg 22

<210> SEQ ID NO 1192
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1192
guugguuuua ugaaaagcua gcagccgaaa ggcugc 36

<210> SEQ ID NO 1193
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1193
uagcuuuuca uaaaaccaac gg 22

<210> SEQ ID NO 1194
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1194
gguaacaaga ugauaaucua gcagccgaaa ggcugc 36

<210> SEQ ID NO 1195
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1195
uagauuauca ucuuguuacc gg 22

<210> SEQ ID NO 1196
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1196
uuucaccuaa cuaaaauaaa gcagccgaaa ggcugc 36

<210> SEQ ID NO 1197
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1197
uuuauuuuag uuaggugaaa gg 22

<210> SEQ ID NO 1198
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1198
aaaauaaugu uuaaagagua gcagccgaaa ggcugc 36

<210> SEQ ID NO 1199
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1199
uacucuuuaa acauuauuuu gg 22

<210> SEQ ID NO 1200
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1200
aaauaauguu uaaagaguua gcagccgaaa ggcugc 36

<210> SEQ ID NO 1201
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1201
uaacucuuua aacauuauuu gg 22

<210> SEQ ID NO 1202
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1202
aauaauguuu aaagaguuua gcagccgaaa ggcugc 36

<210> SEQ ID NO 1203
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1203
uaaacucuuu aaacauuauu gg 22

<210> SEQ ID NO 1204
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1204
guuuaaagag uuuuguauaa gcagccgaaa ggcugc 36

<210> SEQ ID NO 1205
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1205
uuauacaaaa cucuuuaaac gg 22

<210> SEQ ID NO 1206
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1206
uuaaagaguu uuguauaaaa gcagccgaaa ggcugc 36

<210> SEQ ID NO 1207
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1207
uuuuauacaa aacucuuuaa gg 22

<210> SEQ ID NO 1208
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1208
gaguuuugua uaaaaaugua gcagccgaaa ggcugc 36

<210> SEQ ID NO 1209
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1209
uacauuuuua uacaaaacuc gg 22

<210> SEQ ID NO 1210
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1210
gcguuguuac cuguugaaua gcagccgaaa ggcugc 36

<210> SEQ ID NO 1211
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1211
uauucaacag guaacaacgc gg 22

<210> SEQ ID NO 1212
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1212
guuaccuguu gaauuuugua gcagccgaaa ggcugc 36

<210> SEQ ID NO 1213
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1213
uacaaaauuc aacagguaac gg 22

<210> SEQ ID NO 1214
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1214
ccuguugaau uuuguauuaa gcagccgaaa ggcugc 36

<210> SEQ ID NO 1215
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1215
uuaauacaaa auucaacagg gg 22

<210> SEQ ID NO 1216
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1216
cuguugaauu uuguauuaua gcagccgaaa ggcugc 36

<210> SEQ ID NO 1217
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1217
uauaauacaa aauucaacag gg 22

<210> SEQ ID NO 1218
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1218
gaauuuugua uuaugugaaa gcagccgaaa ggcugc 36

<210> SEQ ID NO 1219
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1219
uuucacauaa uacaaaauuc gg 22

<210> SEQ ID NO 1220
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1220
caacguaccc uucauugaua gcagccgaaa ggcugc 36

<210> SEQ ID NO 1221
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1221
uaucaaugaa ggguacguug gg 22

<210> SEQ ID NO 1222
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1222
uggacaucac caagcucaga gcagccgaaa ggcugc 36

<210> SEQ ID NO 1223
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1223
ucugagcuug gugaugucca gg 22

<210> SEQ ID NO 1224
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1224
ugaaagacaa agguggauaa gcagccgaaa ggcugc 36

<210> SEQ ID NO 1225
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1225
uuauccaccu uugucuuuca gg 22

<210> SEQ ID NO 1226
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1226
aagacaaagg uggauacaua gcagccgaaa ggcugc 36

<210> SEQ ID NO 1227
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1227
uauguaucca ccuuugucuu gg 22

<210> SEQ ID NO 1228
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1228
agacaaaggu ggauacauga gcagccgaaa ggcugc 36

<210> SEQ ID NO 1229

<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1229
ucauguaucc accuuugucu gg 22

<210> SEQ ID NO 1230
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1230
uacaugagca agauuugcaa gcagccgaaa ggcugc 36

<210> SEQ ID NO 1231
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1231
uugcaaaucu ugcucaugua gg 22

<210> SEQ ID NO 1232
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1232
ugagcaagau uugcaacuua gcagccgaaa ggcugc 36

<210> SEQ ID NO 1233
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1233
uaaguugcaa aucuugcuca gg 22

<210> SEQ ID NO 1234
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1234
aagauuugca acuugcuaca gcagccgaaa ggcugc 36

<210> SEQ ID NO 1235
<211> LENGTH: 22

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1235
uguagcaagu ugcaaaucuu gg 22

<210> SEQ ID NO 1236
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1236
ugcgauuguc cagagacuga gcagccgaaa ggcugc 36

<210> SEQ ID NO 1237
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1237
ucagucucug gacaaucgca gg 22

<210> SEQ ID NO 1238
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1238
uuuucaccua acuaaaauaa gcagccgaaa ggcugc 36

<210> SEQ ID NO 1239
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1239
uuauuuuagu uaggugaaaa gg 22

<210> SEQ ID NO 1240
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1240
ucugagcuga guugguuuua gcagccgaaa ggcugc 36

<210> SEQ ID NO 1241
<211> LENGTH: 22
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1241
uaaaaccaac ucagcucaga gg 22

<210> SEQ ID NO 1242
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1242
accuuuuuca ccuaacuaaa gcagccgaaa ggcugc 36

<210> SEQ ID NO 1243
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1243
uuuaguuagg ugaaaaaggu gg 22

<210> SEQ ID NO 1244
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1244
cuuuuucacc uaacuaaaaa gcagccgaaa ggcugc 36

<210> SEQ ID NO 1245
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1245
uuuuuaguua ggugaaaaag gg 22

<210> SEQ ID NO 1246
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1246
uucaccuaac uaaaauaaua gcagccgaaa ggcugc 36

<210> SEQ ID NO 1247
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1247
uauuauuuua guuaggugaa gg 22

<210> SEQ ID NO 1248
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1248
caccuaacua aaauaaugua gcagccgaaa ggcugc 36

<210> SEQ ID NO 1249
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1249
uacauuauuu uaguuaggug gg 22

<210> SEQ ID NO 1250
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1250
cuaacuaaaa uaauguuuaa gcagccgaaa ggcugc 36

<210> SEQ ID NO 1251
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1251
uuaaacauua uuuuaguuag gg 22

<210> SEQ ID NO 1252
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1252
caccuuuuuc accuaacuaa gcagccgaaa ggcugc 36

<210> SEQ ID NO 1253
<211> LENGTH: 22
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1253
uuaguuaggu gaaaaaggug gg 22

<210> SEQ ID NO 1254
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1254
cucugagcug aguugguuua gcagccgaaa ggcugc 36

<210> SEQ ID NO 1255
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1255
uaaaccaacu cagcucagag gg 22

<210> SEQ ID NO 1256
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1256
aggugcuaaa guuucccaua gcagccgaaa ggcugc 36

<210> SEQ ID NO 1257
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1257
uaugggaaac uuuagcaccu gg 22

<210> SEQ ID NO 1258
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1258
uguauaaaaa uguaaggaaa gcagccgaaa ggcugc 36

<210> SEQ ID NO 1259
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1259
uuuccuuaca uuuuuauaca gg 22

<210> SEQ ID NO 1260
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1260
augugaauca gugagaugua gcagccgaaa ggcugc 36

<210> SEQ ID NO 1261
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1261
uacaucucac ugauucacau gg 22

<210> SEQ ID NO 1262
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1262
auuaggauaa ugucuuauga gcagccgaaa ggcugc 36

<210> SEQ ID NO 1263
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1263
ucauaagaca uuauccuaau gg 22

<210> SEQ ID NO 1264
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1264
acaccuuuuu caccuaacua gcagccgaaa ggcugc 36

<210> SEQ ID NO 1265
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1265
uaguuaggug aaaaaggugu gg 22

<210> SEQ ID NO 1266
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1266
ugagugacaa cguacccuua gcagccgaaa ggcugc 36

<210> SEQ ID NO 1267
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1267
uaaggguacg uugucacuca gg 22

<210> SEQ ID NO 1268
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1268
agugaagaaa ugaaagacaa gcagccgaaa ggcugc 36

<210> SEQ ID NO 1269
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1269
uugucuuuca uuucuucacu gg 22

<210> SEQ ID NO 1270
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1270
auccucagaa gggauggaua gcagccgaaa ggcugc 36

<210> SEQ ID NO 1271
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1271
uauccauccc uucugaggau gg 22

<210> SEQ ID NO 1272
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1272
ugacaacgua cccuucauua gcagccgaaa ggcugc 36

<210> SEQ ID NO 1273
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1273
uaaugaaggg uacguuguca gg 22

<210> SEQ ID NO 1274
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1274
agguggauac augagcaaga gcagccgaaa ggcugc 36

<210> SEQ ID NO 1275
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1275
ucuugcucau guauccaccu gg 22

<210> SEQ ID NO 1276
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1276
ugcaacuugc uacccauuaa gcagccgaaa ggcugc 36

<210> SEQ ID NO 1277
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1277
uuaaugggua gcaaguugca gg 22

<210> SEQ ID NO 1278
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1278
caagauuugc aacuugcuaa gcagccgaaa ggcugc 36

<210> SEQ ID NO 1279
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1279
uuagcaaguu gcaaaucuug gg 22

<210> SEQ ID NO 1280
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1280
caccuuuccc aguuuuucaa gcagccgaaa ggcugc 36

<210> SEQ ID NO 1281
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1281
uugaaaaacu gggaaaggug gg 22

<210> SEQ ID NO 1282
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1282
uugcaacuug cuacccauua gcagccgaaa ggcugc 36

<210> SEQ ID NO 1283
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1283
uaauggguag caaguugcaa gg 22

<210> SEQ ID NO 1284
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1284
cuugcuaccc auuaggauaa gcagccgaaa ggcugc 36

<210> SEQ ID NO 1285
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1285
uuauccuaau ggguagcaag gg 22

<210> SEQ ID NO 1286
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1286
augaaagaca aagguggaua gcagccgaaa ggcugc 36

<210> SEQ ID NO 1287
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1287
uauccaccuu ugucuuucau gg 22

<210> SEQ ID NO 1288
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1288
agugacaacg uacccuucaa gcagccgaaa ggcugc 36

<210> SEQ ID NO 1289
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1289
uugaagggua cguugucacu gg 22

<210> SEQ ID NO 1290
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1290
acgaacuuuc uucaugugga gcagccgaaa ggcugc 36

<210> SEQ ID NO 1291
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1291
uccacaugaa gaaaguucgu gg 22

<210> SEQ ID NO 1292
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1292
uuucuucaug uggacaucaa gcagccgaaa ggcugc 36

<210> SEQ ID NO 1293
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1293
uugaugucca caugaagaaa gg 22

<210> SEQ ID NO 1294
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1294
uguggacauc accaagcuca gcagccgaaa ggcugc 36

<210> SEQ ID NO 1295
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1295
ugagcuuggu gauguccaca gg 22

<210> SEQ ID NO 1296
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1296
guggacauca ccaagcucaa gcagccgaaa ggcugc 36

<210> SEQ ID NO 1297
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1297
uugagcuugg ugauguccac gg 22

<210> SEQ ID NO 1298
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1298
agauaugccu ucgaggauaa gcagccgaaa ggcugc 36

<210> SEQ ID NO 1299
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1299
uuauccucga aggcauaucu gg 22

<210> SEQ ID NO 1300
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1300
gcguuguuac cuguugaaua gcagccgaaa ggcugc 36

<210> SEQ ID NO 1301
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1301
uauucaacag guaacaacgc gg 22

-continued

```
<210> SEQ ID NO 1302
<211> LENGTH: 58
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (38)..(56)
<223> OTHER INFORMATION: a, c, u, g, unknown or other

<400> SEQUENCE: 1302

nnnnnnnnnn nnnnnnnnna gcagccgaaa ggcugcunnn nnnnnnnnnn nnnnnngg       58


<210> SEQ ID NO 1303
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other

<400> SEQUENCE: 1303

nnnnnnnnnn nnnnnnnnna gcagccgaaa ggcugc                               36
```